US006290969B1

(12) United States Patent
Reed et al.

(10) Patent No.: US 6,290,969 B1
(45) Date of Patent: *Sep. 18, 2001

(54) COMPOUNDS AND METHODS FOR IMMUNOTHERAPY AND DIAGNOSIS OF TUBERCULOSIS

(75) Inventors: Steven G. Reed, Bellevue; Yasir A. W. Skeiky, Seattle; Davin C. Dillon, Redmond; Antonio Campos-Neto, Bainbridge Island; Raymond Houghton, Bothell; Thomas S. Vedvick, Federal Way; Daniel R. Twardzik, Bainbridge Island, all of WA (US)

(73) Assignee: Corixa Corporation, Seattle, WA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/818,112

(22) Filed: Mar. 13, 1997

Related U.S. Application Data

(63) Continuation-in-part of application No. 08/730,510, filed on Oct. 11, 1996, which is a continuation-in-part of application No. 08/680,574, filed on Jul. 12, 1996, which is a continuation-in-part of application No. 08/659,683, filed on Jun. 5, 1996, which is a continuation-in-part of application No. 08/620,874, filed on Mar. 22, 1996, now abandoned, which is a continuation-in-part of application No. 08/533,634, filed on Sep. 22, 1995, now abandoned, which is a continuation-in-part of application No. 08/523,436, filed on Sep. 1, 1995, now abandoned.

(51) Int. Cl.[7] ......................... A61K 39/04; A61K 39/40; C12Q 1/68; G01N 33/53

(52) U.S. Cl. ................................... 424/248.1; 424/168.1; 435/6; 435/7.1; 435/253.1; 435/325

(58) Field of Search ............................ 424/168.1, 248.1; 435/6, 7.1, 172.1, 172.3, 253.1, 320.1, 325

(56) References Cited

U.S. PATENT DOCUMENTS

| | | | |
|---|---|---|---|
| 3,943,119 | 3/1976 | Tsumita et al. | 260/112.5 R |
| 4,689,397 | 8/1987 | Shinnick et al. | 530/327 |
| 4,879,213 | 11/1989 | Fox et al. | 435/5 |
| 4,952,395 | 8/1990 | Shinnick et al. | 424/92 |
| 5,108,745 | 4/1992 | Horwitz | 424/92 |
| 5,330,754 | 7/1994 | Kapoor et al. | 424/190.1 |
| 5,478,726 | 12/1995 | Shinnick et al. | 435/724 |

FOREIGN PATENT DOCUMENTS

| | | |
|---|---|---|
| 419 355 A1 | 3/1991 | (EP) . |
| 519 218 A2 | 12/1992 | (EP) . |
| WO 88/05823 | 8/1988 | (WO) . |
| WO 91/04272 | 4/1991 | (WO) . |
| WO 91/14448 | 10/1991 | (WO) . |
| WO 92/04049 | 3/1992 | (WO) . |
| WO 92/14823 | 9/1992 | (WO) . |
| WO 92/21758 | 12/1992 | (WO) . |
| WO 94/00493 | 1/1994 | (WO) . |
| WO 95/01440 | 1/1995 | (WO) . |
| WO 95/01441 | 1/1995 | (WO) . |
| WO 95/14713 | 6/1995 | (WO) . |
| WO 95/31216 | 11/1995 | (WO) . |
| WO 96/15241 | 5/1996 | (WO) . |

OTHER PUBLICATIONS

Andersen and Heron "Specificity of a Protective Memory Immune Response against *Mycobacterium tuberculosis*" *Infection and Immunity* 61(3):844–851 (1993).

Burgess et al. "Possible Dissociation of the Heparin–binding and Mitogenic Activities of Heparin–Binding (Acidic Fibroblast) Growth Factor–1 from its Receptor–binding Activities by Site–Directed Mutagenesis of a Single Lysine Residue" *J. Cell. Biol.* 111:2129–2138 (1990).

Eiglmeier et al. "Use of an ordered cosmid library to deduce the genomic organization of *Mycobacterium leprae*" *Mol. Microbiol.* 7(2):197–206 (1993).

Fifis et al. "Purification and Characterization of Major Antigens from a *Mycobacterium bovis* Culture Filtrate" *Infection and Immunity* 59(3):800–807 (1991).

Geysen et al. "Cognitive features of continuous antigenic determinants" *J. Mol. Recognition* 1:32–41 (1988).

Greenway et al. "Enhancement of protective immune responses to Venezuelan equine encephalitis (VEE) virus with microencapsulated vaccine" *Vaccine* 13:1411–1420 (1995).

Kadival et al. "Radioimmunoassay of tuberculous antigen" *Indian J. Med. Res.* 75:765–770 (1982).

Lazar et al. "Transforming Growth Factor α: Mutation of Aspartic Acid 47 and Leucine 48 results in Different Biological Activities" *Mol. Cell. Biol.* 8(3):1247–1252 (1988).

Lee et al. "Characterization of the Major Membrane Protein of Virulent *Mycobacterium tuberculosis*" *Infection and Immunity* 60:2066–2074 (1992).

Lerner et al. "Cloning and structure of the *Bacillus subtilis* aspartate transcarbamylas gene (pyrB)" *J. Biol. Chem.* 261(24):11156–11165 (1986).

Mathur and Kolttukudy "Molecular cloning and sequencing of the gene for mycocerosic acid synthase, a novel fatty acid elongating multifunctional enzyme, from *Mycobacterium tuberculosis* var. *bovis* Bacillus Calmette–Guerin" *J. Biol. Chem.* 267:19388–19395 (1992).

(List continued on next page.)

Primary Examiner—Rodney P. Swartz
(74) Attorney, Agent, or Firm—Townsend & Townsend & Crew LLP

(57) ABSTRACT

Compounds and methods for inducing protective immunity against tuberculosis are disclosed. The compounds provided include polypeptides that contain at least one immunogenic portion of one or more *M. tuberculosis* proteins and DNA molecules encoding such polypeptides. Such compounds may be formulated into vaccines and/or pharmaceutical compositions for immunization against *M. tuberculosis* infection, or may be used for the diagnosis of tuberculosis.

98 Claims, 9 Drawing Sheets

U.S. PATENT DOCUMENTS

Figure 1A:
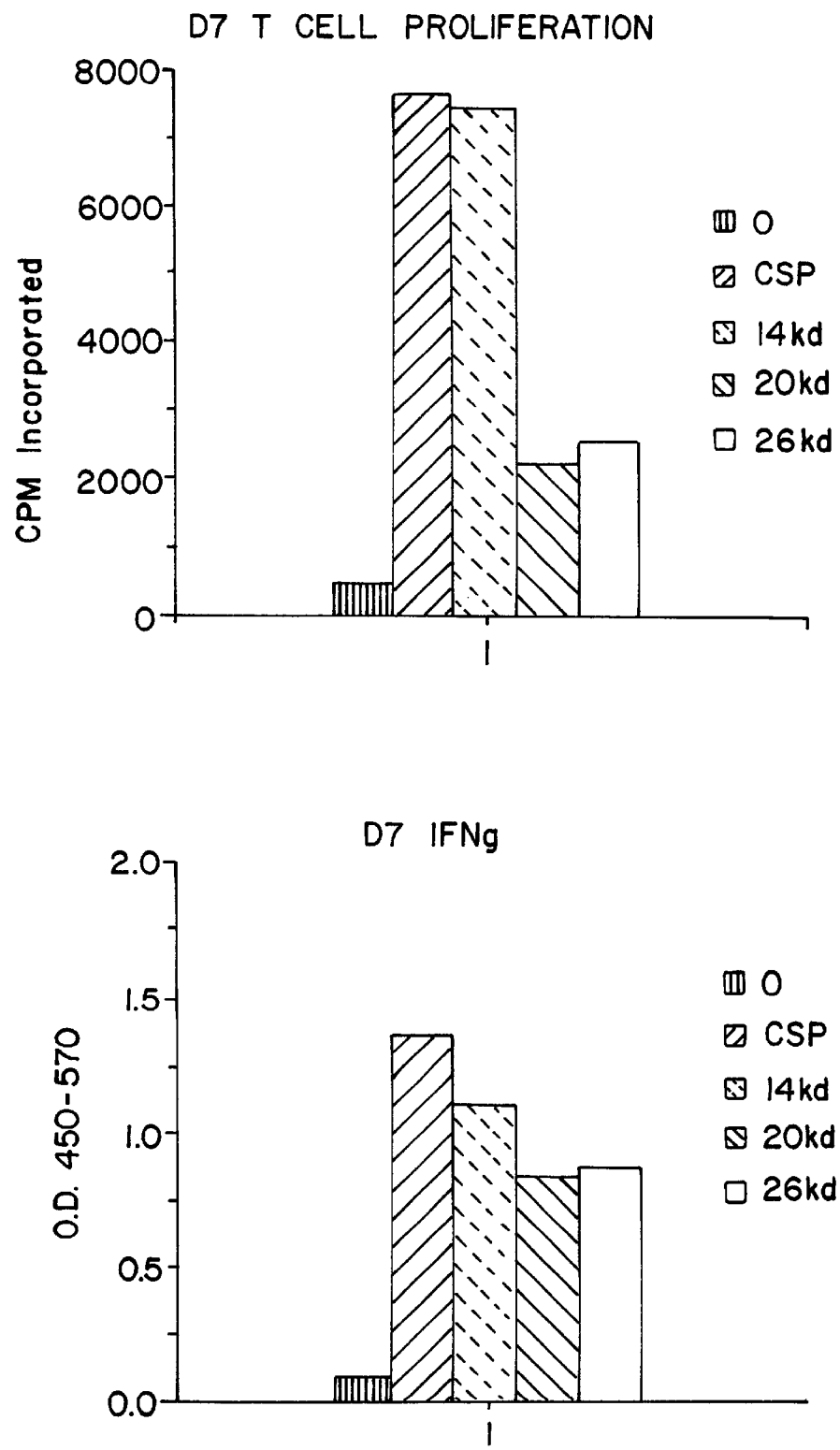
Figure 1B:
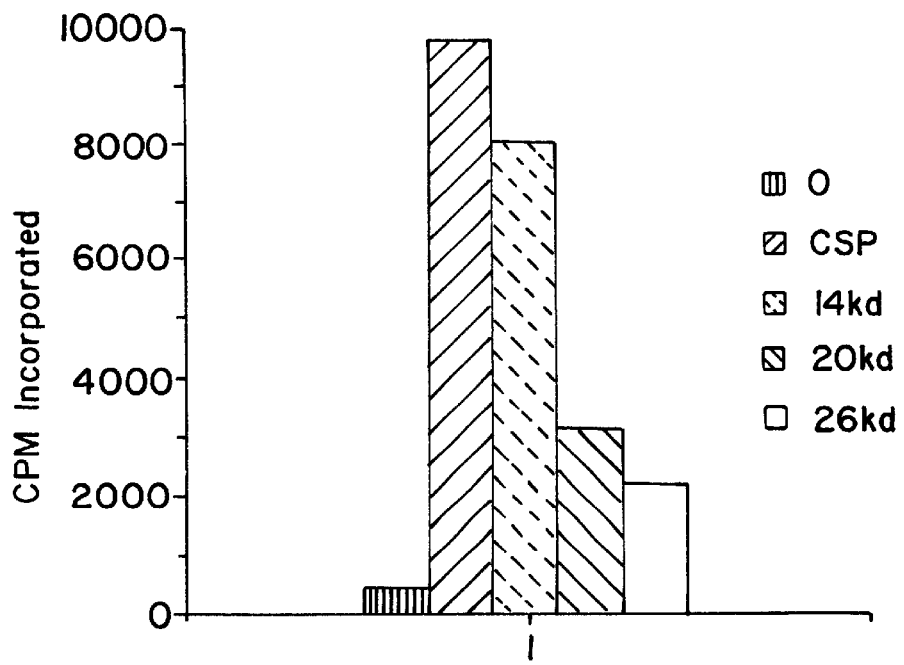
Figure 1B:
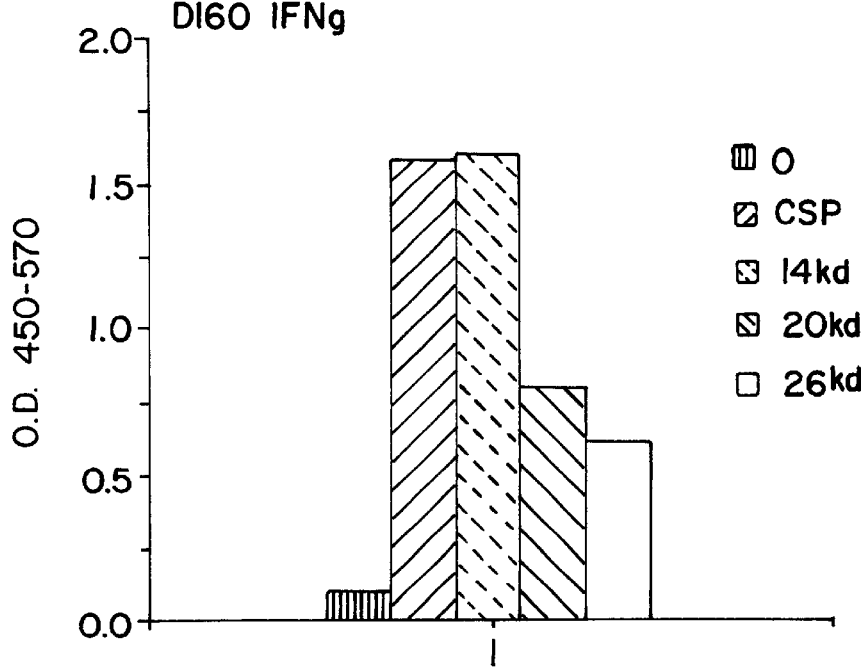
Figure 2:
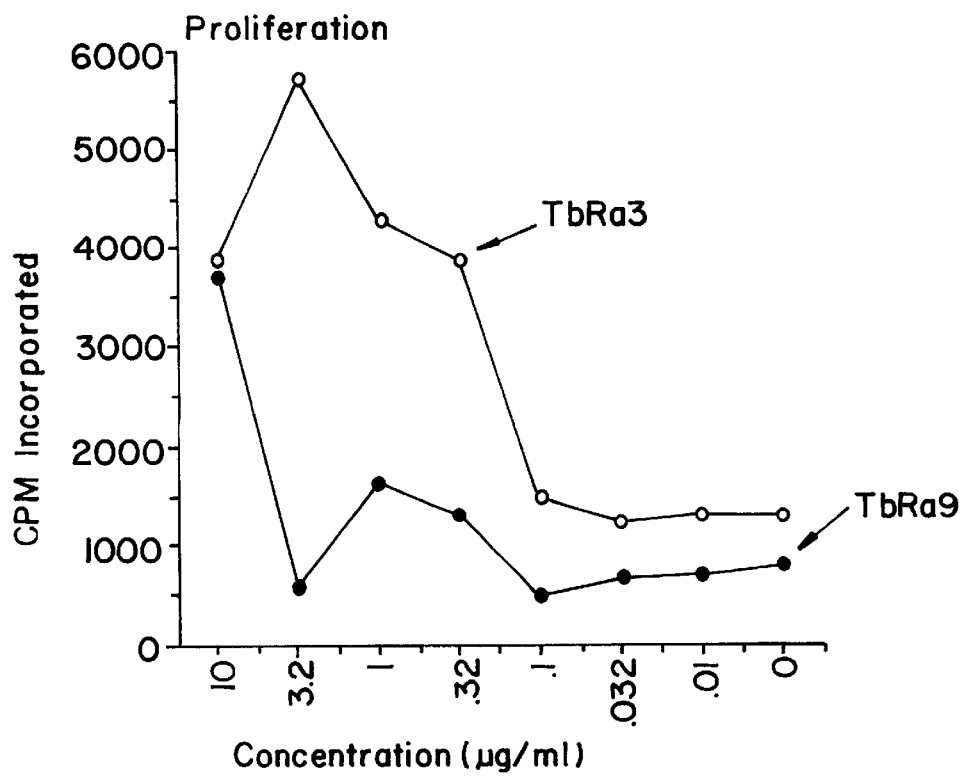
Figure 2:
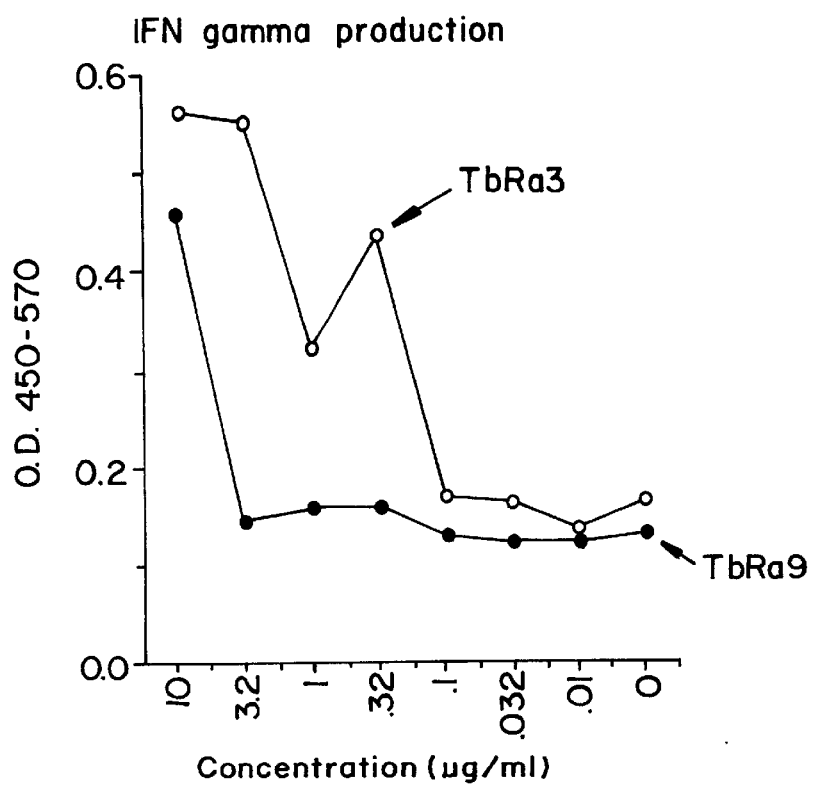
Figure 4A:
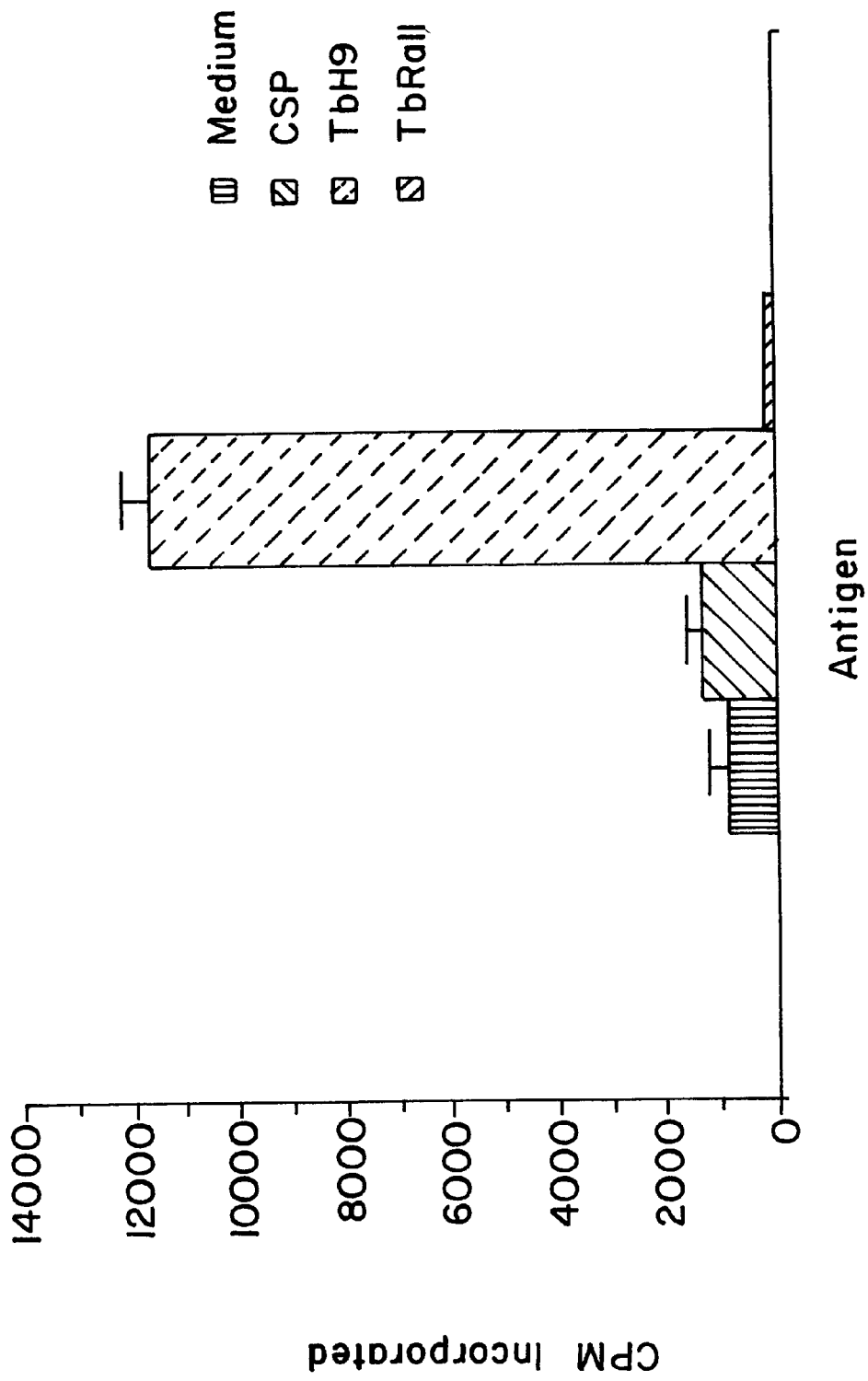
Figure 4B:
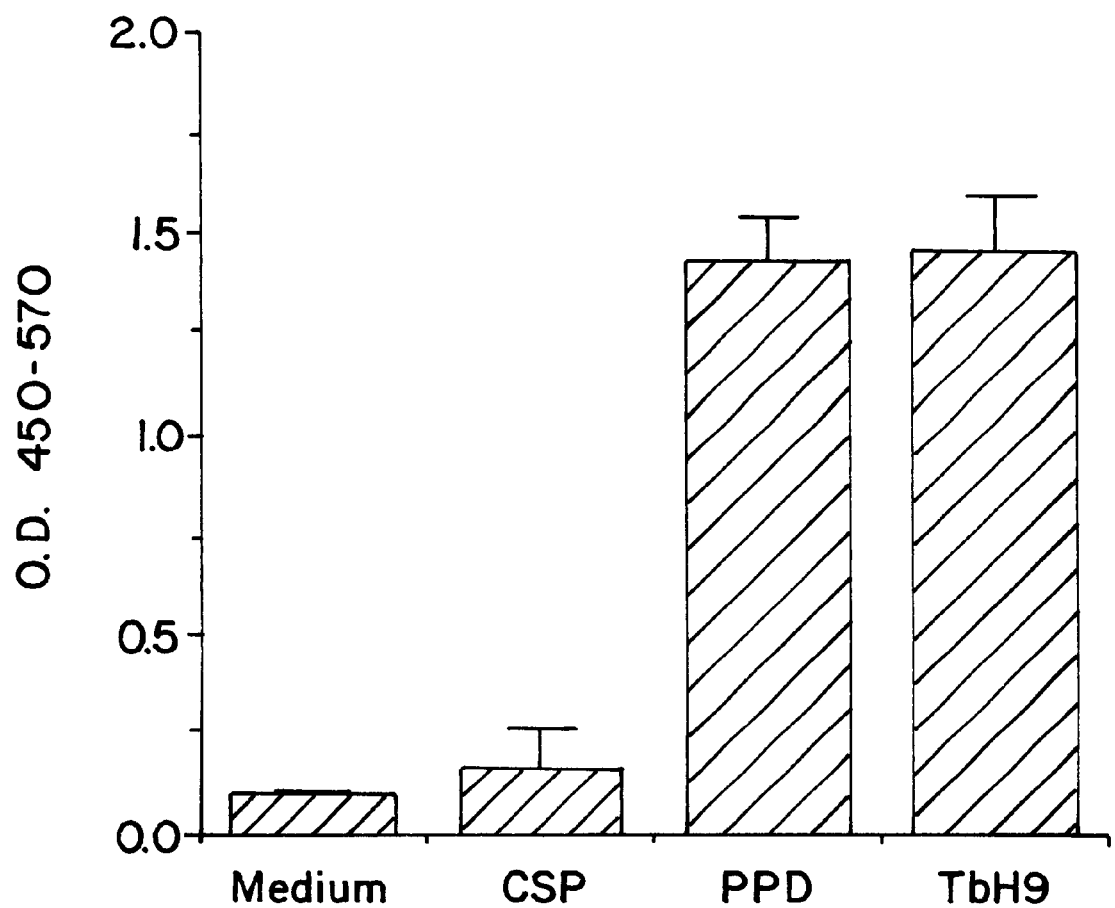
Figure 5A:
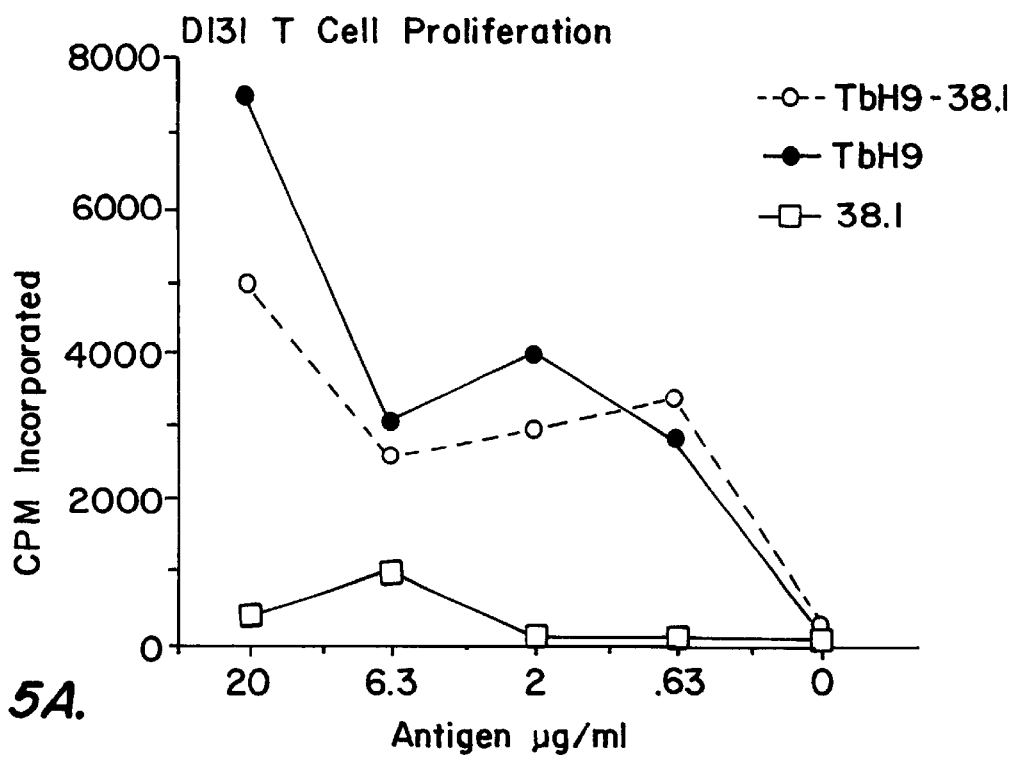
Figure 5B:
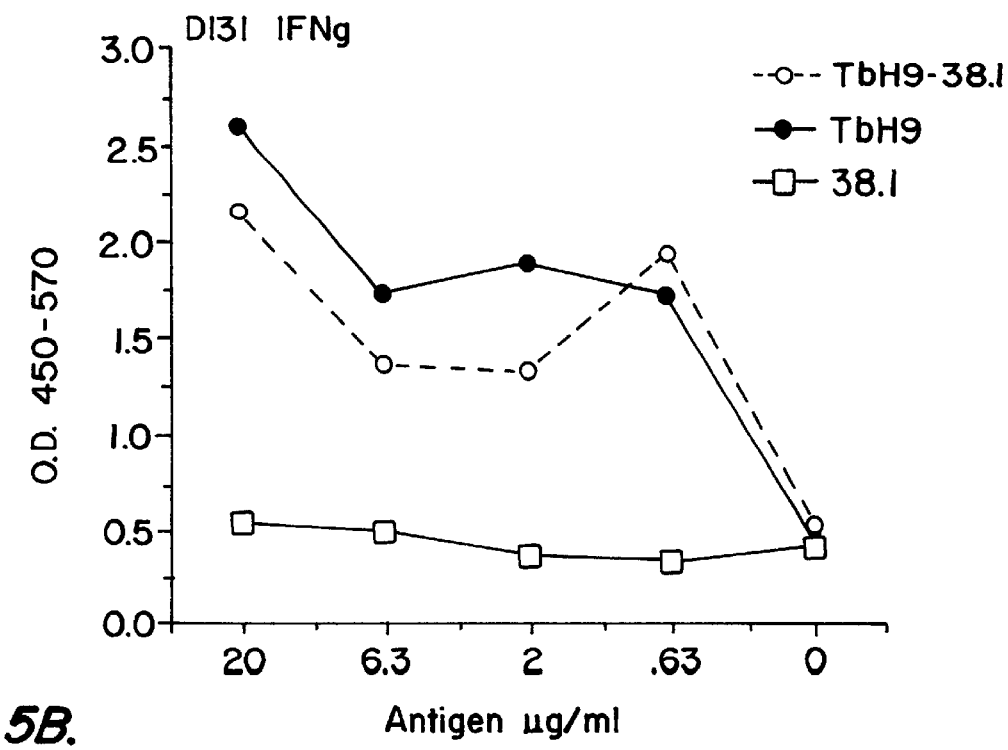
Figure 6A:
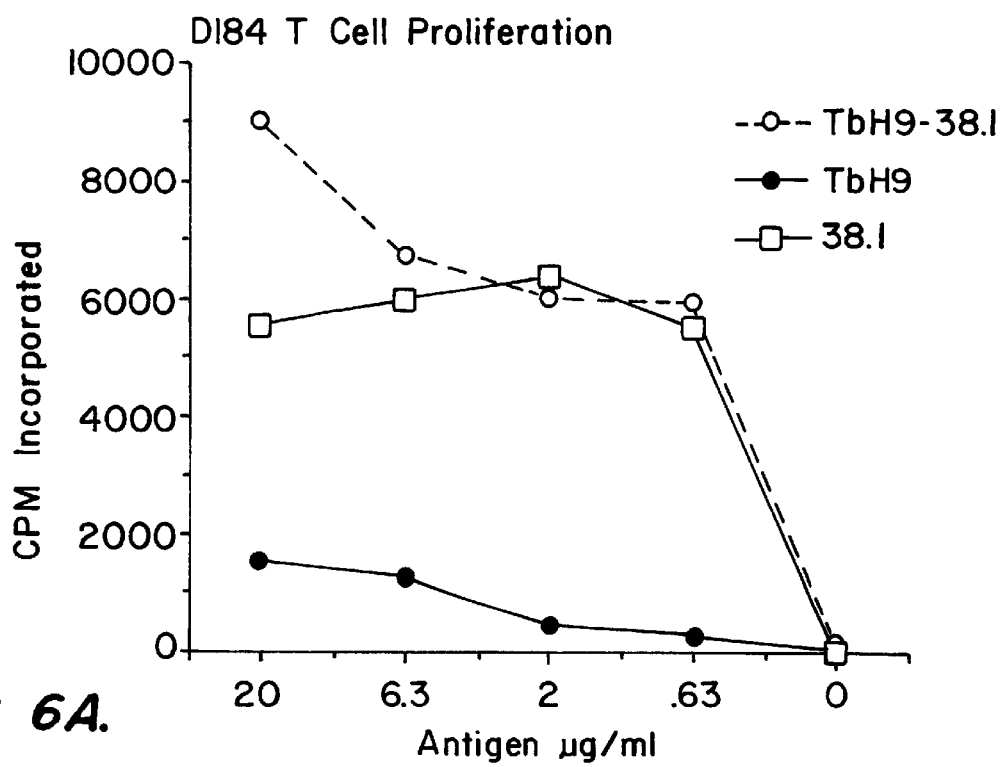
Figure 6B:
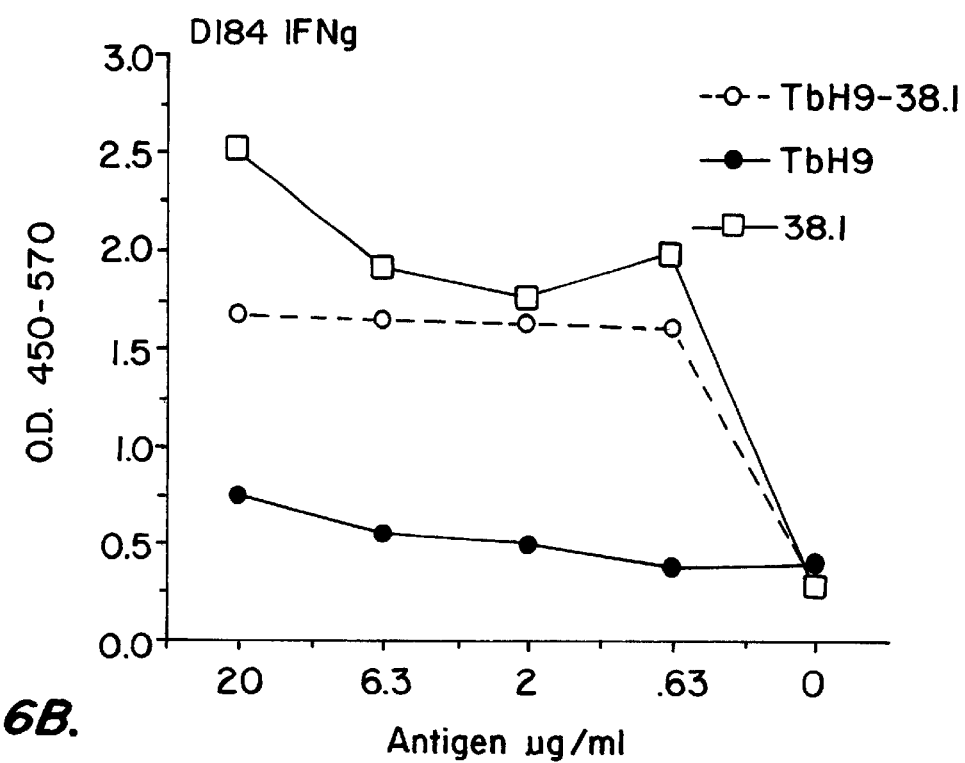
Figure 7A:
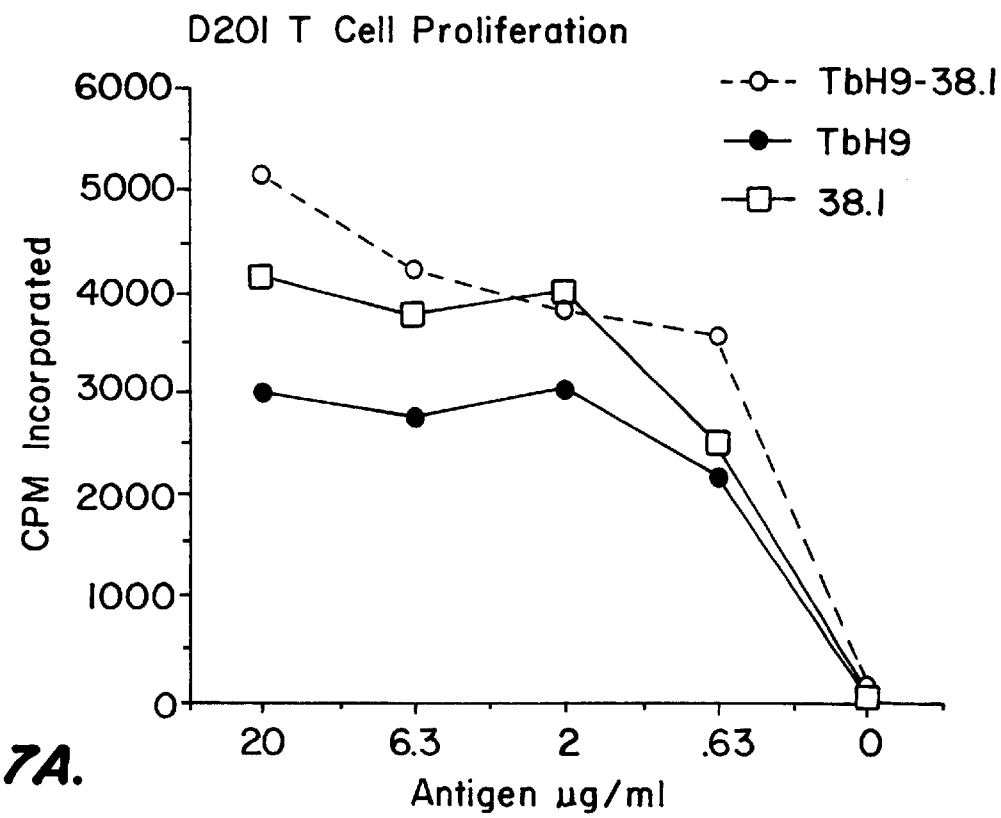
Figure 7B:
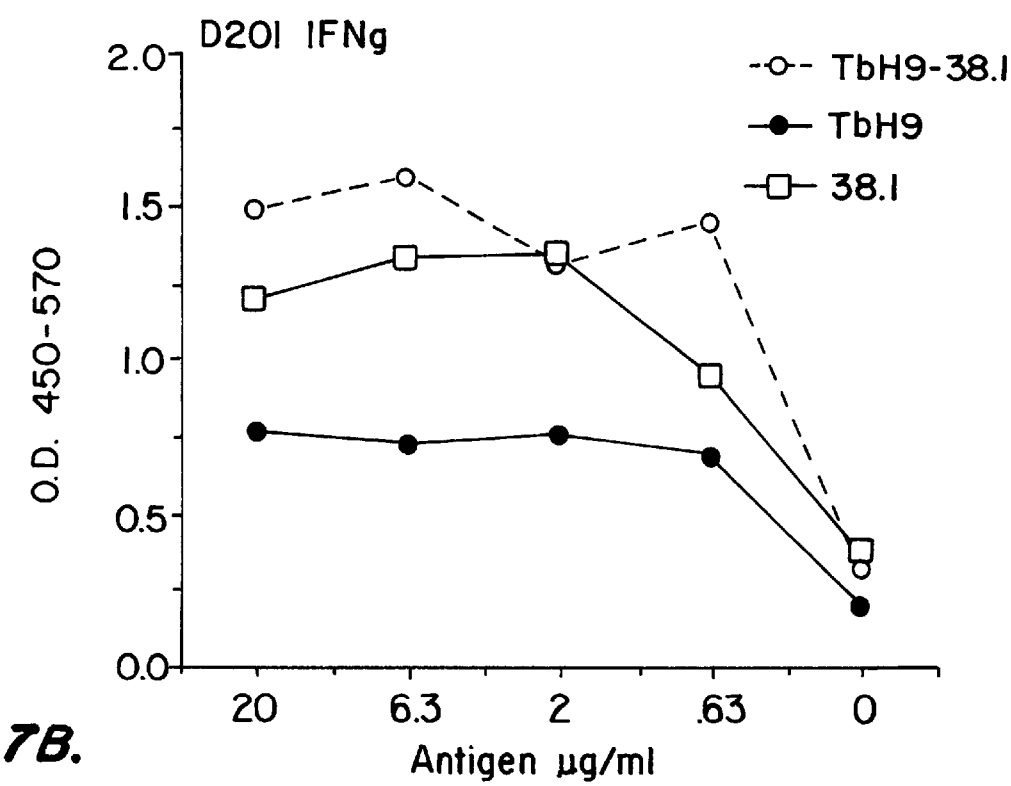

Orme "Prospects for new vaccines against tuberculosis" *Trends in Microbiology* 3(10):401–404 (1995).

Pancholi et al. "Dendritic cells efficiently immunoselect mycobacterial–reactive T cells in human blood, including clonable antigen–reactive precursors" *Immunology* 76(2):217–224 (1992).

Philipp et al. "An integrated map of the genome of the tubercle bacillus, *Mycobacterium tuberculosis* H37Rv, and comparison with *Mycobacterium leprae*" *Proc. Natl. Acad. Sci. USA* 93(7):3132–3137 (1996).

Rinke de Wit et al. "A *Mycobacterium leprae*–specific gene encoding an immunologically recognized 45 kDa protein" *Mol. Microbiol.* 10(4):829–838 (1993).

Rinke de Wit et al. "Mycobacteria contains two groEL genes: the second *Mycobacterium leprae* groEL gene is arranged in an operon with groES" *Mol. Microbiol.* 6(14):1995–2007 (1992).

Romain et al. "Identification of a *Mycobacterium bovis* BCG 45/47–Kilodalton Antigen Complex, an Immunodominant Target for Antibody Response after Immunization with Living Bacteria" *Infection and Immunity* 61(2):742–750 (1993).

Sanderson et al. "Identification of a CD4+ T Cell–stimulating Antigen of Pathogenic Bacteria by Expression Cloning" *J. Exp. Med.* 182(6):1751–1757 (1995).

Vega–Lopez et al. "Sequence and immunological characterization of a serine–rich antigen from *Mycobacterium leprae*" *Infection and Immunity* 61(5):2145–2153 (1993).

Wieles et al. "Characterization of a *Mycobacterium leprae* Antigen Related to the Secreted *Mycobacterium tuberculosis* Protein MPT32" *Infection and Immunity* 62(1):252–258 (1994).

Pal et al, "Immunization with extracellular proteins of Mycobacterium tuberculosis induces cell–mediated immune responses and substantial protective immunity in a guinea pig model of pulmonary tuberculosis", Infection and Immuntiy, vol. 60, No. 11, p. 4781, Nov. 1, 1992.*

Oettinger et al, "cloning and B–cell–epitope mapping of MPT64 from Mycobacterium tuberculosis H37Rv", Infection and Immunity, vol. 62, No. 5, pp. 2058–2064, May 1, 1994.*

Andersen and Hansen, "Structure and Mapping of Antigenic Domains of Protein Antigen b, a 38,000–Molecular–Weight Protein of *Mycobacterium tuberculosis,*" *Infection and Immunity* 37(8):2481–2488, 1989.

Andersen et al., "Identification of Immunodominant Antigens during Infection with *Mycobacterium tuberculosis,*" *Scand. J. Immunol.* 36:823–831, 1992.

Andersen, P., "Effective Vaccination of Mice against *Mycobacterium tuberculosis* Infection with a Soluble Mixture of Secreted Mycobacterial Proteins," *Infection and Immunity* 62(6):2536–2544, 1994.

Ausebel et al., "Isolation of Proteins for Microsequence Analysis," in Current Protocols in Molecular Biology, Wiley & Sons, New York, 1993, pp. 10.19–1–10.19.12.

Barnes et al., "Immunoreactivity of a 10–kDa Antigen of *Mycobacterium tuberculosis,*" *The Journal of Immunology* 148(6):1835–1840, 1992.

Boesen et al., "Human T–Cell Responses to Secreted Antigen Fractions of *Mycobacterium tuberculosis,*" *Infection and Immunity* 63(4):1491–1497, 1995.

Borremans et al., "Cloning, Sequencing Determination, and Expression of a 32–Kilodalton–Protein Gene of *Mycobacterium tuberculosis,*" *Infection and Immunity* 57(10):3123–3130, 1989.

Content et al., "The Genes Coding for the Antigen 85 Complexes of *Mycobacterium tuberculosis* and *Mycobacterium bovis* BCG Are Members of a Gene Family: Cloning, Sequence Determination, and Genomic Orginization of the Gene Coding for Antigen 85–C of *M. tuberculosis,*" *Infection and Immunity,* 59:3205–3212, 1991.

Horowitz et al., "Protective immunity against tuberculosis induced by vaccination with major extracellular proteins of *Mycobacterium tuberculosis,*" *Proc. Natl. Acad. Sci. USA* 92:1530–1534, 1995.

Lowrie et al., "Towards a DNA vaccine against tuberculosis," *Vaccine* 12(16):1537–1540, 1994.

Matsumoto et al., "Cloning and Sequencing of a Unique Antigen MPT70 from *Mycobacterium tuberculosis* H37Rv and Expression in BCG Using *E. coli*–Mycobacteria Shuttle Vector," *Scand. J. Immunol.* 41:281–287, 1995.

Nagai et al., "Isolation and Partial Characterization of Major Protein Antigens in the Culture Fluid of *Mycobacterium tuberculosis,*" *Infection and Immunity* 59(1):372–382, 1991.

Romain et al., "Isolation of a proline–rich mycobacterial protein eliciting delayed–type hypersensitivity reactions only in guinea pigs immunized with living mycobacteria," *Proc. Natl. Acad. Sci. USA* 90:5322–5326, 1993.

Romain et al., "Preparation of Tuberculin Antigen L," *Ann. Inst. Pasteur/Microbiol.* 136B:235–248, 1985.

Wallis et al., "Identification of Antigens of *Mycobacterium tuberculosis* Using Human Monoclonal Antibodies," *J. Clin. Invest.* 84:214–219, 1989.

Wiker and Harboe, "The Antigen 85 Complex: a Major Secretion Product of *Mycobacterium tuberculosis,*" *Microbiological Reviews* 56(4):648–661, 1992.

Yamaguchi et al., "Cloning and Characterization of the Gene for Immunogenic Protein MPB64 of *Mycobacterium bovis* BDG," *Infection and Immunity* 57(1):283–288, 1989.

Young et al., "Screening of a Recombinant Mycobacterial DNA Library with Polyclonal Antiserum and Molecular Weight Analysis of Expressed Antigens," *Infection and Immunity* 55(6):1421–1425, 1987.

* cited by examiner

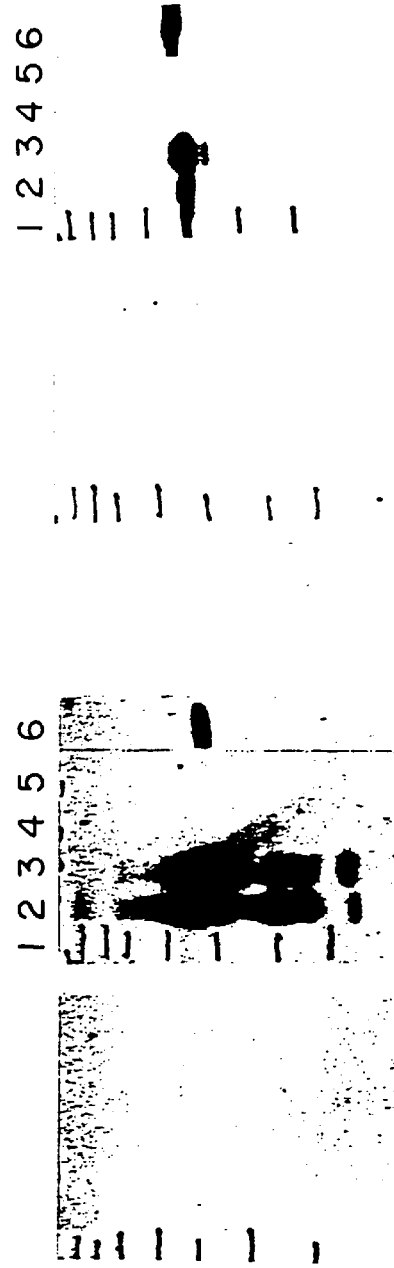
FIG. 3A. FIG. 3B. FIG. 3C. FIG. 3D.

COMPOUNDS AND METHODS FOR IMMUNOTHERAPY AND DIAGNOSIS OF TUBERCULOSIS

CROSS-REFERENCE TO RELATED APPLICATIONS

This application is a continuation-in-part of U.S. application Ser. No. 08/730,510, filed Oct. 11, 1996; which claims priority from PCT Application no. PCT/US 96/14674, filed Aug. 30, 1996; and is a continuation-in-part of U.S. application No. 08/680,574, filed Jul. 12, 1996; which is a continuation-in-part of U.S. application no. 08/659,683, filed Jun. 5, 1996; which is a continuation-in-part of U.S. application No. 08/620,874, filed Mar. 22, 1996 now abandoned; which is a continuation-in-part of U.S. application Ser. No. 08/533,634, filed Sep. 22, 1995 now abandoned; which is a continuation-in-part of U.S. application Ser. No. 08/523,436, filed Sep. 1, 1995, now abandoned.

TECHNICAL FIELD

The present invention relates generally to detecting, treating and preventing *Mycobacterium tuberculosis* infection. The invention is more particularly related to polypeptides comprising a *Mycobacterium tuberculosis* antigen, or a portion or other variant thereof, and the use of such polypeptides for diagnosing and vaccinating against *Mycobacterium tuberculosis* infection.

BACKGROUND OF THE INVENTION

Tuberculosis is a chronic, infectious disease, that is generally caused by infection with *Mycobacterium tuberculosis*. It is a major disease in developing countries, as well as an increasing problem in developed areas of the world, with about 8 million new cases and 3 million deaths each year. Although the infection may be asymptomatic for a considerable period of time, the disease is most commonly manifested as an acute inflammation of the lungs, resulting in fever and a nonproductive cough. If left untreated, serious complications and death typically result.

Although tuberculosis can generally be controlled using extended antibiotic therapy, such treatment is not sufficient to prevent the spread of the disease. Infected individuals may be asymptomatic, but contagious, for some time. In addition, although compliance with the treatment regimen is critical, patient behavior is difficult to monitor. Some patients do not complete the course of treatment, which can lead to ineffective treatment and the development of drug resistance.

Inhibiting the spread of tuberculosis requires effective vaccination and accurate, early diagnosis of the disease. Currently, vaccination with live bacteria is the most efficient method for inducing protective immunity. The most common Mycobacterium employed for this purpose is Bacillus Calmette-Guerin (BCG), an avirulent strain of *Mycobacterium bovis*. However, the safety and efficacy of BCG is a source of controversy and some countries, such as the United States, do not vaccinate the general public. Diagnosis is commonly achieved using a skin test, which involves intradermal exposure to tuberculin PPD (protein-purified derivative). Antigen-specific T cell responses result in measurable induration at the injection site by 48–72 hours after injection, which indicates exposure to Mycobacterial antigens. Sensitivity and specificity have, however, been a problem with this test, and individuals vaccinated with BCG cannot be distinguished from infected individuals.

While macrophages have been shown to act as the principal effectors of *M. tuberculosis* immunity, T cells are the predominant inducers of such immunity. The essential role of T cells in protection against *M. tuberculosis* infection is illustrated by the frequent occurrence of *M. tuberculosis* in AIDS patients, due to the depletion of CD4 T cells associated with human immunodeficiency virus (HIV) infection. Mycobacterium-reactive CD4 T cells have been shown to be potent producers of gamma-interferon (IFN-γ), which, in turn, has been shown to trigger the anti-mycobacterial effects of macrophages in mice. While the role of IFN-γ in humans is less clear, studies have shown that 1,25-dihydroxy-vitamin D3, either alone or in combination with IFN-γ or tumor necrosis factor-alpha, activates human macrophages to inhibit *M. tuberculosis* infection. Furthermore, it is known that IFN-γ stimulates human macrophages to make 1,25-dihydroxy-vitamin D3. Similarly, IL-12 has been shown to play a role in stimulating resistance to *M. tuberculosis* infection. For a review of the immunology of *M. tuberculosis* infection see Chan and Kaufmann in *Tuberculosis: Pathogenesis, Protection and Control,* Bloom (ed.), ASM Press, Washington, DC, 1994.

Accordingly, there is a need in the art for improved vaccines and methods for preventing, treating and detecting tuberculosis. The present invention fulfills these needs and further provides other related advantages.

SUMMARY OF THE INVENTION

Briefly stated, this invention provides compounds and methods for preventing and diagnosing tuberculosis. In one aspect, polypeptides are provided comprising an immunogenic portion of a soluble *M. tuberculosis* antigen, or a variant of such an antigen that differs only in conservative substitutions and/or modifications. In one embodiment of this aspect, the soluble antigen has one of the following N-terminal sequences:

(a) Asp-Pro-Val-Asp-Ala-Val-Ile-Asn-Thr-Thr-Cys-Asn-Tyr-Gly-Gln-Val-Val-Ala-Ala-Leu; (SEQ ID No. 120)

(b) Ala-Val-Glu-Ser-Gly-Met-Leu-Ala-Leu-Gly-Thr-Pro-Ala-Pro-Ser; (SEQ ID No. 121)

(c) Ala-Ala-Met-Lys-Pro-Arg-Thr-Gly-Asp-Gly-Pro-Leu-Glu-Ala-Ala-Lys-Glu-Gly-Arg; (SEQ ID No. 122)

(d) Tyr-Tyr-Trp-Cys-Pro-Gly-Gln-Pro-Phe-Asp-Pro-Ala-Trp-Gly-Pro; (SEQ ID No. 123) (e) Asp-Ile-Gly-Ser-Glu-Ser-Thr-Glu-Asp-Gln-Gln-Xaa-Ala-Val; (SEQ ID No. 124) (f) Ala-Glu-Glu-Ser-Ile-Ser-Thr-Xaa-Glu-Xaa-Ile-Val-Pro; (SEQ ID No. 125)

(g) Asp-Pro-Glu-Pro-Ala-Pro-Pro-Val-Pro-Thr-Thr-Ala-Ala-Ser-Pro-Pro-ger; (SEQ ID No. 126)

(h) Ala-Pro-Lys-Thr-Tyr-Xaa-Glu-Glu-Leu-Lys-Gly-Thr-Asp-Thr-Gly; (SEQ ID No. 127)

(i) Asp -Pro-Ala-Ser-Ala-Pro-Asp-Val-Pro-Thr-Ala-Ala-Gln-Leu-Thr-Ser-Leu-Leu-Asn-Ser-Leu-Ala-Asp-Pro-Asn-Val-Ser-Phe- Ala-Asn; (SEQ ID No. 128)

(j) Xaa-Asp-Ser-Glu-Lys-Ser-Ala-Thr-Ile-Lys-Val-Thr-Asp-Ala-5 Ser; (SEQ ID No. 134)

(k) Ala-Gly-Asp-Thr-Xaa-Ile-Tyr-Ile-Val-Gly-Asn-Leu-Thr-Ala-Asp; (SEQ ID No. 135) or (l) Ala-Pro-Glu-Ser-Gly-Ala-Gly-Leu-Gly-Gly-Thr-Val-Gln-Ala- Gly; (SEQ ID No. 136)

wherein Xaa may be any amino acid.

In a related aspect, polypeptides are provided comprising an immunogenic portion of an *M. tuberculosis* antigen, or a variant of such an antigen that differs only in conservative substitutions and/or modifications, the antigen having one of the following N-terminal sequences:

(m) Xaa-Tyr-Ile-Ala-Tyr-Xaa-Thr-Thr-Ala-Gly-Ile-Val-Pro-Gly-Lys-Ile-Asn-Val-His-Leu-Val; (SEQ ID No. 137) or (n) Asp-Pro-Pro-Asp-Pro-His-Gln-Xaa-Asp-Met-Thr-Lys-Gly-Tyr-Tyr-Pro-Gly-Gly-Arg-Arg-Xaa-Phe; (SEQ ID No. 129) wherein Xaa may be any amino acid.

In another embodiment, the antigen comprises an amino acid sequence encoded by a DNA sequence selected from the group consisting of the sequences recited in SEQ ID Nos.: 1, 2, 4–10, 13–25, 52, 99 and 101, the complements of said sequences, and DNA sequences that hybridize to a sequence recited in SEQ ID Nos.: 1, 2, 4–10, 13–25, 52, 99 and 101 or a complement thereof under moderately stringent conditions.

In a related aspect, the polypeptides comprise an immunogenic portion of a *M. tuberculosis* antigen, or a variant of such an antigen that differs only in conservative substitutions and/or modifications, wherein the antigen comprises an amino acid sequence encoded by a DNA sequence selected from the group consisting of the sequences recited in SEQ ID Nos.: 26–51, 138 and 139, the complements of said sequences, and DNA sequences that hybridize to a sequence recited in SEQ ID Nos.: 26–51, 138 and 139 or a complement thereof under moderately stringent conditions.

In related aspects, DNA sequences encoding the above polypeptides, expression vectors comprising these DNA sequences and host cells transformed or transfected with such expression vectors are also provided.

In another aspect, the present invention provides fusion proteins comprising a first and a second inventive polypeptide or, alternatively, an inventive polypeptide and a known *M. tuberculosis* antigen.

Within other aspects, the present invention provides pharmaceutical compositions that comprise one or more of the above polypeptides, or a DNA molecule encoding such polypeptides, and a physiologically acceptable carrier. The invention also provides vaccines comprising one or more of the polypeptides as described above and a non-specific immune response enhancer, together with vaccines comprising one or more DNA sequences encoding such polypeptides and a non-specific immune response enhancer.

In yet another aspect, methods are provided for inducing protective immunity in a patient, comprising administering to a patient an effective amount of one or more of the above polypeptides.

In further aspects of this invention, methods and diagnostic kits are provided for detecting tuberculosis in a patient. The methods comprise contacting dermal cells of a patient with one or more of the above polypeptides and detecting an immune response on the patient's skin. The diagnostic kits comprise one or more of the above polypeptides in combination with an apparatus sufficient to contact the polypeptide with the dermal cells of a patient.

In yet other aspects, methods are provided for detecting tuberculosis in a patient, such methods comprising contacting dermal cells of a patient with one or more polypeptides encoded by a DNA sequence selected from the group consisting of SEQ ID Nos.: 3, 11, 12, 140 and 141, the complements of said sequences, and DNA sequences that hybridize to a sequence recited in SEQ ID Nos.: 3, 11, 12, 140 and 141; and detecting an immune response on the patient's skin. Diagnostic kits for use in such methods are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIG. 1A and B illustrate the stimulation of proliferation and interferon-γ production in T cells derived from a first and a second *M. tuberculosis*-immune donor, respectively, by the 14 Kd, 20 Kd and 26 Kd antigens described in Example 1.

FIG. 2 illustrates the stimulation of proliferation and interferon-γ production in T cells derived from an *M. tuberculosis-immune* individual by the two representative polypeptides TbRa3 and ThRa9.

FIGS. 3A–D illustrate the reactivity of antisera raised against secretory *M. tuberculosis* proteins, the known *M. tuberculosis* antigen 85b and the inventive antigens Tb38-1 and TbH-9, respectively, with *M. tuberculosis* lysate (lane 2), *M. tuberculosis* secretory proteins (lane 3), recombinant Tb38-1 (lane 4), recombinant TbH-9 (lane 5) and recombinant 85b (lane 5).

FIG. 4A illustrates the stimulation of proliferation in a TbH-9-specific T cell clone by secretory *M. tuberculosis* proteins, recombinant TbH-9 and a control antigen, TbRa11.

FIG. 4B illustrates the stimulation of interferon-γ production in a TbH-9-specific T cell clone by secretory *M. tuberculosis* proteins, PPD and recombinant TbH-9.

FIGS. 5A and B illustrate the stimulation of proliferation and interferon-γ production in TbH9-specific T cells by the fusion protein TbH9-Tb38-1.

FIGS. 6A and B illustrate the stimulation of proliferation and interferon-γ production in Tb38-1-specific T cells by the fusion protein TbH9-Tb38-1.

FIGS. 7A and B illustrate the stimulation of proliferation and interferon-γ production in T cells previously shown to respond to both TbH-9 and Tb38- 1 by the fusion protein TbH9-Tb38-1.

SEQ. ID NO. 1 is the DNA sequence of ThRa1.

SEQ. ID NO. 2 is the DNA sequence of ThRal 0.

SEQ. ID NO. 3 is the DNA sequence of ThRal 1.

SEQ. ID NO. 4 is the DNA sequence of ThRa12.

SEQ. ID NO. 5 is the DNA sequence of ThRa13.

SEQ. ID NO. 6 is the DNA sequence of ThRa16.

SEQ. ID NO. 7 is the DNA sequence of ThRa17.

SEQ. ID NO. 8 is the DNA sequence of ThRa18.

SEQ. ID NO. 9 is the DNA sequence of ThRa19.

SEQ. ID NO. 10 is the DNA sequence of ThRa24.

SEQ. ID NO. 11 is the DNA sequence of TbRa26.

SEQ. ID NO. 12 is the DNA sequence of ThRa28.

SEQ. ID NO. 13 is the DNA sequence of ThRa29.

SEQ. ID NO. 14 is the DNA sequence of ThRa2A.

SEQ. ID NO. 15 is the DNA sequence of ThRa3.

SEQ. ID NO. 16 is the DNA sequence of ThRa32.

SEQ. ID NO. 17 is the DNA sequence of ThRa5.

SEQ. ID NO. 18 is the DNA sequence of ThRa36.

SEQ. ID NO. 19 is the DNA sequence of ThRa4.

SEQ. ID NO. 20 is the DNA sequence of ThRa9.

SEQ. ID NO. 21 is the DNA sequence of ThRaB.

SEQ. ID NO. 22 is the DNA sequence of ThRaC.

SEQ. ID NO. 23 is the DNA sequence of ThRaD.

SEQ. ID NO. 24 is the DNA sequence of YYWCPG.

SEQ. ID NO. 25 is the DNA sequence of AAMK.

SEQ. ID NO. 26 is the DNA sequence of TbL-23.

SEQ. ID NO. 27 is the DNA sequence of TbL-24.
SEQ. ID NO. 28 is the DNA sequence of TbL-25.
SEQ. ID NO. 29 is the DNA sequence of TbL-28.
SEQ. ID NO. 30 is the DNA sequence of TbL-29.
SEQ. ID NO. 31 is the DNA sequence of TbH-5.
SEQ. ID NO. 32 is the DNA sequence of TbH-8.
SEQ. ID NO. 33 is the DNA sequence of TbH-9.
SEQ. ID NO. 34 is the DNA sequence of TbM-1.
SEQ. ID NO. 35 is the DNA sequence of TbM-3.
SEQ. ID NO. 36 is the DNA sequence of TbM-6.
SEQ. ID NO. 37 is the DNA sequence of TbM-7.
SEQ. ID NO. 38 is the DNA sequence of TbM-9.
SEQ. ID NO. 39 is the DNA sequence of TbM-12.
SEQ. ID NO. 40 is the DNA sequence of TbM-13.
SEQ. ID NO. 41 is the DNA sequence of TbM-14.
SEQ. ID NO. 42 is the DNA sequence of TbM-15.
SEQ. ID NO. 43 is the DNA sequence of TbH-4.
SEQ. ID NO. 44 is the DNA sequence of TbH4-FWM.
SEQ. ID NO. 45 is the DNA sequence of TbH-12.
SEQ. ID NO. 46 is the DNA sequence of TbH38-1.
SEQ. ID NO. 47 is the DNA sequence of TbH38-4.
SEQ. ID NO. 48 is the DNA sequence of TbL-17.
SEQ. ID NO. 49 is the DNA sequence of TbL-20.
SEQ. ID NO. 50 is the DNA sequence of TbL-21.
SEQ. ID NO. 51 is the DNA sequence of TbH-16.
SEQ. ID NO. 52 is the DNA sequence of DPEP.
SEQ. ID NO. 53 is the deduced amino acid sequence of DPEP.
SEQ. ID NO. 54 is the protein sequence of DPV N-terminal Antigen.
SEQ. ID NO. 55 is the protein sequence of AVGS N-terminal Antigen.
SEQ. ID NO. 56 is the protein sequence of AAMK N-terminal Antigen.
SEQ. ID NO. 57 is the protein sequence of YYWC N-terminal Antigen.
SEQ. ID NO. 58 is the protein sequence of DIGS N-terminal Antigen.
SEQ. ID NO. 59 is the protein sequence of AEES N-terminal Antigen.
SEQ. ID NO. 60 is the protein sequence of DPEP N-terminal Antigen.
SEQ. ID NO. 61 is the protein sequence of APKT N-terminal Antigen.
SEQ. ID NO. 62 is the protein sequence of DPAS N-terninal Antigen.
SEQ. ID NO. 63 is the deduced amino acid sequence of TbRa1.
SEQ. ID NO. 64 is the deduced amino acid sequence of TbRa10.
SEQ. ID NO. 65 is the deduced amino acid sequence of ThRa11.
SEQ. ID NO. 66 is the deduced amino acid sequence of TbRa12.
SEQ. ID NO. 67 is the deduced amino acid sequence of TbRa13.
SEQ. ID NO. 68 is the deduced amino acid sequence of ThRa16.
SEQ. ID NO. 69 is the deduced amino acid sequence of ThRa17.
SEQ. ID NO. 70 is the deduced amino acid sequence of ThRa18.
SEQ. ID NO. 71 is the deduced amino acid sequence of ThRa19.
SEQ. ID NO. 72 is the deduced amino acid sequence of ThRa24.
SEQ. ID NO. 73 is the deduced amino acid sequence of TbRa6.
SEQ. ID NO. 74 is the deduced amino acid sequence of ThRa28.
SEQ. ID NO. 75 is the deduced amino acid sequence of ThRa9.
SEQ. ID NO. 76 is the deduced amino acid sequence of ThRa2A.
SEQ. ID NO. 77 is the deduced amino acid sequence of TbRa3.
SEQ. ID NO. 78 is the deduced amino acid sequence of ThRa32.
SEQ. ID NO. 79 is the deduced amino acid sequence of TbRa35.
SEQ. ID NO. 80 is the deduced amino acid sequence of TbRa6.
SEQ. ID NO. 81 is the deduced amino acid sequence of TbRa4.
SEQ. ID NO. 82 is the deduced amino acid sequence of ThRa9.
SEQ. ID NO. 83 is the deduced amino acid sequence of TbRaB.
SEQ. ID NO. 84 is the deduced amino acid sequence of TbRaC.
SEQ. ID NO. 85 is the deduced amino acid sequence of TbRaD.
SEQ. ID NO. 86 is the deduced amino acid sequence of YYWCPG.
SEQ. ID NO. 87 is the deduced amino acid sequence of ThAAMK.
SEQ. ID NO.88 is the deduced amino acid sequence of Tb38-1.
SEQ. ID NO.89 is the deduced amino acid sequence of TbH-4.
SEQ. ID NO. 90 is the deduced amino acid sequence of TbH-8.
SEQ. ID NO. 91 is the deduced amino acid sequence of TbH-9.
SEQ. ID NO. 92 is the deduced amino acid sequence of TbH-12.
SEQ. ID NO. 93 is the amino acid sequence of Tb38-1 Peptide 1.
SEQ. ID NO. 94 is the amino acid sequence of Tb38-1 Peptide 2.
SEQ. ID NO.95 is the amino acid sequence of Tb38-1 Peptide 3.
SEQ. ID NO. 96 is the amino acid sequence of Tb38-1 Peptide 4.
SEQ. ID NO.97 is the amino acid sequence of Tb38-1 Peptide 5.
SEQ. ID NO.98 is the amino acid sequence of Tb38-1 Peptide 6.
SEQ. ID NO. 99 is the DNA sequence of DPAS.
SEQ. ID NO. 100 is the deduced amino acid sequence of DPAS.

SEQ. ID NO. 101 is the DNA sequence of DPV.

SEQ. ID NO. 102 is the deduced amino acid sequence of DPV.

SEQ. ID NO. 103 is the DNA sequence of ESAT-6.

SEQ. ID NO. 104 is the deduced amino acid sequence of ESAT-6.

SEQ. ID NO. 105 is the DNA sequence of TbH-8-2.

SEQ. ID NO. 106 is the DNA sequence of TbH-9FL.

SEQ. ID NO. 107 is the deduced amino acid sequence of TbH-9FL.

SEQ. ID NO.108 is the DNA sequence of TbH-9-1.

SEQ. ID NO. 109 is the deduced amino acid sequence of TbH-9-1.

SEQ. ID NO. 1 10 is the DNA sequence of TbH-9-4.

SEQ. ID NO. 111 is the deduced amino acid sequence of TbH-9-4.

SEQ. ID NO. 112 is the DNA sequence of Tb38-1F2 IN.

SEQ. ID NO.113 is the DNA sequence of Tb38-2F2 RP.

SEQ. ID NO. 114 is the deduced amino acid sequence of Tb37-FL.

SEQ. ID NO. 115 is the deduced amino acid sequence of Tb38-IN.

SEQ. ID NO. 116 is the DNA sequence of Tb38-1F3.

SEQ. ID NO. 117 is the deduced amino acid sequence of Tb38-1F3.

SEQ. ID NO. 18is the DNA sequence of Tb38-F5.

SEQ. ID NO. 119 is the DNA sequence of Tb38-1F6.

SEQ. ID NO. 120 is the deduced N-terminal amino acid sequence of DPV.

SEQ. ID NO. 121 is the deduced N-terminal amino acid sequence of AVGS.

SEQ. ID NO. 122 is the deduced N-terminal amino acid sequence of AAMK.

SEQ. ID NO. 123 is the deduced N-terninal amino acid sequence of YYWC.

SEQ. ID NO. 124 is the deduced N-terminal amino acid sequence of DIGS.

SEQ. ID NO. 125 is the deduced N-terminal amino acid sequence of AEES.

SEQ. ID NO. 126 is the deduced N-terminal amino acid sequence of DPEP.

SEQ. ID NO. 127 is the deduced N-terminal amino acid sequence of APKT.

SEQ. ID NO. 128 is the deduced amino acid sequence of DPAS.

SEQ. ID NO. 129 is the protein sequence of DPPD N-terminal Antigen.

SEQ ID NO. 130–133 are the protein sequences of four DPPD cyanogen bromide fragments.

SEQ ID NO. 134 is the N-terminal protein sequence of XDS antigen.

SEQ ID NO. 135 is the N-terminal protein sequence of AGD antigen.

SEQ ID NO. 136 is the N-terminal protein sequence of APE antigen.

SEQ ID NO. 137 is the N-terninal protein sequence of XYI antigen.

SEQ ID NO. 138 is the DNA sequence of TbH-29.

SEQ ID NO. 139 is the DNA sequence of TbH-30.

SEQ ID NO. 140 is the DNA sequence of TbH-32.

SEQ ID NO. 141 is the DNA sequence of TbH-33.

SEQ ID NO. 142 is the predicted amino acid sequence of TbH-29.

SEQ ID NO. 143 is the predicted amino acid sequence of TbH-30.

SEQ ID NO. 144 is the predicted amino acid sequence of TbH-32.

SEQ ID NO. 145 is the predicted amino acid sequence of TbH-33.

SEQ ID NO: 146–151 are PCR primers used in the preparation of a fusion protein containing ThRa3, 38 kD and Tb38-1.

SEQ ID NO: 152 is the DNA sequence of the fusion protein containing ThRa3, 38 kD and Tb38-1.

SEQ ID NO: 153 is the amino acid sequence of the fusion protein containing ThRa3, 38 kD and Tb38-1.

SEQ ID NO: 154 is the DNA sequence of the *M. tuberculosis* antigen 38 kD.

SEQ ID NO: 155 is the amino acid sequence of the *M. tuberculosis* antigen 38 kD.

DETAILED DESCRIPTION OF THE INVENTION

As noted above, the present invention is generally directed to compositions and methods for preventing, treating and diagnosing tuberculosis. The compositions of the subject invention include polypeptides that comprise at least one immunogenic portion of a *M. tuberculosis* antigen, or a variant of such an antigen that differs only in conservative substitutions and/or modifications. Polypeptides within the scope of the present invention include, but are not limited to, immunogenic soluble *M. tuberculosis* antigens. A "soluble *M. tuberculosis* antigen" is a protein of *M. tuberculosis* origin that is present in *M. tuberculosis* culture filtrate. As used herein, the term "polypeptide" encompasses amino acid chains of any length, including full length proteins (i.e., antigens), wherein the amino acid residues are linked by covalent peptide bonds. Thus, a polypeptide comprising an immunogenic portion of one of the above antigens may consist entirely of the immunogenic portion, or may contain additional sequences. The additional sequences may be derived from the native *M. tuberculosis* antigen or may be heterologous, and such sequences may (but need not) be immunogenic.

"Immunogenic," as used herein, refers to the ability to elicit an immune response (e.g., cellular) in a patient, such as a human, and/or in a biological sample. In particular, antigens that are immunogenic (and immunogenic portions or other variants of such antigens) are capable of stimulating cell proliferation, interleukin-12 production and/or interferon i production in biological samples comprising one or more cells selected from the group of T cells, NK cells, B cells and macrophages, where the cells are derived from an *M. tuberculosis*-immune individual. Polypeptides comprising at least an immunogenic portion of one or more *M. tuberculosis* antigens may generally be used to detect tuberculosis or to induce protective immunity against tuberculosis in a patient.

The compositions and methods of this invention also encompass variants of the above polypeptides. A "variant," as used herein, is a polypeptide that differs from the native antigen only in conservative substitutions and/or modifications, such that the ability of the polypeptide to induce an immune response is retained. Such variants may generally be identified by modifying one of the above polypeptide sequences, and evaluating the immunogenic properties of the modified polypeptide using, for example, the representative procedures described herein.

A "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also (or alternatively) be modified by, for example, the deletion or addition of amino acids that have minimal influence on the immunogenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

In a related aspect, combination polypeptides are disclosed. A "combination polypeptide" is a polypeptide comprising at least one of the above immunogenic portions and one or more additional immunogenic M. tuberculosis sequences, which are joined via a peptide linkage into a single amino acid chain. The sequences may be joined directly (i.e., with no intervening amino acids) or may be joined by way of a linker sequence (e.g., Gly-Cys-Gly) that does not significantly diminish the immunogenic properties of the component polypeptides.

In general, M. tuberculosis antigens, and DNA sequences encoding such antigens, may be prepared using any of a variety of procedures. For example, soluble antigens may be isolated from M. tuberculosis culture filtrate by procedures known to those of ordinary skill in the art, including anion-exchange and reverse phase chromatography. Purified antigens are then evaluated for their ability to elicit an appropriate immune response (e.g., cellular) using, for example, the representative methods described herein. Imunogenic antigens may then be partially sequenced using techniques such as traditional Edman chemistry. See Edman and Berg, Eur. J Biochem. 80:116–132, 1967.

Immunogenic antigens may also be produced recombinantly using a DNA sequence that encodes the antigen, which has been inserted into an expression vector and expressed in an appropriate host. DNA molecules encoding soluble antigens may be isolated by screening an appropriate M. tuberculosis expression library with anti-sera (e.g., rabbit) raised specifically against soluble M. tuberculosis antigens. DNA sequences encoding antigens that may or may not be soluble may be identified by screening an appropriate M. tuberculosis genomic or cDNA expression library with sera obtained from patients infected with M. tuberculosis. Such screens may generally be performed using techniques well known to those of ordinary skill in the art, such as those described in Sambrook et al., Molecular Cloning: A Laboratory Manual, Cold Spring Harbor Laboratories, Cold Spring Harbor, N.Y., 1989.

DNA sequences encoding soluble antigens may also be obtained by screening an appropriate M. tuberculosis cDNA or genomic DNA library for DNA sequences that hybridize to degenerate oligonucleotides derived from partial amino acid sequences of isolated soluble antigens. Degenerate oligonucleotide sequences for use in such a screen may be designed and synthesized, and the screen may be performed, as described (for example) in Sambrook et al., Molecular Cloning: A Laboratory Manual, Cold Spring Harbor Laboratories, Cold Spring Harbor, N.Y., 1989 (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

Alternatively, genomic or cDNA libraries derived from M. tuberculosis may be screened directly using peripheral blood mononuclear cells (PBMCs) or T cell lines or clones derived from one or more M. tuberculosis-immune individuals. In general, PBMCs and/or T cells for use in such screens may be prepared as described below. Direct library screens may generally be performed by assaying pools of expressed recombinant proteins for the ability to induce proliferation and/or interferon-γ production in T cells derived from an M. tuberculosis-immune individual. Alternatively, potential T cell antigens may be first selected based on antibody reactivity, as described above.

Regardless of the method of preparation, the antigens (and immunogenic portions thereof) described herein (which may or may not be soluble) have the ability to induce an immunogenic response. More specifically, the antigens have the ability to induce proliferation and/or cytokine production (i e., interferon-γ and/or interleukin-12 production) in T cells, NK cells, B cells and/or macrophages derived from an M. tuberculosis-immune individual. The selection of cell type for use in evaluating an immunogenic response to a antigen will, of course, depend on the desired response. For example, interleukin-12 production is most readily evaluated using preparations containing B cells and/or macrophages. An M. tuberculosis-immune individual is one who is considered to be resistant to the development of tuberculosis by virtue of having mounted an effective T cell response to M. tuberculosis (i.e., substantially free of disease symptoms). Such individuals may be identified based on a strongly positive (i.e., greater than about 10 mn diameter induration) intradermal skin test response to tuberculosis proteins (PPD) and an absence of any signs or symptoms of tuberculosis disease. T cells, NK cells, B cells and macrophages derived from M. tuberculosis-immune individuals may be prepared using methods known to those of ordinary skill in the art. For example, a preparation of PBMCs (i.e., peripheral blood mononuclear cells) may be employed without further separation of component cells. PBMCs may generally be prepared, for example, using density centrifigation through Ficoll™ (Winthrop Laboratories, NY). T cells for use in the assays described herein may also be purified directly from PBMCs. Alternatively, an enriched T cell line reactive against mycobacterial proteins, or T cell clones reactive to individual mycobacterial proteins, may be employed. Such T cell clones may be generated by, for example, culturing PBMCs from M. tuberculosis-immune individuals with mycobacterial proteins for a period of 2–4 weeks. This allows expansion of only the mycobacterial protein-specific T cells, resulting in a line composed solely of such cells. These cells may then be cloned and tested with individual proteins, using methods known to those of ordinary skill in the art, to more accurately define individual T cell specificity. In general, antigens that test positive in assays for proliferation and/or cytokine production (i.e., interferon-γ and/or interleukin-12 production) performed using T cells, NK cells, B cells and/or macrophages derived from an *M. tuberculosis*-immune individual are considered immunogenic. Such assays may be performed, for example, using the representative procedures described below. Immunogenic portions of such antigens may be identified using similar assays, and may be present within the polypeptides described herein.

The ability of a polypeptide (e.g., an immunogenic antigen, or a portion or other variant thereof) to induce cell proliferation is evaluated by contacting the cells (e g., T cells and/or NK cells) with the polypeptide and measuring the proliferation of the cells. In general, the amount of polypeptide that is sufficient for evaluation of about $10^5$ cells ranges from about 10 ng/mL to about 100 $\mu$g/mL and preferably is about 10 $\mu$g/mL. The incubation of polypeptide with cells is typically performed at 37° C. for about six days. Following incubation with polypeptide, the cells are assayed for a proliferative response, which may be evaluated by methods known to those of ordinary skill in the art, such as exposing cells to a pulse of radiolabeled thymidine and measuring the incorporation of label into cellular DNA. In general, a polypeptide that results in at least a three fold increase in proliferation above background (i.e., the proliferation observed for cells cultured without polypeptide) is considered to be able to induce proliferation.

The ability of a polypeptide to stimulate the production of interferon-γ and/or interleukin-12 in cells may be evaluated by contacting the cells with the polypeptide and measuring the level of interferon-γ or interleukin-12 produced by the cells. In general, the amount of polypeptide that is sufficient for the evaluation of about $10^5$ cells ranges from about 10 ng/mL to about 100 $\mu$g/mL and preferably is about 10 $\mu$g/mL. The polypeptide may, but need not, be immobilized on a solid support, such as a bead or a biodegradable microsphere, such as those described in U.S. Pat. Nos. 4,897,268 and 5,075,109. The incubation of polypeptide with the cells is typically performed at 37° C. for about six days. Following incubation with polypeptide, the cells are assayed for interferon-γ and/or interleukin-12 (or one or more subunits thereof), which may be evaluated by methods known to those of ordinary skill in the art, such as an enzyme-linked immunosorbent assay (ELISA) or, in the case of IL-12 P70 subunit, a bioassay such as an assay measuring proliferation of T cells. In general, a polypeptide that results in the production of at least 50pg of interferon-γ per mL of cultured supernatant (containing $10^4$–$10^5$ cells per mL) is considered able to stimulate the production of interferon-γ. A polypeptide that stimulates the production of at least 10 pg/mL of IL-12 P70 subunit, and/or at least 100 pg/mL of IL-12 P40 subunit, per $10^5$ macrophages or B cells (or per $3\div10^5$ PBMC) is considered able to stimulate the production of IL-12.

In general, immunogenic antigens are those antigens that stimulate proliferation and/or cytokine production (ie., interferon-γ and/or interleukin-12 production) in T cells, NK cells, B cells and/or macrophages derived from at least about 25% of *M. tuberculosis*-immune individuals. Among these immunogenic antigens, polypeptides having superior therapeutic properties may be distinguished based on the magnitude of the responses in the above assays and based on the percentage of individuals for which a response is observed. In addition, antigens having superior therapeutic properties will not stimulate proliferation and/or cytokine production in vitro in cells derived from more than about 25% of individuals that are not *M. tuberculosis*-immune, thereby eliminating responses that are not specifically due to *M. tuberculosis*-responsive cells. Those antigens that induce a response in a high percentage of T cell, NK cell, B cell and/or macrophage preparations from *M. tuberculosis*-immune individuals (with a low incidence of responses in cell preparations from other individuals) have superior therapeutic properties.

Antigens with superior therapeutic properties may also be identified based on their ability to diminish the severity of *M. tuberculosis* infection in experimental animals, when administered as a vaccine. Suitable vaccine preparations for use on experimental animals are described in detail below. Efficacy may be determined based on the ability of the antigen to provide at least about a 50% reduction in bacterial numbers and/or at least about a 40% decrease in mortality following experimental infection. Suitable experimental animals include mice, guinea pigs and primates.

Antigens having superior diagnostic properties may generally be identified based on the ability to elicit a response in an intradermal skin test performed on an individual with active tuberculosis, but not in a test performed on an individual who is not infected with *M. tuberculosis*. Skin tests may generally be performed as described below, with a response of at least 5 mm induration considered positive.

Immunogenic portions of the antigens described herein may be prepared and identified using well known techniques, such as those summarized in Paul, *Fundamental Immunology,* 3d ed., Raven Press, 1993, pp. 243–247 and references cited therein. Such techniques include screening polypeptide portions of the native antigen for immunogenic properties. The representative proliferation and cytokine production assays described herein may generally be employed in these screens. An immunogenic portion of a polypeptide is a portion that, within such representative assays, generates an immune response (e.g., proliferation, interferon-γ production and/or interleukin-12 production) that is substantially similar to that generated by the full length antigen. In other words, an immunogenic portion of an antigen may generate at least about 20%, and preferably about 100%, of the proliferation induced by the full length antigen in the model proliferation assay described herein. An immunogenic portion may also, or alternatively, stimulate the production of at least about 20%, and preferably about 100%, of the interferon-γ and/or interleukin-12 induced by the full length antigen in the model assay described herein.

Portions and other variants of *M. tuberculosis* antigens may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc., Foster City, Calif., and may be operated according to the manufacturer's instructions. Variants of a native antigen may generally be prepared using standard mutagenesis techniques, such as oligonucleotide-directed site-specific mutagenesis. Sections of the DNA sequence may also be removed using standard techniques to permit preparation of truncated polypeptides.

Recombinant polypeptides containing portions and/or variants of a native antigen may be readily prepared from a DNA sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides of this invention. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E. coli*, yeast or a mammalian cell line such as COS or CHO. The DNA sequences expressed in this manner may encode naturally occurring antigens, portions of naturally occurring antigens, or other variants thereof.

In general, regardless of the method of preparation, the polypeptides disclosed herein are prepared in substantially pure form. Preferably, the polypeptides are at least about 80% pure, more preferably at least about 90% pure and most preferably at least about 99% pure. In certain preferred embodiments, described in detail below, the substantially pure polypeptides are incorporated into pharmaceutical compositions or vaccines for use in one or more of the methods disclosed herein.

In certain specific embodiments, the subject invention discloses polypeptides comprising at least an immunogenic portion of a soluble *M. tuberculosis* antigen having one of the following N-terminal sequences, or a variant thereof that differs only in conservative substitutions and/or modifications:

(a) Asp-Pro-Val-Asp-Ala-Val-Ile-Asn-Thr-Thr-Cys-Asn-Tyr-Gly-Gln-Val-Val-Ala-Ala-Leu; (SEQ ID No. 120)

(b) Ala-Val-Glu-Ser-Gly-Met-Leu-Ala-Leu-Gly-Thr-Pro-Ala-Pro-Ser; (SEQ ID No. 121)

(c) Ala-Ala-Met-Lys-Pro-Arg-Thr-Gly-Asp-Gly-Pro-Leu-Glu-Ala-Ala-Lys-Glu-Gly-Arg; (SEQ ID No. 122)

(d) Tyr-Tyr-Trp-Cys-Pro-Gly-Gln-Pro-Phe-Asp-Pro-Ala-Trp-Gly-Pro; (SEQ ID No. 123)

(e) Asp-Ile-Gly-Ser-Glu-Ser-Thr-Glu-Asp-Gln-Gln-Xaa-Ala-Val;
(SEQ ID No. 124)

(f) Ala-Glu-Glu-Ser-Ile-Ser-Thr-Xaa-Glu-Xaa-Ile-Val-Pro; (SEQ ID No. 125)

(g) Asp-Pro-Glu-Pro-Ala-Pro-Pro-Val-Pro-Thr-Ala-Ala-Ala-Ser-Pro-Pro-Ser; (SEQ ID No. 126)

(h) Ala-Pro-Lys-Thr-Tyr-Xaa-Glu-Glu-Leu-Lys-Gly-Thr-Asp-Thr-Gly; (SEQ ID No. 127)

(i) Asp-Pro-Ala-Ser-Ala-Pro-Asp-Val-Pro-Thr-Ala-Ala-Gln-Leu-Thr-Ser-Leu-Leu-Asn-Ser-Leu-Ala-Asp-Pro-Asn-Val-Ser-Phe- Ala-Asn; (SEQ ID No. 128)

(j) Xaa-Asp-Ser-Glu-Lys-Ser-Ala-Thr-Ile-Lys-Val-Thr-Asp-Ala-Ser; (SEQ ID No. 134)

(k) Ala-Gly-Asp-Thr-Xaa-Ile-Tyr-Ile-Val-Gly-Asn-Leu-Thr-Ala-Asp; (SEQ ID No. 135) or (l) Ala-Pro-Glu-Ser- Gly-Ala-Gly-Leu-Gly-Gly-Thr-Val-Gln-Ala-Gly; (SEQ ID No. 136)

wherein Xaa may be any amino acid, preferably a cysteine residue. A DNA sequence encoding the antigen identified as (g) above is provided in SEQ ID No. 52, and the polypeptide encoded by SEQ ID No. 52 is provided in SEQ ID No. 53. A DNA sequence encoding the antigen defined as (a) above is provided in SEQ ID No. 101; its deduced amino acid sequence is provided in SEQ ID No. 102. A DNA sequence corresponding to antigen (d) above is provided in SEQ ID No. 24 a DNA sequence corresponding to antigen (c) is provided in SEQ ID No. 25 and a DNA sequence corresponding to antigen (i) is provided in SEQ ID No. 99; its deduced amino acid sequence is provided in SEQ ID No. 100.

In a further specific embodiment, the subject invention discloses polypeptides comprising at least an immunogenic portion of an *M. tuberculosis* antigen having one of the following N-terminal sequences, or a variant thereof that differs only in conservative substitutions and/or modifications:

(m) Xaa-Tyr-Ile-Ala-Tyr-Xaa-Thr-Thr-Ala-Gly-Ile-Val-Pro-Gly-Lys-Ile-Asn-Val-His-Leu-Val; (SEQ ID No 137) or (n) Asp-Pro-Pro-Asp-Pro-His-Gln-Xaa-Asp-Met-Thr-Lys-Gly-Tyr-Tyr-Pro-Gly-Gly-Arg-Arg-Xaa-Phe; (SEQ ID No. 129)

wherein Xaa may be any amino acid, preferably a cysteine residue.

In other specific embodiments, the subject invention discloses polypeptides comprising at least an immunogenic portion of a soluble *M. tuberculosis* antigen (or a variant of such an antigen) that comprises one or more of the amino acid sequences encoded by (a) the DNA sequences of SEQ ID Nos.: 1, 2, 4–10, 13–25 and 52; (b) the complements of such DNA sequences, or (c) DNA sequences substantially homologous to a sequence in (a) or (b).

In further specific embodiments, the subject invention discloses polypeptides comprising at least an immunogenic portion of a *M. tuberculosis* antigen (or a variant of such an antigen), which may or may not be soluble, that comprises one or more of the amino acid sequences encoded by (a) the DNA sequences of SEQ ID Nos.: 26–51, 138 and 139, (b) the complements of such DNA sequences or (c) DNA sequences substantially homologous to a sequence in (a) or (b).

In the specific embodiments discussed above, the *M. tuberculosis* antigens include variants that are encoded by DNA sequences which are substantially homologous to one or more of DNA sequences specifically recited herein. "Substantial homology," as used herein, refers to DNA sequences that are capable of hybridizing under moderately stringent conditions. Suitable moderately stringent conditions include prewashing in a solution of 5X SSC, 0.5% SDS, 1.0 mM EDTA (pH 8.0); hybridizing at 50° C.–65° C., 5X SSC, overnight or, in the case of cross-species homology at 45° C., 0.5X SSC; followed by washing twice at 65° C. for 20 minutes with each of 2X, 0.5X and 0.2X SSC containing 0.1% SDS). Such hybridizing DNA sequences are also within the scope of this invention, as are nucleotide sequences that, due to code degeneracy, encode an immunogenic polypeptide that is encoded by a hybridizing DNA sequence.

In a related aspect, the present invention provides f uision proteins comprising a first and a second inventive polypeptide or, alternatively, a polypeptide of the present invention and a known *M tuberculosis* antigen, such as the 38 kD antigen described in Andersen and Hansen, *Infect. Immun.* 57:2481–2488, 1989, (Genbank Accession No. M30046) or ESAT-6 (SEQ ID Nos. 103 and 104), together with variants of such fusion proteins. The fusion proteins of the present invention may also include a linker peptide between the first and second polypeptides.

A DNA sequence encoding a fusion protein of the present invention is constructed using known recombinant DNA techniques to assemble separate DNA sequences encoding the first and second polypeptides into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit MRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons require to end translation and transcription termination signals are only present 3' to the DNA sequence encoding the second polypeptide.

In another aspect, the present invention provides methods for using one or more of the above polypeptides or fusion proteins (or DNA molecules encoding such polypeptides) to induce protective immunity against tuberculosis in a patient. As used herein, a "patient" refers to any warm-blooded animal, preferably a human. A patient may be afflicted with a disease, or may be free of detectable disease and/or infection. In other words, protective immunity may be induced to prevent or treat tuberculosis.

In this aspect, the polypeptide, fusion protein or DNA molecule is generally present within a pharmaceutical composition and/or a vaccine. Pharmaceutical compositions may comprise one or more polypeptides, each of which may contain one or more of the above sequences (or variants thereof), and a physiologically acceptable carrier. Vaccines may comprise one or more of the above polypeptides and a non-specific immune response enhancer, such as an adjuvant or a liposome (into which the polypeptide is incorporated). Such pharmaceutical compositions and vaccines may also contain other *M. tuberculosis* antigens, either incorporated into a combination polypeptide or present within a separate polypeptide.

Alternatively, a vaccine may contain DNA encoding one or more polypeptides as described above, such that the polypeptide is generated in situ. In such vaccines, the DNA may be present within any of a variety of delivery systems known to those of ordinary skill in the art, including nucleic acid expression systems, bacterial and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

In a related aspect, a DNA vaccine as described above may be administered simultaneously with or sequentially to either a polypeptide of the present invention or a known *M. tuberculosis* antigen, such as the 38 kD antigen described above. For example, administration of DNA encoding a polypeptide of the present invention, either "naked" or in a delivery system as described above, may be followed by administration of an antigen in order to enhance the protective immune effect of the vaccine.

Routes and frequency of administration, as well as dosage, will vary from individual to individual and may parallel those currently being used in immunization using BCG. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from *M. tuberculosis* infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Any of a variety of adjuvants may be employed in the vaccines of this invention to nonspecifically enhance the immune response. Most adjuvants contain a substance designed to protect the antigen from rapid catabolism, such as aluminum hydroxide or mineral oil, and a nonspecific stimulator of immune responses, such as lipid A, *Bortadella pertussis* or *Mycobacterium tuberculosis*. Suitable adjuvants are commercially available as, for example, Freund's Incomplete Adjuvant and Freund's Complete Adjuvant (Difco Laboratories) and Merck Adjuvant 65 (Merck and Company, Inc., Rahway, N.J.). Other suitable adjuvants include alum, biodegradable microspheres, monophosphoryl lipid A and quil A.

In another aspect, this invention provides methods for using one or more of the polypeptides described above to diagnose tuberculosis using a skin test. As used herein, a "skin test" is any assay performed directly on a patient in which a delayed-type hypersensitivity (DTH) reaction (such as swelling, reddening or dermatitis) is measured following intradermal injection of one or more polypeptides as described above. Such injection may be achieved using any suitable device sufficient to contact the polypeptide or polypeptides with dermal cells of the patient, such as a tuberculin syringe or 1 mL syringe. Preferably, the reaction is measured at least 48 hours after injection, more preferably 48–72 hours.

The DTH reaction is a cell-mediated immune response, which is greater in patients that have been exposed previously to the test antigen (ie., the immunogenic portion of the polypeptide employed, or a variant thereof). The response may be measured visually, using a ruler. In general, a response that is greater than about 0.5 cm in diameter, preferably greater than about 1.0 cm in diameter, is a positive response, indicative of tuberculosis infection, which may or may not be manifested as an active disease.

The polypeptides of this invention are preferably formulated, for use in a skin test, as pharmaceutical compositions containing a polypeptide and a physiologically acceptable carrier, as described above. Such compositions typically contain one or more of the above polypeptides in an amount ranging from about 1 µg to about 100 µg, preferably from about 10 µg to about 50 µg in a volume of 0.1 mL. Preferably, the carrier employed in such pharmaceutical compositions is a saline solution with appropriate preservatives, such as phenol and/or Tween 80™.

In a preferred embodiment, a polypeptide employed in a skin test is of sufficient size such that it remains at the site of injection for the duration of the reaction period. In general, a polypeptide that is at least 9 amino acids in length is sufficient. The polypeptide is also preferably broken down by macrophages within hours of injection to allow presentation to T-cells. Such polypeptides may contain repeats of one or more of the above sequences and/or other immunogenic or nonimmunogenic sequences.

The following Examples are offered by way of illustration and not by way of limitation.

EXAMPLES

EXAMPLE 1

Purification and Characterization of Polypeptides FROM *M. Tuberculosis* Culture Filtrate This example illustrates the preparation of *M. tuberculosis* soluble polypeptides from culture filtrate. Unless otherwise noted, all percentages in the following example are weight per volume.

*M. tuberculosis* (either H37Ra, ATCC No. 25177, or H37Rv, ATCC No. 25618) was cultured in sterile GAS media at 37° C. for fourteen days. The media was then vacuum filtered (leaving the bulk of the cells) through a 0.45$\mu$ filter into a sterile 2.5 L bottle. The media was next filtered through a 0.2$\mu$filter into a sterile 4 L bottle and $NaN_3$ was added to the culture filtrate to a concentration of 0.04%. The bottles were then placed in a 4° C. cold room.

The culture filtrate was concentrated by placing the filtrate in a 12 L reservoir that had been autoclaved and feeding the filtrate into a 400 ml Amicon stir cell which had been rinsed with ethanol and contained a 10,000 kDa MWCO membrane. The pressure was maintained at 60 psi using nitrogen gas. This procedure reduced the 12 L volume to approximately 50 ml.

The culture filtrate was dialyzed into 0.1% ammonium bicarbonate using a 8,000 kDa MWCO cellulose ester membrane, with two changes of ammonium bicarbonate solution. Protein concentration was then determined by a commercially available BCA assay (Pierce, Rockford, Ill.).

The dialyzed culture filtrate was then lyophilized, and the polypeptides resuspended in distilled water. The polypeptides were dialyzed against 0.01 mM 1,3 bis[tris (hydroxymethyl)-methylamino]propane, pH 7.5 (Bis-Tris propane buffer), the initial conditions for anion exchange chromatography. Fractionation was performed using gel profusion chromatography on a POROS 146 II Q/M anion exchange column 4.6 mm×100 mm (Perseptive BioSystems, Framingham, Mass.) equilibrated in 0.01 mM Bis-Tris propane buffer pH 7.5. Polypeptides were eluted with a linear 0–0.5 M NaCl gradient in the above buffer system. The column eluent was monitored at a wavelength of 220 nm.

The pools of polypeptides eluting from the ion exchange column were dialyzed against distilled water and lyophilized. The resulting material was dissolved in 0.1% trifluoroacetic acid (TFA) pH 1.9 in water, and the polypeptides were purified on a Delta-Pak C18 column (Waters, Milford, Mass.) 300 Angstrom pore size, 5 micron particle size (3.9×150 mm). The polypeptides were eluted from the column with a linear gradient from 0–60% dilution buffer (0.1% TFA in acetonitrile). The flow rate was 0.75 ml/minute and the HPLC eluent was monitored at 214 nm. Fractions containing the eluted polypeptides were collected to maximize the purity of the individual samples. Approximately 200 purified polypeptides were obtained.

The purified polypeptides were then screened for the ability to induce T-cell proliferation in PBMC preparations. The PBMCs from donors known to be PPD skin test positive and whose T-cells were shown to proliferate in response to PPD and crude soluble proteins from MTB were cultured in medium comprising RPMI 1640 supplemented with 10% pooled human serum and 50 $\mu$g/ml gentamicin. Purified polypeptides were added in duplicate at concentrations of 0.5 to 10 $\mu$g/mL. After six days of culture in 96-well round-bottom plates in a volume of 200 $\mu$l, 50 $\mu$l of medium was removed from each well for determination of IFN-γ levels, as described below. The plates were then pulsed with 1 $\mu$Ci/well of tritiated thymidine for a further 18 hours, harvested and tritium uptake determined using a gas scintillation counter. Fractions that resulted in proliferation in both replicates three fold greater than the proliferation observed in cells cultured in medium alone were considered positive.

IFN-γ was measured using an enzyme-linked immunosorbent assay (ELISA). ELISA plates were coated with a mouse monoclonal antibody directed to human IFN-γ

(PharMingen, San Diego, Calif.) in PBS for four hours at room temperature. Wells were then blocked with PBS containing 5% (W IV) non-fat dried milk for 1 hour at room temperature. The plates were then washed six times in PBS/0.2% TWEEN-20 and samples diluted 1:2 in culture medium in the ELISA plates were incubated overnight at room temperature. The plates were again washed and a polyclonal rabbit anti-human IFN-γ serum diluted 1:3000 in PBS/10% normal goat serum was added to each well. The plates were then incubated for two hours at room temperature, washed and horseradish peroxidase-coupled anti-rabbit IgG (Sigma Chemical So., St. Louis, Mo.) was added at a 1:2000 dilution in PBS/5% non-fat dried milk. After a further two hour incubation at room temperature, the plates were washed and TMB substrate added. The reaction was stopped after 20 min with 1 N sulfuric acid. Optical density was determined at 450 nm using 570 nm as a reference wavelength. Fractions that resulted in both replicates giving an OD two fold greater than the mean OD from cells cultured in medium alone, plus 3 standard deviations, were considered positive.

For sequencing, the polypeptides were individually dried onto Biobrene™ (Perkin Elmer/Applied BioSystems Division, Foster City, Calif.) treated glass fiber filters. The filters with polypeptide were loaded onto a Perkin Elmer/ Applied BioSystems Division Procise 492 protein sequencer. The polypeptides were sequenced from the amino terminal and using traditional Edman chemistry. The amino acid sequence was determined for each polypeptide by comparing the retention time of the PTH amino acid derivative to the appropriate PTH derivative standards.

Using the procedure described above, antigens having the following N-terminal sequences were isolated:

(a) Asp-Pro-Val-Asp-Ala-Val-Ile-Asn-Thr-Thr-Xaa-Asn-Tyr-Gly-Gln-Val-Val-Ala-Ala-Leu; (SEQ ID No. 54)

10 P (b) Ala-Val-Glu-Ser-Gly-Met-Leu-Ala-Leu-Gly-Thr-Pro-Ala-Pro-Ser; (SEQ ID No. 55)

(c) Ala-Ala-Met-Lys-Pro-Arg-Thr-Gly-Asp-Gly-Pro-Leu-Glu-Ala-Ala-Lys-Glu-Gly-Arg; (SEQ ID No. 56)

(d) Tyr-Tyr-Trp-Cys-Pro-Gly-Gln-Pro-Phe-Asp-Pro-Ala-Trp-Gly-Pro; (SEQ ID No. 57)

(e) Asp-Ile-Gly-Ser-Glu-Ser-Thr-Glu-Asp-Gln-Gln-Xaa-Ala-Val; (SEQ ID No. 58)

(f) Ala-Glu-Glu-Ser-Ile-Ser-Thr-Xaa-Glu-Xaa-Ile-Val-Pro; (SEQ ID No. 59)

(g) Asp-Pro-Glu-Pro-Ala-Pro-Pro-Val-Pro-Thr-Ala-Ala-Ala-Ala-Pro-Pro-Ala; (SEQ ID No. 60) and (h) Ala-Pro-Lys-Thr-Tyr-Xaa-Glu-Glu-Leu-Lys-Gly-Thr-Asp-Thr-Gly; (SEQ ID No. 61)

wherein Xaa may be any amino acid.

An additional antigen was isolated employing a microbore HPLC purification step in addition to the procedure described above. Specifically, 20 μl of a fraction comprising a mixture of antigens from the chromatographic purification step previously described, was purified on an Aquapore C1 8 column (Perkin Elmer/Applied Biosystems Division, Foster City, Calif.) with a 7 micron pore size, column size 1 mm×100 mm, in a Perkin Elmer/Applied Biosystems Division Model 172 HPLC. Fractions were eluted from the column with a linear gradient of 1%/minute of acetonitrile (containing 0.05% TFA) in water (0.05% TFA) at a flow rate of 80 μl/minute. The eluent was monitored at 250 nm. The original fraction was separated into 4 major peaks plus other smaller components and a polypeptide was obtained which was shown to have a molecular weight of 12.054 Kd (by mass spectrometry) and the following N-terminal sequence:

(i) Asp-Pro-Ala-Ser-Ala-Pro-Asp-Val-Pro-Thr-Ala-Ala-Gln-Gln-Thr-Ser-Leu-Leu-Asn-Asn-Leu-Ala-Asp-Pro-Asp-Val-Ser-Phe- Ala-Asp (SEQ ID No. 62).

This polypeptide was shown to induce proliferation and IFN-γ production in PBMC preparations using the assays described above.

Additional soluble antigens were isolated from *M. tuberculosis* culture filtrate as follows. *M. tuberculosis* culture filtrate was prepared as described above. Following dialysis against Bis-Tris propane buffer, at pH 5.5, fractionation was performed using anion exchange chromatography on a Poros QE column 4.6×100 mm (Perseptive Biosystems) equilibrated in Bis-Tris propane buffer pH 5.5. Polypeptides were eluted with a linear 0–1.5 M NaCl gradient in the above buffer system at a flow rate of 10 ml/min. The column eluent was monitored at a wavelength of 214 nm.

The fractions eluting from the ion exchange column were pooled and subjected to reverse phase chromatography using a Poros R2 column 4.6×100 mm (Perseptive Biosystems). Polypeptides were eluted from the column with a linear gradient from 0–100% acetonitrile (0.1% TFA) at a flow rate of 5 ml/min. The eluent was monitored at 214 nm.

Fractions containing the eluted polypeptides were lyophilized and resuspended in 80 μl of aqueous 0.1% TFA and further subjected to reverse phase chromatography on a Vydac C4 column 4.6×150 mm (Western Analytical, Temecula, Calif.) with a linear gradient of 0–100% acetonitrile (0.1% TFA) at a flow rate of 2 ml/min. Eluent was monitored at 214 nm.

The fraction with biological activity was separated into one major peak plus other smaller components. Western blot of this peak onto PVDF membrane revealed three major bands of molecular weights 14 Kd, 20 Kd and 26 Kd. These polypeptides were determined to have the following N-terminal sequences, respectively:

(j) Xaa-Asp-Ser-Glu-Lys-Ser-Ala-Thr-Ile-Lys-Val-Thr-Asp-Ala-Ser; (SEQ ID No. 134)

(k) Ala-Gly-Asp-Thr-Xaa-Ile-Tyr-Ile-Val-Gly-Asn-Leu-Thr-Ala-Asp; (SEQ ID No. 135) and (l) Ala-Pro-Glu-Ser-Gly-Ala-Gly-Leu-Gly-Gly-Thr-Val-Gln-Ala-Gly; (SEQ ID No. 136), wherein Xaa may be any amino acid.

Using the assays described above, these polypeptides were shown to induce proliferation and IFN-γ production in PBMC preparations. FIGS. 1A and B show the results of such assays using PBMC preparations from a first and a second donor, respectively.

DNA sequences that encode the antigens designated as (a), (c), (d) and (g) above were obtained by screening a genomic *M. tuberculosis* library using $^{32}$P end labeled degenerate oligonucleotides corresponding to the N-terminal sequence and containing *M. tuberculosis* codon bias. The screen performed using a probe corresponding to antigen (a) above identified a clone having the sequence provided in SEQ ID No. 101. The polypeptide encoded by SEQ ID No. 101 is provided in SEQ ID No. 102. The screen performed using a probe corresponding to antigen (g) above identified a clone having the sequence provided in SEQ ID No. 52. The polypeptide encoded by SEQ ID No. 52 is provided in SEQ ID No. 53. The screen performed using a probe corresponding to antigen (d) above identified a clone having the sequence provided in SEQ ID No. 24, and the screen performed with a probe corresponding to antigen (c) identified a clone having the sequence provided in SEQ ID No: 25.

The above amino acid sequences were compared to known amino acid sequences in the gene bank using the DNA STAR system. The database searched contains some 173,000 proteins and is a combination of the Swiss, PIR databases along with translated protein sequences (Version 87). No significant homologies to the amino acid sequences for antigens (a)–(h) and (l) were detected.

The amino acid sequence for antigen (i) was found to be homologous to a sequence from M. leprae. The full length M. leprae sequence was amplified from genomic DNA using the sequence obtained from GENBANK. This sequence was then used to screen the M. tuberculosis library described below in Example 2 and a full length copy of the M. tuberculosis homologue was obtained (SEQ ID No. 99).

The amino acid sequence for antigen (j) was found to be homologous to a known M. tuberculosis protein translated from a DNA sequence. To the best of the inventors' knowledge, this protein has not been previously shown to possess T-cell stimulatory activity. The amino acid sequence for antigen (k) was found to be related to a sequence from M leprae.

In the proliferation and IFN-γ assays described above, using three PPD positive donors, the results for representative antigens provided above are presented in Table 1:

TABLE 1

RESULTS OF PBMC PROLIFERATION AND IFN-γ ASSAYS

| Sequence | Proliferation | IFN-γ |
|---|---|---|
| (a) | + | − |
| (c) | +++ | +++ |
| (d) | ++ | ++ |
| (g) | +++ | +++ |
| (h) | +++ | +++ |

In Table 1, responses that gave a stimulation index (SI) of between 2 and 4 (compared to cells cultured in medium alone) were scored as +, an SI of 4–8 or 2–4 at a concentration of 1 μg or less was scored as ++ and an SI of greater than 8 was scored as +++. The antigen of sequence (i) was found to have a high SI (+++) for one donor and lower SI (++ and +) for the two other donors in both proliferation and IFN-γ assays. These results indicate that these antigens are capable of inducing proliferation and/or interferon-γ production.

EXAMPLE 2

Use of Patient Sera to Isolate M. Tuberculosis Antigens

This example illustrates the isolation of antigens from M. tuberculosis lysate by screening with serum from M. tuberculosis-infected individuals.

Dessicated M. tuberculosis H37Ra (Difco Laboratories) was added to a 2% NP40 solution, and alternately homogenized and sonicated three times. The resulting suspension was centrifuged at 13,000 rpm in microfuge tubes and the supernatant put through a 0.2 micron syringe filter. The filtrate was bound to Macro Prep DEAE beads (BioRad, Hercules, Calif.). The beads were extensively washed with 20 mM Tris pH 7.5 and bound proteins eluted with IM NaCl. The IM NaCl elute was dialyzed overnight against 10 mM Tris, pH 7.5. Dialyzed solution was treated with DNase and RNase at 0.05 mg/ml for 30 min. at room temperature and then with α-D-mannosidase, 0.5 U/mg at pH 4.5 for 3–4 hours at room temperature. After returning to pH 7.5, the material was fractionated via FPLC over a Bio Scale-Q-20 column (BioRad). Fractions were combined into nine pools, concentrated in a Centriprep 10 (Amicon, Beverley, Mass.) and then screened by Western blot for serological activity using a serum pool from M. tuberculosis-infected patients which was not immunoreactive with other antigens of the present invention.

The most reactive fraction was run in SDS-PAGE and transferred to PVDF. A band at approximately 85 Kd was cut out yielding the sequence:

(m) Xaa-Tyr-Ile-Ala-Tyr-Xaa-Thr-Thr-Ala-Gly-Ile-Val-Pro-Gly-Lys-Ile-Asn-Val-His-Leu-Val; (SEQ ID No. 137), wherein Xaa may be any amino acid.

Comparison of this sequence with those in the gene bank as described above, revealed no significant homologies to known sequences.

EXAMPLE 3

Preparation of DNA Sequences Encoding M. tuberculosis Antigens

This example illustrates the preparation of DNA sequences encoding M. tuberculosis antigens by screening a M. tuberculosis expression library with sera obtained from patients infected with M. tuberculosis, or with anti-sera raised against soluble M. tuberculosis antigens.

A. PREPARATION OF M. TUBERCULOSIS SOLUBLE ANTIGENS USING RABBIT ANTI-SERA

Genomic DNA was isolated from the M. tuberculosis strain H37Ra. The DNA was randomly sheared and used to construct an expression library using the Lambda ZAP expression system (Stratagene, La Jolla, Calif.). Rabbit anti-sera was generated against secretory proteins of the M. tuberculosis strains H37Ra, H37Rv and Erdman by immunizing a rabbit with concentrated supernatant of the M. tuberculosis cultures. Specifically, the rabbit was first immunized subcutaneously with 200 μg of protein antigen in a total volume of 2 ml containing 10 μg muramyl dipeptide (Calbiochem, La Jolla, Calif.) and 1 ml of incomplete Freund's adjuvant. Four weeks later the rabbit was boosted subcutaneously with 100 μg antigen in incomplete Freund's adjuvant. Finally, the rabbit was immunized intravenously four weeks later with 50 μg protein antigen. The anti-sera were used to screen the expression library as described in Sambrook et al., Molecular Cloning: A Laboratory Manual, Cold Spring Harbor Laboratories, Cold Spring Harbor, N.Y., 1989. Bacteriophage plaques expressing immunoreactive antigens were purified. Phagemid from the plaques was rescued and the nucleotide sequences of the M. tuberculosis clones deduced.

Thirty two clones were purified. Of these, 25 represent sequences that have not been previously identified in human M. tuberculosis. Recombinant antigens were expressed and purified antigens used in the immunological analysis described in Example 1. Proteins were induced by IPTG and purified by gel elution, as described in Skeiky et al., J Exp. Med. 181:1527–1537, 1995. Representative sequences of DNA molecules identified in this screen are provided in SEQ ID Nos.: 1–25. The corresponding predicted amino acid sequences are shown in SEQ ID Nos. 63–87.

On comparison of these sequences with known sequences in the gene bank using the databases described above, it was found that the clones referred to hereinafter as TbRA2A, TbRA16, TbRA18, and ThRA29 (SEQ ID Nos. 76, 68, 70, 75) show some homology to sequences previously identified in Mycobacterium leprae but not in M. tuberculosis. ThRA11, ThRA26, ThRA28 and TbDPEP (SEQ ID Nos.:

65, 73, 74, 53) have been previously identified in *M. tuberculosis*. No significant homologies were found to ThRA1, ThRA3, ThRA4, ThRA9, TBRA10, TbRA13, TbRA17, TbRal9, ThRA29, ThRA32, TbRA36 and the overlapping clones TbRA35 and ThRA12 (SEQ ID Nos. 63, 77, 81, 82, 64, 67, 69, 71, 75, 78, 80, 79, 66). The clone ThRa24 is overlapping with clone ThRa29.

The results of PBMC proliferation and interferon-γ assays performed on representative recombinant antigens, and using T-cell preparations from several different *M. tuberculosis*-immune patients, are presented in Tables 2 and 3, respectively.

TABLE 2

RESULTS OF PBMC PROLIFERATION TO REPRESENTATIVE SOLUBLE ANTIGENS

| Antigen | Patient | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| TbRa1 | – | – | ± | ++ | – | – | ± | ± | – | – | + | ± | – |
| TbRa3 | – | ± | ++ | – | ± | – | – | ++ | ± | – | – | – | – |
| TbRa9 | – | – | nt | nt | ++ | ++ | nt | nt | nt | nt | nt | nt | nt |
| TbRa10 | – | – | ± | ± | ± | + | nt | ± | – | + | ± | ± | – |
| TbRa11 | ± | ± | + | ++ | ++ | + | nt | – | ++ | ++ | ++ | ± | nt |
| TbRa12 | – | – | + | + | ± | ++ | + | ± | ± | – | + | – | – |
| TbRa16 | nt | nt | nt | nt | – | + | nt | nt | nt | nt | nt | nt | nt |
| TbRa24 | nt | nt | nt | nt | – | – | nt | nt | nt | nt | nt | nt | nt |
| TbRa26 | – | + | nt | nt | – | – | nt | nt | nt | nt | nt | nt | nt |
| TbRa29 | nt | nt | nt | nt | – | – | nt | nt | nt | nt | nt | nt | nt |
| TbRa35 | ++ | nt | ++ | ++ | ++ | ++ | nt | ++ | ++ | ++ | ++ | ++ | nt |
| TbRaB | nt | nt | nt | nt | – | – | nt | nt | nt | nt | nt | nt | nt |
| TbRaC | nt | nt | nt | nt | – | – | nt | nt | nt | nt | nt | nt | nt |
| TbRaD | nt | nt | nt | nt | – | – | nt | nt | nt | nt | nt | nt | nt |
| AAMK | – | – | ± | – | – | – | nt | – | – | – | nt | ± | nt |
| YY | – | – | – | – | – | – | nt | – | – | – | nt | + | nt |
| DPEP | – | + | – | ++ | – | – | nt | ++ | ± | + | ± | ± | nt |
| Control | – | – | – | – | – | – | – | – | – | – | – | – | – | nt = not tested

TABLE 3

RESULTS OF PBMC INTERFERON-γ PRODUCTION TO REPRESENTATIVE SOLUBLE ANTIGENS

| Antigen | Patient | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| TbRa1 | + | ++ | | +++ | + | – | | ± | – | – | + | ± | – |
| TbRa3 | – | ± | ++ | – | ± | – | – | ++ | ± | – | – | – | – |
| TbRa9 | ++ | + | nt | nt | ++ | – | nt | nt | nt | nt | nt | nt | nt |
| TbRa10 | + | + | ± | ± | ± | + | nt | ± | – | + | ± | ± | – |
| TbRa11 | | ± | + | ++ | ++ | + | nt | – | ++ | ++ | ++ | ± | nt |
| TbRa12 | – | – | + | + | ± | +++ | + | ± | ± | – | + | – | – |
| TbRa16 | nt | nt | nt | nt | + | + | nt | nt | nt | nt | nt | nt | nt |
| TbRa24 | nt | nt | nt | nt | + | – | nt | nt | nt | nt | nt | nt | nt |
| TbRa26 | ++ | ++ | nt | nt | + | + | nt | nt | nt | nt | nt | nt | nt |
| TbRa29 | nt | nt | nt | nt | + | – | nt | nt | nt | nt | nt | nt | nt |
| TbRa35 | ++ | nt | ++ | ++ | +++ | +++ | nt | ++ | ++ | +++ | +++ | ++ | nt |
| TbRaB | nt | nt | nt | nt | ++ | + | nt | nt | nt | nt | nt | nt | nt |
| TbRaC | nt | nt | nt | nt | + | + | nt | nt | nt | nt | nt | nt | nt |
| TbRaD | nt | nt | nt | nt | + | + | nt | nt | nt | nt | nt | nt | nt |
| AAMK | – | – | ± | – | – | – | nt | – | – | – | nt | ± | nt |
| YY | – | – | – | – | – | – | nt | – | – | – | nt | + | nt |
| DPEP | + | + | + | +++ | + | – | nt | +++ | ± | + | ± | ± | nt |
| Control | – | – | – | – | – | – | – | – | – | – | – | – | – |

In Tables 2 and 3, responses that gave a stimulation index (SI) of between 1.2 and 2 (compared to cells cultured in medium alone) were scored as ±, a SI of 2–4 was scored as +, as SI of 4–8 or 2–4 at a concentration of 1 µg or less was scored as ++ and an SI of greater than 8 was scored as +++. In addition, the effect of concentration on proliferation and interferon-γ production is shown for two of the above antigens in the attached Figure. For both proliferation and interferon-γ production, ThRa3 was scored as ++ and ThRa9 as +.

These results indicate that these soluble antigens can induce proliferation and/or interferon-γ production in T-cells derived from an *M. tuberculosis*-immune individual.

B. USE OF PATIENT SERA TO IDENTIFY DNA SEQUENCES ENCODING *M. TUBERCULOSIS* ANTIGENS

The genomic DNA library described above, and an additional H37Rv library, were screened using pools of sera obtained from patients with active tuberculosis. To prepare the H37Rv library, *M. tuberculosis* strain H37Rv genomic DNA was isolated, subjected to partial Sau3A digestion and used to construct an expression library using the Lambda Zap expression system (Stratagene, La Jolla, Calif.). Three different pools of sera, each containing sera obtained from three individuals with active pulmonary or pleural disease, were used in the expression screening. The pools were designated TbL, ThM and ThH, referring to relative reactivity with H37Ra lysate (i.e., TbL=low reactivity, TbM=medium reactivity and TbH=high reactivity) in both ELISA and immunoblot format. A fourth pool of sera from seven patients with active pulmonary tuberculosis was also employed. All of the sera lacked increased reactivity with the recombinant 38 kD *M. tuberculosis* H37Ra phosphate-binding protein.

All pools were pre-adsorbed with *E. coli* lysate and used to screen the H37Ra and H37Rv expression libraries, as described in Sambrook et al., *Molecular Cloning: A Laboratory Manual*, Cold Spring Harbor Laboratories, Cold Spring Harbor, N.Y., 1989. Bacteriophage plaques expressing immunoreactive antigens were purified. Phagemid from the plaques was rescued and the nucleotide sequences of the *M. tuberculosis* clones deduced.

Thirty two clones were purified. Of these, 31 represented sequences that had not been previously identified in human *M. tuberculosis*. Representative sequences of the DNA molecules identified are provided in SEQ ID Nos.: 26–51 and 105. Of these, TbH-8-2 (SEQ. ID NO. 105) is a partial clone of TbH-8, and TbH-4 (SEQ. ID NO. 43) and TbH-4-FWD (SEQ. ID NO. 44) are non-contiguous sequences from the same clone. Amino acid sequences for the antigens hereinafter identified as Tb38-1, TbH-4, TbH-8, TbH-9, and TbH-12 are shown in SEQ ID Nos.: 88–92. Comparison of these sequences with known sequences in the gene bank using the databases identified above revealed no significant homologies to TbH-4, TbH-8, TbH-9 and TbM-3, although weak homologies were found to TbH-9. TbH-12 was found to be homologous to a 34 kD antigenic protein previously identified in M. paratuberculosis (Acc. No. S28515). Tb38-1 was found to be located 34 base pairs upstream of the open reading frame for the antigen ESAT-6 previously identified in M. bovis (Acc. No. U34848) and in M. tuberculosis (Sorensen et al., Infec. Immun. 63:1710–1717, 1995).

Probes derived from Tb38-1 and TbH-9, both isolated from an H37Ra library, were used to identify clones in an H37Rv library. Tb38-1 hybridized to Tb38-1F2, Tb38-1F3, Tb38-1F5 and Tb38-1F6 (SEQ. ID NOS. 112, 113, 116, 118, and 119). (SEQ ID NOS. 112 and 113 are non-contiguous sequences from clone Tb38-1F2.) Two open reading frames were deduced in Tb38-1F2; one corresponds to Tb37FL (SEQ. ID. NO. 114), the second, a partial sequence, may be the homologue of Tb38-1 and is called Tb38-IN (SEQ. ID NO. 115). The deduced amino acid sequence of Tb38-1F3 is presented in SEQ. ID. NO. 117. A TbH-9 probe identified three clones in the H37Rv library: TbH-9-FL (SEQ. ID NO. 106), which may be the homologue of TbH-9 (R37Ra), TbH-9-1 (SEQ. ID NO. 108), and TbH-9-4 (SEQ. ID NO. 110), all of which are highly related sequences to TbH-9. The deduced amino acid sequences for these three clones are presented in SEQ ID NOS. 107, 109 and 111.

Further screening of the *M. tuberculosis* genomic DNA library, as described above, resulted in the recovery of ten additional reactive clones, representing seven different genes. One of these genes was identified as the 38 Kd antigen discussed above, one was determined to be identical to the 14Kd alpha crystalline heat shock protein previously shown to be present in *M. tuberculosis,* and a third was determined to be identical to the antigen TbH-8 described above. The determined DNA sequences for the remaining five clones (hereinafter referred to as TbH-29, TbH-30, TbH-32 and TbH-33) are provided in SEQ ID NO: 138–141, respectively, with the corresponding predicted amino acid sequences being provided in SEQ ID NO: 142–145, respectively. The DNA and amino acid sequences for these antigens were compared with those in the gene bank as described above. No homologies were found to the 5' end of TbH-29 (which contains the reactive open reading frame), although the 3' end of TbH-29 was found to be identical to the *M. tuberculosis* cosmid Y227. TbH-32 and TbH-33 were found to be identical to the previously identified *M. tuberculosis* insertion element IS6110 and to the *M. tuberculosis* cosmid Y50, respectively. No significant homologies to TbH-30 were found.

Positive phagemid from this additional screening were used to infect *E. coli* XL-1 Blue MRF', as described in Sambrook et al., supra. Induction of recombinant protein was accomplished by the addition of IPTG. Induced and uninduced lysates were run in duplicate on SDS-PAGE and transferred to nitrocellulose filters. Filters were reacted with human *M. tuberculosis* sera (1:200 dilution) reactive with TbH and a rabbit sera (1:200 or 1:250 dilution) reactive with the N-terminal 4 Kd portion of lacZ. Sera incubations were performed for 2 hours at room temperature. Bound antibody was detected by addition of $^{125}$I-labeled Protein A and subsequent exposure to film for variable times ranging from 16 hours to 11 days. The results of the immunoblots are summarized in Table 4.

TABLE 4

| Antigen | Human M. tb Sera | Anti-lacZ Sera |
|---|---|---|
| TbH-29 | 45 Kd | 45 Kd |
| TbH-30 | No reactivity | 29 Kd |
| TbH-32 | 12 Kd | 12 Kd |
| TbH-33 | 16 Kd | 16 Kd |

Positive reaction of the recombinant human *M. tuberculosis* antigens with both the human *M. tuberculosis* sera and anti-lacZ sera indicate that reactivity of the human *M. tuberculosis* sera is directed towards the fusion protein. Antigens reactive with the anti-lacZ sera but not with the human *M. tuberculosis* sera may be the result of the human *M. tuberculosis* sera recognizing conformational epitopes, or the antigen-antibody binding kinetics may be such that the 2 hour sera exposure in the immunoblot is not sufficient.

The results of T-cell assays performed on Tb38-1, ESAT-6 and other representative recombinant antigens are presented in Tables 5A, B and 6, respectively, below:

TABLE 5A

RESULTS OF PBMC PROLIFERATION TO REPRESENTATIVE ANTIGENS

| Antigen | Donor 1 | 2 | 3 | 4 | 5 | 6 | 7 | 8 | 9 | 10 |
|---|---|---|---|---|---|---|---|---|---|---|
| Th38.1 | +++ | + | − | − | − | ++ | − | + | − | ++ |
| ESAT-6 | +++ | + | + | + | − | + | − | + | + | ++ |
| TbH-9 | ++ | ++ | − | ++ | ± | ± | ++ | ++ | ++ | ++ |

TABLE 5B

RESULTS OF PBMC INTERFERON-γ PRODUCTION TO REPRESENTATIVE ANTIGENS

| Antigen | Donor 1 | 2 | 3 | 4 | 5 | 6 | 7 | 8 | 9 | 10 | 11 |
|---|---|---|---|---|---|---|---|---|---|---|---|
| Th38.1 | +++ | + | − | + | + | +++ | − | ++ | − | +++ | +++ |
| ESAT-6 | +++ | + | + | + | +− | + | − | + | + | +++ | +++ |
| TbH-9 | ++ | ++ | − | +++ | ± | ± | +++ | +++ | ++ | +++ | ++ |

TABLE 6

SUMMARY OF T-CELL RESPONSES TO REPRESENTATIVE ANTIGENS

| Antigen | Proliferation | | | Interferon-γ | | | total |
|---|---|---|---|---|---|---|---|
| | patient 4 | patient 5 | patient 6 | patient 4 | patient 5 | patient 6 | |
| TbH9 | ++ | ++ | ++ | +++ | ++ | ++ | 13 |
| TbM7 | − | + | − | ++ | + | − | 4 |
| TbH5 | − | + | + | ++ | ++ | ++ | 8 |
| TbL23 | − | + | ± | ++ | ++ | + | 7.5 |
| TbH4 | − | ++ | ± | ++ | ++ | ± | 7 |
| - control | − | − | − | − | − | − | 0 |

These results indicate that both the inventive *M. tuberculosis* antigens and ESAT-6 can induce proliferation and/or interferon-γ production in T-cells derived from an *M. tuberculosis*-immune individual. To the best of the inventors' knowledge, ESAT-6 has not been previously shown to stimulate human immune responses A set of six overlapping peptides covering the amino acid sequence of the antigen T h38-1 was constructed using the method described in Example 6. The sequences of these peptides, hereinafter referred to as pep1-6, are provided in SEQ ID Nos. 93–98, respectively. The results of T-cell assays using these peptides are shown in Tables 7 and 8. These results confirm the existence, and help to localize T-cell epitopes within Tb38-1 capable of inducing proliferation and interferon-γ production in T-cells derived from an *M. tuberculosis* immune individual.

TABLE 7

RESULTS OF PBMC PROLIFERATION TO TB38-1 PEPTIDES

| | Patient | | | | | | | | | | | | |
|---|---|---|---|---|---|---|---|---|---|---|---|---|---|
| Peptide | 1 | 2 | 3 | 4 | 5 | 6 | 7 | 8 | 9 | 10 | 11 | 12 | 13 |
| pep1 | – | – | – | – | ± | – | – | – | – | ± | – | – | + |
| pep2 | ± | – | – | – | ± | – | – | – | ± | ± | – | – | + |
| pep3 | – | – | – | – | – | – | – | – | ± | – | – | – | ± |
| pep4 | ++ | – | – | – | – | – | + | – | ± | ± | – | – | + |
| pep5 | ++ | ± | – | – | – | – | + | – | ± | – | – | – | + |
| pep6 | – | ++ | – | – | – | – | ± | – | ± | + | – | – | + |
| Control | – | – | – | – | – | – | – | – | – | – | – | – | – |

TABLE 8

RESULTS OF PBMC INTERFERON-γ PRODUCTION TO TB38-1 PEPTIDES

| | Patient | | | | | | | | | | | | |
|---|---|---|---|---|---|---|---|---|---|---|---|---|---|
| Peptide | 1 | 2 | 3 | 4 | 5 | 6 | 7 | 8 | 9 | 10 | 11 | 12 | 13 |
| pep1 | + | – | – | – | ± | – | – | – | – | ± | – | – | + |
| pep2 | | – | – | – | ± | – | – | – | ± | ± | – | – | + |
| pep3 | – | – | – | – | – | – | – | – | ± | – | – | – | ± |
| pep4 | ++ | – | – | – | – | – | + | – | ± | ± | – | – | + |
| pep5 | ++ | ± | – | – | – | – | + | – | ± | – | – | – | + |
| pep6 | + | ++ | – | – | – | – | ± | – | ± | + | – | – | + |
| Control | – | – | – | – | – | – | – | – | – | – | – | – | – |

Studies were undertaken to determine whether the antigens TbH-9 and Tb38-1 represent cellular proteins or are secreted into *M. tuberculosis* culture media. In the first study, rabbit sera were raised against A) secretory proteins of *M. tuberculosis,* B) the known secretory recombinant *M. tuberculosis* antigen 85b, C) recombinant Tb38-1 and D) recombinant TbH-9, using protocols substantially the same as that as described in Example 3A. Total *M. tuberculosis* lysate, concentrated supernatant of *M. tuberculosis* cultures and the recombinant antigens 85b, TbH-9 and Tb38-1 were resolved on denaturing gels, immobilized on nitrocellulose membranes and duplicate blots were probed using the rabbit sera described above.

The results of this analysis using control sera (panel I) and antisera (panel II) against secretory proteins, recombinant 85b, recombinant Tb38-1 and recombinant TbH-9 are shown in FIGS. 3A–D, respectively, wherein the lane designations are as follows: 1) molecular weight protein standards; 2) 5 μg of *M. tuberculosis* lysate; 3) 5 μg secretory proteins; 4) 50 ng recombinant Tb38-l; 5) 50 ng recombinant TbH-9; and 6) 50 ng recombinant 85b. The recombinant antigens were engineered with six terminal histidine residues and would therefore be expected to migrate with a mobility approximately 1 kD larger that the native protein. In FIG. 3D, recombinant TbH-9 is lacking approximately 10 kD of the full-length 42 kD antigen, hence the significant difference in the size of the immunoreactive native TbH-9 antigen in the lysate lane (indicated by an arrow). These results demonstrate that Tb38-1 and TbH-9 are intracellular antigens and are not actively secreted by *M. tuberculosis.*

The finding that TbH-9 is an intracellular antigen was confirmed by determining the reactivity of TbH-9-specific human T cell clones to recombinant TbH-9, secretory *M. tuberculosis* proteins and PPD. A TbH-9-specific T cell clone (designated 131TbH-9) was generated from PBMC of a healthy PPD-positive donor. The proliferative response of 131TbH-9 to secretory proteins, recombinant TbH-9 and a control *M. tuberculosis* antigen, TbRa11, was determined by measuring uptake of tritiated thymidine, as described in Example 1. As shown in FIG. 4A, the clone 131TbH-9 responds specifically to TbH-9, showing that TbH-9 is not a significant component of *M. tuberculosis* secretory proteins. FIG. 4B shows the production of IFN-γ by a second TbH-9-specific T cell clone (designated PPD 800-10) prepared from PBMC from a healthy PPD-positive donor, following stimulation of the T cell clone with secretory proteins, PPD or recombinant TbH-9. These results further confirm that TbH-9 is not secreted by *M. tuberculosis.*

EXAMPLE 4

Purification and Characterization of a Polypeptide from Tuberculin Purified Protein Derivative An *M. tuberculosis* polypeptide was isolated from tuberculin purified protein derivative (PPD) as follows.

PPD was prepared as published with some modification (Seibert, F. et al., Tuberculin purified protein derivative. Preparation and analyses of a large quantity for standard. *The American Review of Tuberculosis* 44:9–25, 1941).

M. tuberculosis Rv strain was grown for 6 weeks in synthetic medium in roller bottles at 37° C. Bottles containing the bacterial growth were then heated to 100° C. in water vapor for 3 hours. Cultures were sterile filtered using a 0.22μ filter and the liquid phase was concentrated 20 times using a 3 kD cut-off membrane. Proteins were precipitated once with 50% ammonium sulfate solution and eight times with 25% ammonium sulfate solution. The resulting proteins (PPD) were fractionated by reverse phase liquid chromatography (RP-HPLC) using a C18 column (7.8×300 mM; Waters, Milford, Mass.) in a Biocad HPLC system (Perseptive Biosystems, Framingham, Mass.). Fractions were eluted from the column with a linear gradient from 0–100% buffer (0.1% TFA in acetonitrile). The flow rate was 10 ml/minute and eluent was monitored at 214 nm and 280 nm.

Six fractions were collected, dried, suspended in PBS and tested individually in *M. tuberculosis*-infected guinea pigs for induction of delayed type hypersensitivity (DTH) reaction. One fraction was found to induce a strong DTH reaction and was subsequently fractionated further by RP-HPLC on a microbore Vydac C18 column (Cat. No. 218TP5115) in a Perkin Elmer/Applied Biosystems Division Model 172 IPLC. Fractions were eluted with a linear gradient from 5–100% buffer (0.05% TFA in acetonitrile) with a flow rate of 80 μl/minute. Eluent was monitored at 215 nm. Eight fractions were collected and tested for induction of DTH in *M. tuberculosis*-infected guinea pigs. One fraction was found to induce strong DTH of about 16 mm induration. The other fractions did not induce detectable DTH. The positive fraction was submitted to SDS-PAGE gel electrophoresis and found to contain a single protein band of approximately 12 kD molecular weight.

This polypeptide, herein after referred to as DPPD, was sequenced from the amino terminal using a Perkin Elmer/Applied Biosystems Division Procise 492 protein sequencer as described above and found to have the N-terminal sequence shown in SEQ ID No.: 129. Comparison of this sequence with known sequences in the gene bank as described above revealed no known homologies. Four cyanogen bromide fragments of DPPD were isolated and found to have the sequences shown in SEQ ID Nos.: 130–133.

The ability of the antigen DPPD to stimulate human PBMC to proliferate and to produce IFN-γ was assayed as described in Example 1. As shown in Table 9, DPPD was found to stimulate proliferation and elicit production of large quantities of IFN-γ more than that elicited by commercial PPD.

TABLE 9

RESULTS OF PROLIFERATION AND INTERFERON-γ ASSAYS TO DPPD

| PBMC Donor | Stimulator | Proliferation (CPM) | IFN-γ ($OD_{450}$) |
|---|---|---|---|
| A | Medium | 1,089 | 0.17 |
| | PPD (commercial) | 8,394 | 1.29 |
| | DPPD | 13,451 | 2.21 |
| B | Medium | 450 | 0.09 |
| | PPD (commercial) | 3,929 | 1.26 |
| | DPPD | 6,184 | 1.49 |
| C | Medium | 541 | 0.11 |
| | PPD (commercial) | 8,907 | 0.76 |
| | DPPD | 23,024 | >2.70 |

EXAMPLE 5

Use of Representative Antigens for Diagnoses of Tuberculosis

This example illustrates the effectiveness of several representative polypeptides in skin tests for the diagnosis of *M. tuberculosis* infection.

Individuals were injected intradermally with 100 μl of either PBS or PBS plus Tween 20™ containing either 0.1 μg of protein (for TbH-9 and ThRa35) or 1.0 pg of protein (for TbRa38-1). Induration was measured between 5–7 days after injection, with a response of 5 mm or greater being considered positive. Of the 20 individuals tested, 2 were PPD negative and 18 were PPD positive. Of the PPD positive individuals, 3 had active tuberculosis, 3 had been previously infected with tuberculosis and 9 were healthy. In a second study, 13 PPD positive individuals were tested with 0.1 pg TbRa11 in either PBS or PBS plus Tween 20™ as described above. The results of both studies are shown in Table 10.

TABLE 10

RESULTS OF DTH TESTING WITH REPRESENTATIVE ANTIGENS

| | TbH-9 Pos/Total | Tb38-1 Pos/Total | TbRa35 Pos/Total | Cumulative Pos/Total | TbRa11 Pos/Total |
|---|---|---|---|---|---|
| PPD negative | 0/2 | 0/2 | 0/2 | 0/2 | |
| PPD positive | | | | | |
| healthy | 5/9 | 4/9 | 4/9 | 6/9 | 1/4 |
| prior TB | 3/5 | 2/5 | 2/5 | 4/5 | 3/5 |
| active | 3/4 | 3/4 | 0/4 | 4/4 | 1/4 |
| TOTAL | 11/18 | 9/18 | 6/18 | 14/18 | 5/13 |

EXAMPLE 6

Synthesis of Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

EXAMPLE 7

Preparation and Characterization of *M. Tuberculosis* Fusion Proteins

A fusion protein containing ThRa3, the 38 kD antigen and Tb38-1 was prepared as follows.

Each of the DNA constructs ThRa3, 38 kD and Tb38-1 were modified by PCR in order to facilitate their fusion and the subsequent expression of the fusion protein ThRa3-38 kD-Tb38-1. ThRa3, 38 kD and Tb38-1 DNA was used to perform PCR using the primers PDM-64 and PDM-65 (SEQ ID NO: 146 and 147), PDM-57 and PDM-58 (SEQ ID NO: 148 and 149), and PDM-69 and PDM-60 (SEQ ID NO: 150 and 151), respectively. In each case, the DNA amplification was performed using 10 μl 10X Pfu buffer, 2 μg 10 mM dNTPs, 2 pI each of the PCR primers at 10 μM concentration, 81.5 μl water, 1.5 μl Pfu DNA polymerase (Stratagene, La Jolla, Calif.) and 1 μl DNA at either 70 ng /μl (for ThRa3) or 50 ng/μl (for 38 kD and Tb38-1). For TbRa3, denaturation at 94° C. was performed for 2 min, followed by 40 cycles of 96° C. for 15 sec and 72° C. for 1 min, and lastly by 72° C. for 4 min. For 38 kD, denaturation at 96° C. was performed for 2 min, followed by 40 cycles of 96° C. for 30 sec, 68° C. for 15 sec and 72° C. for 3 min, and finally by 72° C. for 4 min. For Tb38-1 denaturation at 94° C. for 2 min was followed by 10 cycles of 96° C. for 15 sec, 68° C. for 15 sec and 72° C. for 1.5 min, 30 cycles of 96° C. for 15 sec, 64° C. for 15 sec and 72° C. for 1.5, and finally by 72° C. for 4 min.

The TbRa3 PCR fragment was digested with NdeI and EcoRI and cloned directly into pT7AL2 IL 1 vector using NdeI and EcoRI sites. The 38 kD PCR fragment was digested with Sse8387I, treated with T4 DNA polymerase to make blunt ends and then digested with EcoRI for direct cloning into the pT7^L2Ra3-1 vector which was digested with StuI and EcoRI. The 38-1 PCR fragment was digested with Eco47III and EcoRI and directly subcloned into pT7^L2Ra3/38kD-17 digested with the same enzymes. The whole f uision was then transferred to pET28b NT LMEIF-1 using NdeI and EcoRI sites. The fusion construct was confirmed by DNA sequencing.

The expression construct was transformed to BLR pLys S *E. coli* (Novagen, Madison, Wis.) and grown overnight in LB broth with kanamycin (30 μg/ml) and chloramphenicol (34 μl/ml). This culture (12 ml) was used to inoculate 500 ml 2XYT with the same antibiotics and the culture was induced with IPTG at an OD560 of 0.44 to a final concentration of 1.2 mM. Four hours post-induction, the bacteria were harvested and sonicated in 20 mM Tris (8.0), 100 mM NaCl, 0.1% DOC, 20 μg/ml Leupeptin, 20 mM PMSF followed by centrifugation at 26,000 X g. The resulting pellet was resuspended in 8 M urea, 20 mM Tris (8.0), 100 mM NaCl and bound to Pro-bond nickel resin (Invitrogen, Carlsbad, Calif.). The column was washed several times with the above buffer then eluted with an imidazole gradient (50 mM, 100 mM, 500 mM imidazole was added to 8 M urea, 20 mM Tris (8.0), 100 mM NaCI). The eluates containing the protein of interest were then dialzyed against 10 mM Tris (8.0).

The DNA and amino acid sequences for the resulting fusion protein (hereinafter referred to as ThRa3-38 kD-Tb38-1) are provided in SEQ ID NO: 152 and 153, respectively.

A fusion protein containing the two antigens TbH-9 and Tb38-1 (hereinafter referred to as TbH9-Tb38-1) without a hinge sequence, was prepared using a similar procedure to that described above. The DNA sequence for the TbH9-Tb38-1 fusion protein is provided in SEQ ID NO: 156.

The ability of the fusion protein TbH9-Tb38-1 to induce T cell proliferation and IFN-γ production in PBMC preparations was examined using the protocol described above in Example 1. PBMC from three donors were employed: one who had been previously shown to respond to TbH9 but not Tb38-1 (donor 131); one who had been shown to respond to Tb38-1 but not TbH9 (donor 184); and one who had been shown to respond to both antigens (donor 201). The results of these studies (FIGS. 5–7, respectively) demonstrate the functional activity of both the antigens in the fusion protein.

From the foregoing, it will be appreciated that, although specific embodiments of the invention have been described herein for the purpose of illustration, various modifications may be made without deviating from the spirit and scope of the invention.

What is claimed is:

1. An isolated polynucleotide that encodes a polypeptide comprising an amino acid sequence as set forth in SEQ ID NOs: 53, 63, 64, 66–72, 75–89, 91, 92, 100, 102, 120–126, 128, 129, 136, or 137, or that encodes a polypeptide comprising an immunogenic portion of SEQ ID NOs: 53, 63, 64, 66–72, 75–89, 91, 92, 100, 102, 120–126, 128, 129, 136, or 137.

2. The polynucleotide of claim 1, wherein the polypeptide comprises an amino acid sequence as set forth in SEQ ID NO:53 or an immunogenic portion thereof.

3. The polynucleotide of claim 1, wherein the polypeptide comprises an amino acid sequence is as set forth in SEQ ID NO:63 or an in immunogenic portion thereof.

4. The polynucleotide of claim 1, wherein the polypeptide comprises an amino acid sequence as set forth in SEQ ID NO:64 or an immunogenic portion thereof.

5. The polynucleotide of claim 1, wherein the polypeptide comprises an amino acid sequence as set forth in SEQ ID NO:66 or an immunogenic portion thereof.

6. The polynucleotide of claim 1, wherein the polypeptide comprises an amino acid sequence as set forth in SEQ ID NO:67 or an immunogenic portion thereof.

7. The polynucleotide of claim 1, wherein the polypeptide comprises an amino acid sequence as set forth in SEQ ID NO:68 or an immunogenic portion thereof.

8. The poly nucleotide of claim 1, wherein the polypeptide comprises an amino acid sequence as set forth in SEQ ID NO:69 or an immunogenic portion thereof.

9. The polynucleotide of claim 1, wherein the polypeptide comprises an amino acid sequence as set forth in SEQ ID NO:70 or an immunogenic portion thereof.

10. The polynucleotide of claim 1, wherein the polypeptide comprises an amino acid sequence as set forth in SEQ ID NO:71 or an immunogenic portion thereof.

11. The polynucleotide of claim 1, where in the polypeptide comprises an amino acid sequence as set for t k in SEQ ID NO:72 or an immunogenic portion thereof.

12. The polynucleotide of claim 1, wherein the polypeptide comprises an amino acid sequence as set forth in SEQ ID NO:75 or an immunogenic portion thereof.

13. The polynucleotide of claim 1, wherein the polypeptide comprises an amino acid sequence as set forth in SEQ ID NO:76 or an immunogenic portion thereof.

14. The polynucleotide of claim 1, wherein the polypeptide comprises an amino acid sequence as set forth in SEQ ID NO:77 or an immunogenic portion thereof.

15. The polynucleotide of claim 1, wherein the polypeptide comprises an amino acid sequence as set forth in SEQ ID NO:78 or an immunogenic portion thereof.

16. The polynucleotide of claim 1, wherein the polypeptide comprises an amino acid sequence as set forth in SEQ ID NO:79 or an immunogenic portion thereof.

17. The polynucleotide of claim 1, wherein the polypeptide comprises an amino acid sequence as set forth in SEQ ID NO:80 or an immunogenic portion thereof.

18. The polynucleotide of claim 1, wherein the polypeptide comprises an amino acid sequence as set forth in SEQ ID NO:81 or an immunogenic portion thereof.

19. The polynucleotide of claim 1, wherein the polypeptide comprises an amino acid sequence as set forth in SEQ ID NO:82 or an immunogenic portion thereof.

20. The polynucleotide of claim 1, wherein the polypeptide comprises an amino acid sequence as set forth in SEQ ID NO:83 or an immunogenic portion thereof.

21. The polynucleotide of claim 1, wherein the polypeptide comprises an amino acid sequence as set forth in SEQ ID NO:84 or an immunogenic portion thereof.

22. The polynucleotide of claim 1, wherein the polypeptide comprises an amino acid sequence as set forth in SEQ ID NO:85 or an immunogenic portion thereof.

23. The poly nucleotide of claim 1, wherein the polypeptide comprises an amino acid sequence as set forth in SEQ ID NO:86 or an immunogenic portion thereof.

24. The polynucleotide of claim 1, wherein the polypeptide comprises an amino acid sequence as set forth in SEQ ID NO:87 or an immunogenic portion thereof.

25. The polynucleotide of claim 1, wherein the polypeptide comprises an amino acid sequence as set forth in SEQ ED NO:88 or an immunogenic portion thereof.

26. The polynucleotide of claim 1, wherein the polypeptide comprises an amino acid sequence as set forth in SEQ ID NO:89 or an immunogenic portion thereof.

27. The polynucleotide of claim 1, wherein the polypeptide comprises an amino acid sequence as set forth in SEQ ID NO:91 or an immunogenic portion thereof.

28. The polynucleotide of claim 1, wherein the polypeptide comprises an amino acid sequence as set forth in SEQ ID NO:92 or an immunogenic portion thereof.

29. The polynucleotide of claim 1, wherein the polypeptide comprises an amino acid sequence as set forth in SEQ ID NO: 100 or an immunogenic portion thereof.

30. The polynucleotide of claim 1, wherein the polypeptide comprises an amino acid sequence as set for t i in SEQ ID NO:102 or an immunogenic portion thereof.

31. The polynucleotide of claim 1, wherein the polypeptide comprises an amino acid sequence as set forth in SEQ ID NO: 120 or an immunogenic portion thereof.

32. The polynucleotide of claim 1, wherein the polypeptide comprises an amino acid sequence as set forth in SEQ ID NO:121 or an immunogenic portion thereof.

33. The polynucleotide of claim 1, wherein the polypeptide comprises an amino acid sequence as set forth in SEQ ID NO:122 or an immunogenic portion thereof.

34. The polynucleotide of claim 1, wherein the polypeptide comprises an amino acid sequence as set forth in SEQ ID NO:123 or an immunogenic portion thereof.

35. The polynucleotide of claim 1, wherein the polypeptide comprises an amino acid sequence as set forth in SEQ ID NO:124 or an immunogenic portion thereof.

36. The polynucleotide of claim 1, wherein the polypeptide comprises an amino acid sequence as set forth in SEQ ID NO:125 or an immunogenic portion thereof.

37. The polynucleotide of claim 1, wherein the polypeptide comprises an amino acid sequence as set forth in SEQ ID NO:126 or an immunogenic portion thereof.

38. The polynucleotide of claim 1, wherein the polypeptide comprises an amino acid sequence as set forth in SEQ ID NO:128 or an immunogenic portion thereof.

39. The polynucleotide of claim 1, wherein the polypeptide comprises an amino acid sequence as set forth in SEQ ID NO:129 or an immunogenic portion thereof.

40. The polynucleotide of claim 1, wherein the polypeptide comprises an amino acid sequence as set forth in SEQ ID NO:136 or an immunogenic portion thereof.

41. The polynucleotide of claim 1, wherein the polypeptide comprises an amino acid sequence as set forth in SEQ ID NO:137 or an immunogenic portion thereof.

42. An isolated polynucleotide that encodes a polypeptide encoded by SEQ ID NOs:1, 2, 4–10, 13–31, 33, 34–43, 45–52, 99, 101, 138, or 139, or that encodes a polypeptide comprising an immunogenic portion of a polypeptide encoded by SEQ ID NOs: 1, 2, 4–10, 13–31, 33, 34–43, 45–52, 99, 101, 138, or 139.

43. The isolated polynucleotide of claim 42 that encodes a polypeptide encoded by SEQ ID NO:1, or that encodes a polypeptide comprising an immunogenic portion of a polypeptide encoded by SEQ ID NO:1.

44. The isolated polynucleotide of claim 42 that encodes a polypeptide encoded by SEQ ID NO:2, or that encodes a polypeptide comprising an immunogenic portion of a polypeptide encoded by SEQ ID NO:2.

45. The isolated polynucleotide of claim 42 that encodes a polypeptide encoded by SEQ ID NO:4, or that encodes a polypeptide comprising an immunogenic portion of a polypeptide encoded by SEQ ID NO:4.

46. The isolated polynucleotide of claim 42 that encodes a polypeptide encoded by SEQ ID NO:5, or that encodes a polypeptide comprising an immunogenic portion of a polypeptide encoded by SEQ ID NO:5.

47. The isolated polynucleotide of claim 42 that encodes a polypeptide encoded by SEQ ID NO:6, or that encodes a polypeptide comprising an immunogenic portion of a polypeptide encoded by SEQ ID NO:6.

48. The isolated polynucleotide of claim 42 that encodes a polypeptide encoded by SEQ ID NO:7, or that encodes a polypeptide comprising an immunogenic portion of a polypeptide encoded by SEQ ID NO:7.

49. The isolated polynucleotide of claim 42 that encodes a polypeptide encoded by SEQ ID NO:8, or that encodes a polypeptide comprising an immunogenic portion of a polypeptide encoded by SEQ ID NO:8.

50. The isolated polynucleotide of claim 42 that encodes a polypeptide encoded by SEQ ID NO:9, or that encodes a polypeptide comprising an immunogenic portion of a polypeptide encoded by SEQ ID NO:9.

51. The isolated polynucleotide of claim 42 that encodes a polypeptide encoded by SEQ ID NO: 10, or t hat encodes a polypeptide comprising an immunogenic portion of a polypeptide encoded by SEQ ID NO:10.

52. The isolated polynucleotide of claim 42 that encodes a polypeptide encoded by SEQ ID NO:13, or that encodes a polypeptide comprising a n immunogenic portion of a polypeptide encoded by SEQ ID NO:13.

53. The isolated polynucleotide of claim 42 that encodes a polypeptide encoded by SEQ ID NO:14, or that encodes a polypeptide comprising an immunogenic portion of a polypeptide encoded by SEQ ID NO:14.

54. The isolated polynucleotide of claim 42 that encodes a polypeptide encoded by SEQ ID NO:15, or that encodes a polypeptide comprising an in immunogenic portion of a polypeptide encoded by SEQ ID NO:15.

55. The isolated polynucleotide of claim 42 that encodes a polypeptide encoded by SEQ ID NO:16, or that encodes a polypeptide comprising an immunogenic portion of a polypeptide encoded by SEQ ID NO:16.

56. The isolated polynucleotide of claim 42 that encodes a polypeptide encoded by SEQ ID NO:17, or that encodes a polypeptide comprising an immunogenic portion of a polypeptide encoded by SEQ ID NO:17.

57. The isolated polynucleotide of claim 42 that encodes a polypeptide encoded by SEQ ID NO: 18, or that encodes a polypeptide comprising an immunogenic portion of a polypeptide encoded by SEQ ID NO:18.

58. The isolated polynucleotide of claim 42 that encodes a polypeptide encoded by SEQ ID NO:19, or that encodes a polypeptide comprising an immunogenic portion of a polypeptide encoded by SEQ ID NO:19.

59. The isolated polynucleotide of claim 42 that encodes a polypeptide encoded by SEQ ID NO20 , or that encodes a polypeptide comprising an immunogenic portion of a polypeptide encoded by SEQ ID NO:20.

60. The isolated polynucleotide of claim 42 that encodes a polypeptide encoded by SEQ ID NO:21, or that encodes a polypeptide comprising an immunogenic portion of a polypeptide encoded by SEQ ID NO:21.

61. The isolated polynucleotide of claim 42 that encodes a polypeptide encoded by SEQ ID NO:22, or that encodes a polypeptide comprising a u immunogenic portion of a polypeptide encoded by SEQ ID NO:22.

62. The isolated polynucleotide of claim 42 that encodes a polypeptide encoded by SEQ ID NO:23, or that encodes a polypeptide comprising an immunogenic portion of a polypeptide encoded by SEQ ID NO:23.

63. The isolated polynucleotide of claim 42 that encodes a polypeptide encoded by SEQ ID NO:24, or that encodes a polypeptide comprising an imununogenic portion of a polypeptide encoded by SEQ ID NO:24.

64. The isolated polynucleotide of claim 42 that encodes a polypeptide encoded by SEQ ID NO:25, or that encodes a polypeptide comprising an immunogenic portion of a polypeptide encoded by SEQ ID NO:25.

65. The isolated polynucleotide of claim 42 that encodes a polypeptide encoded by SEQ ID NO:26, or that encodes a polypeptide comprising an immunogenic portion of a polypeptide encoded by SEQ ID NO:26.

66. The isolated polynucleotide of claim 42 that encodes a polypeptide encoded by SEQ ID NO:27, or that encodes a polypeptide comprising a n immunogenic portion of a polypeptide encoded by SEQ ID NO:27.

67. The isolated polynucleotide of claim 42 that encodes a polypeptide encoded by SEQ ID NO:28, or that encodes a polypeptide comprising an immunogenic portion of a polypeptide encoded by SEQ ID NO:28.

68. The isolated polynucleotide of claim 42 that encodes a polypeptide encoded by SEQ.ID NO:29, or that encodes a polypeptide comprising an immunogenic portion of a polypeptide encoded by .SEQ ID NO:29.

69. The isolated polynucleotide of claim 42 that encodes a polypeptide encoded by SEQ ID NO:30, or that encodes a polypeptide comprising an immunogenic portion of a polypeptide encoded by SEQ ID NO:30 .

70. The isolated polynucleotide of claim 42 that encodes a polypeptide encoded by SEQ ID NO:31, or that encodes a polypeptide comprising an immunogenic portion of a polypeptide encoded by SEQ ID NO:31.

71. The isolated polynucleotide of claim 42 that encodes a polypeptide encoded by SEQ ID NO:33, or that encodes a polypeptide comprising an immunogenic portion of a polypeptide encoded by SEQ ID NO:33.

72. The isolated polynucleotide of claim 42 that encodes a polypeptide encoded by SEQ ID NO:34, or that encodes a polypeptide comprising an immunogenic portion of a polypeptide encoded by SEQ ID NO:34.

73. The isolated polynucleotide of claim 42 that encodes a polypeptide encoded by SEQ ID NO:35, or that encodes a polypeptide comprising an immunogenic portion of a polypeptide encoded by SEQ ID NO:35.

74. The isolated polynucleotide of claim 42 that encodes a polypeptide encoded by SEQ ID NO-36, or that encodes a polypeptide comprising an immunogenic portion of a polypeptide encoded by SEQ ID NO:36.

75. The isolated polynucleotide of claim 42 hat encodes a polypeptide encoded by SEQ ID NO:37, or that encodes a polypeptide comprising an immunogenic portion of a polypeptide encoded by SEQ ID NO:37.

76. The isolated polynucleotide of claim 42 that encodes a polypeptide encoded by SEQ ID NO:38, or that encodes a polypeptide comprising an immunogenic portion of a polypeptide encoded by SEQ ID NO:38.

77. The isolated polynucleotide of claim 42 that encodes a polypeptide encoded by SEQ ID NO:39, or that encodes a polypeptide comprising an immunogenic portion of a polypeptide encoded by SEQ ID NO:39.

78. The isolated polynucleotide of claim 42 that encodes a polypeptide encoded by SEQ ID NO:40, or that encodes a polypeptide comprising an immunogenic portion of a polypeptide encoded by SEQ ID NO:40.

79. The isolated polynucleotide of claim 42 that encodes a polypeptide encoded by SEQ ID NO:41, or that encodes a polypeptide comprising an immunogenic portion of a polypeptide encoded by SEQ ID NO:41.

80. The isolated polynucleotide of claim 42 that encodes a polypeptide encoded by SEQ ID NO:42, or that encodes a polypeptide comprising an immunogenic portion of a polypeptide encoded by SEQ ID NO:42.

81. The isolated polynucleotide of claim 42 that encodes a polypeptide encoded by SEQ ID NO:43, or that encodes a polypeptide comprising an immunogenic portion of a polypeptide encoded by SEQ ID NO:43.

82. The isolated polynucleotide of claim 42 that encodes a polypeptide encoded by SEQ ID NO:45, or that encodes a polypeptide comprising an immunogenic portion of a polypeptide encoded by SEQ ID NO:45.

83. The isolated polynucleotide of claim 42 that encodes a polypeptide encoded by SEQ ID NO:46, or that encodes a polypeptide comprising an immunogenic portion of a polypeptide encoded by SEQ ID NO:46.

84. The isolated polynucleotide of claim 42 that encodes a polypeptide encoded by SEQ ID NO:47, or that encodes a polypeptide comprising an immunogenic portion of a polypeptide encoded by SEQ ID NO:47.

85. The isolated polynucleotide of claim 42 that encodes a polypeptide encoded by SEQ ID NO:48, or that encodes a polypeptide comprising an immunogenic portion of a polypeptide encoded by SEQ ID NO:48.

86. The isolated polynucleotide of claim 42 that encodes a polypeptide encoded by SEQ ID NO:49, or that encodes a polypeptide comprising an immunogenic portion of a polypeptide encoded by SEQ ID NO:49.

87. The isolated polynucleotide of claim 42 that encodes a polypeptide encoded by SEQ ID NO:50, or that encodes a polypeptide comprising an immunogenic portion of a polypeptide encoded by SEQ ID NO:50.

88. The isolated polynucleotide of claim 42 that encodes a polypeptide encoded by SEQ ID NO:51, or that encodes a polypeptide comprising an immunogenic portion of a polypeptide encoded by SEQ ID NO:51.

89. The isolated polynucleotide of claim 42 that encodes a polypeptide encoded by SEQ ID NO:52, or that encodes a polypeptide comprising an immunogenic portion of a polypeptide encoded by SEQ ID NO:52.

90. The isolated polynucleotide of claim 42 that encodes a polypeptide encoded by SEQ ID NO:99, or that encodes a polypeptide comprising an immunogenic portion of a polypeptide encoded by SEQ ID NO:99.

91. The isolated polynucleotide of claim 42 that encodes a polypeptide encoded by SEQ ID NO:101, or that encodes a polypeptide comprising an immunogenic portion of a polypeptide encoded by SEQ ID NO:101.

92. The isolated polynucleotide of claim 42 that encodes a polypeptide encoded by SEQ ID NO: 138, or that encodes a polypeptide comprising an immunogenic portion of a polypeptide encoded by SEQ ID NO:138.

93. The isolated polynucleotide of claim 42 that encodes a polypeptide encoded by SEQ ID NO: 139, or that encodes a polypeptide comprising an immunogenic portion of a polypeptide encoded by SEQ ID NO: 139.

94. The polynucleotide of any one of claims 1 to 93, further comprising a regulatory sequence operatively linked to the sequence encoding the polypeptide.

95. A cell comprising the polynucleotide of claim 94.

96. The cell of claim 95, which is a prokaryote.

97. The cell of claim 95, which is a eukaryote.

98. A method of making a polypeptide, the method comprising culturing the cell of claim 95 and recovering the polypeptide from the cell or its culture medium.

* * * * *

SEQUENCE LISTING

```
(1) GENERAL INFORMATION:

(iii) NUMBER OF SEQUENCES: 153

(2) INFORMATION FOR SEQ ID NO:1:

(i) SEQUENCE CHARACTERISTICS:
          (A) LENGTH: 766 base pairs
          (B) TYPE: nucleic acid
          (C) STRANDEDNESS: single
          (D) TOPOLOGY: linear (xi) SEQUENCE DESCRIPTION: SEQ ID NO:1:

CGAGGCACCG GTAGTTTGAA CCAAACGCAC AATCGACGGG CAAACGAACG GAAGAACACA      60
```

```
ACCATGAAGA TGGTGAAATC GATCGCCGCA GGTCTGACCG CCGCGGCTGC AATCGGCGCC      120

GCTGCGGCCG GTGTGACTTC GATCATGGCT GGCGGCCCGG TCGTATACCA GATGCAGCCG      180

GTCGTCTTCG GCGCGCCACT GCCGTTGGAC CCGGCATCCG CCCCTGACGT CCCGACCGCC      240

GCCCAGTTGA CCAGCCTGCT CAACAGCCTC GCCGATCCCA ACGTGTCGTT TGCGAACAAG      300

GGCAGTCTGG TCGAGGGCGG CATCGGGGGC ACCGAGGCGC GCATCGCCGA CCACAAGCTG      360

AAGAAGGCCG CCGAGCACGG GGATCTGCCG CTGTCGTTCA GCGTGACGAA CATCCAGCCG      420

GCGGCCGCCG GTTCGGCCAC CGCCGACGTT TCCGTCTCGG GTCCGAAGCT CTCGTCGCCG      480

GTCACGCAGA ACGTCACGTT CGTGAATCAA GGCGGCTGGA TGCTGTCACG CGCATCGGCG      540

ATGGAGTTGC TGCAGGCCGC AGGGNAACTG ATTGGCGGGC CGGNTTCAGC CCGCTGTTCA      600

GCTACGCCGC CCGCCTGGTG ACGCGTCCAT GTCGAACACT CGCGCGTGTA GCACGGTGCG      660

GTNTGCGCAG GGNCGCACGC ACCGCCCGGT GCAAGCCGTC CTCGAGATAG GTGGTGNCTC      720

GNCACCAGNG ANCACCCCCN NNTCGNCNNT TCTCGNTGNT GNATGA                    766

(2) INFORMATION FOR SEQ ID NO:2:

(i) SEQUENCE CHARACTERISTICS:
        (A) LENGTH: 752 base pairs
        (B) TYPE: nucleic acid
        (C) STRANDEDNESS: single
        (D) TOPOLOGY: linear (xi) SEQUENCE DESCRIPTION: SEQ ID NO:2:

ATGCATCACC ATCACCATCA CGATGAAGTC ACGGTAGAGA CGACCTCCGT CTTCCGCGCA       60

GACTTCCTCA GCGAGCTGGA CGCTCCTGCG CAAGCGGGTA CGGAGAGCGC GGTCTCCGGG      120

GTGGAAGGGC TCCCGCCGGG CTCGGCGTTG CTGGTAGTCA AACGAGGCCC CAACGCCGGG      180

TCCCGGTTCC TACTCGACCA AGCCATCACG TCGGCTGGTC GGCATCCCGA CAGCGACATA      240

TTTCTCGACG ACGTGACCGT GAGCCGTCGC CATGCTGAAT TCCGGTTGGA AAACAACGAA      300

TTCAATGTCG TCGATGTCGG GAGTCTCAAC GGCACCTACG TCAACCGCGA GCCCGTGGAT      360

TCGGCGGTGC TGGCGAACGG CGACGAGGTC CAGATCGGCA AGCTCCGGTT GGTGTTCTTG      420

ACCGGACCCA AGCAAGGCGA GGATGACGGG AGTACCGGGG GCCCGTGAGC GCACCCGATA      480

GCCCCGCGCT GGCCGGGATG TCGATCGGGG CGGTCCTCCG ACCTGCTACG ACCGGATTTT      540

CCCTGATGTC CACCATCTCC AAGATTGATT TCTTGGGAGG CTTGAGGGTC NGGGTGACCC      600

CCCCGCGGGC CTCATTCNGG GGTNTCGGCN GGTTTCACCC CNTACCNACT GCCNCCCGGN      660

TTGCNAATTC NTTCTTCNCT GCCCNNAAAG GGACCNTTAN CTTGCCGCTN GAAANGGTNA      720

TCCNGGGCCC NTCCTNGAAN CCCCNTCCCC CT                                   752

(2) INFORMATION FOR SEQ ID NO:3:

(i) SEQUENCE CHARACTERISTICS:
        (A) LENGTH: 813 base pairs
        (B) TYPE: nucleic acid
        (C) STRANDEDNESS: single
        (D) TOPOLOGY: linear (xi) SEQUENCE DESCRIPTION: SEQ ID NO:3:

CATATGCATC ACCATCACCA TCACACTTCT AACCGCCCAG CGCGTCGGGG GCGTCGAGCA       60

CCACGCGACA CCGGGCCCGA TCGATCTGCT AGCTTGAGTC TGGTCAGGCA TCGTCGTCAG      120

CAGCGCGATG CCCTATGTTT GTCGTCGACT CAGATATCGC GGCAATCCAA TCTCCCGCCT      180
```

```
GCGGCCGGCG GTGCTGCAAA CTACTCCCGG AGGAATTTCG ACGTGCGCAT CAAGATCTTC      240

ATGCTGGTCA CGGCTGTCGT TTTGCTCTGT TGTTCGGGTG TGGCCACGGC CGCGCCCAAG      300

ACCTACTGCG AGGAGTTGAA AGGCACCGAT ACCGGCCAGG CGTGCCAGAT TCAAATGTCC      360

GACCCGGCCT ACAACATCAA CATCAGCCTG CCCAGTTACT ACCCCGACCA GAAGTCGCTG      420

GAAAATTACA TCGCCCAGAC GCGCGACAAG TTCCTCAGCG CGGCCACATC GTCCACTCCA      480

CGCGAAGCCC CCTACGAATT GAATATCACC TCGGCCACAT ACCAGTCCGC GATACCGCCG      540

CGTGGTACGC AGGCCGTGGT GCTCAMGGTC TACCACAACG CCGGCGGCAC GCACCCAACG      600

ACCACGTACA AGGCCTTCGA TTGGGACCAG GCCTATCGCA AGCCAATCAC CTATGACACG      660

CTGTGGCAGG CTGACACCGA TCCGCTGCCA GTCGTCTTCC CCATTGTTGC AAGGTGAACT      720

GAGCAACGCA GACCGGGACA ACWGGTATCG ATAGCCGCCN AATGCCGGCT TGGAACCCNG      780

TGAAATTATC ACAACTTCGC AGTCACNAAA NAA                                  813

(2) INFORMATION FOR SEQ ID NO:4:

(i) SEQUENCE CHARACTERISTICS:
        (A) LENGTH: 447 base pairs
        (B) TYPE: nucleic acid
        (C) STRANDEDNESS: single
        (D) TOPOLOGY: linear (xi) SEQUENCE DESCRIPTION: SEQ ID NO:4:

CGGTATGAAC ACGGCCGCGT CCGATAACTT CCAGCTGTCC CAGGGTGGGC AGGGATTCGC       60

CATTCCGATC GGGCAGGCGA TGGCGATCGC GGGCCAGATC CGATCGGGTG GGGGGTCACC      120

CACCGTTCAT ATCGGGCCTA CCGCCTTCCT CGGCTTGGGT GTTGTCGACA CAACGGCAA      180

CGGCGCACGA GTCCAACGCG TGGTCGGGAG CGCTCCGGCG GCAAGTCTCG GCATCTCCAC      240

CGGCGACGTG ATCACCGCGG TCGACGGCGC TCCGATCAAC TCGGCCACCG CGATGGCGGA      300

CGCGCTTAAC GGGCATCATC CCGGTGACGT CATCTCGGTG AACTGGCAAA CCAAGTCGGG      360

CGGCACGCGT ACAGGGAACG TGACATTGGC CGAGGGACCC CCGGCCTGAT TCGTCGYGG      420

ATACCACCCG CCGGCCGGCC AATTGGA                                         447

(2) INFORMATION FOR SEQ ID NO:5:

(i) SEQUENCE CHARACTERISTICS:
        (A) LENGTH: 604 base pairs
        (B) TYPE: nucleic acid
        (C) STRANDEDNESS: single
        (D) TOPOLOGY: linear (xi) SEQUENCE DESCRIPTION: SEQ ID NO:5:

GTCCCACTGC GGTCGCCGAG TATGTCGCCC AGCAAATGTC TGGCAGCCGC CCAACGGAAT       60

CCGGTGATCC GACGTCGCAG GTTGTCGAAC CCGCCGCCGC GGAAGTATCG GTCCATGCCT      120

AGCCCGGCGA CGGCGAGCGC CGGAATGGCG CGAGTGAGGA GGCGGGCAAT TTGGCGGGGC      180

CCGGCGACGG NGAGCGCCGG AATGGCGCGA GTGAGGAGGT GGNCAGTCAT GCCCAGNGTG      240

ATCCAATCAA CCTGNATTCG GNCTGNGGGN CCATTTGACA ATCGAGGTAG TGAGCGCAAA      300

TGAATGATGG AAAACGGGNG NGACGTCCG NTGTTCTGGT GGTGNTAGGT GNCTGNCTGG       360

NGTNGNGGNT ATCAGGATGT TCTTCGNCGA AANCTGATGN CGAGGAACAG GGTGTNCCCG      420

NNANNCCNAN GGNGTCCNAN CCCNNNNTCC TCGNCGANAT CANANAGNCG NTTGATGNGA      480

NAAAAGGGTG GANCAGNNNN AANTNGNGGN CCNAANAANC NNNANNGNNG NNAGNTNGNT      540

NNNTNTTNNC ANNNNNNNTG NNGNNGNNCN NNNCAANCNN NTNNNNGNAA NNGGNTTNTT      600
```

NAAT                                                             604

(2) INFORMATION FOR SEQ ID NO:6:

(i) SEQUENCE CHARACTERISTICS:
        (A) LENGTH: 633 base pairs
        (B) TYPE: nucleic acid
        (C) STRANDEDNESS: single
        (D) TOPOLOGY: linear (xi) SEQUENCE DESCRIPTION: SEQ ID NO:6:

```
TTGCANGTCG AACCACCTCA CTAAAGGGAA CAAAAGCTNG AGCTCCACCG CGGTGGCGGC    60
CGCTCTAGAA CTAGTGKATM YYYCKGGCTG CAGSAATYCG GYACGAGCAT TAGGACAGTC   120
TAACGGTCCT GTTACGGTGA TCGAATGACC GACGACATCC TGCTGATCGA CACCGACGAA   180
CGGGTGCGAA CCCTCACCCT CAACCGGCCG CAGTCCCGYA ACGCGCTCTC GGCGGCGCTA   240
CGGGATCGGT TTTTCGCGGY GTTGGYCGAC GCCGAGGYCG ACGACGACAT CGACGTCGTC   300
ATCCTCACCG GYGCCGATCC GGTGTTCTGC GCCGGACTGG ACCTCAAGGT AGCTGGCCGG   360
GCAGACCGCG CTGCCGGACA TCTCACCGCG GTGGGCGGCC ATGACCAAGC CGGTGATCGG   420
CGCGATCAAC GGCGCCGCGG TCACCGGCGG GCTCGAACTG GCGCTGTACT GCGACATCCT   480
GATCGCCTCC GAGCACGCCC GCTTCGNCGA CACCCACGCC CGGGTGGGGC TGCTGCCCAC   540
CTGGGGACTC AGTGTGTGCT TGCCGCAAAA GGTCGGCATC GGNCTGGGCC GGTGGATGAG   600
CCTGACCGGC GACTACCTGT CCGTGACCGA CGC                                633
```

(2) INFORMATION FOR SEQ ID NO:7:

(i) SEQUENCE CHARACTERISTICS:
        (A) LENGTH: 1362 base pairs
        (B) TYPE: nucleic acid
        (C) STRANDEDNESS: single
        (D) TOPOLOGY: linear (xi) SEQUENCE DESCRIPTION: SEQ ID NO:7:

```
CGACGACGAC GGCGCCGGAG AGCGGGCGCG AACGGCGATC GACGCGGCCC TGGCCAGAGT    60
CGGCACCACC CAGGAGGGAG TCGAATCATG AAATTTGTCA ACCATATTGA GCCCGTCGCG   120
CCCCGCCGAG CCGGCGGCGC GGTCGCCGAG GTCTATGCCG AGGCCCGCCG CGAGTTCGGC   180
CGGCTGCCCG AGCCGCTCGC CATGCTGTCC CCGGACGAGG GACTGCTCAC CGCCGGCTGG   240
GCGACGTTGC GCGAGACACT GCTGGTGGGC CAGGTGCCGC GTGGCCGCAA GGAAGCCGTC   300
GCCGCCGCCG TCGCGGCCAG CCTGCGCTGC CCCTGGTGCG TCGACGCACA CACCACCATG   360
CTGTACGCGG CAGGCCAAAC CGACACCGCC GCGGCGATCT TGGCCGGCAC AGCACCTGCC   420
GCCGGTGACC CGAACGCGCC GTATGTGGCG TGGGCGGCAG GAACCGGGAC ACCGGCGGGA   480
CCGCCGGCAC CGTTCGGCCC GGATGTCGCC GCCGAATACC TGGGCACCGC GGTGCAATTC   540
CACTTCATCG CACGCCTGGT CCTGGTGCTG CTGGACGAAA CCTTCCTGCC GGGGGGCCCG   600
CGCGCCCAAC AGCTCATGCG CCGCGCCGGT GGACTGGTGT CGCCCCGCAA GGTGCGCGCG   660
GAGCATCGGC CGGGCCGCTC CACCCGCCGG CTCGAGCCGC GAACGCTGCC CGACGATCTG   720
GCATGGGCAA CACCGTCCGA GCCCATAGCA ACCGCGTTCG CCGCGCTCAG CCACCACCTG   780
GACACCGCGC CGCACCTGCC GCCACCGACT CGTCAGGTGG TCAGGCGGGT CGTGGGGTCG   840
TGGCACGGCG AGCCAATGCC GATGAGCAGT CGCTGGACGA ACGAGCACAC CGCCGAGCTG   900
CCCGCCGACC TGCACGCGCC CACCCGTCTT GCCCTGCTGA CCGGCCTGGC CCCGCATCAG   960
```

-continued

| | |
|---|---|
| GTGACCGACG ACGACGTCGC CGCGGCCCGA TCCCTGCTCG ACACCGATGC GGCGCTGGTT | 1020 |
| GGCGCCCTGG CCTGGGCCGC CTTCACCGCC GCGCGGCGCA TCGGCACCTG GATCGGCGCC | 1080 |
| GCCGCCGAGG GCCAGGTGTC GCGGCAAAAC CCGACTGGGT GAGTGTGCGC GCCCTGTCGG | 1140 |
| TAGGGTGTCA TCGCTGGCCC GAGGGATCTC GCGGCGGCGA ACGGAGGTGG CGACACAGGT | 1200 |
| GGAAGCTGCG CCCACTGGCT TGCGCCCCAA CGCCGTCGTG GGCGTTCGGT TGGCCGCACT | 1260 |
| GGCCGATCAG GTCGGCGCCG GCCCTTGGCC GAAGGTCCAG CTCAACGTGC CGTCACCGAA | 1320 |
| GGACCGGACG GTCACCGGGG GTCACCCTGC GCGCCCAAGG AA | 1362 |

(2) INFORMATION FOR SEQ ID NO:8:

(i) SEQUENCE CHARACTERISTICS:
        (A) LENGTH: 1458 base pairs
        (B) TYPE: nucleic acid
        (C) STRANDEDNESS: single
        (D) TOPOLOGY: linear (xi) SEQUENCE DESCRIPTION: SEQ ID NO:8:

| | |
|---|---|
| GCGACGACCC CGATATGCCG GGCACCGTAG CGAAAGCCGT CGCCGACGCA CTCGGGCGCG | 60 |
| GTATCGCTCC CGTTGAGGAC ATTCAGGACT GCGTGGAGGC CCGGCTGGGG GAAGCCGGTC | 120 |
| TGGATGACGT GGCCCGTGTT TACATCATCT ACCGGCAGCG GCGCGCCGAG CTGCGGACGG | 180 |
| CTAAGGCCTT GCTCGGCGTG CGGGACGAGT TAAAGCTGAG CTTGGCGGCC GTGACGGTAC | 240 |
| TGCGCGAGCC CTATCTGCTG CACGACGAGC AGGGCCGGCC GGCCGAGTCG ACCGGCGAGC | 300 |
| TGATGGACCG ATCGGCGCGC TGTGTCGCGG CGGCCGAGGA CCAGTATGAG CCGGGCTCGT | 360 |
| CGAGGCGGTG GGCCGAGCGG TTCGCCACGC TATTACGCAA CCTGGAATTC CTGCCGAATT | 420 |
| CGCCCACGTT GATGAACTCT GGCACCGACC TGGGACTGCT CGCCGGCTGT TTTGTTCTGC | 480 |
| CGATTGAGGA TTCGCTGCAA TCGATCTTTG CGACGCTGGG ACAGGCCGCC GAGCTGCAGC | 540 |
| GGGCTGGAGG CGGCACCGGA TATGCGTTCA GCCACCTGCG ACCCGCCGGG GATCGGGTGG | 600 |
| CCTCCACGGG CGGCACGGCC AGCGGACCGG TGTCGTTTCT ACGGCTGTAT GACAGTGCCG | 660 |
| CGGGTGTGGT CTCCATGGGC GGTCGCCGGC GTGGCGCCTG TATGGCTGTG CTTGATGTGT | 720 |
| CGCACCCGGA TATCTGTGAT TTCGTCACCG CCAAGGCCGA ATCCCCCAGC GAGCTCCCGC | 780 |
| ATTTCAACCT ATCGGTTGGT GTGACCGACG CGTTCCTGCG GGCCGTCGAA CGCAACGGCC | 840 |
| TACACCGGCT GGTCAATCCG CGAACCGGCA AGATCGTCGC GCGGATGCCC GCCGCCGAGC | 900 |
| TGTTCGACGC CATCTGCAAA GCCGCGCACG CCGGTGGCGA TCCCGGGCTG GTGTTTCTCG | 960 |
| ACACGATCAA TAGGGCAAAC CCGGTGCCGG GGAGAGGCCG CATCGAGGCG ACCAACCCGT | 1020 |
| GCGGGGAGGT CCCACTGCTG CCTTACGAGT CATGTAATCT CGGCTCGATC AACCTCGCCC | 1080 |
| GGATGCTCGC CGACGGTCGC GTCGACTGGG ACCGGCTCGA GGAGGTCGCC GGTGTGGCGG | 1140 |
| TGCGGTTCCT TGATGACGTC ATCGATGTCA GCCGCTACCC CTTCCCCGAA CTGGGTGAGG | 1200 |
| CGGCCCGCGC CACCCGCAAG ATCGGGCTGG GAGTCATGGG TTTGGCGGAA CTGCTTGCCG | 1260 |
| CACTGGGTAT TCCGTACGAC AGTGAAGAAG CCGTGCGGTT AGCCACCCGG CTCATGCGTC | 1320 |
| GCATACAGCA GGCGGCGCAC ACGGCATCGC GGAGGCTGGC CGAAGAGCGG GGCGCATTCC | 1380 |
| CGGCGTTCAC CGATAGCCGG TTCGCGCGGT CGGGCCCGAG CGCAACGCA CAGGTCACCT | 1440 |
| CCGTCGCTCC GACGGGCA | 1458 |

(2) INFORMATION FOR SEQ ID NO:9:

(i) SEQUENCE CHARACTERISTICS:

(A) LENGTH: 862 base pairs
    (B) TYPE: nucleic acid
    (C) STRANDEDNESS: single
    (D) TOPOLOGY: linear (xi) SEQUENCE DESCRIPTION: SEQ ID NO:9:

```
ACGGTGTAAT CGTGCTGGAT CTGGAACCGC GTGGCCCGCT ACCTACCGAG ATCTACTGGC    60

GGCGCAGGGG GCTGGCCCTG GGCATCGCGG TCGTCGTAGT CGGGATCGCG GTGGCCATCG   120

TCATCGCCTT CGTCGACAGC AGCGCCGGTG CCAAACCGGT CAGCGCCGAC AAGCCGGCCT   180

CCGCCCAGAG CCATCCGGGC TCGCCGGCAC CCCAAGCACC CCAGCCGGCC GGGCAAACCG   240

AAGGTAACGC CGCCGCGGCC CCGCCGCAGG GCCAAAACCC CGAGACACCC ACGCCCACCG   300

CCGCGGTGCA GCCGCCGCCG GTGCTCAAGG AAGGGGACGA TTGCCCCGAT TCGACGCTGG   360

CCGTCAAAGG TTTGACCAAC GCGCCGCAGT ACTACGTCGG CGACCAGCCG AAGTTCACCA   420

TGGTGGTCAC CAACATCGGC CTGGTGTCCT GTAAACGCGA CGTTGGGGCC GCGGTGTTGG   480

CCGCCTACGT TTACTCGCTG GACAACAAGC GGTTGTGGTC CAACCTGGAC TGCGCGCCCT   540

CGAATGAGAC GCTGGTCAAG ACGTTTTCCC CCGGTGAGCA GGTAACGACC GCGGTGACCT   600

GGACCGGGAT GGGATCGGCG CCGCGCTGCC CATTGCCGCG GCCGGCGATC GGGCCGGGCA   660

CCTACAATCT CGTGGTACAA CTGGGCAATC TGCGCTCGCT GCCGGTTCCG TTCATCCTGA   720

ATCAGCCGCC GCCGCCGCCC GGGCCGGTAC CCGCTCCGGG TCCAGCGCAG GCGCCTCCGC   780

CGGAGTCTCC CGCGCAAGGC GGATAATTAT TGATCGCTGA TGGTCGATTC CGCCAGCTGT   840

GACAACCCCT CGCCTCGTGC CG                                           862
```

(2) INFORMATION FOR SEQ ID NO:10:

(i) SEQUENCE CHARACTERISTICS:
        (A) LENGTH: 622 base pairs
        (B) TYPE: nucleic acid
        (C) STRANDEDNESS: single
        (D) TOPOLOGY: linear (xi) SEQUENCE DESCRIPTION: SEQ ID NO:10:

```
TTGATCAGCA CCGGCAAGGC GTCACATGCC TCCCTGGGTG TGCAGGTGAC CAATGACAAA    60

GACACCCCGG GCGCCAAGAT CGTCGAAGTA GTGGCCGGTG GTGCTGCCGC GAACGCTGGA   120

GTGCCGAAGG GCGTCGTTGT CACCAAGGTC GACGACCGCC CGATCAACAG CGCGGACGCG   180

TTGGTTGCCG CCGTGCGGTC CAAAGCGCCG GGCGCCACGG TGGCGCTAAC CTTTCAGGAT   240

CCCTCGGGCG GTAGCCGCAC AGTGCAAGTC ACCCTCGGCA AGGCGGAGCA GTGATGAAGG   300

TCGCCGCGCA GTGTTCAAAG CTCGGATATA CGGTGGCACC CATGGAACAG CGTGCGGAGT   360

TGGTGGTTGG CCGGGCACTT GTCGTCGTCG TTGACGATCG CACGGCGCAC GGCGATGAAG   420

ACCACAGCGG GCCGCTTGTC ACCGAGCTGC TCACCGAGGC CGGGTTTGTT GTCGACGGCG   480

TGGTGGCGGT GTCGGCCGAC GAGGTCGAGA TCCGAAATGC GCTGAACACA GCGGTGATCG   540

GCGGGGTGGA CCTGGTGGTG TCGGTCGGCG GGACCGGNGT GACGNCTCGC GATGTCACCC   600

CGGAAGCCAC CCGNGACATT CT                                           622
```

(2) INFORMATION FOR SEQ ID NO:11:

(i) SEQUENCE CHARACTERISTICS:
        (A) LENGTH: 1200 base pairs
        (B) TYPE: nucleic acid
        (C) STRANDEDNESS: single
        (D) TOPOLOGY: linear -continued (xi) SEQUENCE DESCRIPTION: SEQ ID NO:11:

```
GGCGCAGCGG TAAGCCTGTT GGCCGCCGGC ACACTGGTGT TGACAGCATG CGGCGGTGGC      60

ACCAACAGCT CGTCGTCAGG CGCAGGCGGA ACGTCTGGGT CGGTGCACTG CGGCGGCAAG     120

AAGGAGCTCC ACTCCAGCGG CTCGACCGCA CAAGAAAATG CCATGGAGCA GTTCGTCTAT     180

GCCTACGTGC GATCGTGCCC GGGCTACACG TTGGACTACA ACGCCAACGG GTCCGGTGCC     240

GGGGTGACCC AGTTTCTCAA CAACGAAACC GATTTCGCCG GCTCGGATGT CCCGTTGAAT     300

CCGTCGACCG GTCAACCTGA CCGGTCGGCG GAGCGGTGCG GTTCCCCGGC ATGGGACCTG     360

CCGACGGTGT TCGGCCCGAT CGCGATCACC TACAATATCA AGGGCGTGAG CACGCTGAAT     420

CTTGACGGAC CCACTACCGC CAAGATTTTC AACGGCACCA TCACCGTGTG GAATGATCCA     480

CAGATCCAAG CCCTCAACTC CGGCACCGAC CTGCCGCCAA CACCGATTAG CGTTATCTTC     540

CGCAGCGACA AGTCCGGTAC GTCGGACAAC TTCCAGAAAT ACCTCGACGG TGTATCCAAC     600

GGGGCGTGGG GCAAAGGCGC CAGCGAAACG TTCAGCGGGG GCGTCGGCGT CGGCGCCAGC     660

GGGAACAACG GAACGTCGGC CCTACTGCAG ACGACCGACG GGTCGATCAC CTACAACGAG     720

TGGTCGTTTG CGGTGGGTAA GCAGTTGAAC ATGGCCCAGA TCATCACGTC GGCGGGTCCG     780

GATCCAGTGG CGATCACCAC CGAGTCGGTC GGTAAGACAA TCGCCGGGGC CAAGATCATG     840

GGACAAGGCA ACGACCTGGT ATTGGACACG TCGTCGTTCT ACAGACCCAC CCAGCCTGGC     900

TCTTACCCGA TCGTGCTGGC GACCTATGAG ATCGTCTGCT CGAAATACCC GGATGCGACG     960

ACCGGTACTG CGGTAAGGGC GTTTATGCAA GCCGCGATTG GTCCAGGCCA AGAAGGCCTG    1020

GACCAATACG GCTCCATTCC GTTGCCCAAA TCGTTCCAAG CAAAATTGGC GGCCGCGGTG    1080

AATGCTATTT CTTGACCTAG TGAAGGGAAT TCGACGGTGA GCGATGCCGT TCCGCAGGTA    1140

GGGTCGCAAT TTGGGCCGTA TCAGCTATTG CGGCTGCTGG GCCGAGGCGG GATGGGCGAG    1200
```

(2) INFORMATION FOR SEQ ID NO:12:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (xi) SEQUENCE DESCRIPTION: SEQ ID NO:12:

```
GCAAGCAGCT GCAGGTCGTG CTGTTCGACG AACTGGGCAT GCCGAAGACC AAACGCACCA      60

AGACCGGCTA CACCACGGAT GCCGACGCGC TGCAGTCGTT GTTCGACAAG ACCGGGCATC     120

CGTTTCTGCA ACATCTGCTC GCCCACCGCG ACGTCACCCG GCTCAAGGTC ACCGTCGACG     180

GGTTGCTCCA AGCGGTGGCC GCCGACGGCC GCATCCACAC CACGTTCAAC CAGACGATCG     240

CCGCGACCGG CCGGCTCTCC TCGACCGAAC CCAACCTGCA GAACATCCCG ATCCGCACCG     300

ACGCGGGCCG GCGGATCCGG GACGCGTTCG TGGTCGGGGA CGGTTACGCC GAGTTGATGA     360

CGGCCGACTA CAGCCAGATC GAGATGCGGA TCATGGGGCA CCTGTCCGGG GACGAGGGCC     420

TCATCGAGGC GTTCAACACC GGGGAGGACC TGTATTCGTT CGTCGCGTCC CGGGTGTTCG     480

GTGTGCCCAT CGACGAGGTC ACCGGCGAGT TGCGGCGCCG GGTCAAGGCG ATGTCCTACG     540

GGCTGGTTTA CGGGTTGAGC GCCTACGGCC TGTCGCAGCA GTTGAAAATC TCCACCGAGG     600

AAGCCAACGA GCAGATGGAC GCGTATTTCG CCCGATTCGG CGGGGTGCGC GACTACCTGC     660

GCGCCGTAGT CGAGCGGGCC CGCAAGGACG GCTACACCTC GACGGTGCTG GGCCGTCGCC     720

GCTACCTGCC CGAGCTGGAC AGCAGCAACC GTCAAGTGCG GGAGGCCGCC GAGCGGGCGG     780
```

-continued

| CGCTGAACGC GCCGATCCAG GGCAGCGCGG CCGACATCAT CAAGGTGGCC ATGATCCAGG | 840 |
| TCGACAAGGC GCTCAACGAG GCACAGCTGG CGTCGCGCAT GCTGCTGCAG GTCCACGACG | 900 |
| AGCTGCTGTT CGAAATCGCC CCCGGTGAAC GCGAGCGGGT CGAGGCCCTG GTGCGCGACA | 960 |
| AGATGGGCGG CGCTTACCCG CTCGACGTCC CGCTGGAGGT GTCGGTGGGC TACGGCCGCA | 1020 |
| GCTGGGACGG GGCGGCGCAC TGAGTGCCGA GCGTGCATCT GGGGCGGGAA TTCGGCGATT | 1080 |
| TTTCCGCCCT GAGTTCACGC TCGGCGCAAT CGGGACCGAG TTTGTCCAGC GTGTACCCGT | 1140 |
| CGAGTAGCCT CGTCA | 1155 |

(2) INFORMATION FOR SEQ ID NO:13:

(i) SEQUENCE CHARACTERISTICS:
        (A) LENGTH: 1771 base pairs
        (B) TYPE: nucleic acid
        (C) STRANDEDNESS: single
        (D) TOPOLOGY: linear (xi) SEQUENCE DESCRIPTION: SEQ ID NO:13:

| GAGCGCCGTC TGGTGTTTGA ACGGTTTTAC CGGTCGGCAT CGGCACGGGC GTTGCCGGGT | 60 |
| TCGGGCCTCG GGTTGGCGAT CGTCAAACAG GTGGTGCTCA ACCACGGCGG ATTGCTGCGC | 120 |
| ATCGAAGACA CCGACCCAGG CGGCCAGCCC CCTGGAACGT CGATTTACGT GCTGCTCCCC | 180 |
| GGCCGTCGGA TGCCGATTCC GCAGCTTCCC GGTGCGACGG CTGGCGCTCG GAGCACGGAC | 240 |
| ATCGAGAACT CTCGGGGTTC GGCGAACGTT ATCTCAGTGG AATCTCAGTC CACGCGCGCA | 300 |
| ACCTAGTTGT GCAGTTACTG TTGAAAGCCA CACCCATGCC AGTCCACGCA TGGCCAAGTT | 360 |
| GGCCCGAGTA GTGGGCCTAG TACAGGAAGA GCAACCTAGC GACATGACGA ATCACCCACG | 420 |
| GTATTCGCCA CCGCCGCAGC AGCCGGGAAC CCCAGGTTAT GCTCAGGGGC AGCAGCAAAC | 480 |
| GTACAGCCAG CAGTTCGACT GGCGTTACCC ACCGTCCCCG CCCCCGCAGC CAACCCAGTA | 540 |
| CCGTCAACCC TACGAGGCGT TGGGTGGTAC CCGGCCGGGT CTGATACCTG GCGTGATTCC | 600 |
| GACCATGACG CCCCCTCCTG GGATGGTTCG CCAACGCCCT CGTGCAGGCA TGTTGGCCAT | 660 |
| CGGCGCGGTG ACGATAGCGG TGGTGTCCGC CGGCATCGGC GGCGCGGCCG CATCCCTGGT | 720 |
| CGGGTTCAAC CGGGCACCCG CCGGCCCCAG CGGCGGCCCA GTGGCTGCCA GCGCGGCGCC | 780 |
| AAGCATCCCC GCAGCAAACA TGCCGCCGGG GTCGGTCGAA CAGGTGGCGG CCAAGGTGGT | 840 |
| GCCCAGTGTC GTCATGTTGG AAACCGATCT GGGCCGCCAG TCGGAGGAGG GCTCCGGCAT | 900 |
| CATTCTGTCT GCCGAGGGGC TGATCTTGAC CAACAACCAC GTGATCGCGG CGGCCGCCAA | 960 |
| GCCTCCCCTG GGCAGTCCGC CGCCGAAAAC GACGGTAACC TTCTCTGACG GCGGACCGC | 1020 |
| ACCCTTCACG GTGGTGGGGG CTGACCCCAC CAGTGATATC GCCGTCGTCC GTGTTCAGGG | 1080 |
| CGTCTCCGGG CTCACCCCGA TCTCCCTGGG TTCCTCCTCG GACCTGAGGG TCGGTCAGCC | 1140 |
| GGTGCTGGCG ATCGGGTCGC CGCTCGGTTT GGAGGGCACC GTGACCACGG GGATCGTCAG | 1200 |
| CGCTCTCAAC CGTCCAGTGT CGACGACCGG CGAGGCCGGC AACCAGAACA CCGTGCTGGA | 1260 |
| CGCCATTCAG ACCGACGCCG CGATCAACCC CGGTAACTCC GGGGCGCGC TGGTGAACAT | 1320 |
| GAACGCTCAA CTCGTCGGAG TCAACTCGGC CATTGCCACG CTGGGCGCGG ACTCAGCCGA | 1380 |
| TGCGCAGAGC GGCTCGATCG GTCTCGGTTT TGCGATTCCA GTCGACCAGG CCAAGCGCAT | 1440 |
| CGCCGACGAG TTGATCAGCA CCGGCAAGGC GTCACATGCC TCCCTGGGTG TGCAGGTGAC | 1500 |
| CAATGACAAA GACACCCCGG CGCCAAGAT CGTCGAAGTA GTGGCCGGTG GTGCTGCCGC | 1560 |
| GAACGCTGGA GTGCCGAAGG GCGTCGTTGT CACCAAGGTC GACGACCGCC CGATCAACAG | 1620 |

```
CGCGGACGCG TTGGTTGCCG CCGTGCGGTC CAAAGCGCCG GGCGCCACGG TGGCGCTAAC    1680

CTTTCAGGAT CCCTCGGGCG GTAGCCGCAC AGTGCAAGTC ACCCTCGGCA AGGCGGAGCA    1740

GTGATGAAGG TCGCCGCGCA GTGTTCAAAG C                                   1771

(2) INFORMATION FOR SEQ ID NO:14:

(i) SEQUENCE CHARACTERISTICS:
        (A) LENGTH: 1058 base pairs
        (B) TYPE: nucleic acid
        (C) STRANDEDNESS: single
        (D) TOPOLOGY: linear (xi) SEQUENCE DESCRIPTION: SEQ ID NO:14:

CTCCACCGCG GTGGCGGCCG CTCTAGAACT AGTGGATCCC CCGGGCTGCA GGAATTCGGC      60

ACGAGGATCC GACGTCGCAG GTTGTCGAAC CCGCCGCCGC GGAAGTATCG GTCCATGCCT     120

AGCCCGGCGA CGGCGAGCGC CGGAATGGCG CGAGTGAGGA GGCGGGCAAT TTGGCGGGGC     180

CCGGCGACGG CGAGCGCCGG AATGGCGCGA GTGAGGAGGC GGGCAGTCAT GCCCAGCGTG     240

ATCCAATCAA CCTGCATTCG GCCTGCGGGC CCATTTGACA ATCGAGGTAG TGAGCGCAAA     300

TGAATGATGG AAAACGGGCG GTGACGTCCG CTGTTCTGGT GGTGCTAGGT GCCTGCCTGG     360

CGTTGTGGCT ATCAGGATGT TCTTCGCCGA AACCTGATGC CGAGGAACAG GGTGTTCCCG     420

TGAGCCCGAC GGCGTCCGAC CCCGCGCTCC TCGCCGAGAT CAGGCAGTCG CTTGATGCGA     480

CAAAAGGGTT GACCAGCGTG CACGTAGCGG TCCGAACAAC CGGGAAAGTC GACAGCTTGC     540

TGGGTATTAC CAGTGCCGAT GTCGACGTCC GGGCCAATCC GCTCGCGGCA AAGGGCGTAT     600

GCACCTACAA CGACGAGCAG GGTGTCCCGT TTCGGGTACA AGGCGACAAC ATCTCGGTGA     660

AACTGTTCGA CGACTGGAGC AATCTCGGCT CGATTTCTGA ACTGTCAACT TCACGCGTGC     720

TCGATCCTGC CGCTGGGGTG ACGCAGCTGC TGTCCGGTGT CACGAACCTC CAAGCGCAAG     780

GTACCGAAGT GATAGACGGA ATTTCGACCA CCAAAATCAC CGGGACCATC CCCGCGAGCT     840

CTGTCAAGAT GCTTGATCCT GGCGCCAAGA GTGCAAGGCC GGCGACCGTG TGGATTGCCC     900

AGGACGGCTC GCACCACCTC GTCCGAGCGA GCATCGACCT CGGATCCGGG TCGATTCAGC     960

TCACGCAGTC GAAATGGAAC GAACCCGTCA ACGTCGACTA GGCCGAAGTT GCGTCGACGC    1020

GTTGNTCGAA ACGCCCTTGT GAACGGTGTC AACGGNAC                            1058

(2) INFORMATION FOR SEQ ID NO:15:

(i) SEQUENCE CHARACTERISTICS:
        (A) LENGTH: 542 base pairs
        (B) TYPE: nucleic acid
        (C) STRANDEDNESS: single
        (D) TOPOLOGY: linear (xi) SEQUENCE DESCRIPTION: SEQ ID NO:15:

GAATTCGGCA CGAGAGGTGA TCGACATCAT CGGGACCAGC CCCACATCCT GGGAACAGGC      60

GGCGGCGGAG GCGGTCCAGC GGGCGCGGGA TAGCGTCGAT GACATCCGCG TCGCTCGGGT     120

CATTGAGCAG GACATGGCCG TGGACAGCGC CGGCAAGATC ACCTACCGCA TCAAGCTCGA     180

AGTGTCGTTC AAGATGAGGC CGGCGCAACC GCGCTAGCAC GGGCCGGCGA GCAAGACGCA     240

AAATCGCACG GTTTGCGGTT GATTCGTGCG ATTTTGTGTC TGCTCGCCGA GGCCTACCAG     300

GCGCGGCCCA GGTCCGCGTG CTGCCGTATC CAGGCGTGCA TCGCGATTCC GGCGGCCACG     360

CCGGAGTTAA TGCTTCGCGT CGACCCGAAC TGGGCGATCC GCCGGNGAGC TGATCGATGA     420

CCGTGGCCAG CCCGTCGATG CCCGAGTTGC CGAGGAAAC GTGCTGCCAG GCCGGTAGGA     480
```

```
AGCGTCCGTA GGCGGCGGTG CTGACCGGCT CTGCCTGCGC CCTCAGTGCG GCCAGCGAGC    540

GG                                                                  542

(2) INFORMATION FOR SEQ ID NO:16:

(i) SEQUENCE CHARACTERISTICS:
        (A) LENGTH: 913 base pairs
        (B) TYPE: nucleic acid
        (C) STRANDEDNESS: single
        (D) TOPOLOGY: linear (xi) SEQUENCE DESCRIPTION: SEQ ID NO:16:

CGGTGCCGCC CGCGCCTCCG TTGCCCCCAT TGCCGCCGTC GCCGATCAGC TGCGCATCGC     60

CACCATCACC GCCTTTGCCG CCGGCACCGC CGGTGGCGCC GGGGCCGCCG ATGCCACCGC    120

TTGACCCTGG CCGCCGGCGC CGCCATTGCC ATACAGCACC CCGCCGGGGG CACCGTTACC    180

GCCGTCGCCA CCGTCGCCGC CGCTGCCGTT TCAGGCCGGG GAGGCCGAAT GAACCGCCGC    240

CAAGCCCGCC GCCGGCACCG TTGCCGCCTT TTCCGCCCGC CCCGCCGGCG CCGCCAATTG    300

CCGAACAGCC AMGCACCGTT GCCGCCAGCC CCGCCGCCGT TAACGGCGCT GCCGGGCGCC    360

GCCGCCGGAC CCGCCATTAC CGCCGTTCCC GTTCGGTGCC CCGCCGTTAC CGGCGCCGCC    420

GTTTGCCGCC AATATTCGGC GGGCACCGCC AGACCCGCCG GGGCCACCAT TGCCGCCGGG    480

CACCGAAACA ACAGCCCAAC GGTGCCGCCG GCCCCGCCGT TTGCCGCCAT CACCGGCCAT    540

TCACCGCCAG CACCGCCGTT AATGTTTATG AACCCGGTAC CGCCAGCGCG GCCCCTATTG    600

CCGGGCGCCG GAGNGCGTGC CGCCGGCGC CGCCAACGCC CAAAAGCCCG GGGTTGCCAC    660

CGGCCCCGCC GGACCCACCG GTCCCGCCGA TCCCCCCGTT GCCGCCGGTG CCGCCGCCAT    720

TGGTGCTGCT GAAGCCGTTA GCGCCGGTTC CGCSGGTTCC GGCGGTGGCG CCNTGGCCGC    780

CGGCCCCGCC GTTGCCGTAC AGCCACCCCC CGGTGGCGCC GTTGCCGCCA TTGCCGCCAT    840

TGCCGCCGTT GCCGCCATTG CCGCCGTTCC CGCCGCCACC GCCGGNTTGG CCGCCGGCGC    900

CGCCGGCGGC CGC                                                      913

(2) INFORMATION FOR SEQ ID NO:17:

(i) SEQUENCE CHARACTERISTICS:
        (A) LENGTH: 1872 base pairs
        (B) TYPE: nucleic acid
        (C) STRANDEDNESS: single
        (D) TOPOLOGY: linear (xi) SEQUENCE DESCRIPTION: SEQ ID NO:17:

GACTACGTTG GTGTAGAAAA ATCCTGCCGC CCGGACCCTT AAGGCTGGGA CAATTTCTGA     60

TAGCTACCCC GACACAGGAG GTTACGGGAT GAGCAATTCG CGCCGCCGCT CACTCAGGTG    120

GTCATGGTTG CTGAGCGTGC TGGCTGCCGT CGGGCTGGGC CTGGCCACGG CGCCGGCCCA    180

GGCGGCCCCG CCGGCCTTGT CGCAGGACCG GTTCGCCGAC TTCCCCGCGC TGCCCCTCGA    240

CCCGTCCGCG ATGGTCGCCC AAGTGGCGCC ACAGGTGGTC AACATCAACA CCAAACTGGG    300

CTACAACAAC GCCGTGGGCG CCGGGACCGG CATCGTCATC GATCCCAACG GTGTCGTGCT    360

GACCAACAAC CACGTGATCG CGGGCGCCAC CGACATCAAT GCGTTCAGCG TCGGCTCCGG    420

CCAAACCTAC GGCGTCGATG TGGTCGGGTA TGACCGCACC CAGGATGTCG CGGTGCTGCA    480

GCTGCGCGGT GCCGGTGGCC TGCCGTCGGC GGCGATCGGT GGCGGCGTCG CGGTTGGTGA    540

GCCCGTCGTC GCGATGGGCA ACAGCGGTGG GCAGGGCGGA ACGCCCCGTG CGGTGCCTGG    600
```

```
CAGGGTGGTC GCGCTCGGCC AAACCGTGCA GGCGTCGGAT TCGCTGACCG GTGCCGAAGA    660

GACATTGAAC GGGTTGATCC AGTTCGATGC CGCAATCCAG CCCGGTGATT CGGGCGGGCC    720

CGTCGTCAAC GGCCTAGGAC AGGTGGTCGG TATGAACACG GCCGCGTCCG ATAACTTCCA    780

GCTGTCCCAG GGTGGGCAGG GATTCGCCAT TCCGATCGGG CAGGCGATGG CGATCGCGGG    840

CCAAATCCGA TCGGGTGGGG GGTCACCCAC CGTTCATATC GGGCCTACCG CCTTCCTCGG    900

CTTGGGTGTT GTCGACAACA ACGGCAACGG CGCACGAGTC CAACGCGTGG TCGGAAGCGC    960

TCCGGCGGCA AGTCTCGGCA CTCCACCGG CGACGTGATC ACCGCGGTCG ACGGCGCTCC   1020

GATCAACTCG GCCACCGCGA TGGCGGACGC GCTTAACGGG CATCATCCCG GTGACGTCAT   1080

CTCGGTGAAC TGGCAAACCA AGTCGGGCGG CACGCGTACA GGGAACGTGA CATTGGCCGA   1140

GGGACCCCCG GCCTGATTTG TCGCGGATAC CACCCGCCGG CCGGCCAATT GGATTGGCGC   1200

CAGCCGTGAT TGCCGCGTGA GCCCCGAGT TCCGTCTCCC GTGCGCGTGG CATTGTGGAA   1260

GCAATGAACG AGGCAGAACA CAGCGTTGAG CACCCTCCCG TGCAGGGCAG TTACGTCGAA   1320

GGCGGTGTGG TCGAGCATCC GGATGCCAAG GACTTCGGCA GCGCCGCCGC CCTGCCCGCC   1380

GATCCGACCT GGTTTAAGCA CGCCGTCTTC TACGAGGTGC TGGTCCGGGC GTTCTTCGAC   1440

GCCAGCGCGG ACGGTTCCGN CGATCTGCGT GGACTCATCG ATCGCCTCGA CTACCTGCAG   1500

TGGCTTGGCA TCGACTGCAT CTGTTGCCGC CGTTCCTACG ACTCACCGCT GCGCGACGGC   1560

GGTTACGACA TTCGCGACTT CTACAAGGTG CTGCCCGAAT TCGGCACCGT CGACGATTTC   1620

GTCGCCCTGG TCGACACCGC TCACCGGCGA GGTATCCGCA TCATCACCGA CCTGGTGATG   1680

AATCACACCT CGGAGTCGCA CCCCTGGTTT CAGGAGTCCC GCCGCGACCC AGACGGACCG   1740

TACGGTGACT ATTACGTGTG GAGCGACACC AGCGAGCGCT ACACCGACGC CCGGATCATC   1800

TTCGTCGACA CCGAAGAGTC GAACTGGTCA TTCGATCCTG TCCGCCGACA GTTNCTACTG   1860

GCACCGATTC TT                                                      1872
```

(2) INFORMATION FOR SEQ ID NO:18:

(i) SEQUENCE CHARACTERISTICS:
        (A) LENGTH: 1482 base pairs
        (B) TYPE: nucleic acid
        (C) STRANDEDNESS: single
        (D) TOPOLOGY: linear (xi) SEQUENCE DESCRIPTION: SEQ ID NO:18:

```
CTTCGCCGAA ACCTGATGCC GAGGAACAGG GTGTTCCCGT GAGCCCGACG GCGTCCGACC     60

CCGCGCTCCT CGCCGAGATC AGGCAGTCGC TTGATGCGAC AAAAGGGTTG ACCAGCGTGC    120

ACGTAGCGGT CCGAACAACC GGGAAAGTCG ACAGCTTGCT GGGTATTACC AGTGCCGATG    180

TCGACGTCCG GGCCAATCCG CTCGCGGCAA AGGGCGTATG CACCTACAAC GACGAGCAGG    240

GTGTCCCGTT TCGGGTACAA GGCGACAACA TCTCGGTGAA ACTGTTCGAC GACTGGAGCA    300

ATCTCGGCTC GATTTCTGAA CTGTCAACTT CACGCGTGCT CGATCCTGCC GCTGGGGTGA    360

CGCAGCTGCT GTCCGGTGTC ACGAACCTCC AAGCGCAAGG TACCGAAGTG ATAGACGGAA    420

TTTCGACCAC CAAAATCACC GGGACCATCC CCGCGAGCTC TGTCAAGATG CTTGATCCTG    480

GCGCCAAGAG TGCAAGGCCG GCGACCGTGT GGATTGCCCA GGACGGCTCG CACCACCTCG    540

TCCGAGCGAG CATCGACCTC GGATCCGGGT CGATTCAGCT CACGCAGTCG AAATGGAACG    600

AACCCGTCAA CGTCGACTAG GCCGAAGTTG CGTCGACGCG TTGCTCGAAA CGCCCTTGTG    660

AACGGTGTCA ACGGCACCCG AAAACTGACC CCCTGACGGC ATCTGAAAAT TGACCCCCTA    720
```

```
GACCGGGCGG TTGGTGGTTA TTCTTCGGTG GTTCCGGCTG GTGGGACGCG GCCGAGGTCG      780

CGGTCTTTGA GCCGGTAGCT GTCGCCTTTG AGGGCGACGA CTTCAGCATG GTGGACGAGG      840

CGGTCGATCA TGGCGGCAGC AACGACGTCG TCGCCGCCGA AAACCTCGCC CCACCGGCCG      900

AAGGCCTTAT TGGACGTGAC GATCAAGCTG GCCCGCTCAT ACCGGGAGGA CACCAGCTGG      960

AAGAAGAGGT TGGCGGCCTC GGGCTCAAAC GGAATGTAAC CGACTTCGTC AACCACCAGG     1020

AGCGGATAGC GGCCAAACCG GGTGAGTTCG GCGTAGATGC GCCCGGCGTG GTGAGCCTCG     1080

GCGAACCGTG CTACCCATTC GGCGGCGGTG GCGAACAGCA CCCGATGACC GGCCTGACAC     1140

GCGCGTATCG CCAGGCCGAC CGCAAGATGA GTCTTCCCGG TGCCAGGCGG GGCCCAAAAA     1200

CACGACGTTA TCGCGGGCGG TGATGAAATC CAGGGTGCCC AGATGTGCGA TGGTGTCGCG     1260

TTTGAGGCCA CGAGCATGCT CAAAGTCGAA CTCTTCCAAC GACTTCCGAA CCGGGAAGCG     1320

GGCGGCGCGG ATGCGGCCCT CACCACCATG GGACTCCCGG GCTGACACTT CCCGCTGCAG     1380

GCAGGCGGCC AGGTATTCTT CGTGGCTCCA GTTCTCGGCG CGGGCGCGAT CGGCCAGCCG     1440

GGACACTGAC TCACGCAGGG TGGGAGCTTT CAATGCTCTT GT                       1482

(2) INFORMATION FOR SEQ ID NO:19:

(i) SEQUENCE CHARACTERISTICS:
        (A) LENGTH: 876 base pairs
        (B) TYPE: nucleic acid
        (C) STRANDEDNESS: single
        (D) TOPOLOGY: linear (xi) SEQUENCE DESCRIPTION: SEQ ID NO:19:

GAATTCGGCA CGAGCCGGCG ATAGCTTCTG GGCCGCGGCC GACCAGATGG CTCGAGGGTT       60

CGTGCTCGGG GCCACCGCCG GGCGCACCAC CCTGACCGGT GAGGGCCTGC AACACGCCGA      120

CGGTCACTCG TTGCTGCTGG ACGCCACCAA CCCGGCGGTG GTTGCCTACG ACCCGGCCTT      180

CGCCTACGAA ATCGGCTACA TCGNGGAAAG CGGACTGGCC AGGATGTGCG GGGAGAACCC      240

GGAGAACATC TTCTTCTACA TCACCGTCTA CAACGAGCCG TACGTGCAGC CGCCGGAGCC      300

GGAGAACTTC GATCCCGAGG GCGTGCTGGG GGGTATCTAC CGNTATCACG CGGCCACCGA      360

GCAACGCACC AACAAGGNGC AGATCCTGGC CTCCGGGGTA GCGATGCCCG CGGCGCTGCG      420

GGCAGCACAG ATGCTGGCCG CCGAGTGGGA TGTCGCCGCC GACGTGTGGT CGGTGACCAG      480

TTGGGGCGAG CTAAACCGCG ACGGGGTGGT CATCGAGACC GAGAAGCTCC GCCACCCCGA      540

TCGGCCGGCG GGCGTGCCCT ACGTGACGAG AGCGCTGGAG AATGCTCGGG GCCCGGTGAT      600

CGCGGTGTCG GACTGGATGC GCGCGGTCCC CGAGCAGATC CGACCGTGGG TGCCGGGCAC      660

ATACCTCACG TTGGGCACCG ACGGGTTCGG TTTTTCCGAC ACTCGGCCCG CCGGTCGTCG      720

TTACTTCAAC ACCGACGCCG AATCCCAGGT TGGTCGCGGT TTTGGGAGGG GTTGGCCGGG      780

TCGACGGGTG AATATCGACC CATTCGGTGC CGGTCGTGGG CCGCCCGCCC AGTTACCCGG      840

ATTCGACGAA GGTGGGGGGT TGCGCCCGAN TAAGTT                               876

(2) INFORMATION FOR SEQ ID NO:20:

(i) SEQUENCE CHARACTERISTICS:
        (A) LENGTH: 1021 base pairs
        (B) TYPE: nucleic acid
        (C) STRANDEDNESS: single
        (D) TOPOLOGY: linear (xi) SEQUENCE DESCRIPTION: SEQ ID NO:20:

ATCCCCCCGG GCTGCAGGAA TTCGGCACGA GAGACAAAAT TCCACGCGTT AATGCAGGAA       60
```

```
CAGATTCATA ACGAATTCAC AGCGGCACAA CAATATGTCG CGATCGCGGT TTATTTCGAC      120

AGCGAAGACC TGCCGCAGTT GGCGAAGCAT TTTTACAGCC AAGCGGTCGA GGAACGAAAC      180

CATGCAATGA TGCTCGTGCA ACACCTGCTC GACCGCGACC TTCGTGTCGA AATTCCCGGC      240

GTAGACACGG TGCGAAACCA GTTCGACAGA CCCCGCGAGG CACTGGCGCT GGCGCTCGAT      300

CAGGAACGCA CAGTCACCGA CCAGGTCGGT CGGCTGACAG CGGTGGCCCG CGACGAGGGC      360

GATTTCCTCG GCGAGCAGTT CATGCAGTGG TTCTTGCAGG AACAGATCGA AGAGGTGGCC      420

TTGATGGCAA CCCTGGTGCG GGTTGCCGAT CGGGCCGGGG CCAACCTGTT CGAGCTAGAG      480

AACTTCGTCG CACGTGAAGT GGATGTGGCG CCGGCCGCAT CAGGCGCCCC GCACGCTGCC      540

GGGGGCCGCC TCTAGATCCC TGGGGGGGAT CAGCGAGTGG TCCCGTTCGC CCGCCCGTCT      600

TCCAGCCAGG CCTTGGTGCG GCCGGGGTGG TGAGTACCAA TCCAGGCCAC CCCGACCTCC      660

CGGNAAAAGT CGATGTCCTC GTACTCATCG ACGTTCCAGG AGTACACCGC CCGGCCCTGA      720

GCTGCCGAGC GGTCAACGAG TTGCGGATAT TCCTTTAACG CAGGCAGTGA GGGTCCCACG      780

GCGGTTGGCC CGACCGCCGT GGCCGCACTG CTGGTCAGGT ATCGGGGGGT CTTGGCGAGC      840

AACAACGTCG GCAGGAGGGG TGGAGCCCGC CGGATCCGCA GACCGGGGGG GCGAAAACGA      900

CATCAACACC GCACGGGATC GATCTGCGGA GGGGGGTGCG GGAATACCGA ACCGGTGTAG      960

GAGCGCCAGC AGTTGTTTTT CCACCAGCGA AGCGTTTTCG GGTCATCGGN GGCNNTTAAG     1020

T                                                                    1021

(2) INFORMATION FOR SEQ ID NO:21:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:21:

CGTGCCGACG AACGGAAGAA CACAACCATG AAGATGGTGA AATCGATCGC CGCAGGTCTG       60

ACCGCCGCGG CTGCAATCGG CGCCGCTGCG GCCGGTGTGA CTTCGATCAT GGCTGGCGGN      120

CCGGTCGTAT ACCAGATGCA GCCGGTCGTC TTCGGCGCGC CACTGCCGTT GGACCCGGNA      180

TCCGCCCCTG ANGTCCCGAC CGCCGCCCAG TGGACCAGNC TGCTCAACAG NCTCGNCGAT      240

CCCAACGTGT CGTTTGNGAA CAAGGGNAGT CTGGTCGAGG GNGGNATCGG NGGNANCGAG      300

GGNGNGNATC GNCGANCACA A                                                321

(2) INFORMATION FOR SEQ ID NO:22:

(i) SEQUENCE CHARACTERISTICS:
        (A) LENGTH: 373 base pairs
        (B) TYPE: nucleic acid
        (C) STRANDEDNESS: single
        (D) TOPOLOGY: linear (xi) SEQUENCE DESCRIPTION: SEQ ID NO:22:

TCTTATCGGT TCCGGTTGGC GACGGGTTTT GGGNGCGGGT GGTTAACCCG CTCGGCCAGC       60

CGATCGACGG GCGCGGAGAC GTCGACTCCG ATACTCGGCG CGCGCTGGAG CTCCAGGCGC      120

CCTCGGTGGT GNACCGGCAA GGCGTGAAGG AGCCGTTGNA GACCGGGATC AAGGCGATTG      180

ACGCGATGAC CCCGATCGGC CGCGGGCAGC GCCAGCTGAT CATCGGGGAC CGCAAGACCG      240

GCAAAAACCG CCGTCTGTGT CGGACACCAT CCTCAAACCA GCGGGAAGAA CTGGGAGTCC      300
```

```
GGTGGATCCC AAGAAGCAGG TGCGCTTGTG TATACGTTGG CCATCGGGCA AGAAGGGGAA      360

CTTACCATCG CCG                                                         373

(2) INFORMATION FOR SEQ ID NO:23:

(i) SEQUENCE CHARACTERISTICS:
        (A) LENGTH: 352 base pairs
        (B) TYPE: nucleic acid
        (C) STRANDEDNESS: single
        (D) TOPOLOGY: linear (xi) SEQUENCE DESCRIPTION: SEQ ID NO:23:

GTGACGCCGT GATGGGATTC CTGGGCGGGG CCGGTCCGCT GGCGGTGGTG GATCAGCAAC       60

TGGTTACCCG GGTGCCGCAA GGCTGGTCGT TTGCTCAGGC AGCCGCTGTG CCGGTGGTGT      120

TCTTGACGGC CTGGTACGGG TTGGCCGATT TAGCCGAGAT CAAGGCGGGC GAATCGGTGC      180

TGATCCATGC CGGTACCGGC GGTGTGGGCA TGGCGGCTGT GCAGCTGGCT CGCCAGTGGG      240

GCGTGGAGGT TTTCGTCACC GCCAGCCGTG GNAAGTGGGA CACGCTGCGC GCCATNGNGT      300

TTGACGACGA NCCATATCGG NGATTCCCNC ACATNCGAAG TTCCGANGGA GA              352

(2) INFORMATION FOR SEQ ID NO:24:

(i) SEQUENCE CHARACTERISTICS:
        (A) LENGTH: 726 base pairs
        (B) TYPE: nucleic acid
        (C) STRANDEDNESS: single
        (D) TOPOLOGY: linear (xi) SEQUENCE DESCRIPTION: SEQ ID NO:24:

GAAATCCGCG TTCATTCCGT TCGACCAGCG GCTGGCGATA ATCGACGAAG TGATCAAGCC       60

GCGGTTCGCG GCGCTCATGG GTCACAGCGA GTAATCAGCA AGTTCTCTGG TATATCGCAC      120

CTAGCGTCCA GTTGCTTGCC AGATCGCTTT CGTACCGTCA TCGCATGTAC CGGTTCGCGT      180

GCCGCACGCT CATGCTGGCG GCGTGCATCC TGGCCACGGG TGTGGCGGGT CTCGGGGTCG      240

GCGCGCAGTC CGCAGCCCAA ACCGCGCCGG TGCCCGACTA CTACTGGTGC CCGGGGCAGC      300

CTTTCGACCC CGCATGGGGG CCCAACTGGG ATCCCTACAC CTGCCATGAC GACTTCCACC      360

GCGACAGCGA CGGCCCCGAC CACAGCCGCG ACTACCCCGG ACCCATCCTC GAAGGTCCCG      420

TGCTTGACGA TCCCGGTGCT GCGCCGCCGC CCCCGGCTGC CGGTGGCGGC GCATAGCGCT      480

CGTTGACCGG GCCGCATCAG CGAATACGCG TATAAACCCG GGCGTGCCCC CGGCAAGCTA      540

CGACCCCCGG CGGGGCAGAT TTACGCTCCC GTGCCGATGG ATCGCGCCGT CCGATGACAG      600

AAAATAGGCG ACGGTTTTGG CAACCGCTTG GAGGACGCTT GAAGGGAACC TGTCATGAAC      660

GGCGACAGCG CCTCCACCAT CGACATCGAC AAGGTTGTTA CCCGCACACC CGTTCGCCGG      720

ATCGTG                                                                 726

(2) INFORMATION FOR SEQ ID NO:25:

(i) SEQUENCE CHARACTERISTICS:
        (A) LENGTH: 580 base pairs
        (B) TYPE: nucleic acid
        (C) STRANDEDNESS: single
        (D) TOPOLOGY: linear (xi) SEQUENCE DESCRIPTION: SEQ ID NO:25:

CGCGACGACG ACGAACGTCG GGCCCACCAC CGCCTATGCG TTGATGCAGG CGACCGGGAT       60

GGTCGCCGAC CATATCCAAG CATGCTGGGT GCCCACTGAG CGACCTTTTG ACCAGCCGGG      120
```

```
CTGCCCGATG GCGGCCCGGT GAAGTCATTG CGCCGGGGCT TGTGCACCTG ATGAACCCGA      180

ATAGGGAACA ATAGGGGGT GATTTGGCAG TTCAATGTCG GGTATGGCTG GAAATCCAAT       240

GGCGGGGCAT GCTCGGCGCC GACCAGGCTC GCGCAGGCGG GCCAGCCCGA ATCTGGAGGG      300

AGCACTCAAT GGCGGCGATG AAGCCCCGGA CCGGCGACGG TCCTTTGGAA GCAACTAAGG      360

AGGGGCGCGG CATTGTGATG CGAGTACCAC TTGAGGGTGG CGGTCGCCTG GTCGTCGAGC      420

TGACACCCGA CGAAGCCGCC GCACTGGGTG ACGAACTCAA AGGCGTTACT AGCTAAGACC      480

AGCCCAACGG CGAATGGTCG GCGTTACGCG CACACCTTCC GGTAGATGTC CAGTGTCTGC      540

TCGGCGATGT ATGCCCAGGA GAACTCTTGG ATACAGCGCT                            580
```

(2) INFORMATION FOR SEQ ID NO:26:

(i) SEQUENCE CHARACTERISTICS:
        (A) LENGTH: 160 base pairs
        (B) TYPE: nucleic acid
        (C) STRANDEDNESS: single
        (D) TOPOLOGY: linear (xi) SEQUENCE DESCRIPTION: SEQ ID NO:26:

```
AACGGAGGCG CCGGGGGTTT TGGCGGGGCC GGGGCGGTCG GCGGCAACGG CGGGGCCGGC       60

GGTACCGCCG GGTTGTTCGG TGTCGGCGGG GCCGGTGGGG CCGGAGGCAA CGGCATCGCC      120

GGTGTCACGG GTACGTCGGC CAGCACACCG GGTGGATCCG                            160
```

(2) INFORMATION FOR SEQ ID NO:27:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (xi) SEQUENCE DESCRIPTION: SEQ ID NO:27:

```
GACACCGATA CGATGGTGAT GTACGCCAAC GTTGTCGACA CGCTCGAGGC GTTCACGATC       60

CAGCGCACAC CCGACGGCGT GACCATCGGC GATGCGGCCC CGTTCGCGGA GGCGGCTGCC      120

AAGGCGATGG GAATCGACAA GCTGCGGGTA ATTCATACCG GAATGGACCC CGTCGTCGCT      180

GAACGCGAAC AGTGGGACGA CGGCAACAAC ACGTTGGCGT TGGCGCCCGG TGTCGTTGTC      240

GCCTACGAGC GCAACGTACA GACCAACGCC CG                                    272
```

(2) INFORMATION FOR SEQ ID NO:28:

(i) SEQUENCE CHARACTERISTICS:
        (A) LENGTH: 317 base pairs
        (B) TYPE: nucleic acid
        (C) STRANDEDNESS: single
        (D) TOPOLOGY: linear (xi) SEQUENCE DESCRIPTION: SEQ ID NO:28:

```
GCAGCCGGTG GTTCTCGGAC TATCTGCGCA CGGTGACGCA GCGCGACGTG CGCGAGCTGA       60

AGCGGATCGA GCAGACGGAT CGCCTGCCGC GGTTCATGCG CTACCTGGCC GCTATCACCG      120

CGCAGGAGCT GAACGTGGCC GAAGCGGCGC GGGTCATCGG GGTCGACGCG GGGACGATCC      180

GTTCGGATCT GGCGTGGTTC GAGACGGTCT ATCTGGTACA TCGCCTGCCC GCCTGGTCGC      240

GGAATCTGAC CGCGAAGATC AAGAAGCGGT CAAAGATCCA CGTCGTCGAC AGTGGCTTCG      300

CGGCCTGGTT GCGCGGG                                                     317
```

(2) INFORMATION FOR SEQ ID NO:29:

(i) SEQUENCE CHARACTERISTICS:
(A) LENGTH: 182 base pairs
(B) TYPE: nucleic acid
(C) STRANDEDNESS: single
(D) TOPOLOGY: linear (xi) SEQUENCE DESCRIPTION: SEQ ID NO:29:

| | | |
|---|---|---|
| GATCGTGGAG CTGTCGATGA ACAGCGTTGC CGGACGCGCG GCGGCCAGCA CGTCGGTGTA | 60 |
| GCAGCGCCGG ACCACCTCGC CGGTGGGCAG CATGGTGATG ACCACGTCGG CCTCGGCCAC | 120 |
| CGCTTCGGGC GCGCTACGAA ACACCGCGAC ACCGTGCGCG GCGGCGCCGG ACGCCGCCGT | 180 |
| GG | 182 |

(2) INFORMATION FOR SEQ ID NO:30:

(i) SEQUENCE CHARACTERISTICS:
(A) LENGTH: 308 base pairs
(B) TYPE: nucleic acid
(C) STRANDEDNESS: single
(D) TOPOLOGY: linear (xi) SEQUENCE DESCRIPTION: SEQ ID NO:30:

| | |
|---|---|
| GATCGCGAAG TTTGGTGAGC AGGTGGTCGA CGCGAAAGTC TGGGCGCCTG CGAAGCGGGT | 60 |
| CGGCGTTCAC GAGGCGAAGA CACGCCTGTC CGAGCTGCTG CGGCTCGTCT ACGGCGGGCA | 120 |
| GAGGTTGAGA TTGCCCGCCG CGGCGAGCCG GTAGCAAAGC TTGTGCCGCT GCATCCTCAT | 180 |
| GAGACTCGGC GGTTAGGCAT TGACCATGGC GTGTACCGCG TGCCCGACGA TTTGGACGCT | 240 |
| CCGTTGTCAG ACGACGTGCT CGAACGCTTT CACCGGTGAA GCGCTACCTC ATCGACACCC | 300 |
| ACGTTTGG | 308 |

(2) INFORMATION FOR SEQ ID NO:31:

(i) SEQUENCE CHARACTERISTICS:
(A) LENGTH: 267 base pairs
(B) TYPE: nucleic acid
(C) STRANDEDNESS: single
(D) TOPOLOGY: linear (xi) SEQUENCE DESCRIPTION: SEQ ID NO:31:

| | |
|---|---|
| CCGACGACGA GCAACTCACG TGGATGATGG TCGGCAGCGG CATTGAGGAC GGAGAGAATC | 60 |
| CGGCCGAAGC TGCCGCGCGG CAAGTGCTCA TAGTGACCGG CCGTAGAGGG CTCCCCCGAT | 120 |
| GGCACCGGAC TATTCTGGTG TGCCGCTGGC CGGTAAGAGC GGGTAAAAGA ATGTGAGGGG | 180 |
| ACACGATGAG CAATCACACC TACCGAGTGA TCGAGATCGT CGGGACCTCG CCCGACGGCG | 240 |
| TCGACGCGGC AATCCAGGGC GGTCTGG | 267 |

(2) INFORMATION FOR SEQ ID NO:32:

(i) SEQUENCE CHARACTERISTICS:
(A) LENGTH: 1539 base pairs
(B) TYPE: nucleic acid
(C) STRANDEDNESS: single
(D) TOPOLOGY: linear (xi) SEQUENCE DESCRIPTION: SEQ ID NO:32:

| | |
|---|---|
| CTCGTGCCGA AAGAATGTGA GGGGACACGA TGAGCAATCA CACCTACCGA GTGATCGAGA | 60 |
| TCGTCGGGAC CTCGCCCGAC GGCGTCGACG CGGCAATCCA GGGCGGTCTG GCCCGAGCTG | 120 |
| CGCAGACCAT GCGCGCGCTG GACTGGTTCG AAGTACAGTC AATTCGAGGC CACCTGGTCG | 180 |
| ACGGAGCGGT CGCGCACTTC CAGGTGACTA TGAAAGTCGG CTTCCGCTGG AGGATTCCTG | 240 |

```
AACCTTCAAG CGCGGCCGAT AACTGAGGTG CATCATTAAG CGACTTTTCC AGAACATCCT        300

GACGCGCTCG AAACGCGGTT CAGCCGACGG TGGCTCCGCC GAGGCGCTGC CTCCAAAATC        360

CCTGCGACAA TTCGTCGGCG GCGCCTACAA GGAAGTCGGT GCTGAATTCG TCGGGTATCT        420

GGTCGACCTG TGTGGGCTGC AGCCGGACGA AGCGGTGCTC GACGTCGGCT GCGGCTCGGG        480

GCGGATGGCG TTGCCGCTCA CCGGCTATCT GAACAGCGAG GGACGCTACG CCGGCTTCGA        540

TATCTCGCAG AAAGCCATCG CGTGGTGCCA GGAGCACATC ACCTCGGCGC ACCCCAACTT        600

CCAGTTCGAG GTCTCCGACA TCTACAACTC GCTGTACAAC CCGAAAGGGA AATACCAGTC        660

ACTAGACTTT CGCTTTCCAT ATCCGGATGC GTCGTTCGAT GTGGTGTTTC TTACCTCGGT        720

GTTCACCCAC ATGTTTCCGC CGGACGTGGA GCACTATCTG GACGAGATCT CCCGCGTGCT        780

GAAGCCCGGC GGACGATGCC TGTGCACGTA CTTCTTGCTC AATGACGAGT CGTTAGCCCA        840

CATCGCGGAA GGAAAGAGTG CGCACAACTT CCAGCATGAG GGACCGGGTT ATCGGACAAT        900

CCACAAGAAG CGGCCCGAAG AAGCAATCGG CTTGCCGGAG ACCTTCGTCA GGGATGTCTA        960

TGGCAAGTTC GGCCTCGCCG TGCACGAACC ATTGCACTAC GGCTCATGGA GTGGCCGGGA       1020

ACCACGCCTA AGCTTCCAGG ACATCGTCAT CGCGACCAAA ACCGCGAGCT AGGTCGGCAT       1080

CCGGGAAGCA TCGCGACACC GTGGCGCCGA GCGCCGCTGC CGGCAGGCCG ATTAGGCGGG       1140

CAGATTAGCC CGCCGCGGCT CCCGGCTCCG AGTACGGCGC CCCGAATGGC GTCACCGGCT       1200

GGTAACCACG CTTGCGCGCC TGGGCGGCGG CCTGCCGGAT CAGGTGGTAG ATGCCGACAA       1260

AGCCTGCGTG ATCGGTCATC ACCAACGGTG ACAGCAGCCG GTTGTGCACC AGCGCGAACG       1320

CCACCCCGGT CTCCGGGTCT GTCCAGCCGA TCGAGCCGCC CAAGCCCACA TGACCAAACC       1380

CCGGCATCAC GTTGCCGATC GGCATACCGT GATAGCCAAG ATGAAAATTT AAGGGCACCA       1440

ATAGATTTCG ATCCGGCAGA ACTTGCCGTC GGTTGCGGGT CAGGCCCGTG ACCAGCTCCC       1500

GCGACAAGAA CCGTATGCCG TCGATCTCGC CTCGTGCCG                             1539

(2) INFORMATION FOR SEQ ID NO:33:

(i) SEQUENCE CHARACTERISTICS:
           (A) LENGTH: 851 base pairs
           (B) TYPE: nucleic acid
           (C) STRANDEDNESS: single
           (D) TOPOLOGY: linear (xi) SEQUENCE DESCRIPTION: SEQ ID NO:33:

CTGCAGGGTG GCGTGGATGA GCGTCACCGC GGGGCAGGCC GAGCTGACCG CCGCCCAGGT         60

CCGGGTTGCT GCGGCGGCCT ACGAGACGGC GTATGGGCTG ACGGTGCCCC CGCCGGTGAT        120

CGCCGAGAAC CGTGCTGAAC TGATGATTCT GATAGCGACC AACCTCTTGG GGCAAAACAC        180

CCCGGCGATC GCGGTCAACG AGGCCGAATA CGGCGAGATG TGGGCCCAAG ACGCCGCCGC        240

GATGTTTGGC TACGCCGCGG CGACGGCGAC GGCGACGGCG ACGTTGCTGC CGTTCGAGGA        300

GGCGCCGGAG ATGACCAGCG CGGGTGGGCT CCTCGAGCAG GCCGCCGCGG TCGAGGAGGC        360

CTCCGACACC GCCGCGGCGA ACCAGTTGAT GAACAATGTG CCCCAGGCGC TGAAACAGTT        420

GGCCCAGCCC ACGCAGGGCA CCACGCCTTC TTCCAAGCTG GGTGGCCTGT GGAAGACGGT        480

CTCGCCGCAT CGGTCGCCGA TCAGCAACAT GGTGTCGATG GCCAACAACC ACATGTCGAT        540

GACCAACTCG GGTGTGTCGA TGACCAACAC CTTGAGCTCG ATGTTGAAGG CTTTGCTCC         600

GGCGGCGGCC GCCCAGGCCG TGCAAACCGC GGCGCAAAAC GGGGTCCGGG CGATGAGCTC        660

GCTGGGCAGC TCGCTGGGTT CTTCGGGTCT GGGCGGTGGG GTGGCCGCCA ACTTGGGTCG        720
```

```
GGCGGCCTCG GTACGGTATG GTCACCGGGA TGGCGGAAAA TATGCANAGT CTGGTCGGCG        780

GAACGGTGGT CCGGCGTAAG GTTTACCCCC GTTTTCTGGA TGCGGTGAAC TTCGTCAACG        840

GAAACAGTTA C                                                             851

(2) INFORMATION FOR SEQ ID NO:34:

(i) SEQUENCE CHARACTERISTICS:
        (A) LENGTH: 254 base pairs
        (B) TYPE: nucleic acid
        (C) STRANDEDNESS: single
        (D) TOPOLOGY: linear (xi) SEQUENCE DESCRIPTION: SEQ ID NO:34:

GATCGATCGG GCGGAAATTT GGACCAGATT CGCCTCCGGC GATAACCCAA TCAATCGAAC         60

CTAGATTTAT TCCGTCCAGG GGCCCGAGTA ATGGCTCGCA GGAGAGGAAC CTTACTGCTG        120

CGGGCACCTG TCGTAGGTCC TCGATACGGC GGAAGGCGTC GACATTTTCC ACCGACACCC        180

CCATCCAAAC GTTCGAGGGC CACTCCAGCT TGTGAGCGAG GCGACGCAGT CGCAGGCTGC        240

GCTTGGTCAA GATC                                                         254

(2) INFORMATION FOR SEQ ID NO:35:

(i) SEQUENCE CHARACTERISTICS:
        (A) LENGTH: 1227 base pairs
        (B) TYPE: nucleic acid
        (C) STRANDEDNESS: single
        (D) TOPOLOGY: linear (xi) SEQUENCE DESCRIPTION: SEQ ID NO:35:

GATCCTGACC GAAGCGGCCG CCGCCAAGGC GAAGTCGCTG TTGGACCAGG AGGGACGGGA         60

CGATCTGGCG CTGCGGATCG CGGTTCAGCC GGGGGGGTGC GCTGGATTGC GCTATAACCT        120

TTTCTTCGAC GACCGGACGC TGGATGGTGA CCAAACCGCG GAGTTCGGTG GTGTCAGGTT        180

GATCGTGGAC CGGATGAGCG CGCCGTATGT GGAAGGCGCG TCGATCGATT TCGTCGACAC        240

TATTGAGAAG CAAGGTTCAC CATCGACAAT CCCAACGCCA CCGGCTCCTG CGCGTGCGGG        300

GATTCGTTCA ACTGATAAAA CGCTAGTACG ACCCCGCGGT GCGCAACACG TACGAGCACA        360

CCAAGACCTG ACCGCGCTGG AAAAGCAACT GAGCGATGCC TTGCACCTGA CCGCGTGGCG        420

GGCCGCCGGC GGCAGGTGTC ACCTGCATGG TGAACAGCAC CTGGGCCTGA TATTGCGACC        480

AGTACACGAT TTTGTCGATC GAGGTCACTT CGACCTGGGA GAACTGCTTG CGGAACGCGT        540

CGCTGCTCAG CTTGGCCAAG GCCTGATCGG AGCGCTTGTC GCGCACGCCG TCGTGGATAC        600

CGCACAGCGC ATTGCGAACG ATGGTGTCCA CATCGCGGTT CTCCAGCGCG TTGAGGTATC        660

CCTGAATCGC GGTTTTGGCC GGTCCCTCCG AGAATGTGCC TGCCGTGTTG GCTCCGTTGG        720

TGCGGACCCC GTATATGATC GCCGCCGTCA TAGCCGACAC CAGCGCGAGG GCTACCACAA        780

TGCCGATCAG CAGCCGCTTG TGCCGTCGCT TCGGGTAGGA CACCTGCGGC GGCACGCCGG        840

GATATGCGGC GGGCGGCAGC GCCGCGTCGT CTGCCGGTCC CGGGGCGAAG GCCGGTTCGG        900

CGGCGCCGAG GTCGTGGGGG TAGTCCAGGG CTTGGGGTTC GTGGGATGAG GGCTCGGGGT        960

ACGGCGCCGG TCCGTTGGTG CCGACACCGG GGTTCGGCGA GTGGGACCG GGCATTGTGG       1020

TTCTCCTAGG GTGGTGGACG GGACCAGCTG CTAGGGCGAC AACCGCCCGT CGCGTCAGCC       1080

GGCAGCATCG GCAATCAGGT GAGCTCCCTA GGCAGGCTAG CGCAACAGCT GCCGTCAGCT       1140

CTCAACGCGA CGGGGCGGGC CGCGGCGCCG ATAATGTTGA AGACTAGGC AACCTTAGGA       1200
```

```
ACGAAGGACG GAGATTTTGT GACGATC                                          1227

(2) INFORMATION FOR SEQ ID NO:36:

(i) SEQUENCE CHARACTERISTICS:
        (A) LENGTH: 181 base pairs
        (B) TYPE: nucleic acid
        (C) STRANDEDNESS: single
        (D) TOPOLOGY: linear (xi) SEQUENCE DESCRIPTION: SEQ ID NO:36:

GCGGTGTCGG CGGATCCGGC GGGTGGTTGA ACGGCAACGG CGGGGCCGGC GGGGCCGGCG       60

GGACCGGCGC TAACGGTGGT GCCGGCGGCA ACGCCTGGTT GTTCGGGGCC GGCGGGTCCG      120

GCGGNGCCGG CACCAATGGT GGNGTCGGCG GGTCCGGCGG ATTTGTCTAC GGCAACGGCG      180

G                                                                     181

(2) INFORMATION FOR SEQ ID NO:37:

(i) SEQUENCE CHARACTERISTICS:
        (A) LENGTH: 290 base pairs
        (B) TYPE: nucleic acid
        (C) STRANDEDNESS: single
        (D) TOPOLOGY: linear (xi) SEQUENCE DESCRIPTION: SEQ ID NO:37:

GCGGTGTCGG CGGATCCGGC GGGTGGTTGA ACGGCAACGG CGGTGTCGGC GGCCGGGGCG       60

GCGACGGCGT CTTTGCCGGT GCCGGCGGCC AGGGCGGCCT CGGTGGGCAG GGCGGCAATG      120

GCGGCGGCTC CACCGGCGGC AACGGCGGTC TTGGCGGCGC GGGCGGTGGC GGAGGCAACG      180

CCCCGGACGG CGGCTTCGGT GGCAACGGCG GTAAGGGTGG CCAGGGCGGN ATTGGCGGCG      240

GCACTCAGAG CGCGACCGGC CTCGGNGGTG ACGGCGGTGA CGGCGGTGAC                 290

(2) INFORMATION FOR SEQ ID NO:38:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:38:

GATCCAGTGG CATGGNGGGT GTCAGTGGAA GCAT                                   34

(2) INFORMATION FOR SEQ ID NO:39:

(i) SEQUENCE CHARACTERISTICS:
        (A) LENGTH: 155 base pairs
        (B) TYPE: nucleic acid
        (C) STRANDEDNESS: single
        (D) TOPOLOGY: linear (xi) SEQUENCE DESCRIPTION: SEQ ID NO:39:

GATCGCTGCT CGTCCCCCCC TTGCCGCCGA CGCCACCGGT CCCACCGTTA CCGAACAAGC       60

TGGCGTGGTC GCCAGCACCC CCGGCACCGC CGACGCCGGA GTCGAACAAT GGCACCGTCG      120

TATCCCCACC ATTGCCGCCG GNCCCACCGG CACCG                                 155

(2) INFORMATION FOR SEQ ID NO:40:

(i) SEQUENCE CHARACTERISTICS:
        (A) LENGTH: 53 base pairs
        (B) TYPE: nucleic acid
        (C) STRANDEDNESS: single
```

(D) TOPOLOGY: linear (xi) SEQUENCE DESCRIPTION: SEQ ID NO:40:

| ATGGCGTTCA CGGGGCGCCG GGGACCGGGC AGCCCGGNGG GGCCGGGGGG TGG | 53 |
|---|---|

(2) INFORMATION FOR SEQ ID NO:41:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (xi) SEQUENCE DESCRIPTION: SEQ ID NO:41:

| GATCCACCGC GGGTGCAGAC GGTGCCCGCG GCGCCACCCC GACCAGCGGC GGCAACGGCG | 60 |
|---|---|
| GCACCGGCGG CAACGGCGCG AACGCCACCG TCGTCGGNGG GGCCGGCGGG GCCGGCGGCA | 120 |
| AGGGCGGCAA CG | 132 |

(2) INFORMATION FOR SEQ ID NO:42:

(i) SEQUENCE CHARACTERISTICS:
        (A) LENGTH: 132 base pairs
        (B) TYPE: nucleic acid
        (C) STRANDEDNESS: single
        (D) TOPOLOGY: linear (xi) SEQUENCE DESCRIPTION: SEQ ID NO:42:

| GATCGGCGGC CGGNACGGNC GGGGACGGCG GCAAGGGCGG NAACGGGGGC GCCGNAGCCA | 60 |
|---|---|
| CCNGCCAAGA ATCCTCCGNG TCCNCCAATG GCGCGAATGG CGGACAGGGC GGCAACGGCG | 120 |
| GCANCGGCGG CA | 132 |

(2) INFORMATION FOR SEQ ID NO:43:

(i) SEQUENCE CHARACTERISTICS:
        (A) LENGTH: 702 base pairs
        (B) TYPE: nucleic acid
        (C) STRANDEDNESS: single
        (D) TOPOLOGY: linear (xi) SEQUENCE DESCRIPTION: SEQ ID NO:43:

| CGGCACGAGG ATCGGTACCC CGCGGCATCG GCAGCTGCCG ATTCGCCGGG TTTCCCCACC | 60 |
|---|---|
| CGAGGAAAGC CGCTACCAGA TGGCGCTGCC GAAGTAGGGC GATCCGTTCG CGATGCCGGC | 120 |
| ATGAACGGGC GGCATCAAAT TAGTGCAGGA ACCTTTCAGT TTAGCGACGA TAATGGCTAT | 180 |
| AGCACTAAGG AGGATGATCC GATATGACGC AGTCGCAGAC CGTGACGGTG GATCAGCAAG | 240 |
| AGATTTTGAA CAGGGCCAAC GAGGTGGAGG CCCCGATGGC GGACCCACCG ACTGATGTCC | 300 |
| CCATCACACC GTGCGAACTC ACGGNGGNTA AAAACGCCGC CCAACAGNTG GTNTTGTCCG | 360 |
| CCGACAACAT GCGGGAATAC CTGGCGGCCG GTGCCAAAGA GCGGCAGCGT CTGGCGACCT | 420 |
| CGCTGCGCAA CGCGGCCAAG GNGTATGGCG AGGTTGATGA GGAGGCTGCG ACCGCGCTGG | 480 |
| ACAACGACGG CGAAGGAACT GTGCAGGCAG AATCGGCCGG GGCCGTCGGA GGGGACAGTT | 540 |
| CGGCCGAACT AACCGATACG CCGAGGGTGG CCACGGCCGG TGAACCCAAC TTCATGGATC | 600 |
| TCAAAGAAGG GGCAAGGAAG CTCGAAACGG GCGACCAAGG CGCATCGCTC GCGCACTGNG | 660 |
| GGGATGGGTG GAACACTTNC ACCCTGACGC TGCAAGGCGA CG | 702 |

(2) INFORMATION FOR SEQ ID NO:44:

(i) SEQUENCE CHARACTERISTICS:

(A) LENGTH: 298 base pairs
(B) TYPE: nucleic acid
(C) STRANDEDNESS: single
(D) TOPOLOGY: linear (xi) SEQUENCE DESCRIPTION: SEQ ID NO:44:

| | | | | | |
|---|---|---|---|---|---|
| GAAGCCGCAG | CGCTGTCGGG | CGACGTGGCG | GTCAAAGCGG | CATCGCTCGG | TGGCGGTGGA | 60 |
| GGCGGCGGGG | TGCCGTCGGC | GCCGTTGGGA | TCCGCGATCG | GGGGCGCCGA | ATCGGTGCGG | 120 |
| CCCGCTGGCG | CTGGTGACAT | TGCCGGCTTA | GGCCAGGGAA | GGGCCGGCGG | CGGCGCCGCG | 180 |
| CTGGGCGGCG | GTGGCATGGG | AATGCCGATG | GGTGCCGCGC | ATCAGGGACA | AGGGGCGCC | 240 |
| AAGTCCAAGG | GTTCTCAGCA | GGAAGACGAG | GCGCTCTACA | CCGAGGATCC | TCGTGCCG | 298 |

(2) INFORMATION FOR SEQ ID NO:45:

(i) SEQUENCE CHARACTERISTICS:
(A) LENGTH: 1058 base pairs
(B) TYPE: nucleic acid
(C) STRANDEDNESS: single
(D) TOPOLOGY: linear (xi) SEQUENCE DESCRIPTION: SEQ ID NO:45:

| | | | | | |
|---|---|---|---|---|---|
| CGGCACGAGG | ATCGAATCGC | GTCGCCGGGA | GCACAGCGTC | GCACTGCACC | AGTGGAGGAG | 60 |
| CCATGACCTA | CTCGCCGGGT | AACCCCGGAT | ACCCGCAAGC | GCAGCCCGCA | GGCTCCTACG | 120 |
| GAGGCGTCAC | ACCCTCGTTC | GCCCACGCCG | ATGAGGGTGC | GAGCAAGCTA | CCGATGTACC | 180 |
| TGAACATCGC | GGTGGCAGTG | CTCGGTCTGG | CTGCGTACTT | CGCCAGCTTC | GGCCCAATGT | 240 |
| TCACCCTCAG | TACCGAACTC | GGGGGGGGTG | ATGGCGCAGT | GTCCGGTGAC | ACTGGGCTGC | 300 |
| CGGTCGGGGT | GGCTCTGCTG | GCTGCGCTGC | TTGCCGGGGT | GGTTCTGGTG | CCTAAGGCCA | 360 |
| AGAGCCATGT | GACGGTAGTT | GCGGTGCTCG | GGGTACTCGG | CGTATTTCTG | ATGGTCTCGG | 420 |
| CGACGTTTAA | CAAGCCCAGC | GCCTATTCGA | CCGGTTGGGC | ATTGTGGGTT | GTGTTGGCTT | 480 |
| TCATCGTGTT | CCAGGCGGTT | GCGGCAGTCC | TGGCGCTCTT | GGTGGAGACC | GGCGCTATCA | 540 |
| CCGCGCCGGC | GCCGCGGCCC | AAGTTCGACC | CGTATGGACA | GTACGGGCGG | TACGGGCAGT | 600 |
| ACGGGCAGTA | CGGGGTGCAG | CCGGGTGGGT | ACTACGGTCA | GCAGGGTGCT | CAGCAGGCCG | 660 |
| CGGGACTGCA | GTCGCCCGGC | CCGCAGCAGT | CTCCGCAGCC | TCCCGGATAT | GGGTCGCAGT | 720 |
| ACGGCGGCTA | TTCGTCCAGT | CCGAGCCAAT | CGGGCAGTGG | ATACACTGCT | CAGCCCCCGG | 780 |
| CCCAGCCGCC | GGCGCAGTCC | GGGTCGCAAC | AATCGCACCA | GGGCCCATCC | ACGCCACCTA | 840 |
| CCGGCTTTCC | GAGCTTCAGC | CCACCACCAC | CGGTCAGTGC | CGGGACGGGG | TCGCAGGCTG | 900 |
| GTTCGGCTCC | AGTCAACTAT | TCAAACCCCA | GCGGGGGCGA | GCAGTCGTCG | TCCCCCGGGG | 960 |
| GGGCGCCGGT | CTAACCGGGC | GTTCCCGCGT | CCGGTCGCGC | GTGTGCGCGA | AGAGTGAACA | 1020 |
| GGGTGTCAGC | AAGCGCGGAC | GATCCTCGTG | CCGAATTC | | | 1058 |

(2) INFORMATION FOR SEQ ID NO:46:

(i) SEQUENCE CHARACTERISTICS:
(A) LENGTH: 327 base pairs
(B) TYPE: nucleic acid
(C) STRANDEDNESS: single
(D) TOPOLOGY: linear (xi) SEQUENCE DESCRIPTION: SEQ ID NO:46:

| | | | | | |
|---|---|---|---|---|---|
| CGGCACGAGA | GACCGATGCC | GCTACCCTCG | CGCAGGAGGC | AGGTAATTTC | GAGCGGATCT | 60 |
| CCGGCGACCT | GAAAACCCAG | ATCGACCAGG | TGGAGTCGAC | GGCAGGTTCG | TTGCAGGGCC | 120 |

```
AGTGGCGCGG CGCGGCGGGG ACGGCCGCCC AGGCCGCGGT GGTGCGCTTC CAAGAAGCAG    180

CCAATAAGCA GAAGCAGGAA CTCGACGAGA TCTCGACGAA TATTCGTCAG GCCGGCGTCC    240

AATACTCGAG GGCCGACGAG GAGCAGCAGC AGGCGCTGTC CTCGCAAATG GGCTTCTGAC    300

CCGCTAATAC GAAAAGAAAC GGAGCAA                                       327
```

(2) INFORMATION FOR SEQ ID NO:47:

(i) SEQUENCE CHARACTERISTICS:
        (A) LENGTH: 170 base pairs
        (B) TYPE: nucleic acid
        (C) STRANDEDNESS: single
        (D) TOPOLOGY: linear (xi) SEQUENCE DESCRIPTION: SEQ ID NO:47:

```
CGGTCGCGAT GATGGCGTTG TCGAACGTGA CCGATTCTGT ACCGCCGTCG TTGAGATCAA     60

CCAACAACGT GTTGGCGTCG GCAAATGTGC CGNACCCGTG GATCTCGGTG ATCTTGTTCT    120

TCTTCATCAG GAAGTGCACA CCGGCCACCC TGCCCTCGGN TACCTTTCGG               170
```

(2) INFORMATION FOR SEQ ID NO:48:

(i) SEQUENCE CHARACTERISTICS:
        (A) LENGTH: 127 base pairs
        (B) TYPE: nucleic acid
        (C) STRANDEDNESS: single
        (D) TOPOLOGY: linear (xi) SEQUENCE DESCRIPTION: SEQ ID NO:48:

```
GATCCGGCGG CACGGGGGGT GCCGGCGGCA GCACCGCTGG CGCTGGCGGC AACGGCGGGG     60

CCGGGGGTGG CGGCGGAACC GGTGGGTTGC TCTTCGGCAA CGGCGGTGCC GGCGGGCACG    120

GGGCCGT                                                             127
```

(2) INFORMATION FOR SEQ ID NO:49:

(i) SEQUENCE CHARACTERISTICS:
        (A) LENGTH: 81 base pairs
        (B) TYPE: nucleic acid
        (C) STRANDEDNESS: single
        (D) TOPOLOGY: linear (xi) SEQUENCE DESCRIPTION: SEQ ID NO:49:

```
CGGCGGCAAG GCGGCACCG CCGGCAACGG GAGCGGCGCG GCCGGCGGCA ACGGCGGCAA      60

CGGCGGCTCC GGCCTCAACG G                                              81
```

(2) INFORMATION FOR SEQ ID NO:50:

(i) SEQUENCE CHARACTERISTICS:
        (A) LENGTH: 149 base pairs
        (B) TYPE: nucleic acid
        (C) STRANDEDNESS: single
        (D) TOPOLOGY: linear (xi) SEQUENCE DESCRIPTION: SEQ ID NO:50:

```
GATCAGGGCT GGCCGGCTCC GGCCAGAAGG GCGGTAACGG AGGAGCTGCC GGATTGTTTG     60

GCAACGGCGG GGCCGGNGGT GCCGGCGCGT CCAACCAAGC CGGTAACGGC GGNGCCGGCG    120

GAAACGGTGG TGCCGGTGGG CTGATCTGG                                     149
```

(2) INFORMATION FOR SEQ ID NO:51:

(i) SEQUENCE CHARACTERISTICS:
        (A) LENGTH: 355 base pairs (B) TYPE: nucleic acid
(C) STRANDEDNESS: single
(D) TOPOLOGY: linear (xi) SEQUENCE DESCRIPTION: SEQ ID NO:51:

| | | | | | |
|---|---|---|---|---|---|
| CGGCACGAGA | TCACACCTAC | CGAGTGATCG | AGATCGTCGG | GACCTCGCCC | GACGGTGTCG | 60 |
| ACGCGGNAAT | CCAGGGCGGT | CTGGCCCGAG | CTGCGCAGAC | CATGCGCGCG | CTGGACTGGT | 120 |
| TCGAAGTACA | GTCAATTCGA | GGCCACCTGG | TCGACGGAGC | GGTCGCGCAC | TTCCAGGTGA | 180 |
| CTATGAAAGT | CGGCTTCCGC | CTGGAGGATT | CCTGAACCTT | CAAGCGCGGC | CGATAACTGA | 240 |
| GGTGCATCAT | TAAGCGACTT | TTCCAGAACA | TCCTGACGCG | CTCGAAACGC | GGTTCAGCCG | 300 |
| ACGGTGGCTC | CGCCGAGGCG | CTGCCTCCAA | AATCCCTGCG | ACAATTCGTC | GGCGG | 355 |

(2) INFORMATION FOR SEQ ID NO:52:

(i) SEQUENCE CHARACTERISTICS:
   (A) LENGTH: 999 base pairs
   (B) TYPE: nucleic acid
   (C) STRANDEDNESS: single
   (D) TOPOLOGY: linear (xi) SEQUENCE DESCRIPTION: SEQ ID NO:52:

| | | | | | |
|---|---|---|---|---|---|
| ATGCATCACC | ATCACCATCA | CATGCATCAG | GTGGACCCCA | ACTTGACACG | TCGCAAGGGA | 60 |
| CGATTGGCGG | CACTGGCTAT | CGCGGCGATG | GCCAGCGCCA | GCCTGGTGAC | CGTTGCGGTG | 120 |
| CCCGCGACCG | CCAACGCCGA | TCCGGAGCCA | GCGCCCCCGG | TACCCACAAC | GGCCGCCTCG | 180 |
| CCGCCGTCGA | CCGCTGCAGC | GCCACCCGCA | CCGGCGACAC | CTGTTGCCCC | CCCACCACCG | 240 |
| GCCGCCGCCA | ACACGCCGAA | TGCCCAGCCG | GGCGATCCCA | ACGCAGCACC | TCCGCCGGCC | 300 |
| GACCCGAACG | CACCGCCGCC | ACCTGTCATT | GCCCCAAACG | CACCCCAACC | TGTCCGGATC | 360 |
| GACAACCCGG | TTGGAGGATT | CAGCTTCGCG | CTGCCTGCTG | GCTGGGTGGA | GTCTGACGCC | 420 |
| GCCCACTTCG | ACTACGGTTC | AGCACTCCTC | AGCAAAACCA | CCGGGGACCC | GCCATTTCCC | 480 |
| GGACAGCCGC | CGCCGGTGGC | CAATGACACC | CGTATCGTGC | TCGGCCGGCT | AGACCAAAAG | 540 |
| CTTTACGCCA | GCGCCGAAGC | CACCGACTCC | AAGGCCGCGG | CCCGGTTGGG | CTCGGACATG | 600 |
| GGTGAGTTCT | ATATGCCCTA | CCCGGGCACC | CGGATCAACC | AGGAAACCGT | CTCGCTCGAC | 660 |
| GCCAACGGGG | TGTCTGGAAG | CGCGTCGTAT | TACGAAGTCA | AGTTCAGCGA | TCCGAGTAAG | 720 |
| CCGAACGGCC | AGATCTGGAC | GGGCGTAATC | GGCTCGCCCG | CGGCGAACGC | ACCGGACGCC | 780 |
| GGGCCCCCTC | AGCGCTGGTT | TGTGGTATGG | CTCGGGACCC | CCAACAACCC | GGTGGACAAG | 840 |
| GGCGCGGCCA | AGGCGCTGGC | CGAATCGATC | CGGCCTTTGG | TCGCCCCGCC | GCCGGCGCCG | 900 |
| GCACCGGCTC | CTGCAGAGCC | CGCTCCGGCG | CCGGCGCCGG | CCGGGGAAGT | CGCTCCTACC | 960 |
| CCGACGACAC | CGACACCGCA | GCGGACCTTA | CCGGCCTGA | | | 999 |

(2) INFORMATION FOR SEQ ID NO:53:

(i) SEQUENCE CHARACTERISTICS:
   (A) LENGTH: 332 amino acids
   (B) TYPE: amino acid
   (C) STRANDEDNESS: single
   (D) TOPOLOGY: linear (xi) SEQUENCE DESCRIPTION: SEQ ID NO:53:

Met His His His His His His Met His Gln Val Asp Pro Asn Leu Thr
1               5                   10                  15

Arg Arg Lys Gly Arg Leu Ala Ala Leu Ala Ile Ala Ala Met Ala Ser
            20                  25                  30

```
Ala Ser Leu Val Thr Val Ala Val Pro Ala Thr Ala Asn Ala Asp Pro
        35                  40                  45

Glu Pro Ala Pro Pro Val Pro Thr Thr Ala Ala Ser Pro Pro Ser Thr
 50                  55                  60

Ala Ala Ala Pro Pro Ala Pro Ala Thr Pro Val Ala Pro Pro Pro Pro
 65                  70                  75                  80

Ala Ala Ala Asn Thr Pro Asn Ala Gln Pro Gly Asp Pro Asn Ala Ala
                 85                  90                  95

Pro Pro Pro Ala Asp Pro Asn Ala Pro Pro Pro Val Ile Ala Pro
                100                 105                 110

Asn Ala Pro Gln Pro Val Arg Ile Asp Asn Pro Val Gly Gly Phe Ser
             115                 120                 125

Phe Ala Leu Pro Ala Gly Trp Val Glu Ser Asp Ala Ala His Phe Asp
         130                 135                 140

Tyr Gly Ser Ala Leu Leu Ser Lys Thr Thr Gly Asp Pro Pro Phe Pro
145                 150                 155                 160

Gly Gln Pro Pro Pro Val Ala Asn Asp Thr Arg Ile Val Leu Gly Arg
                165                 170                 175

Leu Asp Gln Lys Leu Tyr Ala Ser Ala Glu Ala Thr Asp Ser Lys Ala
             180                 185                 190

Ala Ala Arg Leu Gly Ser Asp Met Gly Glu Phe Tyr Met Pro Tyr Pro
         195                 200                 205

Gly Thr Arg Ile Asn Gln Glu Thr Val Ser Leu Asp Ala Asn Gly Val
        210                 215                 220

Ser Gly Ser Ala Ser Tyr Tyr Glu Val Lys Phe Ser Asp Pro Ser Lys
225                 230                 235                 240

Pro Asn Gly Gln Ile Trp Thr Gly Val Ile Gly Ser Pro Ala Ala Asn
                245                 250                 255

Ala Pro Asp Ala Gly Pro Pro Gln Arg Trp Phe Val Val Trp Leu Gly
             260                 265                 270

Thr Ala Asn Asn Pro Val Asp Lys Gly Ala Ala Lys Ala Leu Ala Glu
         275                 280                 285

Ser Ile Arg Pro Leu Val Ala Pro Pro Ala Pro Ala Pro Ala Pro
290                 295                 300

Ala Glu Pro Ala Pro Ala Pro Ala Pro Gly Glu Val Ala Pro Thr
305                 310                 315                 320

Pro Thr Thr Pro Thr Pro Gln Arg Thr Leu Pro Ala
                325                 330

(2) INFORMATION FOR SEQ ID NO:54:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:54:

Asp Pro Val Asp Ala Val Ile Asn Thr Thr Xaa Asn Tyr Gly Gln Val
 1               5                  10                  15

Val Ala Ala Leu
         20

(2) INFORMATION FOR SEQ ID NO:55:

(i) SEQUENCE CHARACTERISTICS:
```

(A) LENGTH: 15 amino acids
(B) TYPE: amino acid
(C) STRANDEDNESS:
(D) TOPOLOGY: linear (xi) SEQUENCE DESCRIPTION: SEQ ID NO:55:

Ala Val Glu Ser Gly Met Leu Ala Leu Gly Thr Pro Ala Pro Ser
1               5                  10                  15

(2) INFORMATION FOR SEQ ID NO:56:

(i) SEQUENCE CHARACTERISTICS:
(A) LENGTH: 19 amino acids
(B) TYPE: amino acid
(C) STRANDEDNESS:
(D) TOPOLOGY: linear (xi) SEQUENCE DESCRIPTION: SEQ ID NO:56:

Ala Ala Met Lys Pro Arg Thr Gly Asp Gly Pro Leu Glu Ala Ala Lys
1               5                  10                  15

Glu Gly Arg (2) INFORMATION FOR SEQ ID NO:57:

(i) SEQUENCE CHARACTERISTICS:
(A) LENGTH: 15 amino acids
(B) TYPE: amino acid
(C) STRANDEDNESS:
(D) TOPOLOGY: linear (xi) SEQUENCE DESCRIPTION: SEQ ID NO:57:

Tyr Tyr Trp Cys Pro Gly Gln Pro Phe Asp Pro Ala Trp Gly Pro
1               5                  10                  15

(2) INFORMATION FOR SEQ ID NO:58:

(i) SEQUENCE CHARACTERISTICS:
(A) LENGTH: 14 amino acids
(B) TYPE: amino acid
(C) STRANDEDNESS:
(D) TOPOLOGY: linear (xi) SEQUENCE DESCRIPTION: SEQ ID NO:58:

Asp Ile Gly Ser Glu Ser Thr Glu Asp Gln Gln Xaa Ala Val
1               5                  10

(2) INFORMATION FOR SEQ ID NO:59:

(i) SEQUENCE CHARACTERISTICS:
(A) LENGTH: 13 amino acids
(B) TYPE: amino acid
(C) STRANDEDNESS:
(D) TOPOLOGY: linear (xi) SEQUENCE DESCRIPTION: SEQ ID NO:59:

Ala Glu Glu Ser Ile Ser Thr Xaa Glu Xaa Ile Val Pro
1               5                  10

(2) INFORMATION FOR SEQ ID NO:60:

(i) SEQUENCE CHARACTERISTICS:
(A) LENGTH: 17 amino acids
(B) TYPE: amino acid
(C) STRANDEDNESS:
(D) TOPOLOGY: linear (xi) SEQUENCE DESCRIPTION: SEQ ID NO:60:

```
Asp Pro Glu Pro Ala Pro Pro Val Pro Thr Ala Ala Ala Ala Pro Pro
1               5                   10                  15

Ala
```

(2) INFORMATION FOR SEQ ID NO:61:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:61:

```
Ala Pro Lys Thr Tyr Xaa Glu Glu Leu Lys Gly Thr Asp Thr Gly
1               5                   10                  15
```

(2) INFORMATION FOR SEQ ID NO:62:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:62:

```
Asp Pro Ala Ser Ala Pro Asp Val Pro Thr Ala Ala Gln Gln Thr Ser
1               5                   10                  15

Leu Leu Asn Asn Leu Ala Asp Pro Asp Val Ser Phe Ala Asp
                20                  25                  30
```

(2) INFORMATION FOR SEQ ID NO:63:

(i) SEQUENCE CHARACTERISTICS:
        (A) LENGTH: 187 amino acids
        (B) TYPE: amino acid
        (C) STRANDEDNESS: single
        (D) TOPOLOGY: linear (xi) SEQUENCE DESCRIPTION: SEQ ID NO:63:

```
Thr Gly Ser Leu Asn Gln Thr His Asn Arg Arg Ala Asn Glu Arg Lys
1               5                   10                  15

Asn Thr Thr Met Lys Met Val Lys Ser Ile Ala Ala Gly Leu Thr Ala
                20                  25                  30

Ala Ala Ala Ile Gly Ala Ala Ala Gly Val Thr Ser Ile Met Ala
            35                  40                  45

Gly Gly Pro Val Val Tyr Gln Met Gln Pro Val Val Phe Gly Ala Pro
        50                  55                  60

Leu Pro Leu Asp Pro Ala Ser Ala Pro Asp Val Pro Thr Ala Ala Gln
65                  70                  75                  80

Leu Thr Ser Leu Leu Asn Ser Leu Ala Asp Pro Asn Val Ser Phe Ala
                85                  90                  95

Asn Lys Gly Ser Leu Val Glu Gly Gly Ile Gly Gly Thr Glu Ala Arg
            100                 105                 110

Ile Ala Asp His Lys Leu Lys Lys Ala Ala Glu His Gly Asp Leu Pro
        115                 120                 125

Leu Ser Phe Ser Val Thr Asn Ile Gln Pro Ala Ala Ala Gly Ser Ala
            130                 135                 140

Thr Ala Asp Val Ser Val Ser Gly Pro Lys Leu Ser Ser Pro Val Thr
145                 150                 155                 160

Gln Asn Val Thr Phe Val Asn Gln Gly Gly Trp Met Leu Ser Arg Ala
                165                 170                 175
```

```
Ser Ala Met Glu Leu Leu Gln Ala Ala Gly Xaa
            180                 185

(2) INFORMATION FOR SEQ ID NO:64:

(i) SEQUENCE CHARACTERISTICS:
        (A) LENGTH: 148 amino acids
        (B) TYPE: amino acid
        (C) STRANDEDNESS: single
        (D) TOPOLOGY: linear (xi) SEQUENCE DESCRIPTION: SEQ ID NO:64:

Asp Glu Val Thr Val Glu Thr Thr Ser Val Phe Arg Ala Asp Phe Leu
1               5                   10                  15

Ser Glu Leu Asp Ala Pro Ala Gln Ala Gly Thr Glu Ser Ala Val Ser
            20                  25                  30

Gly Val Glu Gly Leu Pro Pro Gly Ser Ala Leu Leu Val Val Lys Arg
        35                  40                  45

Gly Pro Asn Ala Gly Ser Arg Phe Leu Leu Asp Gln Ala Ile Thr Ser
    50                  55                  60

Ala Gly Arg His Pro Asp Ser Asp Ile Phe Leu Asp Asp Val Thr Val
65                  70                  75                  80

Ser Arg Arg His Ala Glu Phe Arg Leu Glu Asn Asn Glu Phe Asn Val
                85                  90                  95

Val Asp Val Gly Ser Leu Asn Gly Thr Tyr Val Asn Arg Glu Pro Val
            100                 105                 110

Asp Ser Ala Val Leu Ala Asn Gly Asp Glu Val Gln Ile Gly Lys Leu
        115                 120                 125

Arg Leu Val Phe Leu Thr Gly Pro Lys Gln Gly Glu Asp Asp Gly Ser
    130                 135                 140

Thr Gly Gly Pro
145

(2) INFORMATION FOR SEQ ID NO:65:

(i) SEQUENCE CHARACTERISTICS:
        (A) LENGTH: 230 amino acids
        (B) TYPE: amino acid
        (C) STRANDEDNESS: single
        (D) TOPOLOGY: linear (xi) SEQUENCE DESCRIPTION: SEQ ID NO:65:

Thr Ser Asn Arg Pro Ala Arg Arg Gly Arg Arg Ala Pro Arg Asp Thr
1               5                   10                  15

Gly Pro Asp Arg Ser Ala Ser Leu Ser Leu Val Arg His Arg Arg Gln
            20                  25                  30

Gln Arg Asp Ala Leu Cys Leu Ser Ser Thr Gln Ile Ser Arg Gln Ser
        35                  40                  45

Asn Leu Pro Pro Ala Ala Gly Gly Ala Ala Asn Tyr Ser Arg Arg Asn
    50                  55                  60

Phe Asp Val Arg Ile Lys Ile Phe Met Leu Val Thr Ala Val Val Leu
65                  70                  75                  80

Leu Cys Cys Ser Gly Val Ala Thr Ala Ala Pro Lys Thr Tyr Cys Glu
                85                  90                  95

Glu Leu Lys Gly Thr Asp Thr Gly Gln Ala Cys Gln Ile Gln Met Ser
            100                 105                 110

Asp Pro Ala Tyr Asn Ile Asn Ile Ser Leu Pro Ser Tyr Tyr Pro Asp
        115                 120                 125
```

```
Gln Lys Ser Leu Glu Asn Tyr Ile Ala Gln Thr Arg Asp Lys Phe Leu
    130                 135                 140
Ser Ala Ala Thr Ser Ser Thr Pro Arg Glu Ala Pro Tyr Glu Leu Asn
145                 150                 155                 160
Ile Thr Ser Ala Thr Tyr Gln Ser Ala Ile Pro Pro Arg Gly Thr Gln
                165                 170                 175
Ala Val Val Leu Xaa Val Tyr His Asn Ala Gly Gly Thr His Pro Thr
            180                 185                 190
Thr Thr Tyr Lys Ala Phe Asp Trp Asp Gln Ala Tyr Arg Lys Pro Ile
        195                 200                 205
Thr Tyr Asp Thr Leu Trp Gln Ala Asp Thr Asp Pro Leu Pro Val Val
    210                 215                 220
Phe Pro Ile Val Ala Arg
225             230

(2) INFORMATION FOR SEQ ID NO:66:

(i) SEQUENCE CHARACTERISTICS:
        (A) LENGTH: 132 amino acids
        (B) TYPE: amino acid
        (C) STRANDEDNESS: single
        (D) TOPOLOGY: linear (xi) SEQUENCE DESCRIPTION: SEQ ID NO:66:

Thr Ala Ala Ser Asp Asn Phe Gln Leu Ser Gln Gly Gly Gln Gly Phe
1               5                   10                  15
Ala Ile Pro Ile Gly Gln Ala Met Ala Ile Ala Gly Gln Ile Arg Ser
            20                  25                  30
Gly Gly Gly Ser Pro Thr Val His Ile Gly Pro Thr Ala Phe Leu Gly
        35                  40                  45
Leu Gly Val Val Asp Asn Asn Gly Asn Gly Ala Arg Val Gln Arg Val
    50                  55                  60
Val Gly Ser Ala Pro Ala Ala Ser Leu Gly Ile Ser Thr Gly Asp Val
65                  70                  75                  80
Ile Thr Ala Val Asp Gly Ala Pro Ile Asn Ser Ala Thr Ala Met Ala
                85                  90                  95
Asp Ala Leu Asn Gly His His Pro Gly Asp Val Ile Ser Val Asn Trp
            100                 105                 110
Gln Thr Lys Ser Gly Gly Thr Arg Thr Gly Asn Val Thr Leu Ala Glu
        115                 120                 125
Gly Pro Pro Ala
    130

(2) INFORMATION FOR SEQ ID NO:67:

(i) SEQUENCE CHARACTERISTICS:
        (A) LENGTH: 100 amino acids
        (B) TYPE: amino acid
        (C) STRANDEDNESS: single
        (D) TOPOLOGY: linear (xi) SEQUENCE DESCRIPTION: SEQ ID NO:67:

Val Pro Leu Arg Ser Pro Ser Met Ser Pro Ser Lys Cys Leu Ala Ala
1               5                   10                  15
Ala Gln Arg Asn Pro Val Ile Arg Arg Arg Leu Ser Asn Pro Pro
            20                  25                  30
Pro Arg Lys Tyr Arg Ser Met Pro Ser Pro Ala Thr Ala Ser Ala Gly
        35                  40                  45
```

```
Met Ala Arg Val Arg Arg Ala Ile Trp Arg Gly Pro Ala Thr Xaa
    50                  55                  60

Ser Ala Gly Met Ala Arg Val Arg Arg Trp Xaa Val Met Pro Xaa Val
65              70                  75                      80

Ile Gln Ser Thr Xaa Ile Arg Xaa Xaa Gly Pro Phe Asp Asn Arg Gly
                85                  90                  95

Ser Glu Arg Lys
            100
```

(2) INFORMATION FOR SEQ ID NO:68:

(i) SEQUENCE CHARACTERISTICS:
        (A) LENGTH: 163 amino acids
        (B) TYPE: amino acid
        (C) STRANDEDNESS: single
        (D) TOPOLOGY: linear (xi) SEQUENCE DESCRIPTION: SEQ ID NO:68:

```
Met Thr Asp Asp Ile Leu Leu Ile Asp Thr Asp Glu Arg Val Arg Thr
1               5                   10                  15

Leu Thr Leu Asn Arg Pro Gln Ser Arg Asn Ala Leu Ser Ala Ala Leu
            20                  25                  30

Arg Asp Arg Phe Phe Ala Xaa Leu Xaa Asp Ala Glu Xaa Asp Asp
        35                  40                  45

Ile Asp Val Val Ile Leu Thr Gly Ala Asp Pro Val Phe Cys Ala Gly
50                  55                  60

Leu Asp Leu Lys Val Ala Gly Arg Ala Asp Arg Ala Ala Gly His Leu
65              70                  75                      80

Thr Ala Val Gly Gly His Asp Gln Ala Gly Asp Arg Arg Asp Gln Arg
                85                  90                  95

Arg Arg Gly His Arg Arg Ala Arg Thr Gly Ala Val Leu Arg His Pro
            100                 105                 110

Asp Arg Leu Arg Ala Arg Pro Leu Arg Arg His Pro Arg Pro Gly Gly
            115                 120                 125

Ala Ala Ala His Leu Gly Thr Gln Cys Val Leu Ala Ala Lys Gly Arg
            130                 135                 140

His Arg Xaa Gly Pro Val Asp Glu Pro Asp Arg Arg Leu Pro Val Arg
145                 150                 155                 160

Asp Arg Arg
```

(2) INFORMATION FOR SEQ ID NO:69:

(i) SEQUENCE CHARACTERISTICS:
        (A) LENGTH: 344 amino acids
        (B) TYPE: amino acid
        (C) STRANDEDNESS: single
        (D) TOPOLOGY: linear (xi) SEQUENCE DESCRIPTION: SEQ ID NO:69:

```
Met Lys Phe Val Asn His Ile Glu Pro Val Ala Pro Arg Arg Ala Gly
1               5                   10                  15

Gly Ala Val Ala Glu Val Tyr Ala Glu Ala Arg Arg Glu Phe Gly Arg
            20                  25                  30

Leu Pro Glu Pro Leu Ala Met Leu Ser Pro Asp Glu Gly Leu Leu Thr
            35                  40                  45

Ala Gly Trp Ala Thr Leu Arg Glu Thr Leu Leu Val Gly Gln Val Pro
50                  55                  60
```

```
Arg Gly Arg Lys Glu Ala Val Ala Ala Val Ala Ala Ser Leu Arg
 65                  70                  75                  80

Cys Pro Trp Cys Val Asp Ala His Thr Thr Met Leu Tyr Ala Ala Gly
                 85                  90                  95

Gln Thr Asp Thr Ala Ala Ala Ile Leu Ala Gly Thr Ala Pro Ala Ala
            100                 105                 110

Gly Asp Pro Asn Ala Pro Tyr Val Ala Trp Ala Ala Gly Thr Gly Thr
            115                 120                 125

Pro Ala Gly Pro Pro Ala Pro Phe Gly Pro Asp Val Ala Ala Glu Tyr
        130                 135                 140

Leu Gly Thr Ala Val Gln Phe His Phe Ile Ala Arg Leu Val Leu Val
145                 150                 155                 160

Leu Leu Asp Glu Thr Phe Leu Pro Gly Gly Pro Arg Ala Gln Gln Leu
                165                 170                 175

Met Arg Arg Ala Gly Gly Leu Val Phe Ala Arg Lys Val Arg Ala Glu
            180                 185                 190

His Arg Pro Gly Arg Ser Thr Arg Arg Leu Glu Pro Arg Thr Leu Pro
            195                 200                 205

Asp Asp Leu Ala Trp Ala Thr Pro Ser Glu Pro Ile Ala Thr Ala Phe
        210                 215                 220

Ala Ala Leu Ser His His Leu Asp Thr Ala Pro His Leu Pro Pro Pro
225                 230                 235                 240

Thr Arg Gln Val Val Arg Arg Val Val Gly Ser Trp His Gly Glu Pro
                245                 250                 255

Met Pro Met Ser Ser Arg Trp Thr Asn Glu His Thr Ala Glu Leu Pro
            260                 265                 270

Ala Asp Leu His Ala Pro Thr Arg Leu Ala Leu Leu Thr Gly Leu Ala
        275                 280                 285

Pro His Gln Val Thr Asp Asp Val Ala Ala Ala Arg Ser Leu Leu
290                 295                 300

Asp Thr Asp Ala Ala Leu Val Gly Ala Leu Ala Trp Ala Ala Phe Thr
305                 310                 315                 320

Ala Ala Arg Arg Ile Gly Thr Trp Ile Gly Ala Ala Ala Glu Gly Gln
            325                 330                 335

Val Ser Arg Gln Asn Pro Thr Gly
            340

(2) INFORMATION FOR SEQ ID NO:70:

(i) SEQUENCE CHARACTERISTICS:
        (A) LENGTH: 485 amino acids
        (B) TYPE: amino acid
        (C) STRANDEDNESS: single
        (D) TOPOLOGY: linear (xi) SEQUENCE DESCRIPTION: SEQ ID NO:70:

Asp Asp Pro Asp Met Pro Gly Thr Val Ala Lys Ala Val Ala Asp Ala
 1                   5                  10                  15

Leu Gly Arg Gly Ile Ala Pro Val Glu Asp Ile Gln Asp Cys Val Glu
                 20                  25                  30

Ala Arg Leu Gly Glu Ala Gly Leu Asp Asp Val Ala Arg Val Tyr Ile
             35                  40                  45

Ile Tyr Arg Gln Arg Arg Ala Glu Leu Arg Thr Ala Lys Ala Leu Leu
         50                  55                  60

Gly Val Arg Asp Glu Leu Lys Leu Ser Leu Ala Ala Val Thr Val Leu
 65                  70                  75                  80
```

-continued

```
Arg Glu Arg Tyr Leu Leu His Asp Glu Gln Gly Arg Pro Ala Glu Ser
                85                  90                  95
Thr Gly Glu Leu Met Asp Arg Ser Ala Arg Cys Val Ala Ala Ala Glu
            100                 105                 110
Asp Gln Tyr Glu Pro Gly Ser Ser Arg Arg Trp Ala Glu Arg Phe Ala
        115                 120                 125
Thr Leu Leu Arg Asn Leu Glu Phe Leu Pro Asn Ser Pro Thr Leu Met
    130                 135                 140
Asn Ser Gly Thr Asp Leu Gly Leu Leu Ala Gly Cys Phe Val Leu Pro
145                 150                 155                 160
Ile Glu Asp Ser Leu Gln Ser Ile Phe Ala Thr Leu Gly Gln Ala Ala
                165                 170                 175
Glu Leu Gln Arg Ala Gly Gly Thr Gly Tyr Ala Phe Ser His Leu
            180                 185                 190
Arg Pro Ala Gly Asp Arg Val Ala Ser Thr Gly Gly Thr Ala Ser Gly
        195                 200                 205
Pro Val Ser Phe Leu Arg Leu Tyr Asp Ser Ala Ala Gly Val Val Ser
    210                 215                 220
Met Gly Gly Arg Arg Arg Gly Ala Cys Met Ala Val Leu Asp Val Ser
225                 230                 235                 240
His Pro Asp Ile Cys Asp Phe Val Thr Ala Lys Ala Glu Ser Pro Ser
                245                 250                 255
Glu Leu Pro His Phe Asn Leu Ser Val Gly Val Thr Asp Ala Phe Leu
            260                 265                 270
Arg Ala Val Glu Arg Asn Gly Leu His Arg Leu Val Asn Pro Arg Thr
        275                 280                 285
Gly Lys Ile Val Ala Arg Met Pro Ala Ala Glu Leu Phe Asp Ala Ile
    290                 295                 300
Cys Lys Ala Ala His Ala Gly Gly Asp Pro Gly Leu Val Phe Leu Asp
305                 310                 315                 320
Thr Ile Asn Arg Ala Asn Pro Val Pro Gly Arg Gly Arg Ile Glu Ala
                325                 330                 335
Thr Asn Pro Cys Gly Glu Val Pro Leu Leu Pro Tyr Glu Ser Cys Asn
            340                 345                 350
Leu Gly Ser Ile Asn Leu Ala Arg Met Leu Ala Asp Gly Arg Val Asp
        355                 360                 365
Trp Asp Arg Leu Glu Glu Val Ala Gly Val Ala Val Arg Phe Leu Asp
    370                 375                 380
Asp Val Ile Asp Val Ser Arg Tyr Pro Phe Pro Glu Leu Gly Glu Ala
385                 390                 395                 400
Ala Arg Ala Thr Arg Lys Ile Gly Leu Gly Val Met Gly Leu Ala Glu
                405                 410                 415
Leu Leu Ala Ala Leu Gly Ile Pro Tyr Asp Ser Glu Glu Ala Val Arg
            420                 425                 430
Leu Ala Thr Arg Leu Met Arg Arg Ile Gln Gln Ala Ala His Thr Ala
        435                 440                 445
Ser Arg Arg Leu Ala Glu Glu Arg Gly Ala Phe Pro Ala Phe Thr Asp
    450                 455                 460
Ser Arg Phe Ala Arg Ser Gly Pro Arg Arg Asn Ala Gln Val Thr Ser
465                 470                 475                 480
Val Ala Pro Thr Gly
                485
```

(2) INFORMATION FOR SEQ ID NO:71:

(i) SEQUENCE CHARACTERISTICS:
        (A) LENGTH: 267 amino acids
        (B) TYPE: amino acid
        (C) STRANDEDNESS: single
        (D) TOPOLOGY: linear (xi) SEQUENCE DESCRIPTION: SEQ ID NO:71:

```
Gly Val Ile Val Leu Asp Leu Glu Pro Arg Gly Pro Leu Pro Thr Glu
1               5                  10                 15

Ile Tyr Trp Arg Arg Gly Leu Ala Leu Gly Ile Ala Val Val Val
            20                 25                 30

Val Gly Ile Ala Val Ala Ile Val Ile Ala Phe Val Asp Ser Ser Ala
        35                  40                 45

Gly Ala Lys Pro Val Ser Ala Asp Lys Pro Ala Ser Ala Gln Ser His
    50                  55                 60

Pro Gly Ser Pro Ala Pro Gln Ala Pro Gln Pro Ala Gly Gln Thr Glu
65                  70                 75                 80

Gly Asn Ala Ala Ala Ala Pro Pro Gln Gly Gln Asn Pro Glu Thr Pro
                85                 90                 95

Thr Pro Thr Ala Ala Val Gln Pro Pro Val Leu Lys Glu Gly Asp
            100                105                110

Asp Cys Pro Asp Ser Thr Leu Ala Val Lys Gly Leu Thr Asn Ala Pro
        115                 120                125

Gln Tyr Tyr Val Gly Asp Gln Pro Lys Phe Thr Met Val Val Thr Asn
    130                 135                140

Ile Gly Leu Val Ser Cys Lys Arg Asp Val Gly Ala Ala Val Leu Ala
145                 150                155                160

Ala Tyr Val Tyr Ser Leu Asp Asn Lys Arg Leu Trp Ser Asn Leu Asp
                165                170                175

Cys Ala Pro Ser Asn Glu Thr Leu Val Lys Thr Phe Ser Pro Gly Glu
            180                185                190

Gln Val Thr Thr Ala Val Thr Trp Thr Gly Met Gly Ser Ala Pro Arg
        195                 200                205

Cys Pro Leu Pro Arg Pro Ala Ile Gly Pro Gly Thr Tyr Asn Leu Val
    210                 215                220

Val Gln Leu Gly Asn Leu Arg Ser Leu Pro Val Pro Phe Ile Leu Asn
225                 230                235                240

Gln Pro Pro Pro Pro Gly Pro Val Pro Ala Pro Gly Pro Ala Gln
                245                250                255

Ala Pro Pro Glu Ser Pro Ala Gln Gly Gly
            260                265
```

(2) INFORMATION FOR SEQ ID NO:72:

(i) SEQUENCE CHARACTERISTICS:
        (A) LENGTH: 97 amino acids
        (B) TYPE: amino acid
        (C) STRANDEDNESS: single
        (D) TOPOLOGY: linear (xi) SEQUENCE DESCRIPTION: SEQ ID NO:72:

```
Leu Ile Ser Thr Gly Lys Ala Ser His Ala Ser Leu Gly Val Gln Val
1               5                  10                 15

Thr Asn Asp Lys Asp Thr Pro Gly Ala Lys Ile Val Glu Val Val Ala
            20                 25                 30
```

-continued

```
Gly Gly Ala Ala Ala Asn Ala Gly Val Pro Lys Gly Val Val Thr
         35                  40                  45

Lys Val Asp Asp Arg Pro Ile Asn Ser Ala Asp Ala Leu Val Ala Ala
 50                  55                  60

Val Arg Ser Lys Ala Pro Gly Ala Thr Val Ala Leu Thr Phe Gln Asp
 65                  70                  75                  80

Pro Ser Gly Gly Ser Arg Thr Val Gln Val Thr Leu Gly Lys Ala Glu
                 85                  90                  95

Gln
```

(2) INFORMATION FOR SEQ ID NO:73:

(i) SEQUENCE CHARACTERISTICS:
        (A) LENGTH: 364 amino acids
        (B) TYPE: amino acid
        (C) STRANDEDNESS: single
        (D) TOPOLOGY: linear (xi) SEQUENCE DESCRIPTION: SEQ ID NO:73:

```
Gly Ala Ala Val Ser Leu Leu Ala Ala Gly Thr Leu Val Leu Thr Ala
 1               5                  10                  15

Cys Gly Gly Gly Thr Asn Ser Ser Ser Gly Ala Gly Gly Thr Ser
                 20                  25                  30

Gly Ser Val His Cys Gly Gly Lys Lys Glu Leu His Ser Ser Gly Ser
                 35                  40                  45

Thr Ala Gln Glu Asn Ala Met Glu Gln Phe Val Tyr Ala Tyr Val Arg
 50                  55                  60

Ser Cys Pro Gly Tyr Thr Leu Asp Tyr Asn Ala Asn Gly Ser Gly Ala
 65                  70                  75                  80

Gly Val Thr Gln Phe Leu Asn Asn Glu Thr Asp Phe Ala Gly Ser Asp
                 85                  90                  95

Val Pro Leu Asn Pro Ser Thr Gly Gln Pro Asp Arg Ser Ala Glu Arg
                100                 105                 110

Cys Gly Ser Pro Ala Trp Asp Leu Pro Thr Val Phe Gly Pro Ile Ala
                115                 120                 125

Ile Thr Tyr Asn Ile Lys Gly Val Ser Thr Leu Asn Leu Asp Gly Pro
130                 135                 140

Thr Thr Ala Lys Ile Phe Asn Gly Thr Ile Thr Val Trp Asn Asp Pro
145                 150                 155                 160

Gln Ile Gln Ala Leu Asn Ser Gly Thr Asp Leu Pro Pro Thr Pro Ile
                165                 170                 175

Ser Val Ile Phe Arg Ser Asp Lys Ser Gly Thr Ser Asp Asn Phe Gln
                180                 185                 190

Lys Tyr Leu Asp Gly Val Ser Asn Gly Ala Trp Gly Lys Gly Ala Ser
                195                 200                 205

Glu Thr Phe Ser Gly Gly Val Gly Val Gly Ala Ser Gly Asn Asn Gly
                210                 215                 220

Thr Ser Ala Leu Leu Gln Thr Ser Asp Gly Ser Ile Thr Tyr Asn Glu
225                 230                 235                 240

Trp Ser Phe Ala Val Gly Lys Gln Leu Asn Met Ala Gln Ile Ile Thr
                245                 250                 255

Ser Ala Gly Pro Asp Pro Val Ala Ile Thr Thr Glu Ser Val Gly Lys
                260                 265                 270

Thr Ile Ala Gly Ala Lys Ile Met Gly Gln Gly Asn Asp Leu Val Leu
                275                 280                 285
```

-continued

```
Asp Thr Ser Ser Phe Tyr Arg Pro Thr Gln Pro Gly Ser Tyr Pro Ile
        290                 295                 300

Val Leu Ala Thr Tyr Glu Ile Val Cys Ser Lys Tyr Pro Asp Ala Thr
305                 310                 315                 320

Thr Gly Thr Ala Val Arg Ala Phe Met Gln Ala Ala Ile Gly Pro Gly
                325                 330                 335

Gln Glu Gly Leu Asp Gln Tyr Gly Ser Ile Pro Leu Pro Lys Ser Phe
            340                 345                 350

Gln Ala Lys Leu Ala Ala Ala Val Asn Ala Ile Ser
        355                 360
```

(2) INFORMATION FOR SEQ ID NO:74:

(i) SEQUENCE CHARACTERISTICS:
        (A) LENGTH: 309 amino acids
        (B) TYPE: amino acid
        (C) STRANDEDNESS: single
        (D) TOPOLOGY: linear (xi) SEQUENCE DESCRIPTION: SEQ ID NO:74:

```
Gln Ala Ala Ala Gly Arg Ala Val Arg Arg Thr Gly His Ala Glu Asp
1               5                   10                  15

Gln Thr His Gln Asp Arg Leu His His Gly Cys Arg Arg Ala Ala Val
            20                  25                  30

Val Val Arg Gln Asp Arg Ala Ser Val Ser Ala Thr Ser Ala Arg Pro
        35                  40                  45

Pro Arg Arg His Pro Ala Gln Gly His Arg Arg Arg Val Ala Pro Ser
    50                  55                  60

Gly Gly Arg Arg Arg Pro His Pro His His Val Gln Pro Asp Asp Arg
65                  70                  75                  80

Arg Asp Arg Pro Ala Leu Leu Asp Arg Thr Gln Pro Ala Glu His Pro
                85                  90                  95

Asp Pro His Arg Arg Gly Pro Ala Asp Pro Gly Arg Val Arg Gly Arg
            100                 105                 110

Gly Arg Leu Arg Arg Val Asp Asp Gly Arg Leu Gln Pro Asp Arg Asp
        115                 120                 125

Ala Asp His Gly Ala Pro Val Arg Gly Arg Gly Pro His Arg Gly Val
    130                 135                 140

Gln His Arg Gly Gly Pro Val Phe Val Arg Arg Val Pro Gly Val Arg
145                 150                 155                 160

Cys Ala His Arg Arg Gly His Arg Arg Val Ala Ala Pro Gly Gln Gly
                165                 170                 175

Asp Val Leu Arg Ala Gly Leu Arg Val Glu Arg Leu Arg Pro Val Ala
            180                 185                 190

Ala Val Glu Asn Leu His Arg Gly Ser Gln Arg Ala Asp Gly Arg Val
        195                 200                 205

Phe Arg Pro Ile Arg Arg Gly Ala Arg Leu Pro Ala Arg Arg Ser Arg
    210                 215                 220

Ala Gly Pro Gln Gly Arg Leu His Leu Asp Gly Ala Gly Pro Ser Pro
225                 230                 235                 240

Leu Pro Ala Arg Ala Gly Gln Gln Gln Pro Ser Ser Ala Gly Gly Arg
                245                 250                 255

Arg Ala Gly Gly Ala Glu Arg Ala Asp Pro Gly Gln Arg Gly Arg His
            260                 265                 270

His Gln Gly Gly His Asp Pro Gly Arg Gln Gly Ala Gln Arg Gly Thr
        275                 280                 285
```

```
Ala Gly Val Ala His Ala Ala Gly Pro Arg Ala Ala Val Arg
    290                 295                 300

Asn Arg Pro Arg Arg
305

(2) INFORMATION FOR SEQ ID NO:75:

(i) SEQUENCE CHARACTERISTICS:
        (A) LENGTH: 580 amino acids
        (B) TYPE: amino acid
        (C) STRANDEDNESS: single
        (D) TOPOLOGY: linear (xi) SEQUENCE DESCRIPTION: SEQ ID NO:75:

Ser Ala Val Trp Cys Leu Asn Gly Phe Thr Gly Arg His Arg His Gly
1               5                   10                  15

Arg Cys Arg Val Arg Ala Ser Gly Trp Arg Ser Ser Asn Arg Trp Cys
            20                  25                  30

Ser Thr Thr Ala Asp Cys Cys Ala Ser Lys Thr Pro Thr Gln Ala Ala
            35                  40                  45

Ser Pro Leu Glu Arg Arg Phe Thr Cys Cys Ser Pro Ala Val Gly Cys
    50                  55                  60

Arg Phe Arg Ser Phe Pro Val Arg Leu Ala Leu Gly Ala Arg Thr
65                  70                  75                  80

Ser Arg Thr Leu Gly Val Arg Arg Thr Leu Ser Gln Trp Asn Leu Ser
                85                  90                  95

Pro Arg Ala Gln Pro Ser Cys Ala Val Thr Val Glu Ser His Thr His
            100                 105                 110

Ala Ser Pro Arg Met Ala Lys Leu Ala Arg Val Val Gly Leu Val Gln
            115                 120                 125

Glu Glu Gln Pro Ser Asp Met Thr Asn His Pro Arg Tyr Ser Pro Pro
    130                 135                 140

Pro Gln Gln Pro Gly Thr Pro Gly Tyr Ala Gln Gly Gln Gln Gln Thr
145                 150                 155                 160

Tyr Ser Gln Gln Phe Asp Trp Arg Tyr Pro Pro Ser Pro Pro Pro Gln
                165                 170                 175

Pro Thr Gln Tyr Arg Gln Pro Tyr Glu Ala Leu Gly Gly Thr Arg Pro
            180                 185                 190

Gly Leu Ile Pro Gly Val Ile Pro Thr Met Thr Pro Pro Gly Met
    195                 200                 205

Val Arg Gln Arg Pro Arg Ala Gly Met Leu Ala Ile Gly Ala Val Thr
    210                 215                 220

Ile Ala Val Val Ser Ala Gly Ile Gly Gly Ala Ala Ser Leu Val
225                 230                 235                 240

Gly Phe Asn Arg Ala Pro Ala Gly Pro Ser Gly Gly Pro Val Ala Ala
                245                 250                 255

Ser Ala Ala Pro Ser Ile Pro Ala Ala Asn Met Pro Pro Gly Ser Val
            260                 265                 270

Glu Gln Val Ala Ala Lys Val Val Pro Ser Val Val Met Leu Glu Thr
    275                 280                 285

Asp Leu Gly Arg Gln Ser Glu Glu Gly Ser Gly Ile Ile Leu Ser Ala
    290                 295                 300

Glu Gly Leu Ile Leu Thr Asn Asn His Val Ile Ala Ala Ala Lys
305                 310                 315                 320

Pro Pro Leu Gly Ser Pro Pro Pro Lys Thr Thr Val Thr Phe Ser Asp
```

```
                    325                 330                 335
Gly Arg Thr Ala Pro Phe Thr Val Val Gly Ala Asp Pro Thr Ser Asp
                340                 345                 350
Ile Ala Val Val Arg Val Gln Gly Val Ser Gly Leu Thr Pro Ile Ser
                355                 360                 365
Leu Gly Ser Ser Asp Leu Arg Val Gly Gln Pro Val Leu Ala Ile
                370                 375                 380
Gly Ser Pro Leu Gly Leu Glu Gly Thr Val Thr Thr Gly Ile Val Ser
385                 390                 395                 400
Ala Leu Asn Arg Pro Val Ser Thr Thr Gly Glu Ala Gly Asn Gln Asn
                405                 410                 415
Thr Val Leu Asp Ala Ile Gln Thr Asp Ala Ala Ile Asn Pro Gly Asn
                420                 425                 430
Ser Gly Gly Ala Leu Val Asn Met Asn Ala Gln Leu Val Gly Val Asn
                435                 440                 445
Ser Ala Ile Ala Thr Leu Gly Ala Asp Ser Ala Asp Ala Gln Ser Gly
                450                 455                 460
Ser Ile Gly Leu Gly Phe Ala Ile Pro Val Asp Gln Ala Lys Arg Ile
465                 470                 475                 480
Ala Asp Glu Leu Ile Ser Thr Gly Lys Ala Ser His Ala Ser Leu Gly
                485                 490                 495
Val Gln Val Thr Asn Asp Lys Asp Thr Pro Gly Ala Lys Ile Val Glu
                500                 505                 510
Val Val Ala Gly Gly Ala Ala Asn Ala Gly Val Pro Lys Gly Val
                515                 520                 525
Val Val Thr Lys Val Asp Asp Arg Pro Ile Asn Ser Ala Asp Ala Leu
                530                 535                 540
Val Ala Ala Val Arg Ser Lys Ala Pro Gly Ala Thr Val Ala Leu Thr
545                 550                 555                 560
Phe Gln Asp Pro Ser Gly Gly Ser Arg Thr Val Gln Val Thr Leu Gly
                565                 570                 575
Lys Ala Glu Gln
                580

(2) INFORMATION FOR SEQ ID NO:76:

(i) SEQUENCE CHARACTERISTICS:
        (A) LENGTH: 233 amino acids
        (B) TYPE: amino acid
        (C) STRANDEDNESS: single
        (D) TOPOLOGY: linear (xi) SEQUENCE DESCRIPTION: SEQ ID NO:76:

Met Asn Asp Gly Lys Arg Ala Val Thr Ser Ala Val Leu Val Val Leu
1                   5                  10                  15
Gly Ala Cys Leu Ala Leu Trp Leu Ser Gly Cys Ser Ser Pro Lys Pro
                20                  25                  30
Asp Ala Glu Glu Gln Gly Val Pro Val Ser Pro Thr Ala Ser Asp Pro
            35                  40                  45
Ala Leu Leu Ala Glu Ile Arg Gln Ser Leu Asp Ala Thr Lys Gly Leu
        50                  55                  60
Thr Ser Val His Val Ala Val Arg Thr Thr Gly Lys Val Asp Ser Leu
65                  70                  75                  80
Leu Gly Ile Thr Ser Ala Asp Val Asp Val Arg Ala Asn Pro Leu Ala
                85                  90                  95
```

```
Ala Lys Gly Val Cys Thr Tyr Asn Asp Glu Gln Gly Val Pro Phe Arg
            100                 105                 110

Val Gln Gly Asp Asn Ile Ser Val Lys Leu Phe Asp Asp Trp Ser Asn
        115                 120                 125

Leu Gly Ser Ile Ser Glu Leu Ser Thr Ser Arg Val Leu Asp Pro Ala
    130                 135                 140

Ala Gly Val Thr Gln Leu Leu Ser Gly Val Thr Asn Leu Gln Ala Gln
145                 150                 155                 160

Gly Thr Glu Val Ile Asp Gly Ile Ser Thr Thr Lys Ile Thr Gly Thr
                165                 170                 175

Ile Pro Ala Ser Ser Val Lys Met Leu Asp Pro Gly Ala Lys Ser Ala
            180                 185                 190

Arg Pro Ala Thr Val Trp Ile Ala Gln Asp Gly Ser His His Leu Val
        195                 200                 205

Arg Ala Ser Ile Asp Leu Gly Ser Gly Ser Ile Gln Leu Thr Gln Ser
    210                 215                 220

Lys Trp Asn Glu Pro Val Asn Val Asp
225                 230
```

(2) INFORMATION FOR SEQ ID NO:77:

(i) SEQUENCE CHARACTERISTICS:
        (A) LENGTH: 66 amino acids
        (B) TYPE: amino acid
        (C) STRANDEDNESS: single
        (D) TOPOLOGY: linear (xi) SEQUENCE DESCRIPTION: SEQ ID NO:77:

```
Val Ile Asp Ile Ile Gly Thr Ser Pro Thr Ser Trp Glu Gln Ala Ala
1               5                   10                  15

Ala Glu Ala Val Gln Arg Ala Arg Asp Ser Val Asp Asp Ile Arg Val
            20                  25                  30

Ala Arg Val Ile Glu Gln Asp Met Ala Val Asp Ser Ala Gly Lys Ile
        35                  40                  45

Thr Tyr Arg Ile Lys Leu Glu Val Ser Phe Lys Met Arg Pro Ala Gln
    50                  55                  60

Pro Arg
65
```

(2) INFORMATION FOR SEQ ID NO:78:

(i) SEQUENCE CHARACTERISTICS:
        (A) LENGTH: 69 amino acids
        (B) TYPE: amino acid
        (C) STRANDEDNESS: single
        (D) TOPOLOGY: linear (xi) SEQUENCE DESCRIPTION: SEQ ID NO:78:

```
Val Pro Pro Ala Pro Leu Pro Pro Leu Pro Pro Ser Pro Ile Ser
1               5                   10                  15

Cys Ala Ser Pro Pro Ser Pro Leu Pro Ala Pro Pro Val Ala
            20                  25                  30

Pro Gly Pro Pro Met Pro Pro Leu Asp Pro Trp Pro Pro Ala Pro Pro
        35                  40                  45

Leu Pro Tyr Ser Thr Pro Pro Gly Ala Pro Leu Pro Pro Ser Pro Pro
    50                  55                  60

Ser Pro Pro Leu Pro
65
```

(2) INFORMATION FOR SEQ ID NO:79:

(i) SEQUENCE CHARACTERISTICS:
        (A) LENGTH: 355 amino acids
        (B) TYPE: amino acid
        (C) STRANDEDNESS: single
        (D) TOPOLOGY: linear (xi) SEQUENCE DESCRIPTION: SEQ ID NO:79:

```
Met Ser Asn Ser Arg Arg Arg Ser Leu Arg Trp Ser Trp Leu Leu Ser
1               5                   10                  15

Val Leu Ala Ala Val Gly Leu Gly Leu Ala Thr Ala Pro Ala Gln Ala
            20                  25                  30

Ala Pro Pro Ala Leu Ser Gln Asp Arg Phe Ala Asp Phe Pro Ala Leu
        35                  40                  45

Pro Leu Asp Pro Ser Ala Met Val Ala Gln Val Ala Pro Gln Val Val
    50                  55                  60

Asn Ile Asn Thr Lys Leu Gly Tyr Asn Asn Ala Val Gly Ala Gly Thr
65                  70                  75                  80

Gly Ile Val Ile Asp Pro Asn Gly Val Val Leu Thr Asn Asn His Val
                85                  90                  95

Ile Ala Gly Ala Thr Asp Ile Asn Ala Phe Ser Val Gly Ser Gly Gln
            100                 105                 110

Thr Tyr Gly Val Asp Val Val Gly Tyr Asp Arg Thr Gln Asp Val Ala
        115                 120                 125

Val Leu Gln Leu Arg Gly Ala Gly Gly Leu Pro Ser Ala Ala Ile Gly
    130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
                165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
        195                 200                 205

Gly Gly Pro Val Val Asn Gly Leu Gly Gln Val Val Gly Met Asn Thr
    210                 215                 220

Ala Ala Ser Asp Asn Phe Gln Leu Ser Gln Gly Gly Gln Gly Phe Ala
225                 230                 235                 240

Ile Pro Ile Gly Gln Ala Met Ala Ile Ala Gly Gln Ile Arg Ser Gly
                245                 250                 255

Gly Gly Ser Pro Thr Val His Ile Gly Pro Thr Ala Phe Leu Gly Leu
            260                 265                 270

Gly Val Val Asp Asn Asn Gly Asn Gly Ala Arg Val Gln Arg Val Val
        275                 280                 285

Gly Ser Ala Pro Ala Ala Ser Leu Gly Ile Ser Thr Gly Asp Val Ile
    290                 295                 300

Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Asn Trp Gln
                325                 330                 335

Thr Lys Ser Gly Gly Thr Arg Thr Gly Asn Val Thr Leu Ala Glu Gly
            340                 345                 350

Pro Pro Ala
355
```

(2) INFORMATION FOR SEQ ID NO:80:

(i) SEQUENCE CHARACTERISTICS:
        (A) LENGTH: 205 amino acids
        (B) TYPE: amino acid
        (C) STRANDEDNESS: single
        (D) TOPOLOGY: linear (xi) SEQUENCE DESCRIPTION: SEQ ID NO:80:

```
Ser Pro Lys Pro Asp Ala Glu Glu Gln Gly Val Pro Val Ser Pro Thr
 1               5                  10                  15

Ala Ser Asp Pro Ala Leu Leu Ala Glu Ile Arg Gln Ser Leu Asp Ala
             20                  25                  30

Thr Lys Gly Leu Thr Ser Val His Val Ala Val Arg Thr Thr Gly Lys
         35                  40                  45

Val Asp Ser Leu Leu Gly Ile Thr Ser Ala Asp Val Asp Val Arg Ala
     50                  55                  60

Asn Pro Leu Ala Ala Lys Gly Val Cys Thr Tyr Asn Asp Glu Gln Gly
 65                  70                  75                  80

Val Pro Phe Arg Val Gln Gly Asp Asn Ile Ser Val Lys Leu Phe Asp
             85                  90                  95

Asp Trp Ser Asn Leu Gly Ser Ile Ser Glu Leu Ser Thr Ser Arg Val
            100                 105                 110

Leu Asp Pro Ala Ala Gly Val Thr Gln Leu Leu Ser Gly Val Thr Asn
        115                 120                 125

Leu Gln Ala Gln Gly Thr Glu Val Ile Asp Gly Ile Ser Thr Thr Lys
130                 135                 140

Ile Thr Gly Thr Ile Pro Ala Ser Ser Val Lys Met Leu Asp Pro Gly
145                 150                 155                 160

Ala Lys Ser Ala Arg Pro Ala Thr Val Trp Ile Ala Gln Asp Gly Ser
                165                 170                 175

His His Leu Val Arg Ala Ser Ile Asp Leu Gly Ser Gly Ser Ile Gln
            180                 185                 190

Leu Thr Gln Ser Lys Trp Asn Glu Pro Val Asn Val Asp
        195                 200                 205
```

(2) INFORMATION FOR SEQ ID NO:81:

(i) SEQUENCE CHARACTERISTICS:
        (A) LENGTH: 286 amino acids
        (B) TYPE: amino acid
        (C) STRANDEDNESS: single
        (D) TOPOLOGY: linear (xi) SEQUENCE DESCRIPTION: SEQ ID NO:81:

```
Gly Asp Ser Phe Trp Ala Ala Asp Gln Met Ala Arg Gly Phe Val
 1               5                  10                  15

Leu Gly Ala Thr Ala Gly Arg Thr Thr Leu Thr Gly Glu Gly Leu Gln
             20                  25                  30

His Ala Asp Gly His Ser Leu Leu Asp Ala Thr Asn Pro Ala Val
         35                  40                  45

Val Ala Tyr Asp Pro Ala Phe Ala Tyr Glu Ile Gly Tyr Ile Xaa Glu
     50                  55                  60

Ser Gly Leu Ala Arg Met Cys Gly Glu Asn Pro Glu Asn Ile Phe Phe
 65                  70                  75                  80

Tyr Ile Thr Val Tyr Asn Glu Pro Tyr Val Gln Pro Pro Glu Pro Glu
             85                  90                  95
```

```
Asn Phe Asp Pro Glu Gly Val Leu Gly Gly Ile Tyr Arg Tyr His Ala
                100                 105                 110

Ala Thr Glu Gln Arg Thr Asn Lys Xaa Gln Ile Leu Ala Ser Gly Val
            115                 120                 125

Ala Met Pro Ala Ala Leu Arg Ala Ala Gln Met Leu Ala Ala Glu Trp
        130                 135                 140

Asp Val Ala Ala Asp Val Trp Ser Val Thr Ser Trp Gly Glu Leu Asn
145                 150                 155                 160

Arg Asp Gly Val Val Ile Glu Thr Glu Lys Leu Arg His Pro Asp Arg
                165                 170                 175

Pro Ala Gly Val Pro Tyr Val Thr Arg Ala Leu Glu Asn Ala Arg Gly
            180                 185                 190

Pro Val Ile Ala Val Ser Asp Trp Met Arg Ala Val Pro Glu Gln Ile
        195                 200                 205

Arg Pro Trp Val Pro Gly Thr Tyr Leu Thr Leu Gly Thr Asp Gly Phe
    210                 215                 220

Gly Phe Ser Asp Thr Arg Pro Ala Gly Arg Arg Tyr Phe Asn Thr Asp
225                 230                 235                 240

Ala Glu Ser Gln Val Gly Arg Gly Phe Gly Arg Gly Trp Pro Gly Arg
                245                 250                 255

Arg Val Asn Ile Asp Pro Phe Gly Ala Gly Arg Gly Pro Pro Ala Gln
            260                 265                 270

Leu Pro Gly Phe Asp Glu Gly Gly Leu Arg Pro Xaa Lys
        275                 280                 285

(2) INFORMATION FOR SEQ ID NO:82:

(i) SEQUENCE CHARACTERISTICS:
        (A) LENGTH: 173 amino acids
        (B) TYPE: amino acid
        (C) STRANDEDNESS: single
        (D) TOPOLOGY: linear (xi) SEQUENCE DESCRIPTION: SEQ ID NO:82:

Thr Lys Phe His Ala Leu Met Gln Glu Gln Ile His Asn Glu Phe Thr
1               5                   10                  15

Ala Ala Gln Gln Tyr Val Ala Ile Ala Val Tyr Phe Asp Ser Glu Asp
            20                  25                  30

Leu Pro Gln Leu Ala Lys His Phe Tyr Ser Gln Ala Val Glu Glu Arg
        35                  40                  45

Asn His Ala Met Met Leu Val Gln His Leu Leu Asp Arg Asp Leu Arg
    50                  55                  60

Val Glu Ile Pro Gly Val Asp Thr Val Arg Asn Gln Phe Asp Arg Pro
65                  70                  75                  80

Arg Glu Ala Leu Ala Leu Ala Leu Asp Gln Glu Arg Thr Val Thr Asp
                85                  90                  95

Gln Val Gly Arg Leu Thr Ala Val Ala Arg Asp Glu Gly Asp Phe Leu
            100                 105                 110

Gly Glu Gln Phe Met Gln Trp Phe Leu Gln Glu Gln Ile Glu Glu Val
        115                 120                 125

Ala Leu Met Ala Thr Leu Val Arg Val Ala Asp Arg Ala Gly Ala Asn
    130                 135                 140

Leu Phe Glu Leu Glu Asn Phe Val Ala Arg Glu Val Asp Val Ala Pro
145                 150                 155                 160

Ala Ala Ser Gly Ala Pro His Ala Ala Gly Gly Arg Leu
```

165            170

(2) INFORMATION FOR SEQ ID NO:83:

(i) SEQUENCE CHARACTERISTICS:
        (A) LENGTH: 107 amino acids
        (B) TYPE: amino acid
        (C) STRANDEDNESS: single
        (D) TOPOLOGY: linear (xi) SEQUENCE DESCRIPTION: SEQ ID NO:83:

```
Arg Ala Asp Glu Arg Lys Asn Thr Thr Met Lys Met Val Lys Ser Ile
 1               5                  10                  15

Ala Ala Gly Leu Thr Ala Ala Ala Ile Gly Ala Ala Ala Ala Gly
            20                  25                  30

Val Thr Ser Ile Met Ala Gly Gly Pro Val Val Tyr Gln Met Gln Pro
        35                  40                  45

Val Val Phe Gly Ala Pro Leu Pro Leu Asp Pro Xaa Ser Ala Pro Xaa
    50                  55                  60

Val Pro Thr Ala Ala Gln Trp Thr Xaa Leu Leu Asn Xaa Leu Xaa Asp
65                  70                  75                  80

Pro Asn Val Ser Phe Xaa Asn Lys Gly Ser Leu Val Glu Gly Gly Ile
                85                  90                  95

Gly Gly Xaa Glu Gly Xaa Xaa Arg Arg Xaa Gln
            100                 105
```

(2) INFORMATION FOR SEQ ID NO:84:

(i) SEQUENCE CHARACTERISTICS:
        (A) LENGTH: 125 amino acids
        (B) TYPE: amino acid
        (C) STRANDEDNESS: single
        (D) TOPOLOGY: linear (xi) SEQUENCE DESCRIPTION: SEQ ID NO:84:

```
Val Leu Ser Val Pro Val Gly Asp Gly Phe Trp Xaa Arg Val Val Asn
 1               5                  10                  15

Pro Leu Gly Gln Pro Ile Asp Gly Arg Gly Asp Val Asp Ser Asp Thr
            20                  25                  30

Arg Arg Ala Leu Glu Leu Gln Ala Pro Ser Val Val Xaa Arg Gln Gly
        35                  40                  45

Val Lys Glu Pro Leu Xaa Thr Gly Ile Lys Ala Ile Asp Ala Met Thr
    50                  55                  60

Pro Ile Gly Arg Gly Gln Arg Gln Leu Ile Ile Gly Asp Arg Lys Thr
65                  70                  75                  80

Gly Lys Asn Arg Arg Leu Cys Arg Thr Pro Ser Ser Asn Gln Arg Glu
                85                  90                  95

Glu Leu Gly Val Arg Trp Ile Pro Arg Ser Arg Cys Ala Cys Val Tyr
            100                 105                 110

Val Gly His Arg Ala Arg Arg Gly Thr Tyr His Arg Arg
            115                 120                 125
```

(2) INFORMATION FOR SEQ ID NO:85:

(i) SEQUENCE CHARACTERISTICS:
        (A) LENGTH: 117 amino acids
        (B) TYPE: amino acid
        (C) STRANDEDNESS: single
        (D) TOPOLOGY: linear (xi) SEQUENCE DESCRIPTION: SEQ ID NO:85:

```
Cys Asp Ala Val Met Gly Phe Leu Gly Gly Ala Gly Pro Leu Ala Val
 1               5                  10                  15

Val Asp Gln Gln Leu Val Thr Arg Val Pro Gln Gly Trp Ser Phe Ala
                20                  25                  30

Gln Ala Ala Ala Val Pro Val Val Phe Leu Thr Ala Trp Tyr Gly Leu
                35                  40                  45

Ala Asp Leu Ala Glu Ile Lys Ala Gly Glu Ser Val Leu Ile His Ala
            50                  55                  60

Gly Thr Gly Gly Val Gly Met Ala Ala Val Gln Leu Ala Arg Gln Trp
 65                  70                  75                  80

Gly Val Glu Val Phe Val Thr Ala Ser Arg Gly Lys Trp Asp Thr Leu
                85                  90                  95

Arg Ala Xaa Xaa Phe Asp Asp Xaa Pro Tyr Arg Xaa Phe Pro His Xaa
               100                 105                 110

Arg Ser Ser Xaa Gly
            115
```

(2) INFORMATION FOR SEQ ID NO:86:

(i) SEQUENCE CHARACTERISTICS:
        (A) LENGTH: 103 amino acids
        (B) TYPE: amino acid
        (C) STRANDEDNESS: single
        (D) TOPOLOGY: linear (xi) SEQUENCE DESCRIPTION: SEQ ID NO:86:

```
Met Tyr Arg Phe Ala Cys Arg Thr Leu Met Leu Ala Ala Cys Ile Leu
 1               5                  10                  15

Ala Thr Gly Val Ala Gly Leu Gly Val Gly Ala Gln Ser Ala Ala Gln
                20                  25                  30

Thr Ala Pro Val Pro Asp Tyr Tyr Trp Cys Pro Gly Gln Pro Phe Asp
                35                  40                  45

Pro Ala Trp Gly Pro Asn Trp Asp Pro Tyr Thr Cys His Asp Asp Phe
            50                  55                  60

His Arg Asp Ser Asp Gly Pro Asp His Ser Arg Asp Tyr Pro Gly Pro
 65                  70                  75                  80

Ile Leu Glu Gly Pro Val Leu Asp Pro Gly Ala Ala Pro Pro Pro
                85                  90                  95

Pro Ala Ala Gly Gly Gly Ala
            100
```

(2) INFORMATION FOR SEQ ID NO:87:

(i) SEQUENCE CHARACTERISTICS:
        (A) LENGTH: 88 amino acids
        (B) TYPE: amino acid
        (C) STRANDEDNESS: single
        (D) TOPOLOGY: linear (xi) SEQUENCE DESCRIPTION: SEQ ID NO:87:

```
Val Gln Cys Arg Val Trp Leu Glu Ile Gln Trp Arg Gly Met Leu Gly
 1               5                  10                  15

Ala Asp Gln Ala Arg Ala Gly Gly Pro Ala Arg Ile Trp Arg Glu His
                20                  25                  30

Ser Met Ala Ala Met Lys Pro Arg Thr Gly Asp Gly Pro Leu Glu Ala
                35                  40                  45

Thr Lys Glu Gly Arg Gly Ile Val Met Arg Val Pro Leu Glu Gly Gly
 50                  55                  60
```

```
Gly Arg Leu Val Val Glu Leu Thr Pro Asp Glu Ala Ala Ala Leu Gly
 65                  70                  75                  80

Asp Glu Leu Lys Gly Val Thr Ser
                85
```

(2) INFORMATION FOR SEQ ID NO:88:

(i) SEQUENCE CHARACTERISTICS:
        (A) LENGTH: 95 amino acids
        (B) TYPE: amino acid
        (C) STRANDEDNESS: single
        (D) TOPOLOGY: linear (xi) SEQUENCE DESCRIPTION: SEQ ID NO:88:

```
Thr Asp Ala Ala Thr Leu Ala Gln Glu Ala Gly Asn Phe Glu Arg Ile
 1               5                  10                  15

Ser Gly Asp Leu Lys Thr Gln Ile Asp Gln Val Glu Ser Thr Ala Gly
                20                  25                  30

Ser Leu Gln Gly Gln Trp Arg Gly Ala Ala Gly Thr Ala Ala Gln Ala
                35                  40                  45

Ala Val Val Arg Phe Gln Glu Ala Ala Asn Lys Gln Lys Gln Glu Leu
 50                  55                  60

Asp Glu Ile Ser Thr Asn Ile Arg Gln Ala Gly Val Gln Tyr Ser Arg
 65                  70                  75                  80

Ala Asp Glu Glu Gln Gln Gln Ala Leu Ser Ser Gln Met Gly Phe
                85                  90                  95
```

(2) INFORMATION FOR SEQ ID NO:89:

(i) SEQUENCE CHARACTERISTICS:
        (A) LENGTH: 166 amino acids
        (B) TYPE: amino acid
        (C) STRANDEDNESS: single
        (D) TOPOLOGY: linear (xi) SEQUENCE DESCRIPTION: SEQ ID NO:89:

```
Met Thr Gln Ser Gln Thr Val Thr Val Asp Gln Gln Glu Ile Leu Asn
 1               5                  10                  15

Arg Ala Asn Glu Val Glu Ala Pro Met Ala Asp Pro Pro Thr Asp Val
                20                  25                  30

Pro Ile Thr Pro Cys Glu Leu Thr Xaa Xaa Lys Asn Ala Ala Gln Gln
                35                  40                  45

Xaa Val Leu Ser Ala Asp Asn Met Arg Glu Tyr Leu Ala Ala Gly Ala
     50                  55                  60

Lys Glu Arg Gln Arg Leu Ala Thr Ser Leu Arg Asn Ala Ala Lys Xaa
 65                  70                  75                  80

Tyr Gly Glu Val Asp Glu Glu Ala Ala Thr Ala Leu Asp Asn Asp Gly
                85                  90                  95

Glu Gly Thr Val Gln Ala Glu Ser Ala Gly Ala Val Gly Gly Asp Ser
                100                 105                 110

Ser Ala Glu Leu Thr Asp Thr Pro Arg Val Ala Thr Ala Gly Glu Pro
                115                 120                 125

Asn Phe Met Asp Leu Lys Glu Ala Ala Arg Lys Leu Glu Thr Gly Asp
                130                 135                 140

Gln Gly Ala Ser Leu Ala His Xaa Gly Asp Gly Trp Asn Thr Xaa Thr
145                 150                 155                 160

Leu Thr Leu Gln Gly Asp
                165
```

(2) INFORMATION FOR SEQ ID NO:90:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:90:

```
Arg Ala Glu Arg Met
1               5
```

(2) INFORMATION FOR SEQ ID NO:91:

(i) SEQUENCE CHARACTERISTICS:
        (A) LENGTH: 263 amino acids
        (B) TYPE: amino acid
        (C) STRANDEDNESS: single
        (D) TOPOLOGY: linear (xi) SEQUENCE DESCRIPTION: SEQ ID NO:91:

```
Val Ala Trp Met Ser Val Thr Ala Gly Gln Ala Glu Leu Thr Ala Ala
1               5                   10                  15

Gln Val Arg Val Ala Ala Ala Tyr Glu Thr Ala Tyr Gly Leu Thr
            20                  25                  30

Val Pro Pro Pro Val Ile Ala Glu Asn Arg Ala Glu Leu Met Ile Leu
            35                  40                  45

Ile Ala Thr Asn Leu Leu Gly Gln Asn Thr Pro Ala Ile Ala Val Asn
        50                  55                  60

Glu Ala Glu Tyr Gly Glu Met Trp Ala Gln Asp Ala Ala Met Phe
65                  70                  75                  80

Gly Tyr Ala Ala Ala Thr Ala Thr Ala Thr Leu Leu Pro Phe
                85                  90                  95

Glu Glu Ala Pro Glu Met Thr Ser Ala Gly Gly Leu Leu Glu Gln Ala
                100                 105                 110

Ala Ala Val Glu Glu Ala Ser Asp Thr Ala Ala Ala Asn Gln Leu Met
            115                 120                 125

Asn Asn Val Pro Gln Ala Leu Lys Gln Leu Ala Gln Pro Thr Gln Gly
130                 135                 140

Thr Thr Pro Ser Ser Lys Leu Gly Gly Leu Trp Lys Thr Val Ser Pro
145                 150                 155                 160

His Arg Ser Pro Ile Ser Asn Met Val Ser Met Ala Asn Asn His Met
                165                 170                 175

Ser Met Thr Asn Ser Gly Val Ser Met Thr Asn Thr Leu Ser Ser Met
                180                 185                 190

Leu Lys Gly Phe Ala Pro Ala Ala Ala Gln Ala Val Gln Thr Ala
            195                 200                 205

Ala Gln Asn Gly Val Arg Ala Met Ser Ser Leu Gly Ser Ser Leu Gly
210                 215                 220

Ser Ser Gly Leu Gly Gly Val Ala Ala Asn Leu Gly Arg Ala Ala
225                 230                 235                 240

Ser Val Arg Tyr Gly His Arg Asp Gly Gly Lys Tyr Ala Xaa Ser Gly
                245                 250                 255

Arg Arg Asn Gly Gly Pro Ala
            260
```

(2) INFORMATION FOR SEQ ID NO:92:

(i) SEQUENCE CHARACTERISTICS:
        (A) LENGTH: 303 amino acids
        (B) TYPE: amino acid
        (C) STRANDEDNESS: single
        (D) TOPOLOGY: linear (xi) SEQUENCE DESCRIPTION: SEQ ID NO:92:

```
Met Thr Tyr Ser Pro Gly Asn Pro Gly Tyr Pro Gln Ala Gln Pro Ala
 1               5                  10                  15

Gly Ser Tyr Gly Gly Val Thr Pro Ser Phe Ala His Ala Asp Glu Gly
                20                  25                  30

Ala Ser Lys Leu Pro Met Tyr Leu Asn Ile Ala Val Ala Val Leu Gly
            35                  40                  45

Leu Ala Ala Tyr Phe Ala Ser Phe Gly Pro Met Phe Thr Leu Ser Thr
 50                  55                  60

Glu Leu Gly Gly Asp Gly Ala Val Ser Gly Asp Thr Gly Leu Pro
 65                  70                  75                  80

Val Gly Val Ala Leu Leu Ala Ala Leu Leu Ala Gly Val Val Leu Val
                85                  90                  95

Pro Lys Ala Lys Ser His Val Thr Val Val Ala Val Leu Gly Val Leu
                100                 105                 110

Gly Val Phe Leu Met Val Ser Ala Thr Phe Asn Lys Pro Ser Ala Tyr
                115                 120                 125

Ser Thr Gly Trp Ala Leu Trp Val Val Leu Ala Phe Ile Val Phe Gln
    130                 135                 140

Ala Val Ala Ala Val Leu Ala Leu Leu Val Glu Thr Gly Ala Ile Thr
145                 150                 155                 160

Ala Pro Ala Pro Arg Pro Lys Phe Asp Pro Tyr Gly Gln Tyr Gly Arg
                165                 170                 175

Tyr Gly Gln Tyr Gly Gln Tyr Gly Val Gln Pro Gly Tyr Tyr Gly
                180                 185                 190

Gln Gln Gly Ala Gln Gln Ala Ala Gly Leu Gln Ser Pro Gly Pro Gln
            195                 200                 205

Gln Ser Pro Gln Pro Pro Gly Tyr Gly Ser Gln Tyr Gly Gly Tyr Ser
    210                 215                 220

Ser Ser Pro Ser Gln Ser Gly Ser Gly Tyr Thr Ala Gln Pro Pro Ala
225                 230                 235                 240

Gln Pro Pro Ala Gln Ser Gly Ser Gln Gln Ser His Gln Gly Pro Ser
                245                 250                 255

Thr Pro Pro Thr Gly Phe Pro Ser Phe Ser Pro Pro Pro Val Ser
                260                 265                 270

Ala Gly Thr Gly Ser Gln Ala Gly Ser Ala Pro Val Asn Tyr Ser Asn
                275                 280                 285

Pro Ser Gly Gly Glu Gln Ser Ser Pro Gly Gly Ala Pro Val
    290                 295                 300
```

(2) INFORMATION FOR SEQ ID NO:93:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:93:

```
Gly Cys Gly Glu Thr Asp Ala Ala Thr Leu Ala Gln Glu Ala Gly Asn
 1               5                  10                  15
```

```
Phe Glu Arg Ile Ser Gly Asp Leu Lys Thr Gln Ile
            20                  25
```

(2) INFORMATION FOR SEQ ID NO:94:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:94:

```
Asp Gln Val Glu Ser Thr Ala Gly Ser Leu Gln Gly Gln Trp Arg Gly
1               5                   10                  15
```

(2) INFORMATION FOR SEQ ID NO:95:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:95:

```
Gly Cys Gly Ser Thr Ala Gly Ser Leu Gln Gly Gln Trp Arg Gly Ala
1               5                   10                  15
Ala Gly Thr Ala Ala Gln Ala Ala Val Val Arg
            20                  25
```

(2) INFORMATION FOR SEQ ID NO:96:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:96:

```
Gly Cys Gly Gly Thr Ala Ala Gln Ala Ala Val Val Arg Phe Gln Glu
1               5                   10                  15
Ala Ala Asn Lys Gln Lys Gln Glu Leu Asp Glu
            20                  25
```

(2) INFORMATION FOR SEQ ID NO:97:

(i) SEQUENCE CHARACTERISTICS:
        (A) LENGTH: 27 amino acids
        (B) TYPE: amino acid
        (C) STRANDEDNESS: single
        (D) TOPOLOGY: linear (xi) SEQUENCE DESCRIPTION: SEQ ID NO:97:

```
Gly Cys Gly Ala Asn Lys Gln Lys Gln Glu Leu Asp Glu Ile Ser Thr
1               5                   10                  15
Asn Ile Arg Gln Ala Gly Val Gln Tyr Ser Arg
            20                  25
```

(2) INFORMATION FOR SEQ ID NO:98:

(i) SEQUENCE CHARACTERISTICS:
        (A) LENGTH: 28 amino acids
        (B) TYPE: amino acid
        (C) STRANDEDNESS: single
        (D) TOPOLOGY: linear (xi) SEQUENCE DESCRIPTION: SEQ ID NO:98:

Gly Cys Gly Ile Arg Gln Ala Gly Val Gln Tyr Ser Arg Ala Asp Glu
1               5                   10                  15

Glu Gln Gln Gln Ala Leu Ser Ser Gln Met Gly Phe
            20                  25

(2) INFORMATION FOR SEQ ID NO:99:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:99:

ATGAAGATGG TGAAATCGAT CGCCGCAGGT CTGACCGCCG CGGCTGCAAT CGGCGCCGCT      60

GCGGCCGGTG TGACTTCGAT CATGGCTGGC GGCCCGGTCG TATACCAGAT GCAGCCGGTC     120

GTCTTCGGCG CGCCACTGCC GTTGGACCCG GCATCCGCCC CTGACGTCCC GACCGCCGCC     180

CAGTTGACCA GCCTGCTCAA CAGCCTCGCC GATCCCAACG TGTCGTTTGC GAACAAGGGC     240

AGTCTGGTCG AGGGCGGCAT CGGGGGCACC GAGGCGCGCA TCGCCGACCA CAAGCTGAAG     300

AAGGCCGCCG AGCACGGGGA TCTGCCGCTG TCGTTCAGCG TGACGAACAT CCAGCCGGCG     360

GCCGCCGGTT CGGCCACCGC CGACGTTTCC GTCTCGGGTC CGAAGCTCTC GTCGCCGGTC     420

ACGCAGAACG TCACGTTCGT GAATCAAGGC GGCTGGATGC TGTCACGCGC ATCGGCGATG     480

GAGTTGCTGC AGGCCGCAGG GAACTGA                                        507

(2) INFORMATION FOR SEQ ID NO:100:

(i) SEQUENCE CHARACTERISTICS:
        (A) LENGTH: 168 amino acids
        (B) TYPE: amino acid
        (C) STRANDEDNESS: single
        (D) TOPOLOGY: linear (xi) SEQUENCE DESCRIPTION: SEQ ID NO:100:

Met Lys Met Val Lys Ser Ile Ala Ala Gly Leu Thr Ala Ala Ala Ala
1               5                   10                  15

Ile Gly Ala Ala Ala Ala Gly Val Thr Ser Ile Met Ala Gly Gly Pro
            20                  25                  30

Val Val Tyr Gln Met Gln Pro Val Val Phe Gly Ala Pro Leu Pro Leu
        35                  40                  45

Asp Pro Ala Ser Ala Pro Asp Val Pro Thr Ala Ala Gln Leu Thr Ser
    50                  55                  60

Leu Leu Asn Ser Leu Ala Asp Pro Asn Val Ser Phe Ala Asn Lys Gly
65                  70                  75                  80

Ser Leu Val Glu Gly Gly Ile Gly Gly Thr Glu Ala Arg Ile Ala Asp
                85                  90                  95

His Lys Leu Lys Lys Ala Ala Glu His Gly Asp Leu Pro Leu Ser Phe
            100                 105                 110

Ser Val Thr Asn Ile Gln Pro Ala Ala Ala Gly Ser Ala Thr Ala Asp
        115                 120                 125

Val Ser Val Ser Gly Pro Lys Leu Ser Ser Pro Val Thr Gln Asn Val
    130                 135                 140

Thr Phe Val Asn Gln Gly Gly Trp Met Leu Ser Arg Ala Ser Ala Met
145                 150                 155                 160

Glu Leu Leu Gln Ala Ala Gly Asn
                165

(2) INFORMATION FOR SEQ ID NO:101:

(i) SEQUENCE CHARACTERISTICS:
        (A) LENGTH: 500 base pairs
        (B) TYPE: nucleic acid
        (C) STRANDEDNESS: single
        (D) TOPOLOGY: linear (xi) SEQUENCE DESCRIPTION: SEQ ID NO:101:

```
CGTGGCAATG TCGTTGACCG TCGGGGCCGG GGTCGCCTCC GCAGATCCCG TGGACGCGGT    60

CATTAACACC ACCTGCAATT ACGGGCAGGT AGTAGCTGCG CTCAACGCGA CGGATCCGGG   120

GGCTGCCGCA CAGTTCAACG CCTCACCGGT GGCGCAGTCC TATTTGCGCA ATTTCCTCGC   180

CGCACCGCCA CCTCAGCGCG CTGCCATGGC CGCGCAATTG CAAGCTGTGC CGGGGGCGGC   240

ACAGTACATC GGCCTTGTCG AGTCGGTTGC CGGCTCCTGC AACAACTATT AAGCCCATGC   300

GGGCCCCATC CCGCGACCCG GCATCGTCGC CGGGGCTAGG CCAGATTGCC CCGCTCCTCA   360

ACGGGCCGCA TCCCGCGACC CGGCATCGTC GCCGGGGCTA GGCCAGATTG CCCCGCTCCT   420

CAACGGGCCG CATCTCGTGC CGAATTCCTG CAGCCCGGGG GATCCACTAG TTCTAGAGCG   480

GCCGCCACCG CGGTGGAGCT                                              500
```

(2) INFORMATION FOR SEQ ID NO:102:

(i) SEQUENCE CHARACTERISTICS:
        (A) LENGTH: 96 amino acids
        (B) TYPE: amino acid
        (C) STRANDEDNESS: single
        (D) TOPOLOGY: linear (xi) SEQUENCE DESCRIPTION: SEQ ID NO:102:

```
Val Ala Met Ser Leu Thr Val Gly Ala Gly Val Ala Ser Ala Asp Pro
1               5                  10                  15

Val Asp Ala Val Ile Asn Thr Thr Cys Asn Tyr Gly Gln Val Val Ala
                20                  25                  30

Ala Leu Asn Ala Thr Asp Pro Gly Ala Ala Ala Gln Phe Asn Ala Ser
            35                  40                  45

Pro Val Ala Gln Ser Tyr Leu Arg Asn Phe Leu Ala Ala Pro Pro Pro
        50                  55                  60

Gln Arg Ala Ala Met Ala Ala Gln Leu Gln Ala Val Pro Gly Ala Ala
65                  70                  75                  80

Gln Tyr Ile Gly Leu Val Glu Ser Val Ala Gly Ser Cys Asn Asn Tyr
                85                  90                  95
```

(2) INFORMATION FOR SEQ ID NO:103:

(i) SEQUENCE CHARACTERISTICS:
        (A) LENGTH: 154 base pairs
        (B) TYPE: nucleic acid
        (C) STRANDEDNESS: single
        (D) TOPOLOGY: linear (xi) SEQUENCE DESCRIPTION: SEQ ID NO:103:

```
ATGACAGAGC AGCAGTGGAA TTTCGCGGGT ATCGAGGCCG CGGCAAGCGC AATCCAGGGA    60

AATGTCACGT CCATTCATTC CCTCCTTGAC GAGGGGAAGC AGTCCCTGAC CAAGCTCGCA   120

GCGGCCTGGG GCGGTAGCGG TTCGGAAGCG TACC                              154
```

(2) INFORMATION FOR SEQ ID NO:104:

(i) SEQUENCE CHARACTERISTICS:
    (A) LENGTH: 51 amino acids
    (B) TYPE: amino acid
    (C) STRANDEDNESS: single
    (D) TOPOLOGY: linear (xi) SEQUENCE DESCRIPTION: SEQ ID NO:104:

```
Met Thr Glu Gln Gln Trp Asn Phe Ala Gly Ile Glu Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr
    50
```

(2) INFORMATION FOR SEQ ID NO:105:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (xi) SEQUENCE DESCRIPTION: SEQ ID NO:105:

| | | | | | |
|---|---|---|---|---|---|
| CGGTCGCGCA | CTTCCAGGTG | ACTATGAAAG | TCGGCTTCCG | NCTGGAGGAT | TCCTGAACCT | 60 |
| TCAAGCGCGG | CCGATAACTG | AGGTGCATCA | TTAAGCGACT | TTTCCAGAAC | ATCCTGACGC | 120 |
| GCTCGAAACG | CGGCACAGCC | GACGGTGGCT | CCGNCGAGGC | GCTGNCTCCA | AAATCCCTGA | 180 |
| GACAATTCGN | CGGGGCGCC | TACAAGGAAG | TCGGTGCTGA | ATTCGNCGNG | TATCTGGTCG | 240 |
| ACCTGTGTGG | TCTGNAGCCG | GACGAAGCGG | TGCTCGACGT | CG | | 282 |

(2) INFORMATION FOR SEQ ID NO:106:

(i) SEQUENCE CHARACTERISTICS:
        (A) LENGTH: 3058 base pairs
        (B) TYPE: nucleic acid
        (C) STRANDEDNESS: single
        (D) TOPOLOGY: linear (xi) SEQUENCE DESCRIPTION: SEQ ID NO:106:

| | | | | | |
|---|---|---|---|---|---|
| GATCGTACCC | GTGCGAGTGC | TCGGGCCGTT | TGAGGATGGA | GTGCACGTGT | CTTTCGTGAT | 60 |
| GGCATACCCA | GAGATGTTGG | CGGCGGCGGC | TGACACCCTG | CAGAGCATCG | GTGCTACCAC | 120 |
| TGTGGCTAGC | AATGCCGCTG | CGGCGGCCCC | GACGACTGGG | GTGGTGCCCC | CCGCTGCCGA | 180 |
| TGAGGTGTCG | GCGCTGACTG | CGGCGCACTT | CGCCGCACAT | GCGGCGATGT | ATCAGTCCGT | 240 |
| GAGCGCTCGG | GCTGCTGCGA | TTCATGACCA | GTTCGTGGCC | ACCCTTGCCA | GCAGCGCCAG | 300 |
| CTCGTATGCG | GCCACTGAAG | TCGCCAATGC | GGCGGCGGCC | AGCTAAGCCA | GGAACAGTCG | 360 |
| GCACGAGAAA | CCACGAGAAA | TAGGGACACG | TAATGGTGGA | TTTCGGGGCG | TTACCACCGG | 420 |
| AGATCAACTC | CGCGAGGATG | TACGCCGGCC | CGGGTTCGGC | CTCGCTGGTG | GCCGCGGCTC | 480 |
| AGATGTGGGA | CAGCGTGGCG | AGTGACCTGT | TTTCGCCGCC | GTCGGCGTTT | CAGTCGGTGG | 540 |
| TCTGGGGTCT | GACGGTGGGG | TCGTGGATAG | GTTCGTCGGC | GGGTCTGATG | GTGGCGGCGG | 600 |
| CCTCGCCGTA | TGTGGCGTGG | ATGAGCGTCA | CCGCGGGGCA | GGCCGAGCTG | ACCGCCGCCC | 660 |
| AGGTCCGGGT | TGCTCGGGCG | GCCTACGAGA | CGGCGTATGG | GCTGACGGTG | CCCCCGCCGG | 720 |
| TGATCGCCGA | GAACCGTGCT | GAACTGATGA | TTCTGATAGC | GACCAACCTC | TTGGGGCAAA | 780 |
| ACACCCCGGC | GATCGCGGTC | AACGAGGCCG | AATACGGCGA | GATGTGGGCC | CAAGACGCCG | 840 |

```
CCGCGATGTT TGGCTACGCC GCGGCGACGG CGACGGCGAC GGCGACGTTG CTGCCGTTCG    900
AGGAGGCGCC GGAGATGACC AGCGCGGGTG GGCTCCTCGA GCAGGCCGCC GCGGTCGAGG    960
AGGCCTCCGA CACCGCCGCG GCGAACCAGT TGATGAACAA TGTGCCCCAG GCGCTGCAAC   1020
AGCTGGCCCA GCCCACGCAG GGCACCACGC CTTCTTCCAA GCTGGGTGGC CTGTGGAAGA   1080
CGGTCTCGCC GCATCGGTCG CCGATCAGCA ACATGGTGTC GATGGCCAAC AACCACATGT   1140
CGATGACCAA CTCGGGTGTG TCGATGACCA ACACCTTGAG CTCGATGTTG AAGGGCTTTG   1200
CTCCGGCGGC GGCCGCCCAG GCCGTGCAAA CCGCGGCGCA AAACGGGGTC CGGGCGATGA   1260
GCTCGCTGGG CAGCTCGCTG GGTTCTTCGG GTCTGGGCGG TGGGGTGGCC GCCAACTTGG   1320
GTCGGGCGGC CTCGGTCGGT TCGTTGTCGG TGCCGCAGGC CTGGGCCGCG GCCAACCAGG   1380
CAGTCACCCC GGCGGCGCGG GCGCTGCCGC TGACCAGCCT GACCAGCGCC GCGGAAAGAG   1440
GGCCCGGGCA GATGCTGGGC GGGCTGCCGG TGGGGCAGAT GGGCGCCAGG GCCGGTGGTG   1500
GGCTCAGTGG TGTGCTGCGT GTTCCGCCGC GACCCTATGT GATGCCGCAT TCTCCGGCGG   1560
CCGGCTAGGA GAGGGGCGC  AGACTGTCGT TATTTGACCA GTGATCGGCG GTCTCGGTGT   1620
TTCCGCGGCC GGCTATGACA ACAGTCAATG TGCATGACAA GTTACAGGTA TTAGGTCCAG   1680
GTTCAACAAG GAGACAGGCA ACATGGCCTC ACGTTTTATG ACGGATCCGC ACGCGATGCG   1740
GGACATGGCG GGCCGTTTTG AGGTGCACGC CCAGACGGTG GAGGACGAGG CTCGCCGGAT   1800
GTGGGCGTCC GCGCAAAACA TTTCCGGTGC GGGCTGGAGT GGCATGGCCG AGGCGACCTC   1860
GCTAGACACC ATGGCCCAGA TGAATCAGGC GTTTCGCAAC ATCGTGAACA TGCTGCACGG   1920
GGTGCGTGAC GGGCTGGTTC GCGACGCCAA CAACTACGAG CAGCAAGAGC AGGCCTCCCA   1980
GCAGATCCTC AGCAGCTAAC GTCAGCCGCT GCAGCACAAT ACTTTTACAA GCGAAGGAGA   2040
ACAGGTTCGA TGACCATCAA CTATCAATTC GGGGATGTCG ACGCTCACGG CGCCATGATC   2100
CGCGCTCAGG CCGGGTTGCT GGAGGCCGAG CATCAGGCCA TCATTCGTGA TGTGTTGACC   2160
GCGAGTGACT TTTGGGGCGG CGCCGGTTCG GCGGCCTGCC AGGGGTTCAT TACCCAGTTG   2220
GGCCGTAACT TCCAGGTGAT CTACGAGCAG GCCAACGCCC ACGGGCAGAA GGTGCAGGCT   2280
GCCGGCAACA ACATGGCGCA AACCGACAGC GCCGTCGGCT CCAGCTGGGC CTGACACCAG   2340
GCCAAGGCCA GGGACGTGGT GTACGAGTGA AGTTCCTCGC GTGATCCTTC GGGTGGCAGT   2400
CTAAGTGGTC AGTGCTGGGG TGTTGGTGGT TTGCTGCTTG GCGGGTTCTT CGGTGCTGGT   2460
CAGTGCTGCT CGGGCTCGGG TGAGGACCTC GAGGCCCAGG TAGCGCCGTC CTTCGATCCA   2520
TTCGTCGTGT TGTTCGGCGA GGACGGCTCC GACGAGGCGG ATGATCGAGG CGCGGTCGGG   2580
GAAGATGCCC ACGACGTCGG TTCGGCGTCG TACCTCTCGG TTGAGGCGTT CCTGGGGGTT   2640
GTTGGACCAG ATTTGGCGCC AGATCTGCTT GGGGAAGGCG GTGAACGCCA GCAGGTCGGT   2700
GCGGGCGGTG TCGAGGTGCT CGGCCACCGC GGGGAGTTTG TCGGTCAGAG CGTCGAGTAC   2760
CCGATCATAT TGGGCAACAA CTGATTCGGC GTCGGCTGG  TCGTAGATGG AGTGCAGCAG   2820
GGTGCGCACC CACGGCCAGG AGGGCTTCGG GGTGGCTGCC ATCAGATTGG CTGCGTAGTG   2880
GGTTCTGCAG CGCTGCCAGG CCGCTGCGGG CAGGGTGGCG CCGATCGCGG CCACCAGGCC   2940
GGCGTGGGCG TCGCTGGTGA CCAGCGCGAC CCCGACAGG  CCGCGGGCGA CCAGGTCGCG   3000
GAAGAACGCC AGCCAGCCGG CCCCGTCCTC GGCGGAGGTG ACCTGGATGC CCAGGATC    3058
```

(2) INFORMATION FOR SEQ ID NO:107:

(i) SEQUENCE CHARACTERISTICS:

(A) LENGTH: 391 amino acids
(B) TYPE: amino acid
(C) STRANDEDNESS: single
(D) TOPOLOGY: linear (xi) SEQUENCE DESCRIPTION: SEQ ID NO:107:

```
Met Val Asp Phe Gly Ala Leu Pro Pro Glu Ile Asn Ser Ala Arg Met
  1               5                  10                  15

Tyr Ala Gly Pro Gly Ser Ala Ser Leu Val Ala Ala Gln Met Trp
             20                  25                  30

Asp Ser Val Ala Ser Asp Leu Phe Ser Ala Ala Ser Ala Phe Gln Ser
             35                  40                  45

Val Val Trp Gly Leu Thr Val Gly Ser Trp Ile Gly Ser Ser Ala Gly
 50                  55                  60

Leu Met Val Ala Ala Ser Pro Tyr Val Ala Trp Met Ser Val Thr
 65                  70                  75                  80

Ala Gly Gln Ala Glu Leu Thr Ala Ala Gln Val Arg Val Ala Ala Ala
                 85                  90                  95

Ala Tyr Glu Thr Ala Tyr Gly Leu Thr Val Pro Pro Pro Val Ile Ala
                100                 105                 110

Glu Asn Arg Ala Glu Leu Met Ile Leu Ile Ala Thr Asn Leu Leu Gly
                115                 120                 125

Gln Asn Thr Pro Ala Ile Ala Val Asn Glu Ala Glu Tyr Gly Glu Met
            130                 135                 140

Trp Ala Gln Asp Ala Ala Ala Met Phe Gly Tyr Ala Ala Ala Thr Ala
145                 150                 155                 160

Thr Ala Thr Ala Thr Leu Leu Pro Phe Glu Glu Ala Pro Glu Met Thr
                165                 170                 175

Ser Ala Gly Gly Leu Leu Glu Gln Ala Ala Ala Val Glu Glu Ala Ser
                180                 185                 190

Asp Thr Ala Ala Ala Asn Gln Leu Met Asn Asn Val Pro Gln Ala Leu
                195                 200                 205

Gln Gln Leu Ala Gln Pro Thr Gln Gly Thr Thr Pro Ser Ser Lys Leu
            210                 215                 220

Gly Gly Leu Trp Lys Thr Val Ser Pro His Arg Ser Pro Ile Ser Asn
225                 230                 235                 240

Met Val Ser Met Ala Asn Asn His Met Ser Met Thr Asn Ser Gly Val
                245                 250                 255

Ser Met Thr Asn Thr Leu Ser Ser Met Leu Lys Gly Phe Ala Pro Ala
                260                 265                 270

Ala Ala Ala Gln Ala Val Gln Thr Ala Ala Gln Asn Gly Val Arg Ala
            275                 280                 285

Met Ser Ser Leu Gly Ser Ser Leu Gly Ser Ser Gly Leu Gly Gly Gly
            290                 295                 300

Val Ala Ala Asn Leu Gly Arg Ala Ala Ser Val Gly Ser Leu Ser Val
305                 310                 315                 320

Pro Gln Ala Trp Ala Ala Ala Asn Gln Ala Val Thr Pro Ala Ala Arg
                325                 330                 335

Ala Leu Pro Leu Thr Ser Leu Thr Ser Ala Ala Glu Arg Gly Pro Gly
                340                 345                 350

Gln Met Leu Gly Gly Leu Pro Val Gly Gln Met Gly Ala Arg Ala Gly
            355                 360                 365

Gly Gly Leu Ser Gly Val Leu Arg Val Pro Pro Arg Pro Tyr Val Met
370                 375                 380
```

Pro His Ser Pro Ala Ala Gly
385             390

(2) INFORMATION FOR SEQ ID NO:108:

(i) SEQUENCE CHARACTERISTICS:
        (A) LENGTH: 1725 base pairs
        (B) TYPE: nucleic acid
        (C) STRANDEDNESS: single
        (D) TOPOLOGY: linear (xi) SEQUENCE DESCRIPTION: SEQ ID NO:108:

```
GACGTCAGCA CCCGCCGTGC AGGGCTGGAG CGTGGTCGGT TTTGATCTGC GGTCAAGGTG      60
ACGTCCCTCG GCGTGTCGCC GGCGTGGATG CAGACTCGAT GCCGCTCTTT AGTGCAACTA     120
ATTTCGTTGA AGTGCCTGCG AGGTATAGGA CTTCACGATT GGTTAATGTA GCGTTCACCC     180
CGTGTTGGGG TCGATTTGGC CGGACCAGTC GTCACCAACG CTTGGCGTGC GCGCCAGGCG     240
GGCGATCAGA TCGCTTGACT ACCAATCAAT CTTGAGCTCC CGGGCCGATG CTCGGGCTAA     300
ATGAGGAGGA GCACGCGTGT CTTTCACTGC GCAACCGGAG ATGTTGGCGG CCGCGGCTGG     360
CGAACTTCGT TCCCTGGGGG CAACGCTGAA GGCTAGCAAT GCCGCCGCAG CCGTGCCGAC     420
GACTGGGGTG GTGCCCCCGG CTGCCGACGA GGTGTCGCTG CTGCTTGCCA CACAATTCCG     480
TACGCATGCG GCGACGTATC AGACGGCCAG CGCCAAGGCC GCGGTGATCC ATGAGCAGTT     540
TGTGACCACG CTGGCCACCA GCGCTAGTTC ATATGCGGAC ACCGAGGCCG CCAACGCTGT     600
GGTCACCGGC TAGCTGACCT GACGGTATTC GAGCGGAAGG ATTATCGAAG TGGTGGATTT     660
CGGGGCGTTA CCACCGGAGA TCAACTCCGC GAGGATGTAC GCCGGCCCGG GTTCGGCCTC     720
GCTGGTGGCC GCCGCGAAGA TGTGGGACAG CGTGGCGAGT GACCTGTTTT CGGCCGCGTC     780
GGCGTTTCAG TCGGTGGTCT GGGGTCTGAC GGTGGGGTCG TGGATAGGTT CGTCGGCGGG     840
TCTGATGGCG GCGGCGGCCT CGCCGTATGT GGCGTGGATG AGCGTCACCG CGGGGCAGGC     900
CCAGCTGACC GCCGCCCAGG TCCGGGTTGC TGCGGCGGCC TACGAGACAG CGTATAGGCT     960
GACGGTGCCC CCGCCGGTGA TCGCCGAGAA CCGTACCGAA CTGATGACGC TGACCGCGAC    1020
CAACCTCTTG GGGCAAAACA CGCCGGCGAT CGAGGCCAAT CAGGCCGCAT ACAGCCAGAT    1080
GTGGGGCCAA GACGCGGAGG CGATGTATGG CTACGCCGCC ACGGCGGCGA CGGCGACCGA    1140
GGCGTTGCTG CCGTTCGAGG ACGCCCCACT GATCACCAAC CCCGGCGGGC TCCTTGAGCA    1200
GGCCGTCGCG GTCGAGGAGG CCATCGACAC CGCCGCGGCG AACCAGTTGA TGAACAATGT    1260
GCCCCAAGCG CTGCAACAGC TGGCCCAGCC AGCGCAGGGC GTCGTACCTT CTTCCAAGCT    1320
GGGTGGGCTG TGGACGGCGG TCTCGCCGCA TCTGTCGCCG CTCAGCAACG TCAGTTCGAT    1380
AGCCAACAAC CACATGTCGA TGATGGGCAC GGGTGTGTCG ATGACCAACA CCTTGCACTC    1440
GATGTTGAAG GGCTTAGCTC CGGCGGCGGC TCAGGCCGTG GAAACCGCGG CGGAAAACGG    1500
GGTCTGGGCG ATGAGCTCGC TGGGCAGCCA GCTGGGTTCG TCGCTGGGTT CTTCGGGTCT    1560
GGGCGCTGGG GTGGCCGCCA ACTTGGGTCG GGCGGCCTCG GTCGGTTCGT TGTCGGTGCC    1620
GCCAGCATGG GCCGCGGCCA ACCAGGCGGT CACCCCGGCG GCGCGGGCGC TGCCGCTGAC    1680
CAGCCTGACC AGCGCCGCCC AAACCGCCCC CGGACACATG CTGGG                   1725
```

(2) INFORMATION FOR SEQ ID NO:109:

(i) SEQUENCE CHARACTERISTICS:
        (A) LENGTH: 359 amino acids
        (B) TYPE: amino acid
        (C) STRANDEDNESS:

(D) TOPOLOGY: linear (xi) SEQUENCE DESCRIPTION: SEQ ID NO:109:

```
Val Val Asp Phe Gly Ala Leu Pro Pro Glu Ile Asn Ser Ala Arg Met
1               5                   10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
            35                  40                  45

Val Val Trp Gly Leu Thr Val Gly Ser Trp Ile Gly Ser Ser Ala Gly
50                  55                  60

Leu Met Ala Ala Ala Ser Pro Tyr Val Ala Trp Met Ser Val Thr
65                  70                  75                  80

Ala Gly Gln Ala Gln Leu Thr Ala Ala Gln Val Arg Val Ala Ala Ala
                85                  90                  95

Ala Tyr Glu Thr Ala Tyr Arg Leu Thr Val Pro Pro Val Ile Ala
                100                 105                 110

Glu Asn Arg Thr Glu Leu Met Thr Leu Thr Ala Thr Asn Leu Leu Gly
            115                 120                 125

Gln Asn Thr Pro Ala Ile Glu Ala Asn Gln Ala Ala Tyr Ser Gln Met
130                 135                 140

Trp Gly Gln Asp Ala Glu Ala Met Tyr Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
            195                 200                 205

Gln Gln Leu Ala Gln Pro Ala Gln Gly Val Val Pro Ser Ser Lys Leu
        210                 215                 220

Gly Gly Leu Trp Thr Ala Val Ser Pro His Leu Ser Pro Leu Ser Asn
225                 230                 235                 240

Val Ser Ser Ile Ala Asn Asn His Met Ser Met Met Gly Thr Gly Val
                245                 250                 255

Ser Met Thr Asn Thr Leu His Ser Met Leu Lys Gly Leu Ala Pro Ala
            260                 265                 270

Ala Ala Gln Ala Val Glu Thr Ala Ala Glu Asn Gly Val Trp Ala Met
            275                 280                 285

Ser Ser Leu Gly Ser Gln Leu Gly Ser Ser Leu Gly Ser Ser Gly Leu
290                 295                 300

Gly Ala Gly Val Ala Ala Asn Leu Gly Arg Ala Ala Ser Val Gly Ser
305                 310                 315                 320

Leu Ser Val Pro Pro Ala Trp Ala Ala Asn Gln Ala Val Thr Pro
                325                 330                 335

Ala Ala Arg Ala Leu Pro Leu Ser Leu Thr Ser Ala Ala Gln Thr
            340                 345                 350

Ala Pro Gly His Met Leu Gly
            355
```

(2) INFORMATION FOR SEQ ID NO:110:

(i) SEQUENCE CHARACTERISTICS:
        (A) LENGTH: 3027 base pairs
        (B) TYPE: nucleic acid (C) STRANDEDNESS: single
        (D) TOPOLOGY: linear (xi) SEQUENCE DESCRIPTION: SEQ ID NO:110:

```
AGTTCAGTCG AGAATGATAC TGACGGGCTG TATCCACGAT GGCTGAGACA ACCGAACCAC     60
CGTCGGACGC GGGGACATCG CAAGCCGACG CGATGGCGTT GGCCGCCGAA GCCGAAGCCG    120
CCGAAGCCGA AGCGCTGGCC GCCGCGGCGC GGGCCCGTGC CCGTGCCGCC CGGTTGAAGC    180
GTGAGGCGCT GGCGATGGCC CCAGCCGAGG ACGAGAACGT CCCCGAGGAT ATGCAGACTG    240
GGAAGACGCC GAAGACTATG ACGACTATGA CGACTATGAG GCCGCAGACC AGGAGGCCGC    300
ACGGTCGGCA TCCTGGCGAC GGCGGTTGCG GGTGCGGTTA CCAAGACTGT CCACGATTGC    360
CATGGCGGCC GCAGTCGTCA TCATCTGCGG CTTCACCGGG CTCAGCGGAT ACATTGTGTG    420
GCAACACCAT GAGGCCACCG AACGCCAGCA GCGCGCCGCG GCGTTCGCCG CCGGAGCCAA    480
GCAAGGTGTC ATCAACATGA CCTCGCTGGA CTTCAACAAG GCCAAAGAAG ACGTCGCGCG    540
TGTGATCGAC AGCTCCACCG GCGAATTCAG GGATGACTTC CAGCAGCGGG CAGCCGATTT    600
CACCAAGGTT GTCGAACAGT CCAAAGTGGT CACCGAAGGC ACGGTGAACG CGACAGCCGT    660
CGAATCCATG AACGAGCATT CCGCCGTGGT GCTCGTCGCG GCGACTTCAC GGGTCACCAA    720
TTCCGCTGGG GCGAAAGACG AACCACGTGC GTGGCGGCTC AAAGTGACCG TGACCGAAGA    780
GGGGGGACAG TACAAGATGT CGAAAGTTGA GTTCGTACCG TGACCGATGA CGTACGCGAC    840
GTCAACACCG AAACCACTGA CGCCACCGAA GTCGCTGAGA TCGACTCAGC CGCAGGCGAA    900
GCCGGTGATT CGGCGACCGA GGCATTTGAC ACCGACTCTG CAACGGAATC TACCGCGCAG    960
AAGGGTCAGC GGCACCGTGA CCTGTGGCGA ATGCAGGTTA CCTTGAAACC CGTTCCGGTG   1020
ATTCTCATCC TGCTCATGTT GATCTCTGGG GGCGCGACGG GATGGCTATA CCTTGAGCAA   1080
TACGACCCGA TCAGCAGACG GACTCCGGCC CCGCCCGTGC TGCCGTCGCC GCGGCGTCTG   1140
ACGGGACAAT CGCGCTGTTG TGTATTCACC CGACACGTCG ACCAAGACTT CGCTACCGCC   1200
AGGTCGCACC TCGCCGGCGA TTTCCTGTCC TATACGACCA GTTCACGCAG CAGATCGTGG   1260
CTCCGGCGGC CAAACAGAAG TCACTGAAAA CCACCGCCAA GGTGGTGCGC GCGGCCGTGT   1320
CGGAGCTACA TCCGGATTCG GCCGTCGTTC TGGTTTTTGT CGACCAGAGC ACTACCAGTA   1380
AGGACAGCCC CAATCCGTCG ATGGCGGCCA GCAGCGTGAT GGTGACCCTA GCCAAGGTCG   1440
ACGGCAATTG GCTGATCACC AAGTTCACCC CGGTTTAGGT TGCCGTAGGC GGTCGCCAAG   1500
TCTGACGGGG GCGCGGGTGG CTGCTCGTGC GAGATACCGG CCGTTCTCCG GACAATCACG   1560
GCCCGACCTC AAACAGATCT CGGCCGCTGT CTAATCGGCC GGGTTATTTA AGATTAGTTG   1620
CCACTGTATT TACCTGATGT TCAGATTGTT CAGCTGGATT TAGCTTCGCG GCAGGGCGGC   1680
TGGTGCACTT TGCATCTGGG GTTGTGACTA CTTGAGAGAA TTTGACCTGT TGCCGACGTT   1740
GTTTGCTGTC CATCATTGGT GCTAGTTATG GCCGAGCGGA AGGATTATCG AAGTGGTGGA   1800
CTTCGGGGCG TTACCACCGG AGATCAACTC CGCGAGGATG TACGCCGGCC CGGGTTCGGC   1860
CTCGCTGGTG GCCGCCGCGA AGATGTGGGA CAGCGTGGCG AGTGACCTGT TTTCGGCCGC   1920
GTCGGCGTTT CAGTCGGTGG TCTGGGGTCT GACGACGGGA TCGTGGATAG GTTCGTCGGC   1980
GGGTCTGATG GTGGCGGCGG CCTCGCCGTA TGTGGCGTGG ATGAGCGTCA CCGCGGGGCA   2040
GGCCGAGCTG ACCGCCGCCC AGGTCCGGGT TGCTGCGGCG GCCTACGAGA CGGCGTATGG   2100
GCTGACGGTG CCCCCGCCGG TGATCGCCGA GAACCGTGCT GAACTGATGA TTCTGATAGC   2160
GACCAACCTC TTGGGGCAAA ACACCCCGGC GATCGCGGTC AACGAGGCCG AATACGGGGA   2220
```

-continued

```
GATGTGGGCC CAAGACGCCG CCGCGATGTT TGGCTACGCC GCCACGGCGG CGACGGCGAC    2280

CGAGGCGTTG CTGCCGTTCG AGGACGCCCC ACTGATCACC AACCCCGGCG GGCTCCTTGA    2340

GCAGGCCGTC GCGGTCGAGG AGGCCATCGA CACCGCCGCG GCGAACCAGT TGATGAACAA    2400

TGTGCCCCAA GCGCTGCAAC AACTGGCCCA GCCCACGAAA AGCATCTGGC CGTTCGACCA    2460

ACTGAGTGAA CTCTGGAAAG CCATCTCGCC GCATCTGTCG CCGCTCAGCA ACATCGTGTC    2520

GATGCTCAAC AACCACGTGT CGATGACCAA CTCGGGTGTG TCGATGGCCA GCACCTTGCA    2580

CTCAATGTTG AAGGGCTTTG CTCCGGCGGC GGCTCAGGCC GTGGAAACCG CGGCGCAAAA    2640

CGGGGTCCAG GCGATGAGCT CGCTGGGCAG CCAGCTGGGT TCGTCGCTGG GTTCTTCGGG    2700

TCTGGGCGCT GGGGTGGCCG CCAACTTGGG TCGGGCGGCC TCGGTCGGTT CGTTGTCGGT    2760

GCCGCAGGCC TGGGCCGCGG CCAACCAGGC GGTCACCCCG GCGGCGCGGG CGCTGCCGCT    2820

GACCAGCCTG ACCAGCGCCG CCCAAACCGC CCCCGGACAC ATGCTGGGCG GGCTACCGCT    2880

GGGGCAACTG ACCAATAGCG GCGGCGGGTT CGGCGGGGTT AGCAATGCGT TGCGGATGCC    2940

GCCGCGGGCG TACGTAATGC CCCGTGTGCC CGCCGCCGGG TAACGCCGAT CCGCACGCAA    3000

TGCGGGCCCT CTATGCGGGC AGCGATC                                       3027
```

(2) INFORMATION FOR SEQ ID NO:111:

(i) SEQUENCE CHARACTERISTICS:
        (A) LENGTH: 396 amino acids
        (B) TYPE: amino acid
        (C) STRANDEDNESS:
        (D) TOPOLOGY: linear (xi) SEQUENCE DESCRIPTION: SEQ ID NO:111:

```
Val Val Asp Phe Gly Ala Leu Pro Pro Glu Ile Asn Ser Ala Arg Met
 1               5                  10                  15

Tyr Ala Gly Pro Gly Ser Ala Ser Leu Val Ala Ala Lys Met Trp
            20                  25                  30

Asp Ser Val Ala Ser Asp Leu Phe Ser Ala Ala Ser Ala Phe Gln Ser
        35                  40                  45

Val Val Trp Gly Leu Thr Thr Gly Ser Trp Ile Gly Ser Ser Ala Gly
    50                  55                  60

Leu Met Val Ala Ala Ala Ser Pro Tyr Val Ala Trp Met Ser Val Thr
65                  70                  75                  80

Ala Gly Gln Ala Glu Leu Thr Ala Ala Gln Val Arg Val Ala Ala
                85                  90                  95

Ala Tyr Glu Thr Ala Tyr Gly Leu Thr Val Pro Pro Val Ile Ala
            100                 105                 110

Glu Asn Arg Ala Glu Leu Met Ile Leu Ile Ala Thr Asn Leu Leu Gly
        115                 120                 125

Gln Asn Thr Pro Ala Ile Ala Val Asn Glu Ala Glu Tyr Gly Glu Met
    130                 135                 140

Trp Ala Gln Asp Ala Ala Ala Met Phe Gly Tyr Ala Ala Thr Ala Ala
145                 150                 155                 160

Thr Ala Thr Glu Ala Leu Leu Pro Phe Glu Asp Ala Pro Leu Ile Thr
                165                 170                 175

Asn Pro Gly Gly Leu Leu Glu Gln Ala Val Ala Val Glu Glu Ala Ile
            180                 185                 190

Asp Thr Ala Ala Ala Asn Gln Leu Met Asn Asn Val Pro Gln Ala Leu
        195                 200                 205

Gln Gln Leu Ala Gln Pro Thr Lys Ser Ile Trp Pro Phe Asp Gln Leu
```

```
       210                 215                 220
Ser Glu Leu Trp Lys Ala Ile Ser Pro His Leu Ser Pro Leu Ser Asn
225                 230                 235                 240

Ile Val Ser Met Leu Asn Asn His Val Ser Met Thr Asn Ser Gly Val
                245                 250                 255

Ser Met Ala Ser Thr Leu His Ser Met Leu Lys Gly Phe Ala Pro Ala
                260                 265                 270

Ala Ala Gln Ala Val Glu Thr Ala Ala Gln Asn Gly Val Gln Ala Met
                275                 280                 285

Ser Ser Leu Gly Ser Gln Leu Gly Ser Ser Leu Gly Ser Ser Gly Leu
290                 295                 300

Gly Ala Gly Val Ala Ala Asn Leu Gly Arg Ala Ala Ser Val Gly Ser
305                 310                 315                 320

Leu Ser Val Pro Gln Ala Trp Ala Ala Ala Asn Gln Ala Val Thr Pro
                325                 330                 335

Ala Ala Arg Ala Leu Pro Leu Thr Ser Leu Thr Ser Ala Ala Gln Thr
                340                 345                 350

Ala Pro Gly His Met Leu Gly Gly Leu Pro Leu Gly Gln Leu Thr Asn
                355                 360                 365

Ser Gly Gly Phe Gly Gly Val Ser Asn Ala Leu Arg Met Pro Pro
370                 375                 380

Arg Ala Tyr Val Met Pro Arg Val Pro Ala Ala Gly
385                 390                 395

(2) INFORMATION FOR SEQ ID NO:112:

(i) SEQUENCE CHARACTERISTICS:
        (A) LENGTH: 1616 base pairs
        (B) TYPE: nucleic acid
        (C) STRANDEDNESS: single
        (D) TOPOLOGY: linear (xi) SEQUENCE DESCRIPTION: SEQ ID NO:112:

CATCGGAGGG AGTGATCACC ATGCTGTGGC ACGCAATGCC ACCGGAGTAA ATACCGCACG      60

GCTGATGGCC GGCGCGGGTC CGGCTCCAAT GCTTGCGGCG CCGCGGGAT GGCAGACGCT     120

TTCGGCGGCT CTGGACGCTC AGGCCGTCGA GTTGACCGCG CGCCTGAACT CTCTGGGAGA    180

AGCCTGGACT GGAGGTGGCA GCGACAAGGC GCTTGCGGCT GCAACGCCGA TGGTGGTCTG    240

GCTACAAACC GCGTCAACAC AGGCCAAGAC CCGTGCGATG CAGGCGACGG CGCAAGCCGC    300

GGCATACACC CAGGCCATGG CCACGACGCC GTCGCTGCCG GAGATCGCCG CCAACCACAT    360

CACCCAGGCC GTCCTTACGG CCACCAACTT CTTCGGTATC AACACGATCC CGATCGCGTT    420

GACCGAGATG GATTATTTCA TCCGTATGTG GAACCAGGCA GCCCTGGCAA TGGAGGTCTA    480

CCAGGCCGAG ACCGCGGTTA ACACGCTTTT CGAGAAGCTC GAGCCGATGG CGTCGATCCT    540

TGATCCCGGC GCGAGCCAGA GCACGACGAA CCCGATCTTC GGAATGCCCT CCCCTGGCAG    600

CTCAACACCG GTTGGCCAGT TGCCGCCGGC GGCTACCCAG ACCCTCGGCC AACTGGGTGA    660

GATGAGCGGC CCGATGCAGC AGCTGACCCA GCCGCTGCAG CAGGTGACGT CGTTGTTCAG    720

CCAGGTGGGC GGCACCGGCG GCGGCAACCC AGCCGACGAG GAAGCCGCGC AGATGGGCCT    780

GCTCGGCACC AGTCCGCTGT CGAACCATCC GCTGGCTGGT GGATCAGGCC CCAGCGCGGG    840

CGCGGGCCTG CTGCGCGCGG AGTCGCTACC TGGCGCAGGT GGGTCGTTGA CCCGCACGCC    900

GCTGATGTCT CAGCTGATCG AAAAGCCGGT TGCCCCCTCG GTGATGCCGG CGGCTGCTGC    960

CGGATCGTCG GCGACGGGTG GCGCCGCTCC GGTGGGTGCG GGAGCGATGG GCCAGGGTGC   1020
```

```
GCAATCCGGC GGCTCCACCA GGCCGGGTCT GGTCGCGCCG GCACCGCTCG CGCAGGAGCG    1080

TGAAGAAGAC GACGAGGACG ACTGGGACGA AGAGGACGAC TGGTGAGCTC CCGTAATGAC    1140

AACAGACTTC CCGGCCACCC GGGCCGGAAG ACTTGCCAAC ATTTTGGCGA GGAAGGTAAA    1200

GAGAGAAAGT AGTCCAGCAT GGCAGAGATG AAGACCGATG CCGCTACCCT CGCGCAGGAG    1260

GCAGGTAATT TCGAGCGGAT CTCCGGCGAC CTGAAAACCC AGATCGACCA GGTGGAGTCG    1320

ACGGCAGGTT CGTTGCAGGG CCAGTGGCGC GGCGCGGCGG GGACGGCCGC CCAGGCCGCG    1380

GTGGTGCGCT TCCAAGAAGC AGCCAATAAG CAGAAGCAGG AACTCGACGA GATCTCGACG    1440

AATATTCGTC AGGCCGGCGT CCAATACTCG AGGGCCGACG AGGAGCAGCA GCAGGCGCTG    1500

TCCTCGCAAA TGGGCTTCTG ACCCGCTAAT ACGAAAAGAA ACGGAGCAAA AACATGACAG    1560

AGCAGCAGTG GAATTTCGCG GGTATCGAGG CCGCGGCAAG CGCAATCCAG GGAAAT        1616
```

(2) INFORMATION FOR SEQ ID NO:113:

(i) SEQUENCE CHARACTERISTICS:
        (A) LENGTH: 432 base pairs
        (B) TYPE: nucleic acid
        (C) STRANDEDNESS: single
        (D) TOPOLOGY: linear (xi) SEQUENCE DESCRIPTION: SEQ ID NO:113:

```
CTAGTGGATG GGACCATGGC CATTTTCTGC AGTCTCACTG CCTTCTGTGT TGACATTTTG      60

GCACGCCGGC GGAAACGAAG CACTGGGGTC GAAGAACGGC TGCGCTGCCA TATCGTCCGG     120

AGCTTCCATA CCTTCGTGCG GCCGGAAGAG CTTGTCGTAG TCGGCCGCCA TGACAACCTC     180

TCAGAGTGCG CTCAAACGTA TAAACACGAG AAAGGGCGAG ACCGACGGAA GGTCGAACTC     240

GCCCGATCCC GTGTTTCGCT ATTCTACGCG AACTCGGCGT TGCCCTATGC GAACATCCCA     300

GTGACGTTGC CTTCGGTCGA AGCCATTGCC TGACCGGCTT CGCTGATCGT CCGCGCCAGG     360

TTCTGCAGCG CGTTGTTCAG CTCGGTAGCC GTGGCGTCCC ATTTTGCTG GACACCCTGG     420

TACGCCTCCG AA                                                          432
```

(2) INFORMATION FOR SEQ ID NO:114:

(i) SEQUENCE CHARACTERISTICS:
        (A) LENGTH: 368 amino acids
        (B) TYPE: amino acid
        (C) STRANDEDNESS: single
        (D) TOPOLOGY: linear (xi) SEQUENCE DESCRIPTION: SEQ ID NO:114:

```
Met Leu Trp His Ala Met Pro Pro Glu Xaa Asn Thr Ala Arg Leu Met
1               5                   10                  15

Ala Gly Ala Gly Pro Ala Pro Met Leu Ala Ala Ala Gly Trp Gln
            20                  25                  30

Thr Leu Ser Ala Ala Leu Asp Ala Gln Ala Val Glu Leu Thr Ala Arg
        35                  40                  45

Leu Asn Ser Leu Gly Glu Ala Trp Thr Gly Gly Ser Asp Lys Ala
    50                  55                  60

Leu Ala Ala Ala Thr Pro Met Val Val Trp Leu Gln Thr Ala Ser Thr
65                  70                  75                  80

Gln Ala Lys Thr Arg Ala Met Gln Ala Thr Gln Ala Ala Tyr
            85                  90                  95

Thr Gln Ala Met Ala Thr Thr Pro Ser Leu Pro Glu Ile Ala Ala Asn
                100                 105                 110
```

```
His Ile Thr Gln Ala Val Leu Thr Ala Thr Asn Phe Phe Gly Ile Asn
            115                 120                 125
Thr Ile Pro Ile Ala Leu Thr Glu Met Asp Tyr Phe Ile Arg Met Trp
130                 135                 140
Asn Gln Ala Ala Leu Ala Met Glu Val Tyr Gln Ala Glu Thr Ala Val
145                 150                 155                 160
Asn Thr Leu Phe Glu Lys Leu Glu Pro Met Ala Ser Ile Leu Asp Pro
                165                 170                 175
Gly Ala Ser Gln Ser Thr Thr Asn Pro Ile Phe Gly Met Pro Ser Pro
            180                 185                 190
Gly Ser Ser Thr Pro Val Gly Gln Leu Pro Pro Ala Ala Thr Gln Thr
            195                 200                 205
Leu Gly Gln Leu Gly Glu Met Ser Gly Pro Met Gln Gln Leu Thr Gln
            210                 215                 220
Pro Leu Gln Gln Val Thr Ser Leu Phe Ser Gln Val Gly Gly Thr Gly
225                 230                 235                 240
Gly Gly Asn Pro Ala Asp Glu Glu Ala Ala Gln Met Gly Leu Leu Gly
                245                 250                 255
Thr Ser Pro Leu Ser Asn His Pro Leu Ala Gly Gly Ser Gly Pro Ser
            260                 265                 270
Ala Gly Ala Gly Leu Leu Arg Ala Glu Ser Leu Pro Gly Ala Gly Gly
            275                 280                 285
Ser Leu Thr Arg Thr Pro Leu Met Ser Gln Leu Ile Glu Lys Pro Val
            290                 295                 300
Ala Pro Ser Val Met Pro Ala Ala Ala Gly Ser Ser Ala Thr Gly
305                 310                 315                 320
Gly Ala Ala Pro Val Gly Ala Gly Ala Met Gly Gln Gly Ala Gln Ser
                325                 330                 335
Gly Gly Ser Thr Arg Pro Gly Leu Val Ala Pro Ala Pro Leu Ala Gln
            340                 345                 350
Glu Arg Glu Glu Asp Asp Glu Asp Asp Trp Asp Glu Glu Asp Asp Trp
            355                 360                 365

(2) INFORMATION FOR SEQ ID NO:115:

(i) SEQUENCE CHARACTERISTICS:
        (A) LENGTH: 100 amino acids
        (B) TYPE: amino acid
        (C) STRANDEDNESS:
        (D) TOPOLOGY: linear (xi) SEQUENCE DESCRIPTION: SEQ ID NO:115:

Met Ala Glu Met Lys Thr Asp Ala Ala Thr Leu Ala Gln Glu Ala Gly
1               5                   10                  15
Asn Phe Glu Arg Ile Ser Gly Asp Leu Lys Thr Gln Ile Asp Gln Val
                20                  25                  30
Glu Ser Thr Ala Gly Ser Leu Gln Gly Gln Trp Arg Gly Ala Ala Gly
            35                  40                  45
Thr Ala Ala Gln Ala Ala Val Val Arg Phe Gln Glu Ala Ala Asn Lys
50                  55                  60
Gln Lys Gln Glu Leu Asp Glu Ile Ser Thr Asn Ile Arg Gln Ala Gly
65                  70                  75                  80
Val Gln Tyr Ser Arg Ala Asp Glu Glu Gln Gln Ala Leu Ser Ser
                85                  90                  95
Gln Met Gly Phe
```

(2) INFORMATION FOR SEQ ID NO:116:

(i) SEQUENCE CHARACTERISTICS:
       (A) LENGTH: 396 base pairs
       (B) TYPE: nucleic acid
       (C) STRANDEDNESS: single
       (D) TOPOLOGY: linear (xi) SEQUENCE DESCRIPTION: SEQ ID NO:116:

```
GATCTCCGGC GACCTGAAAA CCCAGATCGA CCAGGTGGAG TCGACGGCAG GTTCGTTGCA        60

GGGCCAGTGG CGCGGCGCGG CGGGGACGGC CGCCCAGGCC GCGGTGGTGC GCTTCCAAGA       120

AGCAGCCAAT AAGCAGAAGC AGGAACTCGA CGAGATCTCG ACGAATATTC GTCAGGCCGG       180

CGTCCAATAC TCGAGGGCCG ACGAGGAGCA GCAGCAGGCG CTGTCCTCGC AAATGGGCTT       240

CTGACCCGCT AATACGAAAA GAAACGGAGC AAAAACATGA CAGAGCAGCA GTGGAATTTC       300

GCGGGTATCG AGGCCGCGGC AAGCGCAATC CAGGGAAATG TCACGTCCAT TCATTCCCTC       360

CTTGACGAGG GGAAGCAGTC CCTGACCAAG CTCGCA                                 396
```

(2) INFORMATION FOR SEQ ID NO:117:

(i) SEQUENCE CHARACTERISTICS:
       (A) LENGTH: 80 amino acids
       (B) TYPE: amino acid
       (C) STRANDEDNESS: single
       (D) TOPOLOGY: linear (xi) SEQUENCE DESCRIPTION: SEQ ID NO:117:

```
Ile Ser Gly Asp Leu Lys Thr Gln Ile Asp Gln Val Glu Ser Thr Ala
1               5                  10                  15

Gly Ser Leu Gln Gly Gln Trp Arg Gly Ala Ala Gly Thr Ala Ala Gln
            20                  25                  30

Ala Ala Val Val Arg Phe Gln Glu Ala Ala Asn Lys Gln Lys Gln Glu
        35                  40                  45

Leu Asp Glu Ile Ser Thr Asn Ile Arg Gln Ala Gly Val Gln Tyr Ser
    50                  55                  60

Arg Ala Asp Glu Glu Gln Gln Gln Ala Leu Ser Ser Gln Met Gly Phe
65                  70                  75                  80
```

(2) INFORMATION FOR SEQ ID NO:118:

(i) SEQUENCE CHARACTERISTICS:
       (A) LENGTH: 387 base pairs
       (B) TYPE: nucleic acid
       (C) STRANDEDNESS: single
       (D) TOPOLOGY: linear (xi) SEQUENCE DESCRIPTION: SEQ ID NO:118:

```
GTGGATCCCG ATCCCGTGTT CGCTATTCT ACGCGAACTC GGCGTTGCCC TATGCGAACA        60

TCCCAGTGAC GTTGCCTTCG GTCGAAGCCA TTGCCTGACC GGCTTCGCTG ATCGTCCGCG       120

CCAGGTTCTG CAGCGCGTTG TTCAGCTCGG TAGCCGTGGC GTCCCATTTT TGCTGGACAC       180

CCTGGTACGC CTCCGAACCG CTACCGCCCC AGGCCGCTGC GAGCTTGGTC AGGGACTGCT       240

TCCCCTCGTC AAGGAGGGAA TGAATGGACG TGACATTTCC CTGGATTGCG CTTGCCGCGG       300

CCTCGATACC CGCGAAATTC CACTGCTGCT CTGTCATGTT TTTGCTCCGT TTCTTTTCGT       360

ATTAGCGGGT CAGAAGCCCA TTTGCGA                                           387
```

(2) INFORMATION FOR SEQ ID NO:119:

(i) SEQUENCE CHARACTERISTICS:
        (A) LENGTH: 272 base pairs
        (B) TYPE: nucleic acid
        (C) STRANDEDNESS: single
        (D) TOPOLOGY: linear (xi) SEQUENCE DESCRIPTION: SEQ ID NO:119:

```
CGGCACGAGG ATCTCGGTTG GCCCAACGGC GCTGGCGAGG GCTCCGTTCC GGGGGCGAGC        60

TGCGCGCCGG ATGCTTCCTC TGCCCGCAGC CGCGCCTGGA TGGATGGACC AGTTGCTACC       120

TTCCCGACGT TTCGTTCGGT GTCTGTGCGA TAGCGGTGAC CCCGGCGCGC ACGTCGGGAG       180

TGTTGGGGGG CAGGCCGGGT CGGTGGTTCG GCCGGGACG CAGACGGTCT GGACGGAACG        240

GGCGGGGGTT CGCCGATTGG CATCTTTGCC CA                                    272
```

(2) INFORMATION FOR SEQ ID NO:120:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:120:

```
Asp Pro Val Asp Ala Val Ile Asn Thr Thr Cys Asn Tyr Gly Gln Val
 1               5                  10                  15

Val Ala Ala Leu
           20
```

(2) INFORMATION FOR SEQ ID NO:121:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:121:

```
Ala Val Glu Ser Gly Met Leu Ala Leu Gly Thr Pro Ala Pro Ser
 1               5                  10                  15
```

(2) INFORMATION FOR SEQ ID NO:122:

(i) SEQUENCE CHARACTERISTICS:
        (A) LENGTH: 19 amino acids
        (B) TYPE: amino acid
        (C) STRANDEDNESS:
        (D) TOPOLOGY: linear (xi) SEQUENCE DESCRIPTION: SEQ ID NO:122:

```
Ala Ala Met Lys Pro Arg Thr Gly Asp Gly Pro Leu Glu Ala Ala Lys
 1               5                  10                  15

Glu Gly Arg
```

(2) INFORMATION FOR SEQ ID NO:123:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:123:

Tyr Tyr Trp Cys Pro Gly Gln Pro Phe Asp Pro Ala Trp Gly Pro (2) INFORMATION FOR SEQ ID NO:124:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:124:

```
Asp Ile Gly Ser Glu Ser Thr Glu Asp Gln Gln Xaa Ala Val
1               5                   10
```

(2) INFORMATION FOR SEQ ID NO:125:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:125:

```
Ala Glu Glu Ser Ile Ser Thr Xaa Glu Xaa Ile Val Pro
1               5                   10
```

(2) INFORMATION FOR SEQ ID NO:126:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:126:

```
Asp Pro Glu Pro Ala Pro Pro Val Pro Thr Thr Ala Ala Ser Pro Pro
1               5                   10                  15
Ser
```

(2) INFORMATION FOR SEQ ID NO:127:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:127:

```
Ala Pro Lys Thr Tyr Xaa Glu Glu Leu Lys Gly Thr Asp Thr Gly
1               5                   10                  15
```

(2) INFORMATION FOR SEQ ID NO:128:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:128:

```
Asp Pro Ala Ser Ala Pro Asp Val Pro Thr Ala Ala Gln Leu Thr Ser
1               5                   10                  15
Leu Leu Asn Ser Leu Ala Asp Pro Asn Val Ser Phe Ala Asn
            20                  25                  30
```

(2) INFORMATION FOR SEQ ID NO:129:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:129:

Asp Pro Pro Asp Pro His Gln Xaa Asp Met Thr Lys Gly Tyr Tyr Pro
1               5                   10                  15

Gly Gly Arg Arg Xaa Phe
            20

(2) INFORMATION FOR SEQ ID NO:130:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:130:

Asp Pro Gly Tyr Thr Pro Gly
1               5

(2) INFORMATION FOR SEQ ID NO:131:

(i) SEQUENCE CHARACTERISTICS:
        (A) LENGTH: 10 amino acids
        (B) TYPE: amino acid
        (C) STRANDEDNESS:
        (D) TOPOLOGY: linear (ix) FEATURE:
        (D) OTHER INFORMATION: /note= "The Second Residue Can Be
            Either a Pro or Thr"

(xi) SEQUENCE DESCRIPTION: SEQ ID NO:131:

Xaa Xaa Gly Phe Thr Gly Pro Gln Phe Tyr
1               5                   10

(2) INFORMATION FOR SEQ ID NO:132:

(i) SEQUENCE CHARACTERISTICS:
        (A) LENGTH: 9 amino acids
        (B) TYPE: amino acid
        (C) STRANDEDNESS:
        (D) TOPOLOGY: linear (ix) FEATURE:
        (D) OTHER INFORMATION: /note= "The Third Residue Can Be Either
            a Gln or Leu"

(xi) SEQUENCE DESCRIPTION: SEQ ID NO:132:

Xaa Pro Xaa Val Thr Ala Tyr Ala Gly
1               5

(2) INFORMATION FOR SEQ ID NO:133:

(i) SEQUENCE CHARACTERISTICS:
        (A) LENGTH: 9 amino acids
        (B) TYPE: amino acid
        (C) STRANDEDNESS:
        (D) TOPOLOGY: linear (xi) SEQUENCE DESCRIPTION: SEQ ID NO:133:

Xaa Xaa Xaa Glu Lys Pro Phe Leu Arg
1               5

(2) INFORMATION FOR SEQ ID NO:134:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:134:

```
Xaa Asp Ser Glu Lys Ser Ala Thr Ile Lys Val Thr Asp Ala Ser
1               5                   10                  15
```

(2) INFORMATION FOR SEQ ID NO:135:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:135:

```
Ala Gly Asp Thr Xaa Ile Tyr Ile Val Gly Asn Leu Thr Ala Asp
1               5                   10                  15
```

(2) INFORMATION FOR SEQ ID NO:136:

(i) SEQUENCE CHARACTERISTICS:
        (A) LENGTH: 15 amino acids
        (B) TYPE: amino acid
        (C) STRANDEDNESS:
        (D) TOPOLOGY: linear (xi) SEQUENCE DESCRIPTION: SEQ ID NO:136:

```
Ala Pro Glu Ser Gly Ala Gly Leu Gly Gly Thr Val Gln Ala Gly
1               5                   10                  15
```

(2) INFORMATION FOR SEQ ID NO:137:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:137:

```
Xaa Tyr Ile Ala Tyr Xaa Thr Thr Ala Gly Ile Val Pro Gly Lys Ile
1               5                   10                  15

Asn Val His Leu Val
            20
```

(2) INFORMATION FOR SEQ ID NO:138:

(i) SEQUENCE CHARACTERISTICS:
        (A) LENGTH: 882 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:138:

```
GCAACGCTGT CGTGGCCTTT GCGGTGATCG GTTTCGCCTC GCTGGCGGTG GCGGTGGCGG      60

TCACCATCCG ACCGACCGCG GCCTCAAAAC CGGTAGAGGG ACACCAAAAC GCCCAGCCAG     120

GGAAGTTCAT GCCGTTGTTG CCGACGCAAC AGCAGGCGCC GGTCCCGCCG CCTCCGCCCG     180

ATGATCCCAC CGCTGGATTC CAGGGCGGCA CCATTCCGGC TGTACAGAAC GTGGTGCCGC     240
```

```
GGCCGGGTAC CTCACCCGGG GTGGGTGGGA CGCCGGCTTC GCCTGCGCCG GAAGCGCCGG      300

CCGTGCCCGG TGTTGTGCCT GCCCCGGTGC CAATCCCGGT CCCGATCATC ATTCCCCCGT      360

TCCCGGGTTG GCAGCCTGGA ATGCCGACCA TCCCCACCGC ACCGCCGACG ACGCCGGTGA      420

CCACGTCGGC GACGACGCCG CCGACCACGC CGCCGACCAC GCCGGTGACC ACGCCGCCAA      480

CGACGCCGCC GACCACGCCG GTGACCACGC CGCCAACGAC GCCGCCGACC ACGCCGGTGA      540

CCACGCCACC AACGACCGTC GCCCCGACGA CCGTCGCCCC GACGACGGTC GCTCCGACCA      600

CCGTCGCCCC GACCACGGTC GCTCCAGCCA CCGCACGCC GACGACCGTC GCTCCGCAGC       660

CGACGCAGCA GCCCACGCAA CAACCAACCC AACAGATGCC AACCCAGCAG CAGACCGTGG      720

CCCCGCAGAC GGTGGCGCCG GCTCCGCAGC CGCCGTCCGG TGGCCGCAAC GGCAGCGGCG      780

GGGGCGACTT ATTCGGCGGG TTCTGATCAC GGTCGCGGCT TCACTACGGT CGGAGGACAT      840

GGCCGGTGAT GCGGTGACGG TGGTGCTGCC CTGTCTCAAC GA                          882
```

(2) INFORMATION FOR SEQ ID NO:139:

(i) SEQUENCE CHARACTERISTICS:
        (A) LENGTH: 815 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:139:

```
CCATCAACCA ACCGCTCGCG CCGCCCGCGC CGCCGGATCC GCCGTCGCCG CCACGCCCGC       60

CGGTGCCTCC GGTGCCCCCG TTGCCGCCGT CGCCGCCGTC GCCGCCGACC GGCTGGGTGC      120

CTAGGGCGCT GTTACCGCCC TGGTTGGCGG GGACGCCGCC GGCACCACCG GTACCGCCGA      180

TGGCGCCGTT GCCGCCGGCG GCACCGTTGC CACCGTTGCC ACCGTTGCCA CCGTTGCCGA      240

CCAGCCACCC GCCGCGACCA CCGGCACCGC CGGCGCCGCC CGCACCGCCG GCGTGCCCGT      300

TCGTGCCCGT ACCGCCGGCA CCGCCGTTGC CGCCGTCACC GCCGACGGAA CTACCGGCGG      360

ACGCGGCCTG CCCGCCGGCG CCGCCCGCAC CGCCATTGGC ACCGCCGTCA CCGCCGGCTG      420

GGAGTGCCGC GATTAGGGCA CTGACCGGCG CAACCAGCGC AAGTACTCTC GGTCACCGAG      480

CACTTCCAGA CGACACCACA GCACGGGGTT GTCGGCGGAC TGGGTGAAAT GGCAGCCGAT      540

AGCGGCTAGC TGTCGGCTGC GGTCAACCTC GATCATGATG TCGAGGTGAC CGTGACCGCG      600

CCCCCCGAAG GAGGCGCTGA ACTCGGCGTT GAGCCGATCG GCGATCGGTT GGGGCAGTGC      660

CCAGGCCAAT ACGGGGATAC CGGGTGTCNA AGCCGCCGCG AGCGCAGCTT CGGTTGCGCG      720

ACNGTGGTCG GGGTGGCCTG TTACGCCGTT GTCNTCGAAC ACGAGTAGCA GGTCTGCTCC      780

GGCGAGGGCA TCCACCACGC GTTGCGTCAG CTCGT                                  815
```

(2) INFORMATION FOR SEQ ID NO:140:

(i) SEQUENCE CHARACTERISTICS:
        (A) LENGTH: 1152 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:140:

```
ACCAGCCGCC GGCTGAGGTC TCAGATCAGA GAGTCTCCGG ACTCACCGGG GCGGTTCAGC       60
```

```
CTTCTCCCAG AACAACTGCT GAAGATCCTC GCCCGCGAAA CAGGCGCTGA TTTGACGCTC      120

TATGACCGGT TGAACGACGA GATCATCCGG CAGATTGATA TGGCACCGCT GGGCTAACAG      180

GTGCGCAAGA TGGTGCAGCT GTATGTCTCG GACTCCGTGT CGCGGATCAG CTTTGCCGAC      240

GGCCGGGTGA TCGTGTGGAG CGAGGAGCTC GGCGAGAGCC AGTATCCGAT CGAGACGCTG      300

GACGGCATCA CGCTGTTTGG GCGGCCGACG ATGACAACGC CCTTCATCGT TGAGATGCTC      360

AAGCGTGAGC GCGACATCCA GCTCTTCACG ACCGACGGCC ACTACCAGGG CCGGATCTCA      420

ACACCCGACG TGTCATACGC GCCGCGGCTC CGTCAGCAAG TTCACCGCAC CGACGATCCT      480

GCGTTCTGCC TGTCGTTAAG CAAGCGGATC GTGTCGAGGA AGATCCTGAA TCAGCAGGCC      540

TTGATTCGGG CACACACGTC GGGGCAAGAC GTTGCTGAGA GCATCCGCAC GATGAAGCAC      600

TCGCTGGCCT GGGTCGATCG ATCGGGCTCC CTGGCGGAGT TGAACGGGTT CGAGGGAAAT      660

GCCGCAAAGG CATACTTCAC CGCGCTGGGG CATCTCGTCC CGCAGGAGTT CGCATTCCAG      720

GGCCGCTCGA CTCGGCCGCC GTTGGACGCC TTCAACTCGA TGGTCAGCCT CGGCTATTCG      780

CTGCTGTACA AGAACATCAT AGGGGCGATC GAGCGTCACA GCCTGAACGC GTATATCGGT      840

TTCCTACACC AGGATTCACG AGGGCACGCA ACGTCTCGTG CCGAATTCGG CACGAGCTCC      900

GCTGAAACCG CTGGCCGGCT GCTCAGTGCC CGTACGTAAT CCGCTGCGCC CAGGCCGGCC      960

CGCCGGCCGA ATACCAGCAG ATCGGACAGC GAATTGCCGC CCAGCCGGTT GGAGCCGTGC     1020

ATACCGCCGG CACACTCACC GGCAGCGAAC AGGCCTGGCA CCGTGGCGGC GCCGGTGTCC     1080

GCGTCTACTT CGACACCGCC CATCACGTAG TGACACGTCG GCCCGACTTC CATTGCCTGC     1140

GTTCGGCACG AG                                                          1152

(2) INFORMATION FOR SEQ ID NO:141:

(i) SEQUENCE CHARACTERISTICS:
        (A) LENGTH: 655 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:141:

CTCGTGCCGA TTCGGCAGGG TGTACTTGCC GGTGGTGTAN GCCGCATGAG TGCCGACGAC       60

CAGCAATGCG GCAACAGCAC GGATCCCGGT CAACGACGCC ACCCGGTCCA CGTGGGCGAT      120

CCGCTCGAGT CCGCCCTGGG CGGCTCTTTC CTTGGGCAGG GTCATCCGAC GTGTTTCCGC      180

CGTGGTTTGC CGCCATTATG CCGGCGCGCC GCGTCGGGCG GCCGGTATGG CCGAANGTCG      240

ATCAGCACAC CCGAGATACG GGTCTGTGCA AGCTTTTTGA GCGTCGCGCG GGGCAGCTTC      300

GCCGGCAATT CTACTAGCGA GAAGTCTGGC CCGATACGGA TCTGACCGAA GTCGCTGCGG      360

TGCAGCCCAC CCTCATTGGC GATGGCGCCG ACGATGGCGC CTGGACCGAT CTTGTGCCGC      420

TTGCCGACGG CGACGCGGTA GGTGGTCAAG TCCGGTCTAC GCTTGGGCCT TGCGGACGG      480

TCCCGACGCT GGTCGCGGTT GCGCCGCGAA AGCGGCGGGT CGGGTGCCAT CAGGAATGCC      540

TCACCGCCGC GGCACTGCAC GGCCAGTGCC GCGGCGATGT CAGCCATCGG GACATCATGC      600

TCGCGTTCAT ACTCCTCGAC CAGTCGGCGG AACAGCTCGA TTCCCGGACC GCCCA           655

(2) INFORMATION FOR SEQ ID NO:142:

(i) SEQUENCE CHARACTERISTICS:
        (A) LENGTH: 267 amino acids
        (B) TYPE: amino acid
```

(C) STRANDEDNESS: single
            (D) TOPOLOGY: linear (ii) MOLECULE TYPE: peptide (xi) SEQUENCE DESCRIPTION: SEQ ID NO:142:

Asn Ala Val Val Ala Phe Ala Val Ile Gly Phe Ala Ser Leu Ala Val
1               5                  10                  15

Ala Val Ala Val Thr Ile Arg Pro Thr Ala Ala Ser Lys Pro Val Glu
            20                  25                  30

Gly His Gln Asn Ala Gln Pro Gly Lys Phe Met Pro Leu Leu Pro Thr
        35                  40                  45

Gln Gln Gln Ala Pro Val Pro Pro Pro Pro Asp Asp Pro Thr Ala
50                  55                  60

Gly Phe Gln Gly Gly Thr Ile Pro Ala Val Gln Asn Val Val Pro Arg
65                  70                  75                  80

Pro Gly Thr Ser Pro Gly Val Gly Gly Thr Pro Ala Ser Pro Ala Pro
                85                  90                  95

Glu Ala Pro Ala Val Pro Gly Val Val Pro Ala Pro Val Pro Ile Pro
                100                 105                 110

Val Pro Ile Ile Ile Pro Pro Phe Pro Gly Trp Gln Pro Gly Met Pro
            115                 120                 125

Thr Ile Pro Thr Ala Pro Pro Thr Thr Pro Val Thr Thr Ser Ala Thr
        130                 135                 140

Thr Pro Pro Thr Thr Pro Pro Thr Thr Pro Val Thr Thr Pro Pro Thr
145                 150                 155                 160

Thr Pro Pro Thr Thr Pro Val Thr Thr Pro Pro Thr Thr Pro Pro Thr
                165                 170                 175

Thr Pro Val Thr Thr Pro Pro Thr Thr Val Ala Pro Thr Thr Val Ala
            180                 185                 190

Pro Thr Thr Val Ala Pro Thr Thr Val Ala Pro Thr Thr Val Ala Pro
        195                 200                 205

Ala Thr Ala Thr Pro Thr Thr Val Ala Pro Gln Pro Thr Gln Gln Pro
    210                 215                 220

Thr Gln Gln Pro Thr Gln Gln Met Pro Thr Gln Gln Gln Thr Val Ala
225                 230                 235                 240

Pro Gln Thr Val Ala Pro Ala Pro Gln Pro Pro Ser Gly Gly Arg Asn
                245                 250                 255

Gly Ser Gly Gly Gly Asp Leu Phe Gly Gly Phe
                260                 265

(2) INFORMATION FOR SEQ ID NO:143:

(i) SEQUENCE CHARACTERISTICS:
        (A) LENGTH: 174 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:143:

Ile Asn Gln Pro Leu Ala Pro Pro Ala Pro Pro Asp Pro Pro Ser Pro
1               5                  10                  15

Pro Arg Pro Pro Val Pro Pro Val Pro Pro Leu Pro Pro Ser Pro Pro
            20                  25                  30

Ser Pro Pro Thr Gly Trp Val Pro Arg Ala Leu Leu Pro Pro Trp Leu
        35                  40                  45

```
Ala Gly Thr Pro Pro Ala Pro Pro Val Pro Pro Met Ala Pro Leu Pro
    50                  55                  60
Pro Ala Ala Pro Leu Pro Pro Leu Pro Pro Leu Pro Pro Leu Pro Thr
65                  70                  75                  80
Ser His Pro Pro Arg Pro Pro Ala Pro Pro Ala Pro Pro Ala Pro Pro
                85                  90                  95
Ala Cys Pro Phe Val Pro Val Pro Pro Ala Pro Pro Leu Pro Pro Ser
            100                 105                 110
Pro Pro Thr Glu Leu Pro Ala Asp Ala Ala Cys Pro Pro Ala Pro Pro
        115                 120                 125
Ala Pro Pro Leu Ala Pro Pro Ser Pro Pro Ala Gly Ser Ala Ala Ile
    130                 135                 140
Arg Ala Leu Thr Gly Ala Thr Ser Ala Ser Thr Leu Gly His Arg Ala
145                 150                 155                 160
Leu Pro Asp Asp Thr Thr Ala Arg Gly Cys Arg Arg Thr Gly
                165                 170

(2) INFORMATION FOR SEQ ID NO:144:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:144:

Gln Pro Pro Ala Glu Val Ser Asp Gln Arg Val Ser Gly Leu Thr Gly
1               5                   10                  15
Ala Val Gln Pro Ser Pro Arg Thr Thr Ala Glu Asp Pro Arg Pro Arg
                20                  25                  30
Asn Arg Arg
        35

(2) INFORMATION FOR SEQ ID NO:145:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:145:

Arg Ala Asp Ser Ala Gly Cys Thr Cys Arg Trp Cys Xaa Pro His Glu
1               5                   10                  15
Cys Arg Arg Pro Ala Met Arg Gln Gln His Gly Ser Arg Ser Thr Thr
                20                  25                  30
Pro Pro Gly Pro Arg Gly Arg Ser Ala Arg Val Arg Pro Gly Arg Leu
            35                  40                  45
Phe Pro Trp Ala Gly Ser Ser Asp Val Phe Pro Pro Trp Phe Ala Ala
    50                  55                  60
Ile Met Pro Ala Arg Arg Val Gly Arg Pro Val Trp Pro Xaa Val Asp
65                  70                  75                  80
Gln His Thr Arg Asp Thr Gly Leu Cys Lys Leu Phe Glu Arg Arg Ala
                85                  90                  95
Gly Gln Leu Arg Arg Gln Phe Tyr
```

(2) INFORMATION FOR SEQ ID NO:146:

(i) SEQUENCE CHARACTERISTICS:
       (A) LENGTH: 53 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PCR primer"

(vi) ORIGINAL SOURCE:
       (A) ORGANISM: Mycobacterium tuberculosis (xi) SEQUENCE DESCRIPTION: SEQ ID NO:146:

GGATCCATAT GGGCCATCAT CATCATCATC ACGTGATCGA CATCATCGGG ACC            53

(2) INFORMATION FOR SEQ ID NO:147:

(i) SEQUENCE CHARACTERISTICS:
       (A) LENGTH: 42 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PCR Primer"

(vi) ORIGINAL SOURCE:
       (A) ORGANISM: Mycobacterium tuberculosis (xi) SEQUENCE DESCRIPTION: SEQ ID NO:147:

CCTGAATTCA GGCCTCGGTT GCGCCGGCCT CATCTTGAAC GA                        42

(2) INFORMATION FOR SEQ ID NO:148:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PCR Primer"

(vi) ORIGINAL SOURCE:
       (A) ORGANISM: Mycobacterium tuberculosis (xi) SEQUENCE DESCRIPTION: SEQ ID NO:148:

GGATCCTGCA GGCTCGAAAC CACCGAGCGG T                                    31

(2) INFORMATION FOR SEQ ID NO:149:

(i) SEQUENCE CHARACTERISTICS:
       (A) LENGTH: 31 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PCR primer"

(vi) ORIGINAL SOURCE:
       (A) ORGANISM: Mycobacterium tuberculosis (xi) SEQUENCE DESCRIPTION: SEQ ID NO:149:

CTCTGAATTC AGCGCTGGAA ATCGTCGCGA T                                    31

```
(2) INFORMATION FOR SEQ ID NO:150:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO:150:

GGATCCAGCG CTGAGATGAA GACCGATGCC GCT                              33

(2) INFORMATION FOR SEQ ID NO:151:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "PCR primer"

(vi) ORIGINAL SOURCE:
        (A) ORGANISM: Mycobacterium tuberculosis (xi) SEQUENCE DESCRIPTION: SEQ ID NO:151:

GAGAGAATTC TCAGAAGCCC ATTTGCGAGG ACA                              33

(2) INFORMATION FOR SEQ ID NO:152:

(i) SEQUENCE CHARACTERISTICS:
        (A) LENGTH: 1993 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Mycobacterium tuberculosis (ix) FEATURE:
        (A) NAME/KEY: CDS
        (B) LOCATION: 152..1273

(xi) SEQUENCE DESCRIPTION: SEQ ID NO:152:

TGTTCTTCGA CGGCAGGCTG GTGGAGGAAG GGCCCACCGA ACAGCTGTTC TCCTCGCCGA     60

AGCATGCGGA AACCGCCCGA TACGTCGCCG GACTGTCGGG GGACGTCAAG GACGCCAAGC    120

GCGGAAATTG AAGAGCACAG AAAGGTATGG C GTG AAA ATT CGT TTG CAT ACG       172
                                  Val Lys Ile Arg Leu His Thr
                                   1               5

CTG TTG GCC GTG TTG ACC GCT GCG CCG CTG CTA GCA GCG GCG GGC          220
Leu Leu Ala Val Leu Thr Ala Ala Pro Leu Leu Ala Ala Ala Gly
         10                  15                  20

TGT GGC TCG AAA CCA CCG AGC GGT TCG CCT GAA ACG GGC GCC GGC GCC      268
Cys Gly Ser Lys Pro Pro Ser Gly Ser Pro Glu Thr Gly Ala Gly Ala
         25                  30                  35

GGT ACT GTC GCG ACT ACC CCC GCG TCG TCG CCG GTG ACG TTG GCG GAG      316
Gly Thr Val Ala Thr Thr Pro Ala Ser Ser Pro Val Thr Leu Ala Glu
 40                  45                  50                  55

ACC GGT AGC ACG CTG CTC TAC CCG CTG TTC AAC CTG TGG GGT CCG GCC      364
Thr Gly Ser Thr Leu Leu Tyr Pro Leu Phe Asn Leu Trp Gly Pro Ala
```

-continued

```
                       60                    65                    70
TTT CAC GAG AGG TAT CCG AAC GTC ACG ATC ACC GCT CAG GGC ACC GGT    412
Phe His Glu Arg Tyr Pro Asn Val Thr Ile Thr Ala Gln Gly Thr Gly
            75                  80                  85

TCT GGT GCC GGG ATC GCG CAG GCC GCC GCC GGG ACG GTC AAC ATT GGG    460
Ser Gly Ala Gly Ile Ala Gln Ala Ala Ala Gly Thr Val Asn Ile Gly
        90                  95                 100

GCC TCC GAC GCC TAT CTG TCG GAA GGT GAT ATG GCC GCG CAC AAG GGG    508
Ala Ser Asp Ala Tyr Leu Ser Glu Gly Asp Met Ala Ala His Lys Gly
        105                 110                 115

CTG ATG AAC ATC GCG CTA GCC ATC TCC GCT CAG CAG GTC AAC TAC AAC    556
Leu Met Asn Ile Ala Leu Ala Ile Ser Ala Gln Gln Val Asn Tyr Asn
120                 125                 130                 135

CTG CCC GGA GTG AGC GAG CAC CTC AAG CTG AAC GGA AAA GTC CTG GCG    604
Leu Pro Gly Val Ser Glu His Leu Lys Leu Asn Gly Lys Val Leu Ala
                140                 145                 150

GCC ATG TAC CAG GGC ACC ATC AAA ACC TGG GAC GAC CCG CAG ATC GCT    652
Ala Met Tyr Gln Gly Thr Ile Lys Thr Trp Asp Asp Pro Gln Ile Ala
                155                 160                 165

GCG CTC AAC CCC GGC GTG AAC CTG CCC GGC ACC GCG GTA GTT CCG CTG    700
Ala Leu Asn Pro Gly Val Asn Leu Pro Gly Thr Ala Val Val Pro Leu
                170                 175                 180

CAC CGC TCC GAC GGG TCC GGT GAC ACC TTC TTG TTC ACC CAG TAC CTG    748
His Arg Ser Asp Gly Ser Gly Asp Thr Phe Leu Phe Thr Gln Tyr Leu
        185                 190                 195

TCC AAG CAA GAT CCC GAG GGC TGG GGC AAG TCG CCC GGC TTC GGC ACC    796
Ser Lys Gln Asp Pro Glu Gly Trp Gly Lys Ser Pro Gly Phe Gly Thr
200                 205                 210                 215

ACC GTC GAC TTC CCG GCG GTG CCG GGT GCG CTG GGT GAG AAC GGC AAC    844
Thr Val Asp Phe Pro Ala Val Pro Gly Ala Leu Gly Glu Asn Gly Asn
                220                 225                 230

GGC GGC ATG GTG ACC GGT TGC GCC GAG ACA CCG GGC TGC GTG GCC TAT    892
Gly Gly Met Val Thr Gly Cys Ala Glu Thr Pro Gly Cys Val Ala Tyr
                235                 240                 245

ATC GGC ATC AGC TTC CTC GAC CAG GCC AGT CAA CGG GGA CTC GGC GAG    940
Ile Gly Ile Ser Phe Leu Asp Gln Ala Ser Gln Arg Gly Leu Gly Glu
                250                 255                 260

GCC CAA CTA GGC AAT AGC TCT GGC AAT TTC TTG TTG CCC GAC GCG CAA    988
Ala Gln Leu Gly Asn Ser Ser Gly Asn Phe Leu Leu Pro Asp Ala Gln
265                 270                 275

AGC ATT CAG GCC GCG GCG GCT GGC TTC GCA TCG AAA ACC CCG GCG AAC   1036
Ser Ile Gln Ala Ala Ala Ala Gly Phe Ala Ser Lys Thr Pro Ala Asn
280                 285                 290                 295

CAG GCG ATT TCG ATG ATC GAC GGG CCC GCC CCG GAC GGC TAC CCG ATC   1084
Gln Ala Ile Ser Met Ile Asp Gly Pro Ala Pro Asp Gly Tyr Pro Ile
                300                 305                 310

ATC AAC TAC GAG TAC GCC ATC GTC AAC AAC CGG CAA AAG GAC GCC GCC   1132
Ile Asn Tyr Glu Tyr Ala Ile Val Asn Asn Arg Gln Lys Asp Ala Ala
                315                 320                 325

ACC GCG CAG ACC TTG CAG GCA TTT CTG CAC TGG GCG ATC ACC GAC GGC   1180
Thr Ala Gln Thr Leu Gln Ala Phe Leu His Trp Ala Ile Thr Asp Gly
                330                 335                 340

AAC AAG GCC TCG TTC CTC GAC CAG GTT CAT TTC CAG CCG CTG CCG CCC   1228
Asn Lys Ala Ser Phe Leu Asp Gln Val His Phe Gln Pro Leu Pro Pro
        345                 350                 355

GCG GTG GTG AAG TTG TCT GAC GCG TTG ATC GCG ACG ATT TCC AGC       1273
Ala Val Val Lys Leu Ser Asp Ala Leu Ile Ala Thr Ile Ser Ser
360                 365                 370

TAGCCTCGTT GACCACCACG CGACAGCAAC CTCCGTCGGG CCATCGGGCT GCTTTGCGGA 1333
```

```
GCATGCTGGC CCGTGCCGGT GAAGTCGGCC GCGCTGGCCC GGCCATCCGG TGGTTGGGTG   1393

GGATAGGTGC GGTGATCCCG CTGCTTGCGC TGGTCTTGGT GCTGGTGGTG CTGGTCATCG   1453

AGGCGATGGG TGCGATCAGG CTCAACGGGT TGCATTTCTT CACCGCCACC GAATGGAATC   1513

CAGGCAACAC CTACGGCGAA ACCGTTGTCA CCGACGCGTC GCCCATCCGG TCGGCGCCTA   1573

CTACGGGGCG TTGCCGCTGA TCGTCGGGAC GCTGGCGACC TCGGCAATCG CCCTGATCAT   1633

CGCGGTGCCG GTCTCTGTAG GAGCGGCGCT GGTGATCGTG GAACGGCTGC CGAAACGGTT   1693

GGCCGAGGCT GTGGGAATAG TCCTGGAATT GCTCGCCGGA ATCCCCAGCG TGGTCGTCGG   1753

TTTGTGGGGG GCAATGACGT TCGGGCCGTT CATCGCTCAT CACATCGCTC CGGTGATCGC   1813

TCACAACGCT CCCGATGTGC CGGTGCTGAA CTACTTGCGC GGCGACCCGG GCAACGGGGA   1873

GGGCATGTTG GTGTCCGGTC TGGTGTTGGC GGTGATGGTC GTTCCCATTA TCGCCACCAC   1933

CACTCATGAC CTGTTCCGGC AGGTGCCGGT GTTGCCCCGG GAGGGCGCGA TCGGGAATTC   1993
```

(2) INFORMATION FOR SEQ ID NO:153:

(i) SEQUENCE CHARACTERISTICS:
        (A) LENGTH: 374 amino acids
        (B) TYPE: amino acid
        (D) TOPOLOGY: linear (ii) MOLECULE TYPE: protein (xi) SEQUENCE DESCRIPTION: SEQ ID NO:153:

```
Val Lys Ile Arg Leu His Thr Leu Leu Ala Val Leu Thr Ala Ala Pro
 1               5                  10                  15

Leu Leu Leu Ala Ala Ala Gly Cys Gly Ser Lys Pro Pro Ser Gly Ser
             20                  25                  30

Pro Glu Thr Gly Ala Gly Ala Gly Thr Val Ala Thr Thr Pro Ala Ser
         35                  40                  45

Ser Pro Val Thr Leu Ala Glu Thr Gly Ser Thr Leu Leu Tyr Pro Leu
     50                  55                  60

Phe Asn Leu Trp Gly Pro Ala Phe His Glu Arg Tyr Pro Asn Val Thr
 65                  70                  75                  80

Ile Thr Ala Gln Gly Thr Gly Ser Gly Ala Gly Ile Ala Gln Ala Ala
                 85                  90                  95

Ala Gly Thr Val Asn Ile Gly Ala Ser Asp Ala Tyr Leu Ser Glu Gly
            100                 105                 110

Asp Met Ala Ala His Lys Gly Leu Met Asn Ile Ala Leu Ala Ile Ser
            115                 120                 125

Ala Gln Gln Val Asn Tyr Asn Leu Pro Gly Val Ser Glu His Leu Lys
        130                 135                 140

Leu Asn Gly Lys Val Leu Ala Ala Met Tyr Gln Gly Thr Ile Lys Thr
145                 150                 155                 160

Trp Asp Asp Pro Gln Ile Ala Ala Leu Asn Pro Gly Val Asn Leu Pro
                165                 170                 175

Gly Thr Ala Val Val Pro Leu His Arg Ser Asp Gly Ser Gly Asp Thr
            180                 185                 190

Phe Leu Phe Thr Gln Tyr Leu Ser Lys Gln Asp Pro Glu Gly Trp Gly
        195                 200                 205

Lys Ser Pro Gly Phe Gly Thr Thr Val Asp Phe Pro Ala Val Pro Gly
    210                 215                 220

Ala Leu Gly Glu Asn Gly Asn Gly Gly Met Val Thr Gly Cys Ala Glu
225                 230                 235                 240
```

```
                Thr Pro Gly Cys Val Ala Tyr Ile Gly Ile Ser Phe Leu Asp Gln Ala
                            245                 250                 255

Ser Gln Arg Gly Leu Gly Glu Ala Gln Leu Gly Asn Ser Ser Gly Asn
                            260                 265                 270

Phe Leu Leu Pro Asp Ala Gln Ser Ile Gln Ala Ala Ala Ala Gly Phe
                            275                 280                 285

Ala Ser Lys Thr Pro Ala Asn Gln Ala Ile Ser Met Ile Asp Gly Pro
                    290                 295                 300

Ala Pro Asp Gly Tyr Pro Ile Ile Asn Tyr Glu Tyr Ala Ile Val Asn
                305                 310                 315                 320

Asn Arg Gln Lys Asp Ala Ala Thr Ala Gln Thr Leu Gln Ala Phe Leu
                            325                 330                 335

His Trp Ala Ile Thr Asp Gly Asn Lys Ala Ser Phe Leu Asp Gln Val
                            340                 345                 350

His Phe Gln Pro Leu Pro Pro Ala Val Val Lys Leu Ser Asp Ala Leu
                            355                 360                 365

Ile Ala Thr Ile Ser Ser
                    370
```